US008779142B2

(12) United States Patent
Kitade et al.

(10) Patent No.: US 8,779,142 B2
(45) Date of Patent: Jul. 15, 2014

(54) AZABICYCLO COMPOUND AND SALT THEREOF

(75) Inventors: Makoto Kitade, Hanno (JP); Shuichi Ohkubo, Hanno (JP); Chihoko Yoshimura, Hanno (JP); Satoshi Yamashita, Hanno (JP); Hiromi Oshiumi, Hanno (JP); Takao Uno, Hanno (JP); Yuichi Kawai, Hanno (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 67 days.

(21) Appl. No.: 13/378,527

(22) PCT Filed: Jul. 9, 2010

(86) PCT No.: PCT/JP2010/004466
§ 371 (c)(1),
(2), (4) Date: Dec. 15, 2011

(87) PCT Pub. No.: WO2011/004610
PCT Pub. Date: Jan. 13, 2011

(65) Prior Publication Data
US 2012/0108589 A1 May 3, 2012

(30) Foreign Application Priority Data

Jul. 10, 2009 (JP) .................................. 2009-164196

(51) Int. Cl.
*A61K 31/4365* (2006.01)
*C07D 471/04* (2006.01)

(52) U.S. Cl.
USPC ........................... 546/118; 546/117; 546/113

(58) Field of Classification Search
USPC .................. 546/113, 117, 118; 514/300, 303
See application file for complete search history.

(56) References Cited

U.S. PATENT DOCUMENTS

| 2007/0185184 A1 | 8/2007 | Hanson et al. |
| 2008/0096868 A1 | 4/2008 | Schmiedeberg et al. |
| 2008/0119457 A1 | 5/2008 | Huang et al. |
| 2008/0234314 A1 | 9/2008 | Cai et al. |
| 2012/0010241 A1 | 1/2012 | Bertin et al. |

FOREIGN PATENT DOCUMENTS

| JP | 2007 505933 | 3/2007 |
| JP | 2008 519790 | 6/2008 |
| JP | 2009 504669 | 2/2009 |
| WO | 2007 035620 | 3/2007 |
| WO | 2008 024978 | 2/2008 |
| WO | 2008 025947 | 3/2008 |
| WO | 2008 115719 | 9/2008 |
| WO | 2008 118391 | 10/2008 |
| WO | WO 2010/106290 A1 | 9/2010 |

OTHER PUBLICATIONS

Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*
Dymock et al. "Inhibitors of HSP90 and Other Chaperones for the Treatment of Cancer", Expert Opinion on Therapeutic Patents 2004, 14(6), 837-847.*
Bagatell et al. "Altered HSP90 Function in Cancer: A Unique Therapeutic Opportunity", Molecular Cancer Therapy, 2004 1021-1030.*
Whitesell et al. "Targeting HSP90 Function to Treat Cancer: Much More to Be Learned", Heat Shock Proteins in Cancer, 2007, Chapter 13, 253-274.*
Trepel et al. "Targeting the Dynamic HSP90 Complex in Cancer", Nat. Rev. Cancer, 10(8); 2010:537-549.*
Extended European Search Report issued Nov. 13, 2012 in Patent Application No. 10796921.4.
Whitesell, L., et al "HSP90 and the Chaperoning of Cancer," Nature Reviews, vol. 5, pp. 761-772, (Oct. 2005).
Kamal, A., et al., "Therapeutic and diagnostic implications of Hsp90 activation," Trends in Molecular Medicine, vol. 10, No. 6, pp. 283-290, (Jun. 6, 2004).
Banerji, U., "Heat Shock protein 90 as a Drug Target: Some Like It Hot," Clin Cancer Res, vol. 15, No. 1, pp. 9-14, (Jan. 1, 2009).
Taldone, T., et al., "Targeting Hsp90: small-molecule inhibitors and their clinical development," Current Opinion in Pharmacology, vol. 8, pp. 370-374, (2008).
Li, Y., et al., "New developments is Hsp90 inhibitors as anti-cancer therapeutics: Mechanisms, clinical perspective and more potential," Drug Resistance Updates, vol. 12, pp. 17-27, (2009).
Luo, W., et al., "Heat shock protein 90: translation from cancer to Alzheimer's disease treatment?," BMC Neuroscience, vol. 9, (Suppl. 2)S7, pp. 1-8, (2008).
International Search Report Issued Sep. 7, 2010 in PCT/JP10/04466 Filed Jul. 9, 2010.

* cited by examiner

*Primary Examiner* — David K O Dell
(74) *Attorney, Agent, or Firm* — Oblon, Spivak, McClelland, Maier & Neustadt, L.L.P.

(57) ABSTRACT

It is intended to provide a novel azabicyclo compound which exhibits both HSP90 inhibitory activity and cell proliferation inhibitory effect. Specifically disclosed is a compound represented by the following general formula (I) or a salt thereof: wherein $X^1$ represents CH or N; any one of $X^2$, $X^3$ and $X^4$ represents N, and the others represent CH; any one or two of $Y^1$, $Y^2$, $Y^3$ and $Y^4$ represent C—$R^4$, and the others are the same or different and represent CH or N; $R^1$ represents an optionally substituted monocyclic or bicyclic unsaturated heterocyclic group having 1 to 4 heteroatoms selected from N, S and O; $R^2$ represents an alkyl group having 1 to 6 carbon atoms, or the like; and $R^3$ and $R^4$ represent —CO—$R^5$ or the like.

12 Claims, No Drawings

AZABICYCLO COMPOUND AND SALT THEREOF

FIELD OF THE INVENTION

The present invention relates to an azabicyclo compound or a salt thereof and a pharmaceutical composition containing the same, particularly, a preventive and/or therapeutic agent for cancer, etc., based on HSP90 inhibitory activity.

BACKGROUND OF THE INVENTION

A group of proteins called molecular chaperons is a multifunctional protein, which promotes the formation of the functional structures of other proteins or maintains these structures, promotes correct association, inhibits unnecessary aggregation, protects other proteins from degradation, and promotes secretion (Non-Patent Document 1). HSP90 is a molecular chaperon as abundant as approximately 1 to 2% of all intracellular soluble proteins and is however unnecessary for the biosynthesis of the majority of polypeptides, unlike other chaperon proteins (Non-Patent Document 1). Signaling-related factors (e.g., ERBB1/EGFR, ERBB2/HER2, MET, IGF1R, KDR/VEGFR, FLT3, ZAP70, KIT, CHUK/IKK, BRAF, RAF1, SRC and AKT), cell cycle regulators (e.g., CDK4, CDK6, Cyclin D, PLK1 and BIRC5), and transcriptional regulators (e.g., HIF-1α, p53, androgen receptor, estrogen receptor and progesterone receptor) are known as the main client proteins whose structure formation or stability is regulated by HSP90 through the interaction therebetween (Non-Patent Documents 2 and 3). HSP90 is deeply involved in cell proliferation or survival by maintaining the normal functions of these proteins. Furthermore, HSP90 is required for the normal functions of mutated or chimeric factors (e.g., BCR-ABL and NPM-ALK) which cause carcinogenesis or exacerbation of cancer. This indicates the importance of HSP90 particularly for processes such as carcinogenesis, cancer survival, growth, exacerbation and metastasis (Non-Patent Document 2).

The inhibition of the chaperon functions of HSP90 by specific inhibitors such as geldanamycin causes the inactivation, destabilization and degradation of the client proteins, resulting in induction of a halt in cell proliferation or apoptosis (Non-Patent Document 4). In terms of the physiological functions of HSP90, HSP90 inhibitors are characterized in that they can simultaneously inhibit a plurality of signaling pathways involved in cancer survival/growth. Thus, the HSP90 inhibitors can serve as drugs having extensive and effective anticancer activity. Moreover, from the findings that cancer cell-derived HSP90 has higher activity and higher affinity for ATP or inhibitors than those of normal cell-derived HSP90, it has been expected that the HSP90 inhibitors would serve as drugs having high cancer selectivity (Non-Patent Document 5). Currently, the clinical development of a plurality of HSP90 inhibitors as anticancer agents is ongoing. The most advancing geldanamycin derivative 17-allylamino-17-demethoxygeldanamycin (17-AAG) is under development as single agents as well as under test on the combined use with various anticancer agents (Non-Patent Documents 3 and 4). However, the problems of 17-AAG, such as poor solubility, instability in solutions, low oral absorption and liver toxicity, have also been pointed out (Non-Patent Documents 4 and 5). Thus, a new type of HSP90 inhibitor has been desired. It has also been reported that HSP90 inhibitors not only have anticancer activity but also can serve as therapeutic agents for autoimmune disease, inflammatory disease, central nervous system disease (e.g., Parkinson's disease, Alzheimer's disease, and Huntington's disease), viral infections, cardiovascular disease, etc. (Non-Patent Documents 2 and 6).

PRIOR ART DOCUMENTS

Patent Document

Patent Document 1: International Publication No. WO2007035620
Patent Document 2: International Publication No. WO2008024978

Non-Patent Document

Non-Patent Document 1: Nature Reviews Cancer 5, 761-772 (2005)
Non-Patent Document 2: TRENDS in Molecular Medicine 6, 283-290 (2007)
Non-Patent Document 3: Clin Can Res 15, 9-14 (2009)
Non-Patent Document 4: Current Opinion in Pharmacology 8, 370-374 (2008)
Non-Patent Document 5: Drug Resistance Updates 12, 17-27 (2009)
Non-Patent Document 6: BMC Neuroscience 9 (Suppl 2), 2008

SUMMARY OF THE INVENTION

Problems to be solved by the Invention

An object of the present invention is to provide a novel azabicyclo compound which has both HSP90 inhibitory activity and cell proliferation inhibitory effect. Another object of the present invention is to provide a pharmaceutical product which is useful for the prevention and/or treatment of disease involving the HSP90, particularly, cancer, based on the HSP90 inhibitory activity.

Means for Solving the Problems

The present inventors have intensively studied various compounds having HSP90 inhibitory activity and consequently completed the present invention by finding that a novel compound represented by the general formula (I) shown below, which has an unsaturated heterocyclic group at position 4 ($R^1$ in the general formula (I)) of the azabicyclo compound, exhibits exceedingly excellent inhibitory activity against HSP90 and further exhibits excellent cell proliferation inhibitory effect on cancer cell lines.

Specifically, the present invention provides a compound represented by the following general formula (I), or a salt thereof:

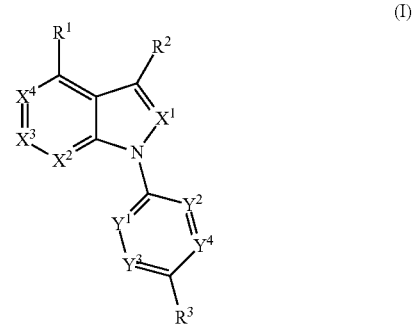

wherein $X^1$ represents CH or N;
any one of $X^2$, $X^3$ and $X^4$ represents N, and the others represent CH;

any one or two of $Y^1$, $Y^2$, $Y^3$ and $Y^4$ represent C—$R^4$, and the others are the same or different and represent CH or N;

$R^1$ represents an optionally substituted monocyclic or bicyclic unsaturated heterocyclic group having 1 to 4 heteroatoms selected from N, S and O;

$R^2$ represents a hydrogen atom, an optionally substituted alkyl group having 1 to 6 carbon atoms or an optionally substituted alkenyl group having 2 to 6 carbon atoms;

$R^3$ represents a cyano group or —CO—$R^5$;

$R^4$(s) are the same or different and represent a hydrogen atom, a halogen atom, a cyano group, an optionally substituted alkyl group having 1 to 6 carbon atoms, an alkenyl group having 2 to 6 carbon atoms, an alkoxy group having 1 to 6 carbon atoms, an aromatic hydrocarbon group, —N($R^6$)($R^7$), —S—$R^8$ or —CO—$R^9$;

$R^5$ represents a hydroxyl group, an amino group optionally having a hydroxyl group, or an optionally substituted mono- or di-alkylamino group;

$R^6$ and $R^7$ are the same or different and represent a hydrogen atom, an optionally substituted alkyl group having 1 to 6 carbon atoms, a halogenoalkyl group having 1 to 6 carbon atoms, an optionally substituted cycloalkyl group having 3 to 7 carbon atoms, an optionally substituted aralkyl group, an optionally substituted aromatic hydrocarbon group, an optionally substituted saturated heterocyclic group or an optionally substituted unsaturated heterocyclic group, or $R^6$ and $R^7$ optionally form a saturated heterocyclic group, together with the nitrogen atom to which they are bonded;

$R^8$ represents an optionally substituted cycloalkyl group having 3 to 7 carbon atoms, or an optionally substituted aromatic hydrocarbon group; and $R^9$ represents a hydrogen atom, a hydroxyl group, an amino group optionally having a hydroxyl group, or an optionally substituted mono- or di-alkylamino group.

The present invention also provides a pharmaceutical product containing the compound represented by the general formula (I), or the salt thereof.

Moreover, the present invention provides a pharmaceutical composition containing the compound represented by the general formula (I), or the salt thereof and a pharmaceutically acceptable carrier.

Moreover, the present invention provides the compound represented by the general formula (I), or the salt thereof, for used in the treatment of cancer.

Furthermore, the present invention provides a method for treating cancer, including administering an effective amount of the compound represented by the general formula (I), or the salts thereof.

Effects of the Invention

The present invention provides a novel compound represented by the general formula (I), or a salt thereof which is useful as an HSP90 inhibitor.

The compound of the present invention, or the salt thereof, has been shown to exhibit excellent HSP90 inhibitory activity and exhibit proliferation inhibitory effect on cancer cell lines. Thus, the compound of the present invention, or the salt thereof, is useful as a preventive and/or therapeutic agent for disease involving HSP90, for example, cancer, based on its excellent HSP90 inhibitory activity.

DETAILED DESCRIPTION OF THE INVENTION

A compound of the present invention represented by the general formula (I) is an azabicyclo compound characterized by having an unsaturated heterocyclic group, such as azaindole or azaindazole, at position 4 of the skeleton, and is a novel compound which is not described in any of the Documents in Citation List, etc.

In the present specification, examples of "substituents" include a halogen atom, a hydroxyl group, a cyano group, a nitro group, an alkyl group, a halogenoalkyl group, a cycloalkyl group, a cycloalkyl-alkyl group, an aralkyl group, a hydroxyalkyl group, an alkenyl group, an alkynyl group, an alkoxy group, a halogenoalkoxy group, an alkoxy-alkyl group, a cycloalkoxy group, a cycloalkyl-alkoxy group, an aralkyloxy group, an aralkyloxy-alkyl group, an alkylthio group, a cycloalkyl-alkylthio group, an amino group, a mono- or dialkylamino group, a cycloalkyl-alkylamino group, an acyl group, an acyloxy group, an oxo group, a carboxyl group, an alkoxycarbonyl group, an aralkyloxycarbonyl group, a carbamoyl group, a saturated or unsaturated heterocyclic group, an aromatic hydrocarbon group and a saturated heterocyclic oxy group. The number of the substituents, if any, is typically 1 to 3.

Examples of the halogen atom included in the substituents include chlorine, bromine, fluorine and iodine atoms.

The alkyl or halogenoalkyl group included in the substituents preferably refers to a linear or branched alkyl group having 1 to 6 carbon atoms, or a group in which one or all hydrogen atoms in such an alkyl group are substituted by the halogen atom exemplified above. Examples thereof include: alkyl groups such as methyl, ethyl, n-propyl, isopropyl, n-butyl, isobutyl, sec-butyl, tert-butyl, pentyl and hexyl groups; and halogenoalkyl groups such as a trifluoromethyl group.

The cycloalkyl group included in the substituents is preferably a cycloalkyl group having 3 to 7 carbon atoms. Examples thereof include cyclopropyl, cyclobutyl, cyclopentyl, cyclohexyl and cycloheptyl groups.

The cycloalkyl-alkyl group included in the substituents is preferably an alkyl group having 1 to 6 carbon atoms which is substituted by cycloalkyl having 3 to 7 carbon atoms. Examples thereof include cyclopropylmethyl, cyclopropylethyl, cyclobutylmethyl, cyclopentylmethyl and cyclohexylmethyl groups.

The aralkyl group included in the substituents preferably refers to a linear or branched alkyl group having 1 to 6 carbon atoms which is substituted by an aromatic hydrocarbon group having 6 to 14 carbon atoms. Examples thereof include benzyl, phenylethyl, phenylpropyl, naphthylmethyl and naphthylethyl groups.

The hydroxyalkyl group included in the substituents preferably refers to the linear or branched alkyl group having 1 to 6 carbon atoms exemplified above which has a hydroxy group. Examples thereof include hydroxymethyl and hydroxyethyl groups.

The alkenyl group included in the substituents preferably refers to an alkenyl group having 2 to 6 carbon atoms which contains a carbon-carbon double bond. Examples thereof include vinyl, allyl, methylvinyl, propenyl, butenyl, pentenyl and hexenyl groups.

The alkynyl group included in the substituents preferably refers to an alkynyl group having 2 to 6 carbon atoms which contains a carbon-carbon triple bond. Examples thereof include ethynyl and propargyl groups.

The alkoxy or halogenoalkoxy group included in the substituents preferably refers to a linear or branched alkoxy group having 1 to 6 carbon atoms, or a group in which such an alkoxy group is substituted by the halogen atom exemplified above. Examples thereof include methoxy, ethoxy, n-propoxy, isopropoxy, 1-methylpropoxy, n-butoxy, isobutoxy, tert-butoxy, 2-methyl-butoxy, neopentyloxy, pentan-2-yloxy, fluoromethoxy, difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 3-fluoro-2-(fluoromethyl)-propoxy, 1,3-difluoropropan-2-yloxy and 2,2,3,3,3-pentafluoro-1-propoxy groups.

The cycloalkoxy group included in the substituents is preferably a cycloalkoxy group having 3 to 7 carbon atoms. Examples thereof include cyclopropoxy, cyclobutoxy, cyclopentyloxy, cyclohexyloxy and cycloheptyloxy groups.

The alkoxy-alkyl group included in the substituents preferably refers to the alkyl group having 1 to 6 carbon atoms exemplified above which is substituted by the linear or branched alkoxy group having 1 to 6 carbon atoms exemplified above. Examples thereof include methoxymethyl and ethoxymethyl groups.

The cycloalkyl-alkoxy group included in the substituents is preferably an alkoxy group having 1 to 6 carbon atoms which is substituted by cycloalkyl having 3 to 7 carbon atoms. Examples thereof include cyclopropylmethoxy, cyclopropylethoxy, cyclobutylmethoxy, cyclopentylmethoxy and cyclohexylmethoxy groups.

The aralkyloxy group included in the substituents preferably refers to an oxy group which has the aralkyl group exemplified above. Examples thereof include benzyloxy, phenethyloxy, phenylpropyloxy, naphthylmethyloxy and naphthylethyloxy groups.

The aralkyloxy-alkyl group included in the substituents preferably refers to the linear or branched alkyl group having 1 to 6 carbon atoms exemplified above which has the aralkyloxy group exemplified above. Examples thereof include benzyloxymethyl and benzyloxyethyl groups.

The alkylthio group included in the substituents is preferably a (C1-C6) alkylthio group which refers to a linear or branched alkylthio group having 1 to 6 carbon atoms. Examples thereof include methylthio, ethylthio, n-propylthio, isopropylthio, n-butylthio, isobutylthio, sec-butylthio, tert-butylthio, pentylthio and hexylthio groups.

The cycloalkyl-alkylthio group included in the substituents is preferably an alkylthio group having 1 to 6 carbon atoms which is substituted by cycloalkyl having 3 to 7 carbon atoms. Examples thereof include cyclopropylmethylthio, cyclopropylethylthio, cyclobutylmethylthio, cyclopentylmethylthio and cyclohexylmethylthio groups.

The mono- or dialkylamino group included in the substituents is a mono- or di-(C1-C6 alkyl)amino group which refers to an amino group which is monosubstituted or disubstituted by the linear or branched alkyl group having 1 to 6 carbon atoms exemplified above. Examples thereof include methylamino, dimethylamino, ethylamino, diethylamino and methylethylamino groups.

The cycloalkyl-alkylamino group included in the substituents refers to an alkylamino group which is substituted by the cycloalkyl group exemplified above. Examples thereof include cyclopropylmethylamino, cyclobutylmethylamino and cyclopentylmethylamino groups.

Examples of the acyl group included in the substituents include: linear or branched acyl groups having 1 to 6 carbon atoms, such as formyl, acetyl, propionyl, n-butyryl, isobutyryl, valeryl, isovaleryl and pivaloyl groups; and a benzoyl group.

Examples of the acyloxy group included in the substituents include: linear or branched acyloxy groups having 1 to 6 carbon atoms, such as formyloxy, acetoxy, propionyloxy, n-butyryloxy, isobutyryloxy, valeryloxy, isovaleryloxy and pivaloyloxy groups; a benzoyloxy group; and amino acid-derived acyloxy groups such as glycyloxy, alanyloxy and leucyloxy groups.

The alkoxycarbonyl group included in the substituents refers to a carbonyl group which is substituted by the alkoxy group exemplified above. Examples thereof include methoxycarbonyl, ethoxycarbonyl, n-propoxycarbonyl, isopropoxycarbonyl, 1-methylpropoxycarbonyl, n-butoxycarbonyl, isobutoxycarbonyl, tert-butoxycarbonyl, 2-methylbutoxycarbonyl, neopentyloxycarbonyl and pentan-2-yloxycarbonyl groups.

The aralkyloxycarbonyl group included in the substituents preferably refers to a carbonyl group which is substituted by the aralkyloxy group exemplified above. Examples thereof include benzyloxycarbonyl, phenethyloxycarbonyl, phenylpropyloxycarbonyl, naphthylmethyloxycarbonyl and naphthylethyloxycarbonyl groups.

Examples of the carbamoyl group included in the substituents include —$CONH_2$, (mono- or dialkyl)carbamoyl, (mono- or diaryl)carbamoyl, (N-alkyl-N-aryl)carbamoyl, pyrrolidinocarbamoyl, piperidinocarbamoyl, piperazinocarbamoyl and morpholinocarbamoyl groups.

The saturated or unsaturated heterocyclic group included in the substituents refers to a monocyclic or bicyclic saturated or 5- to 10-membered unsaturated heterocyclic group preferably having 1 to 4 of any heteroatom of N, S and O. Examples thereof include pyrrolidinyl, piperidinyl, piperazinyl, hexamethyleneimino, morpholino, thiomorpholino, homopiperazinyl, tetrahydrofuranyl, tetrahydropyranyl, imidazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, indazolyl, methylenedioxyphenyl, ethylenedioxyphenyl, benzofuranyl, dihydrobenzofuranyl, benzoimidazolyl, benzoxazolyl, benzothiazolyl, purinyl, quinolyl, isoquinolyl, quinazolinyl and quinoxalyl groups.

The aromatic hydrocarbon group included in the substituents preferably refers to an aromatic hydrocarbon group having 6 to 14 carbon atoms. Examples thereof include phenyl and naphthyl groups.

The saturated heterocyclic oxy group included in the substituents refers to a monocyclic 5- to 7-membered saturated heterocyclic group having one or two of any heteroatom of N, S and O, for example, an oxy group which has a pyrrolidinyl, piperidinyl, piperazinyl, hexamethyleneimino, morpholino, thiomorpholino, homopiperazinyl group or the like. Examples thereof include tetrahydrofuranyloxy and tetrahydropyranyloxy groups.

In the general formula (I), $X^1$ represents CH or N. Moreover, in the general formula (I), any one of $X^2$, $X^3$ and $X^4$ represents N, and the others represent CH. Based on these definitions of $X^1$ to $X^4$, examples of the azabicyclo skeleton in the general formula (I) include the following structures:

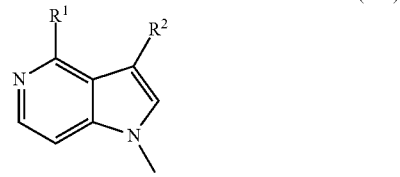

(A-1)

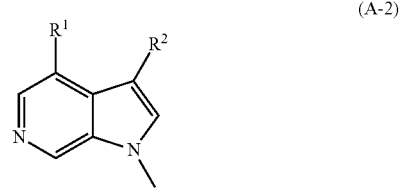

(A-2)

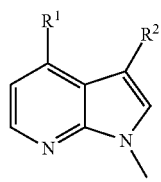

(A-3)

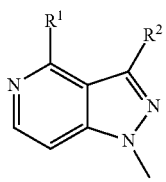

(A-4)

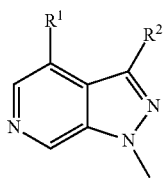

(A-5)

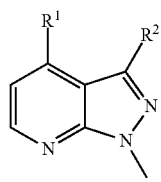

(A-6)

wherein $R^1$ and $R^2$ are as defined above.

Of these skeletons, (A-3) and (A-6) are particularly preferable.

In the general formula (I), the "monocyclic or bicyclic unsaturated heterocyclic group having 1 to 4 heteroatoms selected from N, S and O" in the "optionally substituted monocyclic or bicyclic unsaturated heterocyclic group having 1 to 4 heteroatoms selected from N, S and O", represented by $R^1$ is preferably a monocyclic or bicyclic 5- to 10-membered unsaturated heterocyclic group having 1 to 3 heteroatoms selected from N, S and O, more preferably a monocyclic 5- to 6-membered unsaturated heterocyclic group having 1 to 3 heteroatoms selected from N, S and O, or a bicyclic 9- to 10-membered unsaturated heterocyclic group having 1 to 3 heteroatoms selected from N, S and O. The heterocyclic group is preferably a group having imidazole, pyrazole, thiophene, furan, pyrrole, oxazole, isoxazole, thiazole, isothiazole, triazole, tetrazole, pyridine, pyrazine, pyrimidine, pyridazine, indole, isoindole, pyrrolopyridine, indazole, methylenedioxyphenyl, ethylenedioxyphenyl, benzofuran, dihydrobenzofuran, benzimidazole, benzoxazole, benzothiazole, purine, quinoline, tetrahydroquinoline, isoquinoline, quinazoline or quinoxaline, more preferably a group having imidazole, pyrazole, thiophene, furan, pyridine, indole, pyrrolopyridine, benzofuran, quinoline or tetrahydroquinoline, particularly preferably a group having imidazole, pyridine or quinoline.

Specific examples thereof include 1H-imidazol-1-yl, 1H-imidazol-2-yl, 1H-imidazol-4-yl, 1H-pyrazol-1-yl, 1H-pyrazol-3-yl, 1H-pyrazol-4-yl, thiophen-2-yl, thiophen-3-yl, furan-2-yl, furan-3-yl, pyrrol-1-yl, pyrrol-2-yl, pyrrol-3-yl, oxazol-2-yl, oxazol-4-yl, oxazol-5-yl, isoxazol-3-yl, isoxazol-4-yl, isoxazol-5-yl, thiazol-2-yl, thiazol-3-yl, thiazol-4-yl, thiazol-5-yl, isothiazol-2-yl, isothiazol-4-yl, isothiazol-5-yl, pyrazol-1-yl, pyrazol-3-yl, pyrazol-4-yl, 1,2,3-triazol-1-yl, 1,2,3-triazol-4-yl, 1,2,4-triazol-1-yl, 1,2,4-triazol-3-yl, 1,2,4-triazol-4-yl, tetrazol-1-yl, tetrazol-5-yl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyrimidin-6-yl, pyridazin-3-yl, pyridazin-4-yl, indol-1-yl, indol-2-yl, indol-3-yl, indol-4-yl, indol-5-yl, indol-6-yl, indol-7-yl, isoindol-1-yl, isoindol-2-yl, isoindol-4-yl, isoindol-5-yl, 1H-pyrrolo[2,3-b]pyridin-1-yl, 1H-pyrrolo[2,3-b]pyridin-2-yl, 1H-pyrrolo[2,3-b]pyridin-3-yl, 1H-pyrrolo[2,3-b]pyridin-4-yl, 1H-pyrrolo[2,3-b]pyridin-5-yl, 1H-pyrrolo[2,3-b]pyridin-6-yl, 1H-indazol-1-yl, 1H-indazol-3-yl, 1H-indazol-4-yl, 1H-indazol-5-yl, 1H-indazol-6-yl, 1H-indazol-7-yl, methylenedioxyphenyl, ethylenedioxyphenyl, benzofuran-2-yl, benzofuran-3-yl, benzofuran-4-yl, benzofuran-5-yl, benzofuran-6-yl, benzofuran-7-yl, 2,3-dihydrobenzofuran-2-yl, 2,3-dihydrobenzofuran-3-yl, benzimidazol-1-yl, benzimidazol-2-yl, benzimidazol-4-yl, benzimidazol-5-yl, benzoxazol-2-yl, benzoxazol-4-yl, benzoxazol-5-yl, benzothiazol-2-yl, benzothiazol-4-yl, benzothiazol-5-yl, purin-2-yl, purin-6-yl, purin-7-yl, purin-8-yl, quinolin-2-yl, quinolin-3-yl, quinolin-4-yl, quinolin-5-yl, quinolin-6-yl, quinolin-7-yl, quinolin-8-yl, 5,6,7,8-tetrahydroquinolin-2-yl, 5,6,7,8-tetrahydroquinolin-3-yl, 5,6,7,8-tetrahydroquinolin-4-yl, isoquinolin-1-yl, isoquinolin-3-yl, isoquinolin-4-yl, isoquinolin-5-yl, isoquinolin-6-yl, isoquinolin-7-yl, isoquinolin-8-yl, quinazolin-4-yl, quinoxalin-2-yl, quinoxalin-5-yl and quinoxalin-6-yl groups. The heterocyclic group is preferably a 1H-imidazol-1-yl, pyrazol-4-yl, thiophen-3-yl, furan-2-yl, pyridin-3-yl, pyridin-4-yl, indol-5-yl, 1H-pyrrolo[2,3-b]pyridin-5-yl, benzofuran-2-yl, quinolin-3-yl or 5,6,7,8-tetrahydroquinolin-3-yl group, more preferably a 1H-imidazol-1-yl, pyridin-3-yl, pyridin-4-yl, indol-5-yl, 1H-pyrrolo[2,3-b]pyridin-5-yl, benzofuran-2-yl, quinolin-3-yl or 5,6,7,8-tetrahydroquinolin-3-yl group, particularly preferably a 1H-imidazol-1-yl, pyridin-3-yl or quinolin-3-yl group.

In the general formula (I), examples of the "substituent(s)" in the unsaturated heterocyclic group represented by $R^1$ include the substituents exemplified above. The substituent(s) are preferably 1 to 3 substituents selected from an alkyl group, an alkoxy group, an alkoxy-alkyl group, an aralkyl group, an aralkyloxy-alkyl group, a halogen atom, a halogenoalkyl group, an acyl group, an optionally substituted saturated or unsaturated heterocyclic group and an optionally substituted aromatic hydrocarbon group, more preferably 1 to 3 substituents selected from: an alkyl group; an alkoxy group; an unsaturated heterocyclic group optionally having an alkyl group, a halogenoalkyl group, an aralkyl group or a hydroxyalkyl group; and an aromatic hydrocarbon group optionally having an alkyl group, an alkoxy group or a carbamoyl group. In this context, examples of the unsaturated heterocyclic group which may be substituted on the unsaturated heterocyclic ring represented by $R^1$ include pyrazole, imidazole, pyridine, pyrimidine, furan and thiophene. Moreover, examples of the aromatic hydrocarbon group include phenyl and naphthyl.

Specific examples of the "substituent(s)" in the unsaturated heterocyclic group represented by $R^1$ can include methyl, ethyl, n-propyl, isopropyl, n-butyl, isobutyl, sec-butyl, tert-butyl, methoxy, ethoxy, n-propoxy, isopropoxy, 1-methylpropoxy, n-butoxy, isobutoxy, tert-butoxy, 1H-pyrazol-4-yl, 1-methyl-1H-pyrazol-4-yl, 1-ethyl-1H-pyrazol-4-yl, 1-isopropyl-1H-pyrazol-4-yl, 1-benzyl-1H-pyrazol-4-yl, 1-(difluoromethyl)-1H-pyrazol-4-yl, 1-(hydroxyethyl)-1H-pyrazol-4-yl, 1H-imidazol-1-yl, pyridin-3-yl, pyridin-4-yl, pyrimidine-5-yl, furan-2-yl, furan-3-yl, thiophen-3-yl, phenyl, 4-methoxyphenyl, 4-carbamoylphenyl, 4-isopropylcarbamoylphenyl and 4-dimethylcarbamoylphenyl groups.

Specific examples of preferable $R^1$ include 1H-imidazol-1-yl, 4-phenyl-1H-imidazol-1-yl, 4-(4-carbamoylphenyl)-1H-imidazol-1-yl, 4-(4-methoxyphenyl)-1H-imidazol-1-yl, 4-(thiophen-3-yl)-1H-imidazol-1-yl, 4-(pyridin-3-yl)-1H-imidazol-1-yl, 4-(pyridin-4-yl)-1H-imidazol-1-yl, 5-methyl-4-(pyridin-3-yl)-1H-imidazol-1-yl, 4-(pyrimidin-5-yl)-1H-imidazol-1-yl, 4-(furan-2-yl)-1H-imidazol-1-yl, 4-(furan-3-yl)-1H-imidazol-1-yl, 4-(1H-pyrazol-4-yl)-1H-imidazol-1-yl, 4-(1-methyl-1H-pyrazol-4-yl)-1H-imidazol-1-yl, 4-(1-ethyl-1H-pyrazol-4-yl)-1H-imidazol-1-yl, 4-(1-isopropyl-1H-pyrazol-4-yl)-1H-imidazol-1-yl, 4-(1-hydroxymethyl)-(1H-pyrazol-4-yl)-1H-imidazol-1-yl, 4-(1-(difluoromethyl)-1H-pyrazol-4-yl)-1H-imidazol-1-yl, 4-(1-(hydroxyethyl)-1H-pyrazol-4-yl)-1H-imidazol-1-yl, 4-(1-(hydroxymethyl)-1H-pyrazol-4-yl)-1H-imidazol-1-yl, 4-(1-benzyl-1H-pyrazol-4-yl)-1H-imidazol-1-yl, 4-(1-(benzyloxyethyl)-1H-pyrazol-4-yl)-1H-imidazol-1-yl, 1'H-1,4'-biimidazol-1'-yl, pyridin-3-yl, pyridin-4-yl, 5-methoxypyridin-3-yl, 6-methoxypyridin-3-yl, 1-benzyl-1H-pyrazol-4-yl, 1-methyl-1H-indol-5-yl, 1H-pyrrolo[2,3-b]pyridin-5-yl, 1-methyl-1H-pyrrolo[2,3-b]pyridin-5-yl, 1-methoxymethyl-1H-pyrrolo[2,3-b]pyridin-5-yl, 5,6,7,8-tetrahydroquinolin-3-yl, quinolin-3-yl, thiophen-3-yl, furan-2-yl and benzofuran-2-yl groups. $R^1$ is more preferably a 1H-imidazol-1-yl, 4-(pyridin-3-yl)-1H-imidazol-1-yl, 4-(pyridin-4-yl)-1H-imidazol-1-yl, 4-(1H-pyrazol-4-yl)-1H-imidazol-1-yl, 4-(1-methyl-1H-pyrazol-4-yl)-1H-imidazol-1-yl, 4-(1-ethyl-1H-pyrazol-4-yl)-1H-imidazol-1-yl, 4-(1-isopropyl-1H-pyrazol-4-yl)-1H-imidazol-1-yl, 4-(1-benzyl-1H-pyrazol-4-yl)-1H-imidazol-1-yl, quinolin-3-yl or 4-(1H-pyrazol-4-yl)-1H-imidazol-1-yl group, particularly preferably a 4-(1-methyl-1H-pyrazol-4-yl)-1H-imidazol-1-yl, 4-(pyridin-3-yl)-1H-imidazol-1-yl or quinolin-3-yl group.

In the general formula (I), the "alkyl group having 1 to 6 carbon atoms" in the "optionally substituted alkyl group having 1 to 6 carbon atoms" represented by $R^2$ refers to a linear or branched alkyl group having 1 to 6 carbon atoms, for example, a methyl, ethyl, n-propyl, isopropyl, n-butyl, isobutyl, sec-butyl, tert-butyl, pentyl or hexyl group, and is preferably a methyl, ethyl, n-propyl or isopropyl group.

Examples of the "substituent(s)" in the "optionally substituted alkyl group having 1 to 6 carbon atoms" represented by $R^2$ include the substituents exemplified above. Of them, the substituent(s) are preferably a halogen atom.

The halogen atom-substituted alkyl group is preferably a halogenoalkyl group having 1 to 6 carbon atoms, more preferably a trifluoromethyl group.

The "alkenyl group having 2 to 6 carbon atoms" represented by $R^2$ refers to the alkenyl group having 2 to 6 carbon atoms exemplified above and is preferably a vinyl group. Examples of the "substituent(s)" in the alkenyl group include the substituents exemplified above.

$R^2$ is more preferably an optionally substituted alkyl group having 1 to 6 carbon atoms, or an optionally substituted alkenyl group having 2 to 6 carbon atoms, even more preferably an alkyl group having 1 to 6 carbon atoms which optionally has a halogen atom, or an alkenyl group having 2 to 6 carbon atoms, particularly preferably an alkyl group having 1 to 4 carbon atoms which optionally has a halogen atom.

Any one or two of $Y^1$, $Y^2$, $Y^3$ and $Y^4$ represent C—$R^4$, and the others are the same or different and represent CH or N. Of them, preferably, any one or two of $Y^1$, $Y^2$, $Y^3$ and $Y^4$ are C—$R^4$, and the others are CH. More preferably, $Y^1$ and $Y^3$ are CH, any one or two of $Y^2$ and $Y^4$ are C—$R^4$, and the other is CH. These preferable aspects are represented by the following structural formulas:

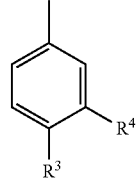
(b1)

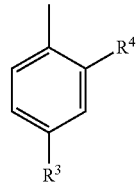
(b2)

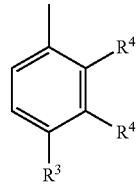
(b3)

wherein $R^3$ and $R^4$ are as defined above.

Of them, (b1) and (b2) are particularly preferable.

In the general formula (I), $R^3$ represents a cyano group or —CO—$R^5$. Of them, —CO—$R^5$ is particularly preferable.

In the general formula (I), $R^4$(s) are the same or different and represent a hydrogen atom, a halogen atom, a cyano group, an optionally substituted alkyl group having 1 to 6 carbon atoms, a cycloalkyl group having 3 to 7 carbon atoms, an alkenyl group having 2 to 6 carbon atoms, an alkoxy group having 1 to 6 carbon atoms, an aromatic hydrocarbon group, —N($R^6$)($R^7$), —S$R^8$ or —CO—$R^9$. Of them, $R^4$ is preferably a halogen atom, an alkyl group having 1 to 6 carbon atoms which optionally has a mono- or di-(C1-C6 alkyl)amino group or a monocyclic 5- to 7-membered saturated heterocyclic group having one or two of any heteroatom of N, S and O, an alkoxy group having 1 to 6 carbon atoms, —N($R^6$)($R^7$), —S$R^8$ or —CO—$R^9$, more preferably a halogen atom, an alkyl group having 1 to 6 carbon atoms or —N($R^6$)($R^7$).

In the general formula (I), the "halogen atom" represented by $R^4$ refers to the halogen atom exemplified above and is preferably a chlorine atom.

In the general formula (I), the "alkyl group having 1 to 6 carbon atoms" in the "optionally substituted alkyl group having 1 to 6 carbon atoms" represented by $R^4$ refers to the alkyl group having 1 to 6 carbon atoms exemplified above and is preferably a methyl, ethyl, n-propyl or isopropyl group. Examples of the "substituent(s)" in the "optionally substituted alkyl group having 1 to 6 carbon atoms" represented by $R^4$ include the substituents exemplified above. The "substituent(s)" are preferably mono- or di-(C1-C6 alkyl)amino groups (e.g., ethylamino and dimethylamino groups) or monocyclic 5- to 7-membered saturated heterocyclic groups having one or two of any heteroatom of N, S and O (e.g., pyrrolidyl and morpholino groups).

In the general formula (I), the "cycloalkyl group having 3 to 7 carbon atoms" represented by $R^4$ refers to the cycloalkyl group having 3 to 7 carbon atoms exemplified above and is preferably a cyclopropyl group.

In the general formula (I), the "alkenyl group having 2 to 6 carbon atoms" represented by $R^4$ refers to the alkenyl group having 2 to 6 carbon atoms exemplified above and is preferably a vinyl or prop-1-en-2-yl group.

In the general formula (I), the "alkoxy group having 1 to 6 carbon atoms" represented by $R^4$ refers to the alkoxy group having 1 to 6 carbon atoms exemplified above and is preferably a methoxy group.

In the general formula (I), the "mono- or di-alkylamino group" in the "optionally substituted mono- or di-alkylamino group" represented by $R^5$ refers to the mono- or dialkylamino group exemplified above and is preferably a mono- or di-(C1-C6 alkyl)amino group. Examples of the "substituent(s)" in the "optionally substituted mono- or di-alkylamino group" represented by $R^5$ include the substituents exemplified above.

$R^5$ is more preferably an amino, hydroxylamino or mono- or di-(C1-C6 alkyl)amino group, particularly preferably an amino group.

In the general formula (I), the "alkyl group having 1 to 6 carbon atoms" in the "optionally substituted alkyl group having 1 to 6 carbon atoms" represented by $R^6$ or $R^7$ refers to the alkyl group having 1 to 6 carbon atoms exemplified above and is preferably an ethyl, n-propyl, n-butyl, isobutyl, sec-butyl or pentyl group. Examples of the "substituent(s)" in the "optionally substituted alkyl group having 1 to 6 carbon atoms" represented by $R^6$ or $R^7$ include the substituents exemplified above. The "substituent(s)" are preferably a hydroxyl group, cycloalkyl groups having 3 to 7 carbon atoms (e.g., a cyclohexyl group), saturated heterocyclic groups (e.g., pyrrolidyl and morpholino groups), unsaturated heterocyclic groups (e.g., a pyridyl group), mono- or di-(C1-C6 alkyl)amino groups (e.g., ethylamino and dimethylamino groups), (C1-C6 alkyl)thio groups (e.g., a methylthio group), or alkoxy groups having 1 to 6 carbon atoms which optionally has a hydroxyl group.

In the general formula (I), the "halogenoalkyl group having 1 to 6 carbon atoms" represented by $R^6$ or $R^7$ refers to the halogenoalkyl group having 1 to 6 carbon atoms exemplified above and is preferably a 2,2-difluoroethyl or 2,2,2-trifluoroethyl group.

In the general formula (I), examples of the "cycloalkyl group having 3 to 7 carbon atoms" in the "optionally substituted cycloalkyl group having 3 to 7 carbon atoms" represented by $R^6$ or $R^7$ include cyclopropyl, cyclobutyl, cyclopentyl, cyclohexyl and cycloheptyl groups. The cycloalkyl group having 3 to 7 carbon atoms is preferably a cyclopropyl, cyclopentyl or cyclohexyl group. Examples of the "substituent(s)" in the "optionally substituted cycloalkyl group having 3 to 7 carbon atoms" represented by $R^6$ or $R^7$ include the substituents exemplified above. The substituent(s) are preferably hydroxyl, amino, amino acid-derived acyloxy, alkanoylamino or alkylsulfonylamino groups, or the like.

In the general formula (I), the "aralkyl group" in the "optionally substituted aralkyl group" represented by $R^6$ or $R^7$ refers to the aralkyl group exemplified above and is preferably an aralkyl group having 7 to 12 carbon atoms, specifically, a benzyl group. Examples of the "substituent(s)" in the "optionally substituted aralkyl group" represented by $R^6$ or $R^7$ include the substituents exemplified above. Specific examples of the substituent(s) include saturated heterocyclic groups such as a pyrrolidinyl group.

In the general formula (I), the "aromatic hydrocarbon group" in the "optionally substituted aromatic hydrocarbon group" represented by $R^6$ or $R^7$ refers to the aromatic hydrocarbon group having 6 to 14 carbon atoms exemplified above and is preferably a phenyl group. Examples of the "substituent(s)" in the "optionally substituted aromatic hydrocarbon group" represented by $R^6$ or $R^7$ include the substituents exemplified above. The substituent(s) are preferably halogen atoms, alkylthio groups (e.g., a methylthio group), saturated heterocyclic groups (e.g., a morpholino group), or substituted carbamoyl groups (e.g., a pyrrolidine-carbonyl group).

In the general formula (I), the "saturated heterocyclic group" in the "optionally substituted saturated heterocyclic group" represented by $R^6$ or $R^7$ refers to the saturated heterocyclic group exemplified above and is preferably a piperidinyl or tetrahydropyranyl group. Examples of the "substituent(s)" in the "optionally substituted saturated heterocyclic group" represented by $R^6$ or $R^7$ include the substituents exemplified above. The substituent(s) are preferably alkyl groups having 1 to 6 carbon atoms (e.g., a methyl group), acyl groups (e.g., an acetyl group), carbonyl groups having a saturated heterocyclic group (e.g., a 2,6-dihydroxypyrimidinyl-4-carbonyl group), or aminoalkylcarbonyl groups (e.g., a 2-aminoacetyl group).

In the general formula (I), the "unsaturated heterocyclic group" in the "optionally substituted unsaturated heterocyclic group" represented by $R^6$ or $R^7$ refers to the unsaturated heterocyclic group exemplified above and is preferably a pyridyl or oxazolyl group. Examples of the "substituent(s)" in the "optionally substituted unsaturated heterocyclic group" represented by $R^6$ or $R^7$ include the substituents exemplified above.

In the general formula (I), the "saturated heterocyclic group" which is optionally formed by $R^6$ and $R^7$ together with the nitrogen atom to which they are bonded refers to a monocyclic or bicyclic saturated heterocyclic group preferably having 1 to 4 of any atom of oxygen, nitrogen and sulfur atoms, for example, a pyrrolidinyl, piperidinyl, piperazinyl, hexamethyleneimino, morpholino, thiomorpholino, homopiperazinyl, tetrahydrofuranyl or tetrahydropyranyl group.

In the general formula (I), it is preferred for the combination of $R^6$ and $R^7$ that $R^6$ should be a hydrogen atom or an optionally substituted alkyl group having 1 to 6 carbon atoms, and $R^7$ should represent a hydrogen atom, an optionally substituted alkyl group having 1 to 6 carbon atoms, an optionally substituted cycloalkyl group having 3 to 7 carbon atoms, an optionally substituted aralkyl group having 7 to 12 carbon atoms, an optionally substituted aromatic hydrocarbon group having 6 to 14 carbon atoms, an optionally substituted monocyclic or bicyclic saturated heterocyclic group having 1 to 4 heteroatoms selected from N, S and O, or an optionally substituted monocyclic or bicyclic unsaturated heterocyclic group having 1 to 4 heteroatoms selected from N, S and O, or $R^6$ and $R^7$ should optionally form a 5- to 7-membered saturated heterocyclic group, together with the nitrogen atom to which they are bonded. More preferably, $R^6$ is a hydrogen atom, and $R^7$ is a hydrogen atom, an optionally substituted alkyl group having 1 to 6 carbon atoms, an optionally substituted cycloalkyl group having 3 to 7 carbon atoms, or an optionally substituted monocyclic or bicyclic saturated heterocyclic group having 1 to 4 heteroatoms selected from N, S and O. Particularly preferably, $R^6$ is a hydrogen atom, and $R^7$ is an optionally substituted alkyl group having 1 to 6 carbon atoms or an optionally substituted cycloalkyl group having 3 to 7 carbon atoms.

In the general formula (I), the "cycloalkyl group having 3 to 7 carbon atoms" in the "optionally substituted cycloalkyl group having 3 to 7 carbon atoms" represented by $R^8$ refers to the cycloalkyl group having 3 to 7 carbon atoms exemplified above and is preferably a cyclohexyl group. Examples of the "substituent(s)" in the "optionally substituted cycloalkyl group having 3 to 7 carbon atoms" represented by $R^8$ include the substituents exemplified above. The substituent(s) are preferably a hydroxyl group.

In the general formula (I), the "aromatic hydrocarbon group" in the "optionally substituted aromatic hydrocarbon group" represented by $R^8$ refers to the aromatic hydrocarbon group having 6 to 14 carbon atoms exemplified above and is preferably a phenyl group. Examples of the "substituent(s)" in the "optionally substituted aromatic hydrocarbon group" represented by $R^8$ include the substituents exemplified above. The substituent(s) are preferably a hydroxyl group.

$R^8$ is preferably an optionally substituted cycloalkyl group having 3 to 7 carbon atoms, or an optionally substituted aromatic hydrocarbon group having 6 to 14 carbon atoms.

In the general formula (I), the "mono- or di-alkylamino group" in the "optionally substituted mono- or di-alkylamino group" represented by $R^9$ refers to the mono- or dialkylamino group exemplified above and is preferably a mono- or di-(C1-C6 alkyl)amino group. Examples of the "substituent(s)" in the "optionally substituted mono- or di-alkylamino group" represented by $R^9$ include the substituents exemplified above.

$R^9$ is preferably a hydrogen atom, a hydroxyl group, an amino group or a mono- or di-(C1-C6 alkyl)amino group, particularly preferably a hydrogen atom.

The compound of the present invention is preferably a compound represented by the general formula (I) or a salt thereof wherein $X^1$ is CH or N; any one of $X^2$, $X^3$ and $X^4$ is N, and the others are CH; any one or two of $Y^1$, $Y^2$, $Y^3$ and $Y^4$ are C—$R^4$, and the others are the same or different and represent CH or N; $R^1$ is an optionally substituted monocyclic or bicyclic unsaturated heterocyclic group having 1 to 4 heteroatoms selected from N, S and O; $R^2$ is an alkyl group having 1 to 6 carbon atoms which optionally has a halogen atom, or an alkenyl group having 2 to 6 carbon atoms; $R^3$ is —CO—$R^5$; $R^4$(s) are the same or different and represent a hydrogen atom, a halogen atom, a cyano group, an optionally substituted alkyl group having 1 to 6 carbon atoms, an alkenyl group having 2 to 6 carbon atoms, an alkoxy group having 1 to 6 carbon atoms, an aromatic hydrocarbon group, —N($R^6$)($R^7$), —S—$R^8$ or —CO—$R^9$; $R^5$ is an amino group or a mono- or di-(C1-C6 alkyl)amino group; $R^6$ and $R^7$ are the same or different and represent a hydrogen atom, an optionally substituted alkyl group having 1 to 6 carbon atoms, a halogenoalkyl group having 1 to 6 carbon atoms, an optionally substituted cycloalkyl group having 3 to 7 carbon atoms, an optionally substituted aralkyl group, an optionally substituted aromatic hydrocarbon group, an optionally substituted saturated heterocyclic group or an optionally substituted unsaturated heterocyclic group, or $R^6$ and $R^7$ form a saturated heterocyclic group, together with the nitrogen atom to which they are bonded; $R^8$ is an optionally substituted cycloalkyl group having 3 to 7 carbon atoms, or an optionally substituted aromatic hydrocarbon group; and $R^9$ is a hydrogen atom, a hydroxyl group, an amino group optionally having a hydroxyl group, or an optionally substituted mono- or di-alkylamino group.

The compound of the present invention is more preferably a compound represented by the general formula (I) or a salt thereof wherein $X^1$ is CH or N; any one of $X^2$, $X^3$ and $X^4$ is N, and the others are CH; any one or two of $Y^1$, $Y^2$, $Y^3$ and $Y^4$ are C—$R^4$, and the others are the same or different and represent CH or N; $R^1$ is an optionally substituted monocyclic 5- to 6-membered unsaturated heterocyclic group having 1 to 3 heteroatoms selected from N, S and O, or an optionally substituted bicyclic 9- to 10-membered unsaturated heterocyclic group having 1 to 3 heteroatoms selected from N, S and O; $R^2$ is an alkyl group having 1 to 6 carbon atoms which optionally has a halogen atom, or an alkenyl group having 2 to 6 carbon atoms; $R^3$ is —CO—$R^5$; $R^4$(s) are the same or different and represent a hydrogen atom, a halogen atom, a cyano group, an optionally substituted alkyl group having 1 to 6 carbon atoms, an alkenyl group having 2 to 6 carbon atoms, an alkoxy group having 1 to 6 carbon atoms, an aromatic hydrocarbon group, —N($R^6$)($R^7$), —S—$R^8$ or —CO—$R^9$; $R^5$ is an amino group or a mono- or di-(C1-C6 alkyl)amino group; $R^6$ and $R^7$ are the same or different and represent a hydrogen atom, an optionally substituted alkyl group having 1 to 6 carbon atoms, a halogenoalkyl group having 1 to 6 carbon atoms, an optionally substituted cycloalkyl group having 3 to 7 carbon atoms, an optionally substituted aralkyl group, an optionally substituted aromatic hydrocarbon group, an optionally substituted saturated heterocyclic group or an optionally substituted unsaturated heterocyclic group, or $R^6$ and $R^7$ form a saturated heterocyclic group, together with the nitrogen atom to which they are bonded; $R^8$ is an optionally substituted cycloalkyl group having 3 to 7 carbon atoms, or an optionally substituted aromatic hydrocarbon group; and $R^9$ is a hydrogen atom, a hydroxyl group, an amino group optionally having a hydroxyl group, or an optionally substituted mono- or di-alkylamino group.

The compound of the present invention is even more preferably a compound represented by the general formula (I) or a salt thereof wherein $X'$ is CH or N; $X^2$ is N, and $X^3$ and $X^4$ are CH; any one or two of $Y^1$, $Y^2$, $Y^3$ and $Y^4$ are C—$R^4$, and the others are the same or different and represent CH or N; $R^1$ is an optionally substituted monocyclic 5- to 6-membered unsaturated heterocyclic group having 1 to 3 heteroatoms selected from N, S and O, or an optionally substituted bicyclic 9- to 10-membered unsaturated heterocyclic group having 1 to 3 heteroatoms selected from N, S and O; $R^2$ is an alkyl group having 1 to 6 carbon atoms which optionally has a halogen atom, or an alkenyl group having 2 to 6 carbon atoms; $R^3$ is —CO—$R^5$; $R^4$(s) are the same or different and represent a hydrogen atom, a halogen atom, a cyano group, an optionally substituted alkyl group having 1 to 6 carbon atoms, an alkenyl group having 2 to 6 carbon atoms, an alkoxy group having 1 to 6 carbon atoms, an aromatic hydrocarbon group, —N($R^6$)($R^7$), —S—$R^8$ or —CO—$R^9$; $R^5$ is an amino group or a mono- or di-(C1-C6 alkyl)amino group; $R^6$ and $R^7$ are the same or different and represent a hydrogen atom, an optionally substituted alkyl group having 1 to 6 carbon atoms, a halogenoalkyl group having 1 to 6 carbon atoms, an optionally substituted cycloalkyl group having 3 to 7 carbon atoms, an optionally substituted aralkyl group, an optionally substituted aromatic hydrocarbon group, an optionally substituted saturated heterocyclic group or an optionally substituted unsaturated heterocyclic group, or $R^6$ and $R^7$ form a saturated heterocyclic group, together with the nitrogen atom to which they are bonded; $R^8$ is an optionally substituted cycloalkyl group having 3 to 7 carbon atoms, or an optionally substituted aromatic hydrocarbon group; and $R^9$ is a hydrogen atom, a hydroxyl group, an amino group optionally having a hydroxyl group, or an optionally substituted mono- or di-alkylamino group.

The compound of the present invention is further preferably a compound represented by the general formula (I) or a salt thereof wherein $X^1$ is CH or N; $X^2$ is N, and $X^3$ and $X^4$ are CH; any one or two of $Y^1$, $Y^2$, $Y^3$ and $Y^4$ are C—$R^4$, and the others are the same or different and represent CH or N; $R^1$ is any of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group and an optionally substituted 5,6,7,8-tetrahydroquinolin-3-yl group; $R^2$ is an alkyl group having 1 to 6 carbon atoms which optionally has a halogen atom, or an alkenyl group having 2 to 6 carbon atoms; $R^3$ is —CO—$R^5$; $R^4$(s) are the same or different and represent a hydrogen atom, a halogen atom, a cyano group, an optionally substituted alkyl group having 1 to 6 carbon atoms, an alkenyl group having 2 to 6 carbon atoms, an alkoxy group having 1 to 6 carbon atoms, an aromatic hydrocarbon group, —N($R^6$)($R^7$), —S—$R^8$ or —CO—$R^9$; $R^5$ is an amino group or a mono- or di-(C1-C6 alkyl)amino group; $R^6$ and $R^7$ are the same or different and represent a hydrogen atom, an optionally substituted alkyl group having 1 to 6 carbon atoms, a halogenoalkyl group having 1 to 6 carbon atoms, an optionally substituted cycloalkyl group having 3 to 7 carbon atoms, an optionally substituted aralkyl group, an optionally substituted aromatic hydrocarbon group, an optionally substituted saturated heterocyclic group or an optionally substituted unsaturated heterocyclic group, or $R^6$ and $R^7$ form a saturated heterocyclic group, together with the nitrogen atom to which they are bonded; $R^8$ is an optionally substituted cycloalkyl group having 3 to 7 carbon atoms, or an optionally substituted aromatic hydrocarbon group; and $R^9$ is a hydrogen atom, a hydroxyl group, an amino group optionally having a hydroxyl group, or an optionally substituted mono- or di-alkylamino group.

The compound of the present invention is further preferably a compound represented by the general formula (I) or a salt thereof wherein $X^1$ is CH or N; $X^2$ is N, and $X^3$ and $X^4$ are CH; $Y^1$ and $Y^3$ are CH, any one or two of $Y^2$ and $Y^4$ are C—$R^4$, and the other is CH; $R^1$ is any of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group and an optionally substituted 5,6,7,8-tetrahydroquinolin-3-yl group; $R^2$ is an alkyl group having 1 to 6 carbon atoms which optionally has a halogen atom, or an alkenyl group having 2 to 6 carbon atoms; $R^3$ is —CO—$R^5$; $R^4$ is a halogen atom, an alkyl group having 1 to 6 carbon atoms which optionally has a mono- or di-(C1-C6 alkyl)amino group or a monocyclic 5- to 7-membered saturated heterocyclic group having one or two of any heteroatom of N, S and O, an alkoxy group having 1 to 6 carbon atoms, —N($R^6$)($R^7$), —S$R^8$ or —CO—$R^9$; $R^5$ is an amino group or a mono- or di-(C1-C6 alkyl)amino group; $R^6$ is a hydrogen atom or an optionally substituted alkyl group having 1 to 6 carbon atoms, and $R^7$ is a hydrogen atom, an optionally substituted alkyl group having 1 to 6 carbon atoms, an optionally substituted cycloalkyl group having 3 to 7 carbon atoms, an optionally substituted aralkyl group having 7 to 12 carbon atoms, an optionally substituted aromatic hydrocarbon group having 6 to 14 carbon atoms, a monocyclic or bicyclic optionally substituted saturated heterocyclic group having 1 to 4 heteroatoms selected from N, S and O, or a monocyclic or bicyclic optionally substituted unsaturated heterocyclic group having 1 to 4 heteroatoms selected from N, S and O, or $R^6$ and $R^7$ form a 5- to 7-membered saturated heterocyclic group, together with the nitrogen atom to which they are bonded; $R^8$ is an optionally substituted cycloalkyl group having 3 to 7 carbon atoms, or an optionally substituted aromatic hydrocarbon group having 6 to 14 carbon atoms; and $R^9$ is a hydrogen atom, a hydroxyl group, an amino group or a mono- or di-(C1-C6 alkyl)amino group.

The compound of the present invention can be produced, for example, according to the following reaction scheme:

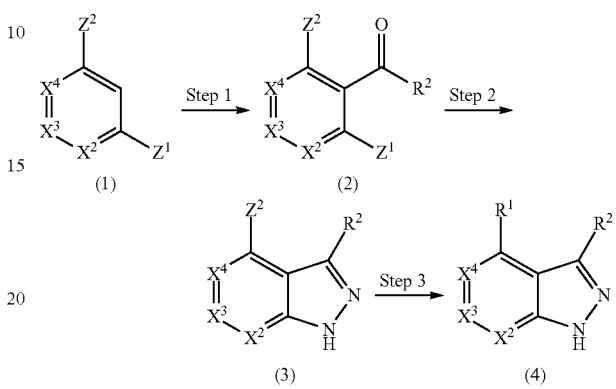

Reaction Scheme 1

In the Reaction Scheme 1, $Z^1$ represents a halogen atom; $Z^2$ represents a hydrogen atom or a halogen atom; and $X^2$, $X^3$, $X^4$, $R^1$ and $R^2$ are as defined above.

<Step 1>

Step 1 is the step of reaction of an easily obtainable compound represented by the general formula (1) with a metal reagent such as a lithium reagent, and then introducing thereto a carbonyl group corresponding to $R^2$.

Examples of the metal reagent used include lithium diisopropylamide, lithium bis(trimethylsilyl)amide, sodium bis(trimethylsilyl)amide and potassium bis(trimethylsilyl)amide. The metal reagent is preferably lithium diisopropylamide and is preferably used at 1 to 2 equivalents with respect to the starting compound (hereinafter, the term "equivalent" means equivalent with respect to the starting compound). The reaction temperature is preferably −78 to 0° C., and the reaction time is preferably 10 minutes to 2 hours. An ether solvent (e.g., tetrahydrofuran (THF) and diethyl ether) or a nonpolar solvent (e.g., benzene and toluene) can be used as a reaction solvent.

Subsequently, a carbonyl group corresponding to $R^2$ can be introduced thereto through reaction with an ester, Weinreb amide or aldehyde form of $R^2$. When the aldehyde form of $R^2$ is used, the obtained hydroxyl form can be subjected to a usual method known in the art, for example, oxidation reaction with active manganese dioxide or the like to produce a carbonyl compound represented by the general formula (2).

<Step 2>

Step 2 is the step of reaction of the compound represented by the general formula (2) with a hydrazine to produce an azaindazole compound represented by the general formula (3).

The hydrazine can be any of hydrazine, hydrazine hydrate and hydrazine hydrochloride and can be used at 1 to 30 equivalents. The reaction temperature is preferably 0° C. to the boiling point of a solvent, and the reaction time is preferably 30 minutes to 50 hours. An alcoholic solvent (e.g., methanol, ethanol and isopropanol), an ether solvent (e.g., tetrahydrofuran and diisopropyl ether), an aprotic highly polar solvent (e.g., dimethylformamide, dimethylacetamide and dimethyl sulfoxide), or a mixed solvent thereof can be used as a reaction solvent.

<Step 3>

Step 3 is the step of introduction of $R^1$ to the azaindazole compound represented by the general formula (3) to produce an azaindazole compound represented by the general formula (4).

When $Z^2$ in the general formula (3) is a hydrogen atom and $X^2$ is a nitrogen atom, the nitrogen atom represented by $X^2$ is converted to an N-oxide form, and $Z^2$ can subsequently be halogenated.

The conversion of the nitrogen atom represented by $X^2$ to an N-oxide form can be performed by producing the N-oxide form through reaction with an oxidizing agent, for example, hydrogen peroxide or m-chloroperbenzoic acid, at 1 to 5 equivalents in a halogen solvent (e.g., chloroform, dichloromethane and dichloroethane), a hydrocarbon solvent (e.g., hexane, heptane and toluene), an ether solvent (e.g., ethylene glycol dimethyl ether and tetrahydrofuran), or a mixed solvent thereof. Subsequently, $Z^2$ can be halogenated through reaction with phosphorus oxychloride, oxalyl chloride, phosphorus oxybromide, thionyl chloride, tetrabutylammonium bromide, or the like at 1 to 5 equivalents in a halogen solvent (e.g., chloroform, dichloromethane and dichloroethane), a hydrocarbon solvent (e.g., hexane, heptane and toluene), an ether solvent (e.g., ethylene glycol dimethyl ether and tetrahydrofuran), or a mixed solvent thereof.

For a compound represented by the general formula (3) having the halogen atom represented by $Z^2$, a Suzuki coupling method or aromatic amine can be used to produce an azaindazole compound represented by the general formula (4).

The Suzuki coupling method can be performed according to a method described in Chemical Review, 1995, 95, 2457-2483. Boronic acid or boronic acid ester corresponding to $R^1$ can be synthesized by a usual method known in the art. When a halogen compound corresponding to $R^1$ is easily obtainable, the compound represented by the general formula (3) is converted to boronic acid or boronic acid ester, which can then be subjected to the Suzuki coupling method in the same way as above to produce an azaindazole compound represented by the general formula (4).

Moreover, the reaction with aromatic amine can be performed by reacting aromatic amine such as imidazole or triazole with halogen-substituted azaindazole represented by the general formula (3) through nucleophilic addition for synthesis. This reaction can usually be carried out at a reaction temperature of room temperature to the boiling point of a solvent for a reaction time of 30 minutes to 50 hours using a nucleophilic reagent at 1 to 10 equivalents in the presence of a base. Moreover, the reaction can also be performed by the addition of a metal such as palladium or copper.

The solvent used is not particularly limited as long as it is inert in this reaction. For example, an ether solvent (e.g., tetrahydrofuran, 1,2-dimethoxyethane and dioxane), an aprotic highly polar solvent (e.g., dimethylformamide, dimethylacetamide and dimethyl sulfoxide), or a mixed solvent thereof can be used.

Reaction Scheme 2

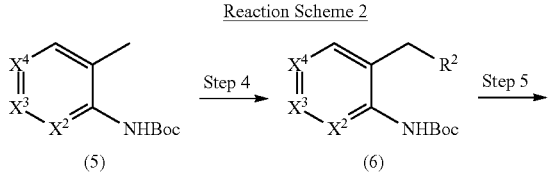

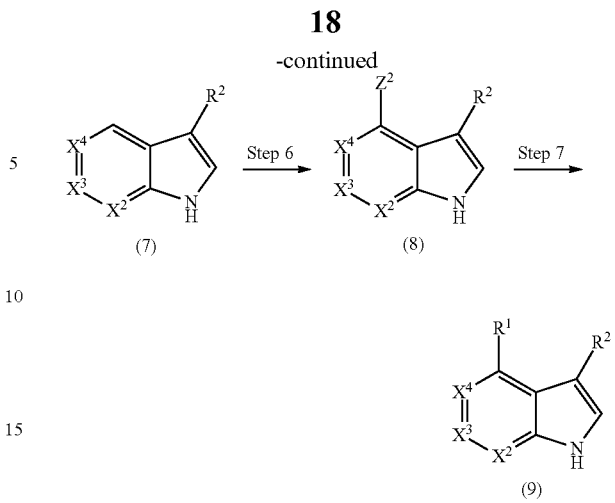

In the Reaction Scheme 2, $Z^2$ represents a halogen atom; Boc represents a tert-butoxycarbonyl group; and $X^2$, $X^3$, $X^4$, $R^1$ and $R^2$ are as defined above.

<Step 4>

Step 4 is the step of formation of an anion of the methyl group of an easily obtainable compound represented by the general formula (5) using a base and then reacting therewith a haloalkyl compound or the like to introduce $R^2$. This reaction can be performed, for example, according to a method described in Synthesis 1996, 877-882.

<Step 5>

Step 5 is the step of formation of an anion of a compound represented by the general formula (6), then introducing thereto a carbonyl group, and performing cyclization under acidic conditions simultaneously with deprotection reaction to obtain an azaindole compound represented by the general formula (7).

The anion of the compound represented by the general formula (6) can be formed in the same way as <Step 4> and then reacted with N,N-dimethylformamide, ethyl formate, or the like, preferably N,N-dimethylformamide, to introduce thereto a carbonyl group. Hydrochloric acid, sulfuric acid, trifluoroacetic acid, acetic acid, or the like can be used as the acidic conditions for performing cyclization simultaneously with deprotection reaction. Hydrochloric acid is preferable. The reaction temperature is usually 0 to 100° C., preferably 0 to 60° C. The reaction time differs depending on the reaction temperature, the starting compound, reagents, and solvents used, and is usually 15 minutes to 5 hours, preferably 30 minutes to 2 hours.

<Step 6>

Step 6 is the step of acquisition of an N-oxide form of the compound represented by the general formula (7) using an oxidizing agent and subsequently halogenating the N-oxide form to obtain a compound represented by the general formula (8).

This step can be performed in the same way as <Step 3>.

<Step 7>

Step 7 is the step of introduction of $R^1$ to the compound represented by the general formula (8).

This step can be performed in the same way as <Step 3> to obtain an azaindole compound represented by the general formula (9).

Reaction Scheme 3

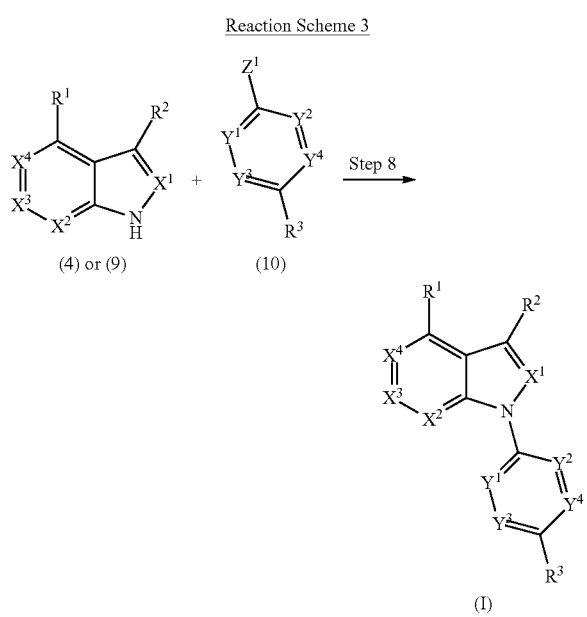

(4) or (9)        (10)

(I)

In the Reaction Scheme 3, $Z^1$ represents an eliminable functional group such as a halogen atom; and $X^1$, $X^2$, $X^3$, $X^4$, $R^1$, $R^2$, $R^3$, $Y^1$, $Y^2$, $Y^3$ and $Y^4$ are as defined above.

<Step 8>

Step 8 is the step of reaction of the nitrogen atom at position 1 of the azaindazole compound represented by the general formula (4) or the azaindole compound represented by the general formula (9) with halo-substituted phenyl, halo-substituted pyridine, halo-substituted pyrimidine, or the like represented by the general formula (10) to obtain the compound represented by the general formula (I).

In this step, $Z^1$ in the compound represented by the general formula (10) can be any eliminable functional group. Examples thereof include a chlorine atom, a bromine atom and a trifluoromethylsulfonyl group. Moreover, $R^3$ is preferably an electron-withdrawing group. Examples thereof include nitrile, ester and nitro groups. The compound represented by the general formula (10) is easily obtainable or can be synthesized, for example, according to a method described in Synthesis 1975, 502 or J. Med. Chem. 1985, 1387-93.

0.5 to 10 mol, preferably 0.8 to 2 mol of the compound represented by the general formula (10) can be used with respect to 1 mol of the compound represented by the general formula (4) or (9) in the reaction at 0 to 180° C., preferably 20 to 150° C. in an appropriate solvent in the presence of 0.5 to 10 mol, preferably 0.8 to 2 mol of a base to obtain the compound represented by the general formula (I).

The solvent used is not particularly limited as long as it does not influence the reaction. Examples thereof include acetonitrile, tetrahydrofuran, dioxane, diethyl ether, diisopropyl ether, benzene, toluene, N,N-dimethylformamide, N,N-dimethylacetamide, N-methylpyrrolidone and dimethyl sulfoxide. These solvents can be used alone or as a mixture. An inorganic base (e.g., lithium hydroxide, sodium hydroxide, potassium hydroxide, calcium hydroxide, barium hydroxide, lithium carbonate, sodium carbonate, potassium carbonate, sodium hydride and cesium carbonate) or an organic base (e.g., pyridine, lutidine, collidine, 4-(N,N-dimethylamino) pyridine, triethylamine, diisopropylethylamine, 1,5-diazabicyclo[4.3.0]non-5-ene and 1,8-diazabicyclo[5.4.0]undec-7-ene) can be used as the base. Moreover, the reaction can also be performed by the addition of copper (I) and 1,2-diamine.

When $Y^2$ and $Y^4$ in the general formula (I) are a carbon atom having a halogen atom, the halogen atom may be converted to amine, thioether, or the like through reaction with amine, thiol, or the like, or the alkyl chain can be elongated by a Suzuki coupling method or the like. Moreover, when $Y^2$ and $Y^4$ are a carbon atom having a nitro group, the nitro group is reduced, by a usual method known in the art, to an amino group, with which a substituent such as an alkyl chain can then be elongated. Moreover, when $Y^2$ and $Y^4$ are a carbon atom having a formyl or ketone group, the formyl or ketone group is converted, by reductive amination using a reducing agent such as a 2-picoline-borane complex, to amine, with which a substituent such as an alkyl chain can then be elongated.

For the substituent such as a nitrile group, an ester group, or a nitro group represented by $R^3$ or for $R^4$ in any of $Y^1$, $Y^2$, $Y^3$ and $Y^4$, the desired compound can be produced by a usual method known in the art.

For example, when $R^3$ is a nitrile group, a carboxamide compound can be produced by a usual hydrolysis method known in the art. Moreover, when $R^3$ is an ester group, a carboxylic acid compound can be produced by hydrolysis and can further be reacted with amine to produce the desired amide compound. When $R^3$ is a nitro group, an amine compound can be produced by catalytic reduction or the like and can further be reacted with carboxylic acid, isocyanate, or the like to obtain the desired amide compound, urea compound, or the like.

Moreover, for example, when $R^4$ is a halogen atom, the desired amine compound or thioether compound can be produced.

The compound of the present invention represented by the general formula (I) can also be obtained by reacting the compound represented by the general formula (3) or (8) with the compound represented by the general formula (10) according to the method of <Step 8> and the converting the halogen atom represented by $Z^2$ to aromatic amine according to the method of <Step 7>.

Reaction Scheme 4

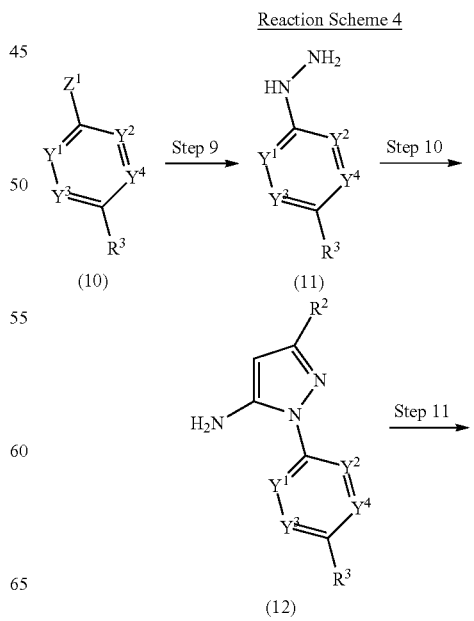

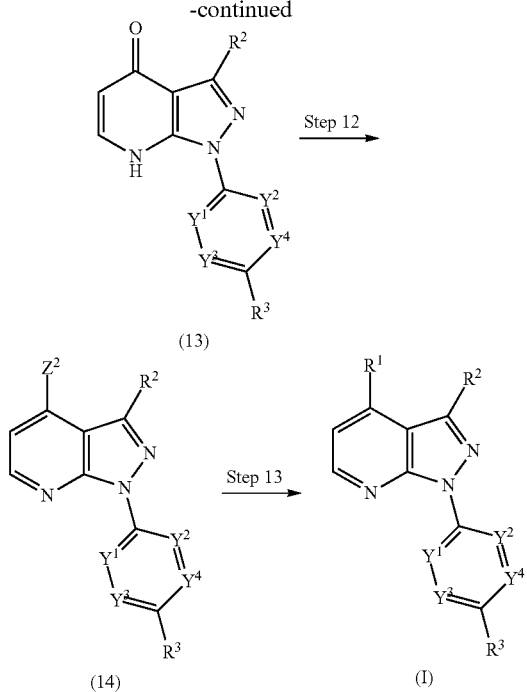

In the Reaction Scheme 4, $Z^1$ and $Z^2$ represent an eliminable functional group such as a halogen atom; and $R^1$, $R^2$, $R^3$, $Y^1$, $Y^2$, $Y^3$ and $Y^4$ are as defined above.

<Step 9>
Step 9 is the step of reaction of the compound represented by the general formula (10) with a hydrazine to produce a hydrazyl compound represented by the general formula (11). The hydrazine can be any of hydrazine, hydrazine hydrate and hydrazine hydrochloride and can be used at 1 to 30 equivalents. The reaction temperature is preferably 60 to 100° C., and the reaction time is preferably 1 to 10 hours. An alcoholic solvent (e.g., methanol, ethanol and isopropanol), an ether solvent (e.g., tetrahydrofuran and diisopropyl ether), or an aprotic highly polar solvent (e.g., dimethylformamide, dimethylacetamide and dimethyl sulfoxide) can be used as a reaction solvent. Alternatively, the reaction can also be performed under solvent-free conditions.

<Step 10>
Step 10 is the step of reaction of the compound represented by the general formula (11) with acetonitrile in $R^2$ to produce a 5-aminopyrazole compound.

The acetonitrile used is easily obtainable acetoacetonitrile, propionylacetonitrile, isopropionylacetonitrile, trifluoroacetoacetonitrile, or the like, which can be used to introduce thereto corresponding $R^2$. A mixed solvent of an alcoholic solvent (e.g., methanol, ethanol and isopropanol) and an acid (e.g., concentrated hydrochloric acid, sulfuric acid, mesylic acid and tosylic acid) can be used as a solvent. The reaction temperature is preferably room temperature to the boiling point of a solvent, and the reaction time is preferably 2 to 24 hours.

<Step 11>
Step 11 is the step of reaction of the compound represented by the general formula (12) with 5-methoxymethylene Meldrum's acid to produce a compound represented by the general formula (13).

The 5-methoxymethylene Meldrum's acid is used at 1 to 3 equivalents. A high-boiling-point solvent (e.g., diphenyl ether, biphenol and Dowtherm) is used as a reaction solvent. The reaction temperature is preferably 150 to 220° C., and the reaction time is preferably 1 to 5 hours.

<Step 12>
Step 12 is the step of halogenation of the compound represented by the general formula (13).

The reaction can be performed using phosphorus oxychloride, phosphorus oxybromide, thionyl chloride, or the like at 1 to 5 equivalents in a halogen solvent (e.g., chloroform and dichloroethane) or an aprotic highly polar solvent (e.g., dimethylformamide, dimethylacetamide and dimethyl sulfoxide) to synthesize a compound represented by the general formula (14).

<Step 14>
Step 14 is the step of introduction of $R^1$ to the compound represented by the general formula (13).

This step can be performed in the same way as <Step 3> to obtain the compound represented by the general formula (I).

When introduction of a substituent or the conversion of a functional group is carried out in the <Step 1> to <Step 14> described above, if there is a reactive substituent which cause reaction other than intended reactions, a protective group may be introduced to the reactive substituent in advance, as appropriate, by means known per se in the art, and the protective group may be removed by means known in the art after the intended reaction, to produce the subject compound. After the completion of reaction, the compound of interest in each of these steps is collected from the reaction mixture according to a routine method. For example, the reaction mixture is appropriately neutralized, or insoluble compound, if any, is removed by filtration. Then, the reaction solution is subjected to extraction with a water-immiscible organic solvent such as toluene, ethyl acetate or chloroform, and the extracts are washed with water or the like. Then, the organic layer containing the compound of interest is concentrated under reduced pressure, and the solvent is distilled off to obtain the compound of interest. The obtained compound of interest can be separated and purified, if necessary, by a routine method, for example, recrystallization, reprecipitation or a method generally used in the usual separation or purification of organic compounds (e.g., adsorption column chromatography using a carrier such as silica gel, alumina or magnesium-silica gel Florisil, partition column chromatography using a carrier such as Sephadex LH-20 (manufactured by Pharmacia), Amberlite XAD-11 (manufactured by Rohm and Haas Company) or Diaion HP-20 (manufactured by Mitsubishi Chemical Corp.), ion-exchange chromatography or normal- or reverse-phase column chromatography using a silica gel or alkylated silica gel, preferably, silica gel column chromatography). When the compound (I) is obtained in a free form, this free form can be converted to its pharmacologically acceptable salt by a method known per se in the art or a method equivalent thereto. Contrarily, when the compound (I) is obtained in a salt form, this salt can be converted to a free form or other salts of interest by a method known per se in the art or a method equivalent thereto.

When the compound (I) has isomers such as optical isomers, stereoisomers, positional isomers or rotational isomers, either of the isomers and a mixture thereof are both encompassed by the compound (I). For example, when the compound (I) has optical isomers, optical isomers resolved from racemic mixtures are also encompassed by the compound (I). Each of these isomers can be obtained as a single product by synthesis and separation (concentration, solvent extraction, column chromatography, recrystallization, etc.) approaches known per se in the art.

The compound (I) may be crystalline. A single crystal form and a polymorphic mixture are both encompassed by the compound (I). These crystals can be produced by crystallizing the compound (I) using a crystallization method known per se in the art. The compound (I) may be a solvate (e.g., a hydrate) or a non-solvate. Both of them are encompassed by the compound (I).

A compound labeled with an isotope (e.g., $^3$H, $^{14}$C, $^{35}$S and $^{125}$I) or the like is also encompassed by the compound (I).

A prodrug of the compound (I) or the salt thereof (hereinafter, abbreviated to the compound (I)) refers to a compound converted to the compound (I) through reaction caused by an enzyme, gastric acid, or the like under physiological conditions in vivo, i.e., a compound converted to the compound (I) by enzymatic oxidation, reduction, hydrolysis, or the like or a compound converted to the compound (I) by hydrolysis or the like caused by gastric acid or the like. Moreover, the prodrug of the compound (I) can be any of those converted to the compound ((I)) under physiological conditions as described in "Pharmaceutical Research and Development" Vol. 7, Molecular Design, published in 1990 by Hirokawa Publishing Company, p. 163-198.

The compound (I) of the present invention exhibits excellent HSP90 inhibitory activity and has excellent cancer cell proliferation inhibitory activity. Thus, the compound (I) of the present invention is useful as a pharmaceutical product such as an anticancer agent. Moreover, the compound (I) of the present invention is highly soluble in water and can be administered orally. Thus, the compound (I) of the present invention is useful as an orally administrable pharmaceutical product such as an anticancer agent. Examples of malignant tumor include head and neck cancer, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, kidney cancer, bladder cancer, prostatic cancer, testicular tumor, osteosarcoma, soft-tissue sarcoma, leukemia, malignant lymphoma, multiple myeloma, skin cancer, brain tumor and mesothelioma.

For using the compound (I) of the present invention as a pharmaceutical product, various dosage forms can be adopted according to the preventive or therapeutic purpose by mixing, as appropriate, the compound (I) with a pharmaceutical carrier. The forms can be any of, for example, oral formulations, injections, suppositories, ointments and patches. Preferably, oral formulations are adopted. Each of these dosage forms can be produced by a general preparation method known by those skilled in the art.

Various organic or inorganic carrier substances generally used as pharmaceutical materials are used as such a pharmaceutical carrier. Solid preparations are formulated using an excipient, a binder, a disintegrant, a lubricant and a coloring agent, and liquid preparations are formulated using a solvent, a solubilizer, a suspending agent, a tonicity agent, a buffer, a soothing agent, and the like. Moreover, pharmaceutical additives such as antiseptics, antioxidants, coloring agents, sweeteners and stabilizers can also be used, if necessary.

When oral solid preparations are prepared, an excipient and an excipient, a binder, a disintegrant, a lubricant, a coloring agent, a corrigent, or the like are added, as appropriate to the compound of the present invention, and then, tablets, coated tablets, granules, powders, capsules, or the like can be produced by a routine method.

When injection agents are prepared, a pH adjuster, a buffer, a stabilizer, a tonicity agent, a local anesthetic, and the like are added to the compound of the present invention, and hypodermic, intramuscular or intravenous injections can be produced by a routine method.

The amount of the compound of the present invention to be contained in each of these unit dosage forms varies depending on the conditions of a patient to which this formulation should be applied, or depending on the dosage form or the like. The amount is generally preferably approximately 0.05 to 1000 mg for the oral formulation, approximately 0.01 to 500 mg for the injection agent, and approximately 1 to 1000 mg for the suppository, per unit dosage form.

Moreover, the daily dose of the drug having the dosage form differs depending on the conditions, body weight, age, sex, or the like of a patient and cannot be generalized. The daily dose in adult (body weight: 50 kg) can be usually approximately 0.05 to 5000 mg, preferably 0.1 to 1000 mg, which is preferably administered in one portion or in approximately two or three divided portions per day.

EXAMPLES

The present invention is specifically described with reference to Examples and Test Examples below, however these Examples are described for the purpose of exemplifications only and do not limit the scope of the present invention.

$^1$H-NMR spectra were measured using tetramethylsilane (TMS) as the internal standard, and chemical shifts are shown in δ values (ppm). The chemical shifts are each shown in parentheses by the number of protons, absorption pattern, and coupling constant (J value).

In the absorption patterns, the following symbols are used: s=singlet, d=doublet, t=triplet, q=quartet, dd=double doublet, ddd=double double doublet, dt=double triplet, m=multiplet, br=broad, and br s=broad singlet.

In some structural formulae of compounds, the following symbols may be used: Me=methyl, Et=ethyl, tBu=tert-butyl, Ph=phenyl, Ac=acetyl, Boc=tert-butoxycarbonyl, TFA=trifluoroacetic acid, and MsOH=methanesulfonic acid.

Example 1

2-(Trans-4-hydroxycyclohexylamino)-4-{4-(quinolin-3-yl)-3-(trifluoromethyl)-1H-pyrazolo[3,4-b]pyridin-1-yl}benzamide (1)

Example 1(1)

3-(Trifluoromethyl)-1H-pyrazolo[3,4-b]pyridine (1a)

Normal-butyllithium (a 2.6 M solution in hexane, 87.2 mL) was dropwise added to a solution of N,N-diisopropylamine (25.0 g) in tetrahydrofuran (hereinafter referred to as THF, 300 mL) under a nitrogen atmosphere at −5 to 0° C., and a solution of 2-fluoropyridine (25 g) in THF (50 mL) was dropwise added thereto at −78° C., followed by stirring for 1 hr. Subsequently, a solution of ethyl trifluoroacetate (47.6 g) in THF (50 mL) was dropwise added to the reaction solution at −78° C., followed by stirring at the same temperature for 1 hr. Hydrazine monohydrate (41.3 g) was added thereto, followed by stirring at 60° C. for 6 hr. Water (500 mL) was added to the reaction solution, followed by stirring at 100° C. for 30 min. The precipitate was collected by filtration and dried under reduced pressure to obtain a compound (1a) (32.8 g, 85%) as a white solid.

$^1$H-NMR (DMSO-d$_6$) δ 14.64 (1H, brs), 8.73 (1H, d, J=4.3 Hz), 8.34 (1H, d, J=8.1 Hz), 7.43 (1H, dd, J=8.1, 4.3 Hz); LRMS (ESI) m/z 188 [M+H]$^+$.

Example 1(2)

3-(Trifluoromethyl)-1H-pyrazolo[3,4-b]pyridine 7-oxide (1b)

Compound (1a) was dissolved in ethylene glycol dimethyl ether (100 mL) and heptane (200 mL), and m-chloroperoxybenzoic acid (33.9 g) was added to the resulting solution at 0° C., followed by stirring at room temperature for 1 hr. The precipitate was collected by filtration to obtain compound (1b) (33.3 g, 96%) as a white solid.

$^1$H-NMR (DMSO-$d_6$) δ 8.53 (1H, d, J=6.1 Hz), 8.87 (1H, d, J=8.3 Hz), 7.36 (1H, dd, J=8.3, 6.1 Hz); LRMS (ESI) m/z 204 [M+H]$^+$.

Example 1(3)

4-Chloro-3-(trifluoromethyl)-1H-pyrazolo[3,4-b]pyridine (1c)

Phosphorus oxychloride (76.4 g) was gradually added to compound (1b) (33.2 g), followed by stirring at 100° C. for 1 hr. The reaction solution was poured into ice water, and sodium hydroxide was added thereto to adjust the pH to 10. The precipitate was collected by filtration to obtain compound (1c) (9.76 g, 27%) as a light pink solid.

$^1$H-NMR (DMSO-$d_6$) δ 14.98 (1H, brs), 8.66 (1H, brd, J=4.9 Hz), 7.61 (1H, brd, J=4.9 Hz); LRMS (ESI) m/z 222 [M+H]$^+$.

Example 1(4)

3-{3-(Trifluoromethyl)-1H-pyrazolo[3,4-b]pyridin-4-yl}quinoline (1d)

A [1,1-bis-(diphenylphosphino)-ferrocene]dichloropalladium(II) dichloromethane complex (0.74 g) was added to a solution of compound (1c) (2.0 g), quinoline-3-boronic acid (2.5 g), and an aqueous sodium carbonate solution (1 M, 18 mL) in 1,4-dioxane (45 mL) under a nitrogen atmosphere, followed by stirring at 100° C. for 3 hr. The reaction solution was distributed between ethyl acetate and water, and the organic layer was washed with saturated saline and then dried over anhydrous sodium sulfate. After distillation of the solvent, the residue was purified by neutral silica gel column chromatography (chloroform/methanol) to obtain compound (1d) (0.94 g, 33%) as a white solid.

$^1$H-NMR (DMSO-$d_6$) δ 14.89 (1H, brs), 9.00 (1H, d, J=2.0 Hz), 8.81 (1H, d, J=4.6 Hz), 8.54 (1H, d, J=2.0 Hz), 8.14 (1H, d, J=8.2 Hz), 8.08 (1H, d, J=8.2 Hz), 7.88 (1H, td, J=6.9, 1.5 Hz), 7.72 (1H, brt, J=6.9 Hz), 7.51 (1H, d, J=4.6 Hz); LRMS (ESI) m/z 315 [M+H]$^+$.

Example 1(5)

2-Bromo-4-{4-(quinolin-3-yl)-3-(trifluoromethyl)-1H-pyrazolo[3,4-b]pyridin-1-yl}benzonitrile (1e)

Sodium hydride (0.183 g, a 55% dispersion in paraffin liquid) was added to a solution of compound (1d) (0.940 g) in N,N-dimethylformamide (hereinafter referred to as DMF, 6 mL) at room temperature, followed by stirring for 30 min. Subsequently, 2-bromo-4-fluorobenzonitrile (0.838 g) was added to the reaction solution, followed by stirring at 60° C. for 1 hr. After cooling, water was added to the reaction solution, followed by extraction with ethyl acetate. The organic layer was washed with water and saturated saline in this order and was dried over anhydrous sodium sulfate. After distillation of the solvent, the residue was purified by neutral silica gel column chromatography (chloroform/methanol) to obtain compound (1e) (0.56 g, 38%) as a white solid.

$^1$H-NMR (DMSO-$d_6$) δ 9.03-9.01 (2H, m), 8.89 (1H, d, J=1.8 Hz), 8.58-8.54 (2H, m), 8.23 (1H, d, J=8.6 Hz), 8.16 (1H, d, J=8.4 Hz), 8.11 (1H, d, J=8.2 Hz), 7.91 (1H, brt, J=7.0 Hz), 7.76-7.71 (2H, m); LRMS (ESI) m/z 494, 496 [M+H]$^+$.

Example 1(6)

2-(Trans-4-hydroxycyclohexylamino)-4-{4-(quinolin-3-yl)-3-(trifluoromethyl)-1H-pyrazolo[3,4-b]pyridin-yl}benzonitrile (1f)

A solution of a mixture of compound (1e) (0.560 g), trans-4-hydroxycyclohexylamine (0.522 g), sodium tert-butoxide (0.218 g), palladium acetate (0.025 g), and 1,1-bis-(diphenylphosphino)-ferrocene (0.126 g) in 1,4-dioxane (12 mL) was stirred under a nitrogen atmosphere at 140° C. for 2 hr. The reaction solution was distributed between ethyl acetate and water, and the organic layer was washed with saturated saline. The organic layer after the washing was dried over anhydrous sodium sulfate, and then the solvent was distilled away. The residue was purified by neutral silica gel column chromatography (chloroform/methanol) to obtain compound (1f) (0.450 g, 75%) as a white solid.

$^1$H-NMR (DMSO-$d_6$) δ 9.03 (1H, d, J=1.6 Hz), 8.95 (1H, d, J=4.8 Hz), 8.58 (1H, d, J=2.1 Hz), 8.16 (1H, d, J=8.7 Hz), 8.10 (1H, d, J=7.3 Hz), 7.90 (1H, td, J=6.9, 1.5 Hz), 7.86 (1H, d, J=2.0 Hz), 7.77-7.68 (3H, m), 7.53 (1H, dd, J=8.6, 2.0 Hz), 4.59 (1H, d, J=4.6 Hz), 3.45 (1H, d, J=7.9 Hz), 3.47-3.43 (1H, m), 3.30 (1H, brs), 2.03-1.98 (2H, m), 1.91-1.86 (2H, m), 1.48-1.14 (4H, m); LRMS (ESI) m/z 529 [M+H]$^+$.

Example 1(7)

2-(Trans-4-hydroxycyclohexylamino)-4-{4-(quinolin-3-yl)-3-(trifluoromethyl)-1H-pyrazolo[3,4-b]pyridin-1-yl}benzamide (1)

Compound (1f) (0.450 g) was dissolved in dimethyl sulfoxide (hereinafter referred to as DMSO, 2 mL) and ethanol (4 mL). An aqueous sodium hydroxide solution (4 M, 0.851 mL) and a 30% hydrogen peroxide solution (0.193 mL) were added to the resulting solution in this order at room temperature, followed by stirring for 30 min. Water was added to the reaction solution, the reaction solution was distributed between ethyl acetate and water, and the organic layer was washed with saturated saline. The organic layer after the washing was dried over anhydrous sodium sulfate, and then the solvent was distilled away. The residue was purified by neutral silica gel column chromatography (chloroform/methanol) to obtain compound (1) (0.300 g, 65%) as a white solid.

$^1$H-NMR (DMSO-$d_6$) δ 9.04 (1H, d, J=2.1 Hz), 8.94 (1H, d, J=4.6 Hz), 8.59 (1H, d, J=2.0 Hz), 8.46 (1H, d, J=7.3 Hz), 8.16 (1H, d, J=8.4 Hz), 8.11 (1H, d, J=7.1 Hz), 7.93-7.84 (3H, m), 7.77-7.65 (3H, m), 7.28 (1H, dd, J=8.6, 2.0 Hz), 7.27 (1H, brs), 4.58 (1H, d, J=4.3 Hz), 3.52 (1H, m), 3.33 (1H, brs), 2.13-2.09 (2H, m), 1.90-1.85 (2H, m), 1.37-1.25 (4H, m); LRMS (ESI) m/z 547 [M+H]$^+$.

Example 2

2-(Trans-4-hydroxycyclohexylamino)-4-{4-(quinolin-3-yl)-3-methyl-1H-pyrazolo[3,4-b]pyridin-1-yl}benzamide (2)

Example 2(1)

3-Methyl-1H-pyrazolo[3,4-b]pyridine (2a)

Normal-butyllithium (a 2.6 M solution in hexane, 87.0 mL) was dropwise added to a solution of N,N-diisopropylamine (11.2 mL) in THF (100 mL) at −78° C. under a nitrogen atmosphere, followed by increasing the temperature to 0° C. Then, the solution was cooled to −78° C., and a solution of 2-fluoropyridine (6.2 g) in THF (100 mL) was dropwise added thereto at −78° C., followed by stirring for 1 hr. Subsequently, a solution of N-methoxy-N-methylacetamide (8.46 mL) in THF (50 mL) was dropwise added to the reaction solution at −78° C., and then hydrazine monohydrate (31.9 mL) was added thereto, followed by stirring at 60° C. for 1 hr. After distillation of the solvent, water was added to the residue, followed by extraction with ethyl acetate. The organic layer was washed with saturated saline. The organic layer after the washing was dried over anhydrous sodium sulfate, and then the solvent was distilled away to obtain compound (2a) (5.90 g, 69%) as a white solid.

$^1$H-NMR (DMSO-$d_6$) δ 8.08 (1H, dd, J=4.27, 1.71 Hz), 7.79 (1H, dd, J=7.81, 1.71 Hz), 6.60 (1H, dd, J=7.81, 4.27 Hz), 2.44 (3H, s); LRMS (ESI) m/z 134 [M+H]$^+$.

Example 2(2)

3-Methyl-1H-pyrazolo[3,4-b]pyridine 7-oxide (2b)

According to Example 1(2), Compound (2b) (99%) was prepared as a white solid using compound (2a) instead of compound (1a). $^1$H-NMR (DMSO-$d_6$) δ 8.31 (1H, d, J=6.16 Hz), 7.79 (1H, dd, J=8.00 Hz), 7.71 (1H, dd, J=8.00, 6.16 Hz), 2.49 (3H, s); LRMS (ESI) m/z 150 [M+H]$^+$.

Example 2(3)

4-Chloro-3-methyl-1H-pyrazolo[3,4-b]pyridine (2c)

According to Example 1(3), compound (2c) (25%) was prepared as a white solid using compound (2b) instead of compound (1b).

$^1$H-NMR (DMSO-$d_6$) δ 8.41 (1H, d, J=5.00 Hz), 7.25 (1H, d, J=5.00 Hz), 2.64 (3H, s); LRMS (ESI) m/z 168 [M+H]$^+$.

Example 2(4)

2-(Trans-4-hydroxycyclohexylamino)-4-{4-(quinolin-3-yl)-3-methyl-1H-pyrazolo[3,4-b]pyridin-1-yl}benzonitrile (2d)

According to Example 1(4), 3-{3-methyl-1H-pyrazolo[3,4-b]pyridin-4-yl}quinoline (17%) was prepared as a white solid using compound (2c) instead of compound (1c). According to Example 1(5), 2-bromo-4-{4-(quinolin-3-yl)-3-methyl-1H-pyrazolo[3,4-b]pyridin-1-yl}benzonitrile was prepared using 3-{3-methyl-1H-pyrazolo[3,4-b]pyridin-4-yl}quinoline instead of compound (1d); and according to Example 1(6), compound (2d) (the second stage yield: 29%) was prepared as a white solid using 2-bromo-4-{4-(quinolin-3-yl)-3-methyl-1H-pyrazolo[3,4-b]pyridin-1-yl}benzonitrile instead of compound (1e).

$^1$H-NMR (DMSO-$d_6$) δ 9.15 (1H, d, J=2.08 Hz), 8.96 (1H, d, J=1.71 Hz), 8.85 (1H, d, J=4.88 Hz), 8.71 (1H, d, J=2.08 Hz), 8.65 (1H, dd, J=8.78, 1.71 Hz), 8.17-8.12 (3H, m), 7.90 (1H, t, J=7.62 Hz), 7.75 (1H, t, J=7.62 Hz), 7.58 (1H, d, J=4.88 Hz), 2.29 (3H, s); LRMS (ESI) m/z 440 [M+H]$^+$.

Example 2(5)

2-(Trans-4-hydroxycyclohexylamino)-4-{4-(quinolin-3-yl)-3-methyl-1H-pyrazolo[3,4-b]pyridin-1-yl}benzamide (2)

According to Example 1(7), compound (2) (92%) was prepared as a white solid using compound (2d) instead of compound (1f).

$^1$H-NMR (DMSO-$d_6$) δ 9.16 (1H, s), 8.76 (1H, d, J=4.63 Hz), 8.71 (1H, s), 8.45 (1H, d, J=7.32 Hz), 8.16 (2H, d, J=8.29 Hz), 7.90 (1H, t, J=7.56 Hz) 7.87 (1H, brs), 7.85 (1H, s), 7.80-7.73 (2H, m), 7.56-7.46 (3H, m), 7.14 (1H, brs), 4.59 (1H, d, J=4.39 Hz), 3.52 (1H, brs), 2.28 (3H, s), 2.12 (2H, 2, J=10.2 Hz), 1.89 (2H, 2, J=10.2 Hz), 1.43-1.22 (4H, m); LRMS (ESI) m/z 493 [M+H]$^+$.

Example 3

2-(Trans-4-hydroxycyclohexylamino)-4-{4-(quinolin-3-yl)-3-ethyl-1H-pyrazolo[3,4-b]pyridin-1-yl}benzamide (3)

Example 3(1)

3-Ethyl-1H-pyrazolo[3,4-b]pyridine (3a)

Normal-butyllithium (a 2.6 M solution in hexane, 87.0 mL) was dropwise added to a solution of N,N-diisopropylamine (23.0 g) in THF (200 mL) at −50° C. under a nitrogen atmosphere, followed by stirring for 10 min. Then, a solution of 2-fluoropyridine (20 g) in THF (100 mL) was dropwise added to the reaction solution at −78° C., followed by stirring for 1 hr. Subsequently, a solution of propionaldehyde (15.6 g) in THF (100 mL) was dropwise added to the reaction solution at −78° C. The reaction solution was warmed to room temperature and was poured in water (100 mL), followed by extraction with ethyl acetate. The organic layer was washed with saturated saline and then dried over anhydrous sodium sulfate. The solvent was distilled away to obtain a colorless oily substance (32.0 g). Without performing purification, celite (28.5 g) and pyridinium chlorochromate (53.0 g) were added to a solution of the colorless oily substance in dichloroethane (200 mL), followed by stirring at 40° C. for 2 hr. Pyridinium chlorochromate (13.0 g) was further added to the reaction solution, followed by stirring at 40° C. for 2 hr. The reaction solution was filtrated using celite, and silica gel (300 g) was added to the filtrate, followed by stirring for 5 min, filtration, and elution with 200 mL of chloroform three times and 200 mL of ethyl acetate twice. The solvent was distilled away to obtain a brown oily substance (31.0 g). Without performing purification, hydrazine monohydrate (25.0 mL) was added to a solution of the brown oily substance (31.0 g) in THF (52 mL), followed by stirring at 90° C. for 30 min. After cooling, the reaction solution was distributed between ethyl acetate and water. The organic layer was washed with saturated saline and was then dried over anhydrous sodium sulfate. Then, the solvent was distilled away to obtain compound (3a) (26.0 g, the third stage yield: 86%) as a yellow oily substance.

¹H-NMR (CDCl₃) δ 11.45 (1H, brs), 8.57 (1H, dd, J=4.6, 1.5 Hz), 8.09 (1H, dd, J=8.0, 1.5 Hz), 7.13 (1H, dd, J=8.0, 4.6 Hz), 3.03 (2H, q, J=7.6 Hz), 1.44 (3H, t, J=7.6 Hz); LRMS (ESI) m/z 148 [M+H]⁺.

Example 3(2)

3-Ethyl-1H-pyrazolo[3,4-b]pyridine 7-oxide (3b)

According to Example 1(2), compound (3b) (69%) was prepared as a white solid using compound (3a) instead of compound (1a).
¹H-NMR (DMSO-d₆) δ 14.02 (1H, brs), 8.32 (1H, d, J=6.1 Hz), 7.84 (1H, d, J=8.1 Hz), 7.11 (1H, dd, J=8.1, 6.1 Hz), 2.91 (2H, q, J=7.6 Hz), 1.29 (3H, t, J=7.6 Hz); LRMS (ESI) m/z 164 [M+H]⁺.

Example 3(3)

4-Chloro-3-ethyl-1H-pyrazolo[3,4-b]pyridine (3c)

Phosphorus oxychloride (11.1 mL) was added to a suspension solution of compound (3b) (19.5 g) in dichloroethane (240 mL) at room temperature, followed by stirring for 30 min. The solvent of the reaction solution was distilled away, and then acetonitrile (40 mL), methanol (40 mL), and water (80 mL) were added to the residue. After adjustment of pH to 9 with an aqueous sodium hydroxide solution, water (400 mL) was added thereto. The precipitate was collected by filtration, washed by sprinkling methanol (40 mL), water (300 mL), ether (60 mL), and hexane (30 mL), sequentially, and dried under reduced pressure to obtain compound (3c) (10.2 g, 47%) as a white solid.
¹H-NMR (CDCl₃) δ 8.42 (1H, d, J=5.1 Hz), 7.13 (1H, d, J=5.1 Hz), 3.19 (2H, q, J=7.6 Hz), 1.43 (3H, t, J=7.6 Hz); LRMS (ESI) m/z 182 [M+H]⁺.

Example 3(4)

4-Chloro-1-(1-ethoxyethyl)-3-ethyl-1H-pyrazolo[3,4-b]pyridine (3d)

Ethyl vinyl ether (3.7 mL) and (+)-10-camphorsulfonic acid (0.162 g) were sequentially added to a solution of compound (3c) (2.36 g) in THF (13.0 mL), followed by stirring at 50° C. for 30 min. After cooling, the reaction solution was distributed between ethyl acetate and a saturated aqueous sodium bicarbonate solution. The organic layer was washed with saturated saline. The organic layer after the washing was dried over anhydrous sodium sulfate, and then the solvent was distilled away. The residue was purified by neutral silica gel column chromatography (n-hexane/ethyl acetate) to obtain compound (3d) (3.01 g, 91%) as an oily substance.
¹H-NMR (CDCl₃) δ 8.34 (1H, d, J=5.1 Hz), 7.09 (1H, d, J=5.1 Hz), 6.22 (1H, q, J=6.1 Hz), 3.43-3.53 (1H, m), 3.11-3.26 (3H, m), 1.84 (3H, d, J=6.1 Hz), 1.40 (3H, t, J=7.6 Hz), 1.12 (3H, t, J=6.8 Hz); LRMS (ESI) m/z 254 [M+H]⁺.

Example 3(5)

3-(3-Ethyl-1H-pyrazolo[3,4-b]pyridin-4-yl)quinoline (3e)

Tetrakis(triphenylphosphine)palladium(0) (0.69 g) was added to a solution of compound (3d) (3.01 g), quinoline-3-boronic acid (2.67 g), and an aqueous sodium carbonate solution (2 M, 23 mL) in ethylene glycol dimethyl ether (30 mL) under a nitrogen atmosphere, followed by stirring at 85° C. for 25 hr. The reaction solution was distributed between ethyl acetate and water. The organic layer was washed with saturated saline and then dried over anhydrous sodium sulfate. After distillation of the solvent, 1,4-dioxane (23 mL) and 6 N hydrochloric acid (23 mL) were added to the residue, and the resulting mixture was stirred at room temperature for 90 min. The pH was adjusted to 7 with an aqueous sodium hydroxide solution, followed by extraction with ethyl acetate. The organic layer was washed with saturated saline. The organic layer after the washing was dried over anhydrous sodium sulfate, and then the solvent was distilled away. The residue was purified by neutral silica gel column chromatography (n-hexane/ethyl acetate) to obtain compound (3e) (0.942 g, the second stage yield: 29%) as a white solid.
¹H-NMR (CDCl₃) δ 11.64 (1H, brs), 9.09 (1H, d, J=2.2 Hz), 8.67 (1H, d, J=4.6 Hz), 8.31 (1H, d, J=2.2 Hz), 8.24 (1H, d, J=8.3 Hz), 7.95 (1H, d, J=7.8 Hz), 7.85 (1H, t, J=8.3 Hz), 7.68 (1H, t, J=7.8 Hz), 7.15 (1H, d, J=4.6 Hz), 2.69 (2H, q, J=7.6 Hz), 1.06 (3H, t, J=7.6 Hz); LRMS (ESI) m/z 275 [M+H]⁺.

Example 3(6)

2-Bromo-4-{4-(quinolin-3-yl)-3-ethyl-1H-pyrazolo[3,4-b]pyridin-1-yl}benzonitrile (3f)

According to Example 1(5), compound (3f) (84%) was prepared as a white solid using compound (3e) instead of compound (1d).
¹H-NMR (DMSO-d₆) δ 9.14 (1H, d, J=2.2 Hz), 8.99 (1H, d, J=2.2 Hz), 8.86 (1H, d, J=4.9 Hz), 8.70 (1H, s), 8.66 (1H, d, J=8.8 Hz), 8.10-8.22 (3H, m), 7.91 (1H, t, J=8.3 Hz), 7.75 (1H, t, J=7.3 Hz), 7.56 (1H, d, J=4.9 Hz), 2.67 (2H, q, J=7.6 Hz), 0.98 (3H, t, J=7.6 Hz); LRMS (ESI) m/z 454 [M+H]⁺.

Example 3(7)

2-(Trans-4-hydroxycyclohexylamino)-4-{4-(quinolin-3-yl)-3-ethyl-1H-pyrazolo[3,4-b]pyridin-1-yl}benzamide (3)

According to Example 1(6), a crude product of 2-(trans-4-hydroxycyclohexylamino)-4-{4-(quinolin-3-yl)-3-ethyl-1H-pyrazolo[3,4-b]pyridin-1-yl}benzonitrile was prepared using compound (3f) instead of compound (1e) and was used in the subsequent reaction without being purified. According to Example 1(7), compound (3) (the second stage yield: 49%) was prepared as a white solid by using 2-(trans-4-hydroxycyclohexylamino)-4-{4-(quinolin-3-yl)-3-ethyl-1H-pyrazolo[3,4-b]pyridin-1-yl}benzonitrile instead of compound (1f).
¹H-NMR (DMSO-d₆) δ 9.14 (1H, d, J=2.2 Hz), 8.76 (1H, d, J=4.9 Hz), 8.69 (1H, s), 8.44 (1H, d, J=7.1 Hz), 8.12-8.20 (2H, m), 7.41-7.94 (5H, m), 7.49 (1H, d, J=8.8 Hz), 7.45 (1H, d, J=4.9 Hz), 7.14 (1H, brs), 4.58 (1H, d, J=4.4 Hz), 3.30-3.60 (2H, m), 2.66 (2H, q, J=7.6 Hz), 1.80-2.20 (4H, m), 1.21-1.50 (4H, m), 0.96 (3H, t, J=7.6 Hz); LRMS (ESI) m/z 507 [M+H]⁺.

Example 4

2-(Trans-4-hydroxycyclohexylamino)-4-{3-isopropyl-4-(quinolin-3-yl)-1H-pyrazolo[4,3-c]pyridin-1-yl}benzamide (4)

Example 4(1)

4-Chloro-3-isopropyl-1H-pyrazolo[4,3-c]pyridine (4a)

Normal-butyllithium (a 1.6 M solution in hexane, 8.13 mL) was dropwise added to a solution of N,N-diisopropylamine (1.99 mL) in THF (30 mL) at −78° C. under a nitrogen atmosphere, followed by increasing the temperature to 0° C. Then, the solution was cooled to −78° C., and a solution of 2,4-dichloropyridine (1.0 g) in THF (3 mL) wad dropwise added thereto at −78° C., followed by stirring for 1.5 hr. Then, a solution of isobutylaldehyde (1.85 mL) in THF (3 mL) was dropwise added to the reaction solution at −78° C., followed by stirring at the same temperature for 30 min. Then, the reaction solution was poured into ice water and was extracted with ethyl acetate. The organic layer was washed with saturated saline, and the organic layer after the washing was dried over anhydrous sodium sulfate. Then, the solvent was distilled away, and the residue was purified by neutral silica gel column chromatography (n-hexane/ethyl acetate) to obtain 1-(2,4-dichloropyridin-3-yl)-2-methylpropan-1-ol (1.48 g, 99%) as a colorless oily substance. A solution of DMSO (0.9 mL) in dichloromethane (5 mL) and a solution of 1-(2,4-dichloropyridin-3-yl)-2-methylpropan-1-ol (1.39 g) in dichloromethane (5 mL) were sequentially added to a solution of oxalyl chloride (0.8 mL) in dichloromethane (30 mL) at −78° C., followed by stirring for 30 min. Then, triethylamine (3.52 mL) was added to the reaction solution at 0° C., followed by stirring for 1 hr. The reaction solution was poured into ice water and was extracted with chloroform. The organic layer was washed with saturated saline. The organic layer after the washing was dried over anhydrous sodium sulfate, and then the solvent was distilled away. The residue was purified by neutral silica gel column chromatography (n-hexane/ethyl acetate) to obtain 1-(2,4-dichloropyridin-3-yl)-2-methylpropan-1-one (1.18 g, 86%) as a colorless oily substance. Hydrazine monohydrate (1.3 mL) was added to a solution of 1-(2,4-dichloropyridin-3-yl)-2-methylpropan-1-one (0.93 g) in THF (13 mL), followed by stirring at room temperature for 12 hr and then at 50° C. for 25 hr. The reaction solvent was distilled away under reduced pressure, and the residue was purified by neutral silica gel column chromatography (n-hexane/ethyl acetate) to obtain compound (4a) (0.55 g, 66%) as a colorless oily substance.

$^1$H-NMR (DMSO-$d_6$) δ 8.06 (1H, d, J=5.73 Hz), 7.48 (1H, d, J=5.73 Hz), 3.69 (1H, q, J=6.83 Hz), 1.35 (1H, d, J=6.83 Hz); LRMS (ESI) m/z 196 [M+H]$^+$.

Example 4(2)

3-{3-Isopropyl-1H-pyrazolo[4,3-c]pyridin-4-yl}quinoline (4b)

Dihydropyran (10.0 mL) and (+)-10-camphorsulfonic acid (0.062 g) were sequentially added to compound (4a) (0.55 g), followed by stirring at 80° C. for 30 min. After cooling, the reaction solution was distributed between ethyl acetate and a saturated aqueous sodium bicarbonate solution, and the organic layer was washed with saturated saline. The organic layer after the washing was dried over anhydrous sodium sulfate, and the solvent was distilled away. The residue was purified by neutral silica gel column chromatography (n-hexane/ethyl acetate) to obtain 4-chloro-3-isopropyl-1-(tetrahydro-2H-pyran-2-yl)-1H-pyrazolo[4,3-c]pyridine (0.727 g, 93%) as a colorless oily substance. Subsequently, tetrakis(triphenylphosphine)palladium(0) (0.149 g) was added to a solution of the colorless oily substance (0.727 g), quinoline-3-boronic acid (0.539 g), and an aqueous sodium carbonate solution (1 M, 13 mL) in ethylene glycol dimethyl ether (26 mL) under a nitrogen atmosphere at 85° C. for 25 hr. The reaction solution was distributed between ethyl acetate and water, and the organic layer was washed with saturated saline and then dried over anhydrous sodium sulfate. After distillation of the solvent, THF (5.2 mL) and concentrated hydrochloric acid (2.6 mL) were added to the residue, followed by stirring at 60° C. for 1 hr. The pH was adjusted to 7 with an aqueous sodium bicarbonate solution, followed by extraction with ethyl acetate. The organic layer was washed with saturated saline. The organic layer after the washing was dried over anhydrous sodium sulfate, and then the solvent was distilled away. The residue was purified by neutral silica gel column chromatography (n-hexane/ethyl acetate) to obtain compound (4b) (0.395 g, the third yield: 52%) as a white solid.

$^1$H-NMR (DMSO-$d_6$) δ 13.3 (1H, s), 9.14 (1H, d, J=2.10 Hz), 8.63 (1H, d, J=2.10 Hz), 8.43 (1H, d, J=5.85 Hz), 8.13 (1H, d, J=8.05 Hz), 8.12 (1H, d, J=8.05 Hz), 7.85 (1H, td, J=8.05, 1.22 Hz), 7.69 (1H, td, J=8.05, 1.22 Hz), 7.55 (1H, d, J=5.85 Hz), 3.00 (1H, d, J=6.83 Hz), 1.01 (1H, d, J=6.83 Hz); LRMS (ESI) m/z 289 [M+H]$^+$.

Example 4(3)

2-Bromo-4-{4-(quinolin-3-yl)-3-isopropyl-1H-pyrazolo[4,3-c]pyridin-1-yl}benzonitrile (4c)

According to Example 1(5), compound (4c) (44%) was prepared as a white solid using compound (4b) instead of compound (1d).

$^1$H-NMR (DMSO-$d_6$) δ 9.18 (1H, d, J=1.95 Hz), 8.70 (1H, d, J=2.20 Hz), 8.68 (1H, d, J=5.98 Hz), 8.31 (1H, d, J=1.95 Hz), 8.15-8.12 (4H, m), 8.06 (1H, d, J=5.98 Hz), 7.88 (1H, t, J=7.31 Hz), 7.72 (1H, t, J=7.31 Hz), 3.05 (1H, q, J=6.71 Hz), 1.07 (6H, d, J=6.71 Hz); LRMS (ESI) m/z 468 [M+H]$^+$.

Example 4(4)

2-(Trans-4-hydroxycyclohexylamino)-4-{3-isopropyl-4-(quinolin-3-yl)-1H-pyrazolo[4,3-c]pyridin-1-yl}benzamide (4)

According to Example 1(6), 2-(trans-4-hydroxycyclohexylamino)-4-{3-isopropyl-4-(quinolin-3-yl)-1H-pyrazolo[4,3-c]pyridin-1-yl}benzonitrile was prepared using compound (4c) instead of compound (1e) and was used in the subsequent reaction without being purified. According to Example 1(7), compound (4) (the second stage yield: 30%) was prepared as a white solid using 2-(trans-4-hydroxycyclohexylamino)-4-{3-isopropyl-4-(quinolin-3-yl)-1H-pyrazolo[4,3-c]pyridin-1-yl}benzonitrile instead of compound (1f).

$^1$H-NMR (DMSO-$d_6$) δ 9.19 (1H, d, J=1.95 Hz), 8.70 (1H, d, J=1.95 Hz), 8.60 (1H, d, J=5.85 Hz), 8.48 (1H, d, J=7.56 Hz), 8.16 (1H, d, J=8.54 Hz), 8.13 (1H, d, J=8.54 Hz), 7.92 (1H, brs), 7.87-7.84 (3H, m) 7.72 (1H, t, J=7.44 Hz), 7.23 (1H, brs), 7.02 (1H, d, J=1.95 Hz), 6.90 (1H, dd, J=8.54, 1.95 Hz), 4.56 (1H, d, J=4.15 Hz), 3.49 (1H, brs), 3.05 (1H, q, J=6.83 Hz), 2.03 (1H, d, J=10.9 Hz), 1.84 (1H, d, J=10.9 Hz), 1.37-1.20 (4H, m), 1.07 (1H, q, J=6.83 Hz); LRMS (ESI) m/z 521 [M+H]⁺.

Example 5

2-(Trans-4-hydroxycyclohexylamino)-4-{3-isopropyl-4-(quinolin-3-yl)-1H-pyrazolo[3,4-c]pyridin-1-yl}benzamide (5)

Example 5(1)

2-Bromo-4-{4-(quinolin-3-yl)-3-isopropyl-1H-pyrazolo[3,4-c]pyridin-1-yl}benzonitrile (5a)

According to Example 4(1), 4-bromo-3-isopropyl-1H-pyrazolo[3,4-c]pyridine (the third stage yield: 45%) was prepared as a white solid using 3,5-dibromo-pyridine instead of 2,4-dichloropyridine. According to Example 4(2), 3-{3-isopropyl-1H-pyrazolo[3,4-c]pyridin-4-yl}quinoline (the third stage yield: 66%) was prepared using 4-bromo-3-isopropyl-1H-pyrazolo[3,4-c]pyridine instead of compound (4a). According to Example 1(5), compound (5a) (73%) was prepared as a white solid using 3-{3-isopropyl-1H-pyrazolo[3,4-c]pyridin-4-yl}quinoline instead of compound (1d).

¹H-NMR (DMSO-d₆) δ 9.53 (1H, s), 9.11 (1H, d, J=1.71 Hz), 8.65 (1H, d, J=1.95 Hz), 8.46 (1H, s), 8.39 (1H, d, J=1.95 Hz), 8.17-8.14 (4H, m), 7.88 (1H, t, J=7.50 Hz), 7.73 (1H, t, J=7.50 Hz), 2.94 (1H, q, J=6.95 Hz), 1.06 (6H, d, J=6.95 Hz); LRMS (ESI) m/z 468 [M+H]⁺.

Example 5(2)

2-(Trans-4-hydroxycyclohexylamino)-4-{3-isopropyl-4-(quinolin-3-yl)-1H-pyrazolo[3,4-c]pyridin-1-yl}benzamide (5)

According to Example 1(6), 2-(trans-4-hydroxycyclohexylamino)-4-{3-isopropyl-4-(quinolin-3-yl)-1H-pyrazolo[3,4-c]pyridin-1-yl}benzonitrile was prepared using compound (5a) instead of compound (1e); and according to Example 1(7), compound (5) (the second stage yield: 41%) was prepared as a white solid using 2-(trans-4-hydroxycyclohexylamino)-4-{3-isopropyl-4-(quinolin-3-yl)-1H-pyrazolo[3,4-c]pyridin-1-yl}benzonitrile instead of compound (1f).

¹H-NMR (DMSO-d₆) δ 9.36 (1H, s), 9.11 (1H, d, J=1.71 Hz), 8.64 (1H, d, J=1.95 Hz), 8.49 (1H, d, J=7.32 Hz), 8.37 (1H, s), 8.15 (1H, d, J=8.29 Hz), 8.12 (1H, d, J=8.29 Hz), 7.94-7.83 (3H, m), 7.72 (1H, t, J=7.56 Hz), 7.23 (1H, brs), 7.09 (1H, s), 6.97 (1H, dd, J=8.29, 1.71 Hz), 4.56 (1H, d, J=4.59 Hz), 3.52-3.38 (2H, m), 2.95 (1H, q, J=7.07 Hz), 2.04 (2H, d, J=10.7 Hz), 1.84 (2H, d, J=10.7 Hz), 1.42-1.22 (4H, m), 1.06 (6H, d, J=7.07 Hz); LRMS (ESI) m/z 521 [M+H]⁺.

Example 6

2-(Trans-4-hydroxycyclohexylamino)-4-{3-isopropyl-4-(quinolin-3-yl)-1H-pyrazolo[3,4-b]pyridin-1-yl}benzamide (6)

Example 6(1)

3-Isopropyl-1H-pyrazolo[3,4-b]pyridine 7-oxide (6a)

According to Example 3(1), 3-isopropyl-1H-pyrazolo[3,4-b]pyridine (the third stage yield: 62%) was prepared as a yellow oily substance using isobutyl aldehyde instead of propionaldehyde; and according to Example 1(2), compound (6a) (81%) was prepared as a white solid using 3-isopropyl-1H-pyrazolo[3,4-b]pyridine instead of compound (1a).

¹H-NMR (CDCl₃) δ 8.37 (1H, d, J=5.9 Hz), 7.80 (1H, d, J=8.3 Hz), 7.05-7.15 (1H, m), 3.39 (1H, q, J=6.8 Hz), 1.45 (6H, d, J=6.8 Hz); LRMS (ESI) m/z 178 [M+H]⁺.

Example 6(2)

4-Chloro-3-isopropyl-1H-pyrazolo[3,4-b]pyridine (6b)

According to Example 1(3), compound (6b) (58%) was prepared as a white solid using compound (6a) instead of compound (1b).

¹H-NMR (DMSO-d₆) δ 8.41 (1H, d, J=4.88 Hz), 7.27 (1H, d, J=4.88 Hz), 3.64 (1H, q, J=6.95 Hz), 1.37 (1H, d, J=6.95 Hz); LRMS (ESI) m/z 196 [M+H]⁺.

Example 6(3)

3-{3-Isopropyl-1H-pyrazolo[3,4-b]pyridin-4-yl}quinoline (6c)

According to Example 1(4), compound (6c) (65%) was prepared as a white solid using compound (6b) instead of compound (1c).

¹H-NMR (DMSO-d₆) δ 13.5 (1H, s), 9.08 (1H, d, J=2.20 Hz), 8.62 (1H, d, J=2.20 Hz), 8.59 (1H, d, J=4.63 Hz), 8.15 (1H, d, J=9.39 Hz), 8.12 (1H, d, J=9.39 Hz), 7.88 (1H, td, J=7.60, 1.46 Hz), 7.73 (1H, t, J=7.60 Hz), 7.21 (1H, d, J=4.63 Hz), 2.90 (1H, q, J=6.83 Hz), 1.00 (6H, d, J=6.83 Hz); LRMS (ESI) m/z 289 [M+H]⁺.

Example 6(4)

2-Bromo-4-{3-isopropyl-4-(quinolin-3-yl)-1H-pyrazolo[3,4-b]pyridin-1-yl}benzonitrile (6d)

According to Example 1(5), compound (6d) (59%) was prepared as a white solid using compound (6c) instead of compound (1d).

¹H-NMR (DMSO-d₆) δ 9.13 (1H, d, J=2.20 Hz), 8.99 (1H, d, J=1.71 Hz), 8.85 (1H, d, J=4.88 Hz), 8.69 (1H, s), 8.65 (1H, dd, J=8.54, 1.95 Hz), 8.18-8.12 (3H, m), 7.90 (1H, t, J=7.25 Hz), 7.74 (1H, t, J=7.25 Hz), 7.53 (1H, d, J=4.88 Hz), 2.97 (1H, q, J=6.83 Hz), 1.05 (1H, d, J=6.83 Hz); LRMS (ESI) m/z 468 [M+H]⁺.

Example 6(5)

2-(Trans-4-hydroxycyclohexylamino)-4-{3-isopropyl-4-(quinolin-3-yl)-1H-pyrazolo[3,4-b]pyridin-1-yl}benzamide (6)

According to Example 1(6), 2-(trans-4-hydroxycyclohexylamino)-4-{3-isopropyl-4-(quinolin-3-yl)-1H-pyrazolo[3,4-b]pyridin-1-yl}benzonitrile was prepared as a white solid using compound (6d) instead of compound (1e); and according to Example 1(7), compound (6) (the second stage yield: 62%) was prepared as a white solid using 2-(trans-4-hydroxycyclohexylamino)-4-{3-isopropyl-4-(quinolin-3-yl)-1H-pyrazolo[3,4-b]pyridin-1-yl}benzonitrile instead of compound (1f).

¹H-NMR (DMSO-d₆) δ 9.07 (1H, d, J=1.95 Hz), 8.69 (1H, d, J=4.88 Hz), 8.63 (1H, s), 8.36 (1H, d, J=7.07 Hz), 8.11 (1H, d, J=9.64 Hz), 8.07 (1H, d, J=9.64 Hz), 7.86-7.66 (5H, m), 7.42 (1H, dd, J=8.54, 1.71 Hz), 7.36 (1H, d, J=4.63 Hz), 7.07 (1H, brs), 4.53 (1H, s), 3.46 (1H, brs), 2.90 (1H, q, J=6.83 Hz), 2.06 (2H, d, J=11.4 Hz), 1.83 (2H, d, J=11.4 Hz), 1.34-1.17 (4H, m), 0.99 (6H, d, J=6.83 Hz); LRMS (ESI) m/z 521 [M+H]$^+$.

Example 7

2-(Trans-4-hydroxycyclohexylamino)-4-{3-isopropyl-4-(pyridin-3-yl)-1H-pyrazolo[3,4-b]pyridin-1-yl}benzamide (7)

Example 7(1)

2-Bromo-4-{3-isopropyl-4-(pyridin-3-yl)-1H-pyrazolo[3,4-b]pyridin-1-yl}benzonitrile (7a)

According to Example 1(4), a crude product of 3-isopropyl-4-(pyridin-3-yl)-1H-pyrazolo[3,4-b]pyridine was prepared using compound (6b) instead of compound (1c) and using pyridine-3-boronic acid instead of quinoline-3-boronic acid and was used in the subsequent reaction without being purified. According to Example 1(5), compound (7a) (the second stage yield: 60%) was prepared using 3-isopropyl-4-(pyridin-3-yl)-1H-pyrazolo[3,4-b]pyridine instead of compound (1d).

$^1$H-NMR (DMSO-d$_6$) δ 8.96 (1H, d, J=2.14 Hz), 8.82-8.77 (3H, m), 8.63 (1H, dd, J=8.60, 2.14 Hz), 8.13 (1H, d, J=8.60 Hz), 8.09 (1H, dt, J=7.85, 1.95 Hz), 7.63 (1H, dd, J=7.85, 4.76 Hz), 7.41 (1H, d, J=4.76 Hz), 2.95 (1H, q, J=6.83 Hz), 1.08 (6H, d, J=6.83 Hz); LRMS (ESI) m/z 418 [M+H]$^+$.

Example 7(2)

2-(Trans-4-hydroxycyclohexylamino)-4-{3-isopropyl-4-(pyridin-3-yl)-1H-pyrazolo[3,4-b]pyridin-1-yl}benzamide (7)

According to Example 1(6), a crude product of 2-(trans-4-hydroxycyclohexylamino)-4-{3-isopropyl-4-(pyridin-3-yl)-1H-pyrazolo[3,4-b]pyridin-1-yl}benzonitrile was prepared using compound (7a) instead of compound (1e) and was used in the subsequent reaction without being purified. According to Example 1(7), compound (7) (the second stage yield: 79%) was prepared as a white solid using 2-(trans-4-hydroxycyclohexylamino)-4-{3-isopropyl-4-(pyridin-3-yl)-1H-pyrazolo[3,4-b]pyridin-1-yl}benzonitrile instead of compound (1f).

$^1$H-NMR (DMSO-d$_6$) δ 8.80 (1H, s), 8.76 (1H, d, J=4.39 Hz), 8.69 (1H, d, J=4.63 Hz), 8.40 (1H, d, J=6.83 Hz), 8.06 (1H, d, J=7.32 Hz), 7.84 (1H, s), 7.80 (1H, brs), 7.77 (1H, d, J=8.23 Hz), 7.65-7.45 (2H, m), 7.28 (1H, d, J=4.39 Hz), 7.12 (1H, brs), 4.59 (1H, d, J=3.90 Hz), 3.51 (1H, m), 2.93 (1H, q, J=6.65 Hz), 2.10 (2H, d, J=10.5 Hz), 1.87 (2H, d, J=10.5 Hz), 1.42-1.22 (4H, m), 1.06 (6H, d, J=6.65 Hz); LRMS (ESI) m/z 471 [M+H]$^+$.

Example 8

2-(Trans-4-hydroxycyclohexylamino)-4-{3-isopropyl-4-(pyridin-4-yl)-1H-pyrazolo[3,4-b]pyridin-1-yl}benzamide (8)

Example 8(1)

2-Bromo-4-{3-isopropyl-4-(pyridin-4-yl)-1H-pyrazolo[3,4-b]pyridin-1-yl}benzonitrile (8a)

According to Example 1(4), a crude product of 3-isopropyl-4-(pyridin-4-yl)-1H-pyrazolo[3,4-b]pyridine was prepared using compound (6b) instead of compound (1c) and using pyridine-4-boronic acid instead of quinoline-3-boronic acid and was used in the subsequent reaction without being purified. According to Example 1(5), compound (8a) (the second stage yield: 62%) was prepared using 3-isopropyl-4-(pyridin-4-yl)-1H-pyrazolo[3,4-b]pyridine instead of compound (1d).

$^1$H-NMR (DMSO-d$_6$) δ 8.92 (1H, d, J=1.22 Hz), 8.82 (1H, d, J=4.63 Hz), 8.79 (1H, d, J=5.12 Hz), 8.63 (1H, dd, J=8.54, 1.22 Hz), 8.14 (1H, d, J=8.54 Hz), 7.66 (2H, d, J=5.12 Hz), 7.38 (1H, d, J=4.63 Hz), 2.99 (1H, q, J=6.58 Hz), 1.09 (6H, d, J=6.58 Hz); LRMS (ESI) m/z 418 [M+H]$^+$.

Example 8(2)

2-(Trans-4-hydroxycyclohexylamino)-4-{3-isopropyl-4-(pyridin-4-yl)-1H-pyrazolo[3,4-b]pyridin-1-yl}benzamide (8)

According to Example 1(6), a crude product of 2-(trans-4-hydroxycyclohexylamino)-4-{3-isopropyl-4-(pyridin-4-yl)-1H-pyrazolo[3,4-b]pyridin-1-yl}benzonitrile was prepared using compound (8a) instead of compound (1e) and was used in the subsequent reaction without being purified. According to Example 1(7), compound (8) (the second stage yield: 58%) was prepared as a white solid using 2-(trans-4-hydroxycyclohexylamino)-4-{3-isopropyl-4-(pyridin-4-yl)-1H-pyrazolo[3,4-b]pyridin-1-yl}benzonitrile instead of compound (1f).

$^1$H-NMR (DMSO-d$_6$) δ 8.77 (2H, d, J=5.85 Hz), 8.70 (1H, d, J=4.63 Hz), 8.40 (1H, d, J=7.32 Hz), 7.83 (1H, d, J=1.71 Hz), 7.77 (1H, d, J=8.78 Hz), 7.77 (1H, brs), 7.63 (2H, d, J=5.85 Hz), 7.44 (1H, dd, J=8.78, 1.71 Hz), 7.25 (1H, d, J=4.63 Hz), 7.12 (1H, brs), 4.58 (1H, d, J=1.22 Hz), 3.50 (1H, brs), 2.96 (1H, q, J=6.83 Hz), 2.10 (2H, d, J=10.6 Hz), 1.87 (2H, d, J=10.6 Hz), 1.42-1.22 (4H, m), 1.07 (6H, d, J=6.83 Hz); LRMS (ESI) m/z 471 [M+H]$^+$.

Example 9

2-(Trans-4-hydroxycyclohexylamino)-4-{3-isopropyl-4-(benzofuran-2-yl)-1H-pyrazolo[3,4-b]pyridin-1-yl}benzamide (9)

Example 9(1)

2-Bromo-4-{3-isopropyl-4-(benzofuran-2-yl)-1H-pyrazolo[3,4-b]pyridin-1-yl}benzonitrile (9a)

According to Example 1(4), a crude product of 3-isopropyl-4-(benzofuran-2-yl)-1H-pyrazolo[3,4-b]pyridine was prepared using compound (6b) instead of compound (1c) and using benzofuran-2-boronic acid instead of quinoline-3-boronic acid and was used in the subsequent reaction without being purified. According to Example 1(5), compound (9a) (the second stage yield: 25%) was prepared using 3-isopropyl-4-(benzofuran-2-yl)-1H-pyrazolo[3,4-b]pyridine instead of compound (1d).

$^1$H-NMR (DMSO-d$_6$) δ 8.96 (1H, d, J=2.00 Hz), 8.81 (1H, d, J=4.88 Hz), 8.62 (1H, dd, J=8.72, 2.00 Hz), 8.14 (1H, d, J=8.71 Hz), 7.83 (1H, d, J=7.56 Hz), 7.80-7.73 (3H, m), 7.48

(1H, t, J=7.31 Hz), 3.83 (1H, q, J=6.59 Hz), 1.29 (6H, d, J=6.59 Hz); LRMS (ESI) m/z 457 [M+H]⁺.

Example 9(2)

2-(Trans-4-hydroxycyclohexylamino)-4-{3-isopropyl-4-(benzofuran-2-yl)-1H-pyrazolo[3,4-b]pyridin-1-yl}benzamide (9)

According to Example 1(6), a crude product of 2-(trans-4-hydroxycyclohexylamino)-4-{3-isopropyl-4-(benzofuran-2-yl)-1H-pyrazolo[3,4-b]pyridin-1-yl}benzonitrile was prepared using compound (9a) instead of compound (1e) and was used in the subsequent reaction without being purified. According to Example 1(7), compound (9) (the second stage yield: 46%) was prepared as a white solid using 2-(trans-4-hydroxycyclohexylamino)-4-{3-isopropyl-4-(benzofuran-2-yl)-1H-pyrazolo[3,4-b]pyridin-1-yl}benzonitrile instead of compound (1f).

$^1$H-NMR (DMSO-$d_6$) δ 8.73 (1H, d, J=4.88 Hz), 8.43 (1H, d, J=7.07 Hz), 7.86-7.76 (5H, m), 7.69 (2H, s), 7.48-7.46 (2H, m), 7.39 (1H, t, J=7.44 Hz), 7.15 (1H, brs), 4.60 (1H, s), 3.80 (1H, q, J=6.83 Hz), 3.52 (1H, brs), 2.13 (2H, d, J=10.0 Hz), 1.90 (2H, d, J=10.0 Hz), 1.41-1.24 (10H, m); LRMS (ESI) m/z 510 [M+H]⁺.

Example 10

2-(Trans-4-hydroxycyclohexylamino)-4-{3-isopropyl-4-(furan-2-yl)-1H-pyrazolo[3,4-b]pyridin-1-yl}benzamide (10)

Example 10(1)

2-Bromo-4-{3-isopropyl-4-(furan-2-yl)-1H-pyrazolo[3,4-b]pyridin-1-yl}benzonitrile (10a)

According to Example 1(4), a crude product of 3-isopropyl-4-(furan-2-yl)-1H-pyrazolo[3,4-b]pyridine was prepared using compound (6b) instead of compound (1c) and using furan-2-boronic acid instead of quinoline-3-boronic acid and was used in the subsequent reaction without being purified. According to Example 1(5), compound (10a) (the second stage yield: 40%) was prepared using 3-isopropyl-4-(furan-2-yl)-1H-pyrazolo[3,4-b]pyridine instead of compound (1d).

$^1$H-NMR (DMSO-$d_6$) δ 8.95 (1H, d, J=2.08 Hz), 8.71 (1H, d, J=5.00 Hz), 8.60 (1H, dd, J=8.78, 2.08 Hz), 8.12 (1H, d, J=8.78 Hz), 8.10 (1H, d, J=1.71 Hz), 7.60 (1H, d, J=5.00 Hz), 7.31 (1H, d, J=3.42 Hz), 6.82 (1H, dd, J=3.42, 1.71 Hz), 3.80 (1H, q, J=6.83 Hz), 1.26 (6H, d, J=6.83 Hz); LRMS (ESI) m/z 407 [M+H]⁺.

Example 10(2)

2-(Trans-4-hydroxycyclohexylamino)-4-{3-isopropyl-4-(furan-2-yl)-1H-pyrazolo[3,4-b]pyridin-1-yl}benzamide (10)

According to Example 1(6), a crude product of 2-(trans-4-hydroxycyclohexylamino)-4-{3-isopropyl-4-(furan-2-yl)-1H-pyrazolo[3,4-b]pyridin-1-yl}benzonitrile was prepared using compound (10a) instead of compound (1e) and was used in the subsequent reaction without being purified. According to Example 1(7), compound (10) (the second stage yield: 59%) was prepared as a white solid using 2-(trans-4-hydroxycyclohexylamino)-4-{3-isopropyl-4-(furan-2-yl)-1H-pyrazolo[3,4-b]pyridin-1-yl}benzonitrile instead of compound (1f).

$^1$H-NMR (DMSO-$d_6$) δ 8.62 (1H, d, J=4.75 Hz), 8.40 (1H, d, J=7.07 Hz), 8.07 (1H, s), 7.83 (1H, s), 7.83 (1H, brs), 7.75 (1H, d, J=8.53 Hz), 7.49 (1H, d, J=4.75 Hz), 7.45 (1H, d, J=8.53 Hz), 7.24 (1H, d, J=2.93 Hz), 7.12 (1H, brs), 6.79 (1H, d, J=2.93 Hz), 4.59 (1H, d, J=3.66 Hz), 3.76 (1H, q, J=6.59 Hz), 3.50 (1H, brs), 2.10 (2H, d, J=10.5 Hz), 1.87 (2H, d, J=10.5 Hz), 1.32-1.30 (10H, m); LRMS (ESI) m/z 460 [M+H]⁺.

Example 11

2-(Trans-4-hydroxycyclohexylamino)-4-{3-isopropyl-4-(5-methoxypyridin-3-yl)-1H-pyrazolo[3,4-b]pyridin-1-yl}benzamide (11)

Example 11(1)

2-Bromo-4-{3-isopropyl-4-(5-methoxypyridin-3-yl)-1H-pyrazolo[3,4-b]pyridin-1-yl}benzonitrile (11a)

According to Example 1(4), a crude product of 3-isopropyl-4-(5-methoxypyridin-3-yl)-1H-pyrazolo[3,4-b]pyridine was prepared using compound (6b) instead of compound (1c) and using 5-methoxypyridine-3-boronic acid pinacol ester instead of quinoline-3-boronic acid and was used in the subsequent reaction without being purified. According to Example 1(5), compound (11a) (the second stage yield: 45%) was prepared using 3-isopropyl-4-(5-methoxypyridin-3-yl)-1H-pyrazolo[3,4-b]pyridine instead of compound (1d).

$^1$H-NMR (DMSO-$d_6$) δ 8.97 (1H, d, J=1.77 Hz), 8.80 (1H, d, J=4.63 Hz), 8.63 (1H, dd, J=8.72, 1.77 Hz), 8.50 (1H, d, J=2.68 Hz), 8.39 (1H, s), 8.13 (1H, d, J=8.72 Hz), 7.70 (1H, s), 7.42 (1H, d, J=4.63 Hz), 3.91 (3H, s), 2.99 (1H, q, J=6.96 Hz), 1.12 (1H, d, J=6.96 Hz); LRMS (ESI) m/z 448 [M+H]⁺.

Example 11(2)

2-(Trans-4-hydroxycyclohexylamino)-4-{3-isopropyl-4-(5-methoxypyridin-3-yl)-1H-pyrazolo[3,4-b]pyridin-1-yl}benzamide (11)

According to Example 1(6), a crude product of 2-(trans-4-hydroxycyclohexylamino)-4-{3-isopropyl-4-(5-methoxypyridin-3-yl)-1H-pyrazolo[3,4-b]pyridin-1-yl}benzonitrile was prepared using compound (11a) instead of compound (1e) and was used in the subsequent reaction without being purified. According to Example 1(7), compound (11) (the second stage yield: 38%) was prepared as a white solid using 2-(trans-4-hydroxycyclohexylamino)-4-{3-isopropyl-4-(5-methoxypyridin-3-yl)-1H-pyrazolo[3,4-b]pyridin-1-yl}benzonitrile instead of compound (1f).

$^1$H-NMR (DMSO-$d_6$) δ 8.71 (1H, d, J=4.63 Hz), 8.49 (1H, d, J=2.80 Hz), 8.42 (1H, d, J=7.07 Hz), 8.39 (1H, d, J=1.89 Hz), 7.85 (1H, d, J=1.95 Hz), 7.83 (1H, brs), 7.78 (1H, d, J=8.60 Hz), 7.69 (1H, dd, J=2.80, 1.95 Hz), 7.46 (1H, dd, J=8.60, 1.89 Hz), 7.31 (1H, d, J=4.63 Hz), 7.14 (1H, brs), 4.59 (1H, d, J=4.15 Hz), 3.91 (3H, s), 3.52 (1H, brs), 2.98 (1H, q, J=6.83 Hz), 2.12 (2H, d, J=10.9 Hz), 1.89 (2H, d, J=10.9 Hz), 1.41-1.22 (4H, m), 1.11 (6H, d, J=6.83 Hz); LRMS (ESI) m/z 501 [M+H]⁺.

Example 12

2-(Trans-4-hydroxycyclohexylamino)-4-{3-isopropyl-4-(1-methyl-1H-indol-5-yl)-1H-pyrazolo[3,4-b]pyridin-1-yl}benzamide (12)

Example 12(1)

2-Bromo-4-{3-isopropyl-4-(1-methyl-1H-indol-5-yl)-1H-pyrazolo[3,4-b]pyridin-1-yl}benzonitrile (12a)

According to Example 1(4), a crude product of 3-isopropyl-4-(1-methyl-1H-indol-5-yl)-1H-pyrazolo[3,4-b]pyridine was prepared using compound (6b) instead of compound (1c) and using 1-methylindole-5-boronic acid pinacol ester instead of quinoline-3-boronic acid and was used in the subsequent reaction without being purified. According to Example 1(5), compound (12a) (the second stage yield: 90%) was prepared using 3-isopropyl-4-(1-methyl-1H-indol-5-yl)-1H-pyrazolo[3,4-b]pyridine instead of compound (1d).

$^1$H-NMR (DMSO-d$_6$) δ 8.97 (1H, d, J=1.95 Hz), 8.69 (1H, d, J=4.88 Hz), 8.64 (1H, dd, J=8.66, 1.95 Hz), 8.10 (1H, d, J=8.66 Hz), 7.74 (1H, s), 7.61 (1H, d, J=8.29 Hz), 7.45 (1H, d, J=3.05 Hz), 7.33 (1H, d, J=8.29 Hz), 7.31 (1H, d, J=4.88 Hz), 6.54 (1H, d, J=3.05 Hz), 3.87 (3H, s), 3.12 (1H, t, J=6.83 Hz), 1.03 (1H, d, J=6.83 Hz); LRMS (ESI) m/z 470 [M+H]$^+$.

Example 12(2)

2-(Trans-4-hydroxycyclohexylamino)-4-{3-isopropyl-4-(1-methyl-1H-indol-5-yl)-1H-pyrazolo[3,4-b]pyridin-1-yl}benzamide (12)

According to Example 1(6), a crude product of 2-(trans-4-hydroxycyclohexylamino)-4-{3-isopropyl-4-(1-methyl-1H-indol-5-yl)-1H-pyrazolo[3,4-b]pyridin-1-yl}benzonitrile was prepared using compound (12a) instead of compound (1e) and was used in the subsequent reaction without being purified. According to Example 1(7), compound (12) (the second stage yield: 58%) was prepared as a white solid using 2-(trans-4-hydroxycyclohexylamino)-4-{3-isopropyl-4-(1-methyl-1H-indol-5-yl)-1H-pyrazolo[3,4-b]pyridin-1-yl}benzonitrile instead of compound (1f).

$^1$H-NMR (DMSO-d$_6$) δ 8.62 (1H, d, J=4.63 Hz), 8.42 (1H, d, J=7.32 Hz), 7.91 (1H, d, J=1.77 Hz), 7.80 (1H, brs), 7.78 (1H, d, J=8.72 Hz), 7.75 (1H, d, J=1.40 Hz), 7.62 (1H, d, J=8.48 Hz), 7.49 (1H, dd, J=8.72, 1.77 Hz), 7.45 (1H, d, J=2.93 Hz), 7.35 (1H, dd, J=8.48, 1.40 Hz), 7.22 (1H, d, J=4.63 Hz), 7.12 (1H, brs), 6.55 (1H, d, J=2.93 Hz), 4.58 (1H, d, J=4.15 Hz), 3.88 (3H, s), 3.52 (1H, brs), 3.12 (1H, q, J=6.83 Hz), 2.13 (2H, d, J=11.5 Hz), 1.89 (2H, d, J=11.5 Hz), 1.41-1.22 (4H, m), 1.04 (6H, d, J=6.83 Hz); LRMS (ESI) m/z 523 [M+H]$^+$.

Example 13

2-(Trans-4-hydroxycyclohexylamino)-4-{3-isopropyl-4-(1H-pyrrolo[2,3-b]pyridin-5-yl)-1H-pyrazolo[3,4-b]pyridin-1-yl}benzamide (13)

Example 13(1)

2-Bromo-4-{3-isopropyl-4-{1-[(2-(trimethylsilyl)ethoxy)methyl]-1H-pyrrolo[2,3-b]pyridin-5-yl}-1H-pyrazolo[3,4-b]pyridin-1-yl}benzonitrile (13a)

According to Example 1(4), a crude product of 3-isopropyl-4-{1-{[2-(trimethylsilyl)ethoxy]methyl}-1H-pyrrolo[2,3-b]pyridin-5-yl}-1H-pyrazolo[3,4-b]pyridine was prepared using compound (6b) instead of compound (1c) and using 1-(2-trimethylsilylethoxymethyl)-1H-pyrrolo[2,3-b]pyridine 5-boronic acid pinacol ester instead of quinoline-3-boronic acid and was used in the subsequent reaction without being purified. According to Example 1(5), compound (13a) (the second stage yield: 58%) was prepared using 3-isopropyl-4-{1-{[2-(trimethylsilyl)ethoxy]methyl}-1H-pyrrolo[2,3-b]pyridin-5-yl}-1H-pyrazolo[3,4-b]pyridine instead of compound (1d).

$^1$H-NMR (DMSO-d$_6$) δ 9.09 (1H, d, J=1.95 Hz), 8.88 (1H, d, J=4.88 Hz), 8.76 (1H, dd, J=8.72, 1.95 Hz), 8.59 (1H, d, J=1.95 Hz), 8.37 (1H, d, J=1.95 Hz), 8.24 (1H, d, J=8.72 Hz), 7.90 (1H, d, J=3.54 Hz), 7.51 (1H, d, J=4.88 Hz), 6.79 (1H, d, J=3.54 Hz), 5.82 (2H, s), 3.67 (2H, t, J=7.99 Hz), 3.13 (1H, d, J=6.83 Hz), 1.15 (6H, d, J=6.83 Hz), 0.95 (2H, d, J=7.99 Hz), 0.00 (9H, s); LRMS (ESI) m/z 587 [M+H]$^+$.

Example 13(2)

2-(Trans-4-hydroxycyclohexylamino)-4-{3-isopropyl-4-{1-[(2-(trimethylsilyl)ethoxy)methyl]-1H-pyrrolo[2,3-b]pyridin-5-yl}-1H-pyrazolo[3,4-b]pyridin-1-yl}benzamide (13b)

According to Example 1(6), a crude product of 2-(trans-4-hydroxycyclohexylamino)-4-{3-isopropyl-4-{1-[(2-(trimethylsilyl)ethoxy)methyl]-1H-pyrrolo[2,3-b]pyridin-5-yl}-1H-pyrazolo[3,4-b]pyridin-1-yl}benzonitrile was prepared using compound (13a) instead of compound (1e) and was used in the subsequent reaction without being purified. According to Example 1(7), compound (13b) (the second stage yield: 55%) was prepared as a white solid using 2-(trans-4-hydroxycyclohexylamino)-4-{3-isopropyl-4-{1-[(2-(trimethylsilyl)ethoxy)methyl]-1H-pyrrolo[2,3-b]pyridin-5-yl}-1H-pyrazolo[3,4-b]pyridin-1-yl}benzonitrile instead of compound (1f).

$^1$H-NMR (DMSO-d$_6$) δ 8.78 (1H, d, J=4.63 Hz), 8.59 (1H, d, J=1.71 Hz), 8.52 (1H, d, J=7.07 Hz), 8.36 (1H, d, J=1.95 Hz), 7.98 (1H, s), 7.93 (1H, brs), 7.85-7.76 (2H, m), 7.58 (1H, dd, J=8.54, 1.71 Hz), 7.39 (1H, d, J=4.63 Hz), 7.22 (1H, brs), 6.78 (1H, d, J=3.66 Hz), 5.82 (2H, s), 4.68 (1H, d, J=4.15 Hz), 3.67 (2H, d, J=8.05 Hz), 3.61 (1H, brs), 3.11 (1H, q, J=6.83 Hz), 2.22 (2H, d, J=10.49 Hz), 1.99 (2H, d, J=10.49 Hz), 1.51-1.33 (4H, m), 1.14 (6H, d, J=6.83 Hz), 0.95 (2H, d, J=8.05 Hz), 0.00 (9H, s); LRMS (ESI) m/z 640 [M+H]$^+$.

Example 13(3)

2-(Trans-4-hydroxycyclohexylamino)-4-{3-isopropyl-4-(1H-pyrrolo[2,3-b]pyridin-5-yl)-1H-pyrazolo[3,4-b]pyridin-1-yl}benzamide (13)

Hydrochloric acid (a 6.0 M solution in water, 0.78 mL) was added to a solution of compound (13b) (0.100 g) in THF (0.78 mL), followed by stirring at 50° C. for 12 hr. The pH was adjusted to 10 with an aqueous sodium hydroxide solution, followed by extraction with ethyl acetate. The organic layer was washed with saturated saline. The organic layer after the washing was dried over anhydrous sodium sulfate, and then the solvent was distilled away. Chloroform and ether were added to the residue, and the precipitate was collected by filtration to obtain compound (13) (0.057 g, 71%) as a white solid.

$^1$H-NMR (DMSO-d$_6$) δ 11.9 (1H, s), 8.67 (1H, d, J=4.63 Hz), 8.44-8.41 (2H, m), 8.20 (1H, d, J=1.95 Hz), 7.90 (1H, d, J=2.20 Hz), 7.84 (1H, brs), 7.78 (1H, d, J=8.54 Hz), 7.62 (1H, d, J=3.18 Hz), 7.48 (1H, dd, J=8.54, 2.20 Hz), 7.29 (1H, d, J=4.63 Hz), 7.14 (1H, brs), 6.59 (1H, dd, J=3.18, 1.95 Hz), 4.59 (1H, d, J=4.39 Hz), 3.53 (1H, brs), 3.03 (1H, q, J=6.83 Hz), 2.12 (2H, d, J=10.9 Hz), 1.89 (2H, d, J=10.9 Hz), 1.42-1.22 (4H, m), 1.06 (6H, d, J=6.83 Hz); LRMS (ESI) m/z 510 [M+H]$^+$.

Example 14

2-(Trans-4-hydroxycyclohexylamino)-4-{3-isopropyl-4-(1-methyl-1H-pyrrolo[2,3-b]pyridin-5-yl)-1H-pyrazolo[3,4-b]pyridin-1-yl}benzamide (14)

Example 14(1)

2-Bromo-4-{3-isopropyl-4-(1-methyl-1H-pyrrolo[2,3-b]pyridin-5-yl)-1H-pyrazolo[3,4-b]pyridin-1-yl}benzonitrile (14a)

According to Example 1(4), a crude product of 3-isopropyl-4-(1-methyl-1H-pyrrolo[2,3-b]pyridin-5-yl)-1H-pyrazolo[3,4-b]pyridine was prepared using compound (6b) instead of compound (1c) and using 1-methyl-1H-pyrrolo[2,3-b]pyridine-5-boronic acid instead of quinoline-3-boronic acid and was used in the subsequent reaction without being purified. According to Example 1(5), compound (14a) (the second stage yield: 34%) was prepared using 3-isopropyl-4-(1-methyl-1H-pyrrolo[2,3-b]pyridin-5-yl)-1H-pyrazolo[3,4-b]pyridine instead of compound (1d).

$^1$H-NMR (DMSO-d$_6$) δ 9.00 (1H, d, J=1.22 Hz), 8.77 (1H, d, J=4.88 Hz), 8.66 (1H, dd, J=8.72, 1.40 Hz), 8.47 (1H, d, J=1.40 Hz), 8.24 (1H, d, J=1.22 Hz), 8.15 (1H, d, J=8.72 Hz), 7.68 (1H, d, J=3.30 Hz), 7.40 (1H, d, J=4.88 Hz), 6.61 (1H, d, J=3.30 Hz), 3.92 (3H, s), 3.04 (1H, q, J=6.58 Hz), 1.06 (1H, d, J=6.58 Hz); LRMS (ESI) m/z 471 [M+H]$^+$.

Example 14(2)

2-(Trans-4-hydroxycyclohexylamino)-4-{3-isopropyl-4-(1-methyl-1H-pyrrolo[2,3-b]pyridin-5-yl)-1H-pyrazolo[3,4-b]pyridin-1-yl}benzamide (14)

According to Example 1(6), a crude product of 2-(trans-4-hydroxycyclohexylamino)-4-(1-methyl-1H-pyrrolo[2,3-b]pyridin-5-yl)-1H-pyrazolo[3,4-b]pyridin-1-yl}benzonitrile was prepared using compound (14a) instead of compound (1e) and was used in the subsequent reaction without being purified. According to Example 1(7), compound (14) (the second stage yield: 30%) was prepared as a white solid using 2-(trans-4-hydroxycyclohexylamino)-4-(1-methyl-1H-pyrrolo[2,3-b]pyridin-5-yl)-1H-pyrazolo[3,4-b]pyridin-1-yl}benzonitrile instead of compound (1f).

$^1$H-NMR (DMSO-d$_6$) δ 8.66 (1H, d, J=4.63 Hz), 8.45 (1H, d, J=1.95 Hz), 8.41 (1H, d, J=7.07 Hz), 8.21 (1H, d, J=1.95 Hz), 7.87 (1H, d, J=1.71 Hz), 7.82 (1H, brs), 7.77 (1H, d, J=8.78 Hz), 7.65 (1H, d, J=3.42 Hz), 7.47 (1H, dd, J=8.78, 1.71 Hz), 7.27 (1H, d, J=4.63 Hz), 7.11 (1H, brs), 6.59 (1H, d, J=3.42 Hz), 4.59 (1H, d, J=3.90 Hz), 3.91 (3H, s), 3.50 (1H, brs), 3.01 (1H, q, J=6.83 Hz), 2.11 (2H, d, J=10.7 Hz), 1.88 (2H, d, J=10.7 Hz), 1.42-1.22 (4H, m), 1.04 (6H, d, J=6.83 Hz); LRMS (ESI) m/z 524 [M+H]$^+$.

Example 15

2-(Trans-4-hydroxycyclohexylamino)-4-{3-isopropyl-4-(1-methoxymethyl-1H-pyrrolo[2,3-b]pyridin-5-yl)-1H-pyrazolo[3,4-b]pyridin-1-yl}benzamide (15)

Example 15(1)

2-Bromo-4-{3-isopropyl-4-(1-methoxymethyl-1H-pyrrolo[2,3-b]pyridin-5-yl)-1H-pyrazolo[3,4-b]pyridin-1-yl}benzonitrile (15a)

According to Example 1(4), a crude product of 3-isopropyl-4-(1-methoxymethyl-1H-pyrrolo[2,3-b]pyridin-5-yl)-1H-pyrazolo[3,4-b]pyridine was prepared using compound (6b) instead of compound (1c) and using 1-methoxymethyl-1H-pyrrolo[2,3-b]pyridine-5-boronic acid instead of quinoline-3-boronic acid and was used in the subsequent reaction without being purified. According to Example 1(5), compound (15a) (the second stage yield: 40%) was prepared using 3-isopropyl-4-(1-methoxymethyl-1H-pyrrolo[2,3-b]pyridin-5-yl)-1H-pyrazolo[3,4-b]pyridine instead of compound (1d).

$^1$H-NMR (DMSO-d$_6$) δ 9.00 (1H, d, J=2.07 Hz), 8.78 (1H, d, J=4.82 Hz), 8.66 (1H, d, J=8.78 Hz), 8.50 (1H, d, J=2.07 Hz), 8.29 (1H, d, J=2.07 Hz), 8.15 (1H, d, J=8.78 Hz), 7.82 (1H, d, J=3.60 Hz), 7.43 (1H, d, J=4.82 Hz), 6.70 (1H, d, J=3.60 Hz), 5.69 (2H, s), 3.27 (3H, s), 3.03 (1H, q, J=6.83 Hz), 1.05 (1H, d, J=6.83 Hz); LRMS (ESI) m/z 501 [M+H]$^+$.

Example 15(2)

2-(Trans-4-hydroxycyclohexylamino)-4-{3-isopropyl-4-(1-methoxymethyl-1H-pyrrolo[2,3-b]pyridin-5-yl)-1H-pyrazolo[3,4-b]pyridin-1-yl}benzamide (15)

According to Example 1(6), a crude product of 2-(trans-4-hydroxycyclohexylamino)-4-{3-isopropyl-4-(1-methoxymethyl-1H-pyrrolo[2,3-b]pyridin-5-yl)-1H-pyrazolo[3,4-b]pyridin-1-yl}benzonitrile was prepared using compound (15a) instead of compound (1e) and was used in the subsequent reaction without being purified. According to Example 1(7), compound (15) (the second stage yield: 45%) was prepared as a white solid using 2-(trans-4-hydroxycyclohexylamino)-4-{3-isopropyl-4-(1-methoxymethyl-1H-pyrrolo[2,3-b]pyridin-5-yl)-1H-pyrazolo[3,4-b]pyridin-1-yl}benzonitrile instead of compound (1f).

$^1$H-NMR (DMSO-d$_6$) δ 8.67 (1H, d, J=4.63 Hz), 8.48 (1H, d, J=1.46 Hz), 8.41 (1H, d, J=6.83 Hz), 8.26 (1H, d, J=1.46 Hz), 7.87 (1H, s), 7.84-7.78 (3H, m), 7.47 (1H, dd, J=8.78, 1.22 Hz), 7.30 (1H, d, J=4.63 Hz), 7.12 (1H, brs), 6.68 (1H, d, J=3.66 Hz), 5.68 (2H, s), 4.59 (1H, d, J=2.93 Hz), 3.50 (1H, brs), 3.26 (3H, s), 3.00 (1H, q, J=6.83 Hz), 2.11 (2H, d, J=11.7 Hz), 1.88 (2H, d, J=10.9 Hz), 1.42-1.22 (4H, m), 1.03 (6H, d, J=6.83 Hz); LRMS (ESI) m/z 554 [M+H]$^+$.

Example 16

4-{4-(1-Benzyl-1H-pyrazol-4-yl)-3-isopropyl-1H-pyrazolo[3,4-b]pyridin-1-yl}-2-(trans-4-hydroxycyclohexylamino)benzamide (16)

Example 16(1)

4-{4-(1-Benzyl-1H-pyrazol-4-yl)-3-isopropyl-1H-pyrazolo[3,4-b]pyridin-1-yl}-2-bromo-benzonitrile (16a)

According to Example 1(4), a crude product of 4-(1-benzyl-1H-pyrazol-4-yl)-3-isopropyl-1H-pyrazolo[3,4-b]pyridine was prepared using compound (6b) instead of compound (1c) and using 1-benzyl-1H-pyrazol-4-yl-boronic acid pinacol ester instead of quinoline-3-boronic acid and was used in the subsequent reaction without being purified. According to Example 1(5), compound (16a) (the second stage yield: 52%) was prepared using 4-(1-benzyl-1H-pyrazol-4-yl)-3-isopropyl-1H-pyrazolo[3,4-b]pyridine instead of compound (1d).

$^1$H-NMR (DMSO-$d_6$) δ 8.94-8.98 (1H, m), 8.67 (1H, dd, J=4.9, 1.0 Hz), 8.58-8.65 (1H, m), 8.37 (1H, s), 8.11 (1H, dd, J=8.6, 1.2 Hz), 7.89 (1H, s), 7.28-7.44 (6H, m), 5.47 (2H, s), 3.35 (1H, q, J=6.8 Hz), 1.13 (6H, d, J=6.8 Hz); LRMS (ESI) m/z 497 [M+H]$^+$.

Example 16(2)

4-{4-(1-Benzyl-1H-pyrazol-4-yl)-3-isopropyl-1H-pyrazolo[3,4-b]pyridin-1-yl}-2-(trans-4-hydroxycyclohexylamino)benzonitrile (16b)

According to Example 1(6), compound (16b) (71%) was prepared using compound (16a) instead of compound (1e).

$^1$H-NMR (DMSO-$d_6$) δ 8.59 (1H, d, J=4.9 Hz), 8.35 (1H, s), 8.03 (1H, d, J=1.9 Hz), 7.88 (1H, s), 7.69 (1H, dd, J=8.6, 1.9 Hz), 7.62 (1H, d, J=8.6 Hz), 7.29-7.43 (5H, m), 7.25 (1H, d, J=4.9 Hz), 5.83 (1H, d, J=7.8 Hz), 5.47 (2H, s), 4.60 (1H, d, J=4.4 Hz), 3.30-3.52 (3H, m), 1.80-2.20 (4H, m), 1.20-1.50 (4H, m), 1.12 (6H, d, J=6.8 Hz); LRMS (ESI) m/z 532 [M+H]$^+$.

Example 16(3)

4-{4-(1-Benzyl-1H-pyrazol-4-yl)-3-isopropyl-1H-pyrazolo[3,4-b]pyridin-1-yl}-2-(trans-4-hydroxycyclohexylamino)benzamide (16)

According to Example 1(7), compound (16) (82%) was prepared as a white solid using compound (16b) instead of compound (1f).

$^1$H-NMR (DMSO-$d_6$) δ 8.57 (1H, d, J=4.6 Hz), 8.40 (1H, d, J=7.3 Hz), 8.34 (1H, s), 7.85-7.90 (2H, m), 7.80 (1H, brs), 7.76 (1H, d, J=8.8 Hz), 7.46 (1H, dd, J=8.8, 2.0 Hz), 7.28-7.43 (5H, m), 7.21 (1H, d, J=4.6 Hz), 7.12 (1H, brs), 5.47 (2H, s), 4.58 (1H, d, J=4.4 Hz), 3.30-3.60 (3H, m), 1.80-2.20 (4H, m), 1.20-1.45 (4H, m), 1.13 (6H, d, J=6.8 Hz); LRMS (ESI) m/z 550 [M+H]$^+$.

Example 17

2-(Trans-4-hydroxycyclohexylamino)-4-{3-isopropyl-4-(thiophen-3-yl)-1H-pyrazolo[3,4-b]pyridin-1-yl}benzamide (17)

Example 17(1)

2-Bromo-4-{3-isopropyl-4-(thiophen-3-yl)-1H-pyrazolo[3,4-b]pyridin-1-yl}benzonitrile (17a)

According to Example 1(4), a crude product of 3-isopropyl-4-(thiophen-3-yl)-1H-pyrazolo[3,4-b]pyridine was prepared using compound (6b) instead of compound (1c) and using thiophen-3-yl-boronic acid instead of quinoline-3-boronic acid and was used in the subsequent reaction without being purified. According to Example 1(5), compound (17a) (the second stage yield: 52%) was prepared using 3-isopropyl-4-(thiophen-3-yl)-1H-pyrazolo[3,4-b]pyridine instead of compound (1d).

$^1$H-NMR (DMSO-$d_6$) δ 8.97 (1H, s), 8.60-8.75 (2H, m), 7.78-8.17 (3H, m), 7.44 (1H, d, J=4.9 Hz), 7.35 (1H, d, J=4.9 Hz), 3.24 (1H, q, J=6.8 Hz), 1.13 (6H, d, J=6.8 Hz); LRMS (ESI) m/z 423 [M+H]$^+$.

Example 17(2)

2-(Trans-4-hydroxycyclohexylamino)-4-{3-isopropyl-4-(thiophen-3-yl)-1H-pyrazolo[3,4-b]pyridin-1-yl}benzonitrile (17b)

According to Example 1(6), compound (17b) (61%) was prepared using compound (17a) instead of compound (1e).

$^1$H-NMR (DMSO-$d_6$) 8.64 (1H, d, J=4.6 Hz), 8.02 (1H, d, J=2.0 Hz), 7.91 (1H, dd, J=3.0, 1.4 Hz), 7.80 (1H, dd, J=4.9, 3.0 Hz), 7.70 (1H, dd, J=8.6, 2.0 Hz), 7.62 (1H, d, J=8.6 Hz), 7.43 (1H, dd, J=4.9, 1.4 Hz), 7.28 (1H, d, J=4.6 Hz), 5.84 (1H, d, J=7.6 Hz), 4.61 (1H, d, J=4.4 Hz), 3.30-3.52 (2H, m), 3.22 (1H, q, J=6.8 Hz), 1.80-2.20 (4H, m), 1.20-1.50 (4H, m), 1.11 (6H, d, J=6.8 Hz); LRMS (ESI) m/z 458 [M+H]$^+$.

Example 17(3)

2-(Trans-4-hydroxycyclohexylamino)-4-{3-isopropyl-4-(thiophen-3-yl)-1H-pyrazolo[3,4-b]pyridin-1-yl}benzamide (17)

According to Example 1(7), compound (17) (89%) was prepared as a white solid using compound (17b) instead of compound (1f).

$^1$H-NMR (DMSO-$d_6$) 8.63 (1H, d, J=4.6 Hz), 8.41 (1H, d, J=7.3 Hz), 7.90 (1H, dd, J=3.0, 1.2 Hz), 7.86 (1H, d, J=2.2 Hz), 7.74-7.82 (3H, m), 7.46 (1H, dd, J=8.5, 2.2 Hz), 7.43 (1H, dd, J=4.9, 1.2 Hz), 7.24 (1H, d, J=4.6 Hz), 7.12 (1H, brs), 4.58 (1H, d, J=4.2 Hz), 3.30-3.60 (2H, m), 3.22 (1H, q, J=6.8 Hz), 1.80-2.20 (4H, m), 1.20-1.45 (4H, m), 1.12 (6H, d, J=6.8 Hz); LRMS (ESI) m/z 476 [M+H]$^+$.

Example 18

2-(Trans-4-hydroxycyclohexylamino)-4-{3-isopropyl-4-(6-methoxypyridin-3-yl)-1H-pyrazolo[3,4-b]pyridin-1-yl}benzamide (18)

Example 18(1)

2-Bromo-4-{3-isopropyl-4-(6-methoxypyridin-3-yl)-1H-pyrazolo[3,4-b]pyridin-1-yl}benzonitrile (18a)

According to Example 1(4), a crude product of 3-isopropyl-4-(6-methoxypyridin-3-yl)-1H-pyrazolo[3,4-b]pyridine was prepared using compound (6b) instead of compound (1c) and using 6-methoxypyridin-3-yl-boronic acid instead of quinoline-3-boronic acid and was used in the subsequent reaction without being purified. According to Example 1(5), compound (18a) (the second stage yield: 60%) was prepared using 3-isopropyl-4-(thiophen-3-yl)-1H-pyrazolo[3,4-b]pyridine instead of compound (1d).

$^1$H-NMR (DMSO-$d_6$) δ 8.97 (1H, d, J=1.7 Hz), 8.76 (1H, d, J=4.9 Hz), 8.63 (1H, dd, J=8.8, 1.7 Hz), 8.42 (1H, d, J=2.4 Hz), 8.13 (1H, d, J=8.8 Hz), 8.00 (1H, dd, J=8.8, 2.4 Hz), 7.36

(1H, d, J=4.9 Hz), 7.03 (1H, d, J=8.8 Hz), 3.96 (3H, s), 3.06 (1H, q, J=6.6 Hz), 1.12 (6H, d, J=6.6 Hz); LRMS (ESI) m/z 448 [M+H]$^+$.

Example 18(2)

2-(Trans-4-hydroxycyclohexylamino)-4-{3-isopropyl-4-(6-methoxypyridin-3-yl)-1H-pyrazolo[3,4-b]pyridin-1-yl}benzonitrile (18b)

According to Example 1(6), compound (18b) (77%) was prepared using compound (18a) instead of compound (1e).
$^1$H-NMR (DMSO-d$_6$) δ 8.68 (1H, d, J=4.6 Hz), 8.41 (1H, d, J=2.4 Hz), 7.95-8.05 (2H, m), 7.70 (1H, dd, J=8.7, 1.7 Hz), 7.63 (1H, d, J=8.7 Hz), 7.28 (1H, d, J=4.6 Hz), 7.03 (1H, d, J=8.5 Hz), 5.86 (1H, d, J=7.6 Hz), 4.61 (1H, d, J=4.4 Hz), 3.96 (3H, s), 3.30-3.52 (2H, m), 3.03 (1H, q, J=6.8 Hz), 1.80-2.20 (4H, m), 1.20-1.50 (4H, m), 1.11 (6H, d, J=6.8 Hz); LRMS (ESI) m/z 483 [M+H]$^+$.

Example 18(3)

2-(Trans-4-hydroxycyclohexylamino)-4-{3-isopropyl-4-(6-methoxypyridin-3-yl)-1H-pyrazolo[3,4-b]pyridin-1-yl}benzamide (18)

According to Example 1(7), compound (18) (63%) was prepared as a white solid using compound (18b) instead of compound (1f).
$^1$H-NMR (DMSO-d$_6$) δ 8.67 (1H, d, J=4.6 Hz), 8.37-8.45 (2H, m), 7.99 (1H, dd, J=8.8, 2.4 Hz), 7.85 (1H, d, J=1.7 Hz), 7.82 (1H, brs), 7.78 (1H, d, J=8.8 Hz), 7.46 (1H, dd, J=8.6, 1.7 Hz), 7.25 (1H, d, J=4.6 Hz), 7.13 (1H, brs), 7.03 (1H, d, J=8.6 Hz), 4.59 (1H, d, J=4.4 Hz), 3.96 (3H, s), 3.30-3.60 (2H, m), 3.03 (1H, q, J=6.8 Hz), 1.80-2.20 (4H, m), 1.20-1.45 (4H, m), 1.12 (6H, d, J=6.8 Hz); LRMS (ESI) m/z 501 [M+H]$^+$.

Example 19

2-(Trans-4-hydroxycyclohexylamino)-4-{3-isopropyl-4-(5,6,7,8-tetrahydroquinolin-3-yl)-1H-pyrazolo[3,4-b]pyridin-1-yl}benzamide (19)

According to Example 1(4), a crude product of 3-isopropyl-4-(5,6,7,8-tetrahydroquinolin-3-yl)-1H-pyrazolo[3,4-b]pyridine was prepared using compound (6b) instead of compound (1c) and using 5,6,7,8-tetrahydroquinolin-3-ylboronic acid instead of quinoline-3-boronic acid and was used in the subsequent reaction without being purified. According to Example 1(5), a crude product of 2-bromo-4-{3-isopropyl-4-(5,6,7,8-tetrahydroquinolin-3-yl)-1H-pyrazolo[3,4-b]pyridin-1-yl}benzonitrile was prepared using 3-isopropyl-4-(5,6,7,8-tetrahydroquinolin-3-yl)-1H-pyrazolo[3,4-b]pyridine instead of compound (1d) and was used in the subsequent reaction without being purified. According to Example 1(6), a crude product of 2-(trans-4-hydroxycyclohexylamino)-4-{3-isopropyl-4-(5,6,7,8-tetrahydroquinolin-3-yl)-1H-pyrazolo[3,4-b]pyridin-1-yl}benzonitrile was prepared using 2-bromo-4-{3-isopropyl-4-(5,6,7,8-tetrahydroquinolin-3-yl)-1H-pyrazolo[3,4-b]pyridin-1-yl}benzonitrile instead of compound (1e) and was used in the subsequent reaction without being purified. According to Example 1(7), compound (19) (the fourth stage yield: 2%) was prepared as a white solid using 2-(trans-4-hydroxycyclohexylamino)-4-{3-isopropyl-4-(5,6,7,8-tetrahydroquinolin-3-yl)-1H-pyrazolo[3,4-b]pyridin-1-yl}benzonitrile instead of compound (1f).

$^1$H-NMR (DMSO-d$_6$) δ 8.67 (1H, d, J=4.6 Hz), 8.50 (1H, s), 8.42 (1H, d, J=7.1 Hz), 7.86 (1H, d, J=1.9 Hz), 7.84 (1H, brs), 7.78 (1H, d, J=8.8 Hz), 7.73 (1H, s), 7.46 (1H, dd, J=8.8, 1.9 Hz), 7.25 (1H, d, J=4.6 Hz), 7.14 (1H, brs), 4.60 (1H, d, J=4.2 Hz), 3.30-3.60 (2H, m), 3.01 (1H, q, J=6.8 Hz), 2.82-2.95 (4H, m), 1.80-2.20 (8H, m), 1.20-1.45 (4H, m), 1.13 (6H, d, J=6.8 Hz); LRMS (ESI) m/z 525 [M+H]$^+$.

Example 20

2-(Benzylamino)-4-{3-isopropyl-4-(quinolin-3-yl)-1H-pyrazolo[3,4-b]pyridin-1-yl}benzamide (20)

According to Example 1(6), 2-(benzylamino)-4-{3-isopropyl-4-(quinolin-3-yl)-1H-pyrazolo[3,4-b]pyridin-1-yl}benzonitrile was prepared using compound (6d) instead of compound (1e) and using benzylamine instead of trans-aminocyclohexanol and was used in the subsequent reaction without being purified. According to Example 1(7), compound (20) (the second stage yield: 22%) was prepared as a white solid using 2-(benzylamino)-4-{3-isopropyl-4-(quinolin-3-yl)-1H-pyrazolo[3,4-b]pyridin-1-yl}benzonitrile instead of (1f).
$^1$H-NMR (DMSO-d$_6$) δ 9.07 (1H, d, J=2.2 Hz), 8.91 (1H, t, J=5.8 Hz), 8.68 (1H, d, J=4.9 Hz), 8.61 (1H, d, J=2.2 Hz), 8.09 (2H, t, J=9.2 Hz), 7.87-7.66 (4H, m), 7.57 (1H, dd, J=1.9, 6.8 Hz), 7.42-7.26 (5H, m), 7.18 (1H, t, J=7.2 Hz), 4.44 (1H, d, J=5.7 Hz), 2.95-2.82 (1H, m), 0.97 (6H, d, J=6.8 Hz); LRMS (ESI) m/z 513 [M+H]$^+$.

Example 21

4-{3-Isopropyl-4-(quinolin-3-yl)-1H-pyrazolo[3,4-b]pyridin-1-yl}-2-(pyridin-2-ylamino)benzamide (21)

According to Example 1(6), 4-{3-isopropyl-4-(quinolin-3-yl)-1H-pyrazolo[3,4-b]pyridin-1-yl}-2-(pyridin-2-ylamino)benzonitrile was prepared using compound (6d) instead of compound (1e) and using 2-aminopyridine instead of trans-aminocyclohexanol and was used in the subsequent reaction without being purified. According to Example 1(7), compound (21) (the second stage yield: 14%) was prepared as a white solid using 4-{3-isopropyl-4-(quinolin-3-yl)-1H-pyrazolo[3,4-b]pyridin-1-yl}-2-(pyridin-2-ylamino)benzonitrile instead of compound (1f).
$^1$H-NMR (DMSO-d$_6$) δ 9.68 (1H, s), 9.16 (1H, d, J=2.4 Hz), 8.79 (1H, d, J=4.6 Hz), 8.71 (1H, s), 8.26-8.24 (2H, m), 8.16 (2H, t, J=8.4 Hz), 7.97 (2H, s), 7.94-7.97 (1H, m), 7.77-7.67 (2H, m), 7.44 (1H, d, J=4.6 Hz), 6.92-6.88 (1H, m), 2.99 (1H, q, J=6.8 Hz), 1.07 (6H, d, J=6.8 Hz); LRMS (ESI) m/z 500 [M+H]$^+$.

Example 22

4-{3-Isopropyl-4-(quinolin-3-yl)-1H-pyrazolo[3,4-b]pyridin-1-yl}-2-{2-(pyrrolidin-1-yl)ethylamino}benzamide (22)

According to Example 1(6), 4-{3-isopropyl-4-(quinolin-3-yl)-1H-pyrazolo[3,4-b]pyridin-1-yl}-2-{2-(pyrrolidin-1-yl)ethylamino}benzonitrile was prepared using compound (6d) instead of compound (1e) and using N-(2-aminoethyl)pyrrolidine instead of trans-aminocyclohexanol and was used in the subsequent reaction without being purified. According to Example 1(7), (22) (the second stage yield: 61%) was prepared as a white solid using 4-{3-isopropyl-4-(quinolin-3- yl)-1H-pyrazolo[3,4-b]pyridin-1-yl}-2-{2-(pyrrolidin-1-yl) ethylamino}benzonitrile instead of compound (1f).

¹H-NMR (DMSO-d₆) δ 9.14 (1H, d, J=1.9 Hz), 8.76 (1H, d, J=4.6 Hz), 8.69 (1H, d, J=1.6 Hz), 8.52 (1H, t, J=5.1 Hz), 8.15 (1H, t, J=8.6 Hz), 7.93-7.87 (1H, m), 7.81-7.72 (3H, m), 7.56 (1H, dd, J=1.9, 6.5 Hz), 7.42 (1H, d, J=4.6 Hz), 2.96 (1H, g, J=6.8 Hz), 2.80-2.70 (2H, m), 2.55-2.49 (6H, m), 1.74-1.68 (4H, m), 1.06 (6H, d, J=6.8 Hz); LRMS (ESI) m/z 520 [M+H]⁺.

Example 23

4-{3-Isopropyl-4-(quinolin-3-yl)-1H-pyrazolo[3,4-b]pyridin-1-yl}-2-{3-(methylthio)propylamino}benzamide (23)

According to Example 1(6), 4-{3-isopropyl-4-(quinolin-3-yl)-1H-pyrazolo[3,4-b]pyridin-1-yl}-2-{3-(methylthio)propylamino}benzonitrile was prepared using compound (6d) instead of compound (1e) and using 3-methylthiopropylamine instead of trans-aminocyclohexanol and was used in the subsequent reaction without being purified. According to Example 1(7), (23) (the second stage yield: 67%) was prepared as a white solid using 4-{3-isopropyl-4-(quinolin-3-yl)-1H-pyrazolo[3,4-b]pyridin-1-yl}-2-{3-(methylthio)propylamino}benzonitrile instead of compound (1f).

¹H-NMR (DMSO-d₆) δ 9.07 (1H, d, J=2.4 Hz), 8.69 (1H, d, J=4.6 Hz), 8.61 (1H, d, J=1.9 Hz), 8.48 (1H, t, J=5.4 Hz), 8.09 (2H, t, J=9.2 Hz), 7.86-7.76 (3H, m), 7.70-7.65 (1H, m), 7.51 (1H, dd, J=1.9, 7.0 Hz), 7.34 (1H, d, J=4.6 Hz), 2.95-2.85 (1H, m), 2.58-2.45 (4H, m), 2.02 (3H, s), 1.93-1.83 (2H, m), 1.00 (6H, d, J=6.8 Hz); LRMS (ESI) m/z 511 [M+H]⁺.

Example 24

4-{3-Isopropyl-4-(quinolin-3-yl)-1H-pyrazolo[3,4-b]pyridin-1-yl}-2-(1-methylpiperidin-4-ylamino)benzamide (24)

According to Example 1(6), 4-{3-isopropyl-4-(quinolin-3-yl)-1H-pyrazolo[3,4-b]pyridin-1-yl}-2-(1-methylpiperidin-4-ylamino)benzonitrile was prepared using compound (6d) instead of (1e) and using 4-amino-1-methylpiperidine instead of trans-aminocyclohexanol and was used in the subsequent reaction without being purified. According to Example 1(7), compound (24) (the second stage yield: 40%) was prepared as a white solid using 4-{3-isopropyl-4-(quinolin-3-yl)-1H-pyrazolo[3,4-b]pyridin-1-yl}-2-(1-methylpiperidin-4-ylamino)benzonitrile instead of compound (1f).

¹H-NMR (DMSO-d₆) δ 9.12 (1H, d, J=2.2 Hz), 8.73 (1H, d, J=4.6 Hz), 8.67 (1H, d, J=2.2 Hz), 8.51 (1H, d, J=7.3 Hz), 8.13 (2H, t, J=8.9 Hz), 7.91-7.70 (4H, m), 7.46 (1H, dd, J=1.9, 6.8 Hz), 7.40 (1H, d, J=4.6 Hz), 2.94 (1H, g, J=6.8 Hz), 2.71-2.67 (2H, m), 2.18-2.02 (8H, m), 1.54-1.47 (2H, m), 1.03 (6H, d, J=6.8 Hz); LRMS (ESI) m/z 520 [M+H]⁺.

Example 25

4-{3-Isopropyl-4-(quinolin-3-yl)-1H-pyrazolo[3,4-b]pyridin-1-yl}-2-(neopentylamino)benzamide (25)

According to Example 1(6), 4-{3-isopropyl-4-(quinolin-3-yl)-1H-pyrazolo[3,4-b]pyridin-1-yl}-2-(neopentylamino)benzonitrile was prepared using compound (6d) instead of compound (1e) and using neopentylamine instead of trans-aminocyclohexanol and was used in the subsequent reaction without being purified. According to Example 1(7), compound (25) (the second stage yield: 60%) was prepared as a white solid using 4-{3-isopropyl-4-(quinolin-3-yl)-1H-pyrazolo[3,4-b]pyridin-1-yl}-2-(neopentylamino)benzonitrile instead of compound (1f).

¹H-NMR (DMSO-d₆) δ 9.12 (1H, d, J=2.4 Hz), 8.75 (1H, d, J=4.9 Hz), 8.67 (1H, d, J=2.2 Hz), 8.13 (2H, t, J=8.6 Hz), 7.91-7.70 (4H, m), 7.49 (1H, dd, J=1.9, 6.8 Hz), 7.40 (1H, d, J=4.9 Hz), 3.01-2.89 (3H, m), 1.06-1.01 (15H, m); LRMS (ESI) m/z 493 [M+H]⁺.

Example 26

4-{3-Isopropyl-4-(quinolin-3-yl)-1H-pyrazolo[3,4-b]pyridin-1-yl}-2-{3-(methylthio)phenylamino}benzamide (26)

According to Example 1(6), 4-{3-isopropyl-4-(quinolin-3-yl)-1H-pyrazolo[3,4-b]pyridin-1-yl}-2-{3-(methylthio)phenylamino}benzonitrile was prepared using compound (6d) instead of compound (1e) and using 3-(methylthio)aniline instead of trans-aminocyclohexanol and was used in the subsequent reaction without being purified. According to Example 1(7), (26) (the second stage yield: 61%) was prepared as a white solid using 4-{3-isopropyl-4-(quinolin-3-yl)-1H-pyrazolo[3,4-b]pyridin-1-yl}-2-{3-(methylthio)phenylamino}benzonitrile instead of compound (1f).

¹H-NMR (DMSO-d₆) δ 9.11 (1H, d, J=2.2 Hz), 8.75 (1H, d, J=4.9 Hz), 8.67 (1H, d, J=2.2 Hz), 8.60 (1H, d, J=1.9 Hz), 7.91-7.70 (4H, m), 7.49 (1H, dd, J=1.9, 6.8 Hz), 8.13 (1H, t, J=8.6 Hz), 7.94-7.85 (2H, m), 7.79-7.70 (2H, m), 7.42 (1H, d, J=4.9 Hz), 7.32-7.25 (2H, m), 7.01 (1H, d, J=7.3 Hz), 6.90 (1H, d, J=7.3 Hz), 2.93 (1H, g, J=6.8 Hz), 1.02 (6H, d, J=6.8 Hz); LRMS (ESI) m/z 545 [M+H]⁺.

Example 27

2-{2-(Dimethylamino)ethylamino}-4-{3-isopropyl-4-(quinolin-3-yl)-1H-pyrazolo[3,4-b]pyridin-1-yl}benzamide (27)

According to Example 1(6), 2-{2-(dimethylamino)ethylamino}-4-{3-isopropyl-4-(quinolin-3-yl)-1H-pyrazolo[3,4-b]pyridin-1-yl}benzonitrile was prepared using compound (6d) instead of (1e) and using N,N-dimethylethylenediamine instead of trans-aminocyclohexanol and was used in the subsequent reaction without being purified. According to Example 1(7), compound (27) (the second stage yield: 57%) was prepared as a white solid using 2-{2-(dimethylamino)ethylamino}-4-{3-isopropyl-4-(quinolin-3-yl)-1H-pyrazolo[3,4-b]pyridin-1-yl}benzonitrile instead of compound (1f).

¹H-NMR (DMSO-d₆) δ 9.14 (1H, d, J=2.4 Hz), 8.76 (1H, d, J=4.6 Hz), 8.69 (1H, d, J=2.4 Hz), 8.46 (1H, t, J=5.1 Hz), 8.15 (1H, t, J=8.3 Hz), 7.93-7.87 (1H, m), 7.83-7.71 (3H, m), 7.56 (1H, dd, J=2.4, 8.4 Hz), 7.42 (1H, d, J=4.9 Hz), 2.96 (1H, g, J=6.8 Hz), 2.58-2.49 (4H, m), 2.24 (6H, s), 1.06 (6H, d, J=6.8 Hz); LRMS (ESI) m/z 494 [M+H]⁺.

Example 28

4-{3-Isopropyl-4-(quinolin-3-yl)-1H-pyrazolo[3,4-b]pyridin-1-yl}-2-{2-(pyridin-2-yl)ethylamino}benzamide (28)

According to Example 1(6), 4-{3-isopropyl-4-(quinolin-3-yl)-1H-pyrazolo[3,4-b]pyridin-1-yl}-2-{2-(pyridin-2-yl)ethylamino}benzonitrile was prepared using compound (6d) instead of compound (1e) and using 3-(2-aminoethyl)pyridine instead of trans-aminocyclohexanol and was used in the subsequent reaction without being purified. According to Example 1(7), (28) (the second stage yield: 67%) was prepared as a white solid using 4-{3-isopropyl-4-(quinolin-3-yl)-1H-pyrazolo[3,4-b]pyridin-1-yl}-2-{2-(pyridin-2-yl)ethylamino}benzonitrile instead of compound (1f).

$^1$H-NMR (DMSO-d$_6$) δ 9.15 (1H, d, J=2.2 Hz), 8.78 (1H, d, J=4.9 Hz), 8.69-8.61 (3H, m), 8.45 (1H, dd, J=1.6, 3.2 Hz), 8.16 (1H, t, J=8.1 Hz), 7.95-7.72 (6H, m), 7.56 (1H, dd, J=1.9, 6.8 Hz), 7.44 (1H, d, J=4.9 Hz), 7.38-7.34 (1H, m), 3.55-3.47 (2H, m), 3.03-2.92 (3H, m), 1.07 (6H, d, J=6.8 Hz); LRMS (ESI) m/z 528 [M+H]$^+$.

Example 29

2-{3-(Dimethylamino)propylamino}-4-{3-isopropyl-4-(quinolin-3-yl)-1H-pyrazolo[3,4-b]pyridin-1-yl}benzamide (29)

According to Example 1(6), 2-{3-(dimethylamino)propylamino}-4-{3-isopropyl-4-(quinolin-3-yl)-1H-pyrazolo[3,4-b]pyridin-1-yl}benzonitrile was prepared using compound (6d) instead of (1e) and using N,N-dimethyl-1,3-propanediamine instead of trans-aminocyclohexanol and was used in the subsequent reaction without being purified. According to Example 1(7), compound (29) (the second stage yield: 14%) was prepared as a white solid using 2-{3-(dimethylamino)propylamino}-4-{3-isopropyl-4-(quinolin-3-yl)-1H-pyrazolo[3,4-b]pyridin-1-yl}benzonitrile instead of compound (1f).

$^1$H-NMR (DMSO-d$_6$) δ 9.12 (1H, d, J=2.2 Hz), 8.75 (1H, d, J=4.9 Hz), 8.67 (1H, d, J=2.2 Hz), 8.50-8.46 (1H, m), 8.14 (1H, t, J=8.4 Hz), 7.91-7.70 (4H, m), 7.52 (1H, dd, J=1.9, 6.8 Hz), 7.41 (1H, d, J=4.9 Hz), 2.94 (1H, q, J=6.8 Hz), 2.80-2.66 (1H, m), 2.50-2.44 (8H, m), 1.97-1.88 (2H, m), 1.04 (6H, d, J=6.8 Hz); LRMS (ESI) m/z 508 [M+H]$^+$.

Example 30

2-(Cyclohexylmethylamino)-4-{3-isopropyl-4-(quinolin-3-yl)-1H-pyrazolo[3,4-b]pyridin-1-yl}benzamide (30)

According to Example 1(6), 2-(cyclohexylmethylamino)-4-{3-isopropyl-4-(quinolin-3-yl)-1H-pyrazolo[3,4-b]pyridin-1-yl}benzonitrile was prepared using compound (6d) instead of (1e) and using aminomethylcyclohexane instead of trans-aminocyclohexanol and was used in the subsequent reaction without being purified. According to Example 1(7), compound (30) (the second stage yield: 56%) was prepared as a white solid using 2-(cyclohexylmethylamino)-4-{3-isopropyl-4-(quinolin-3-yl)-1H-pyrazolo[3,4-b]pyridin-1-yl}benzonitrile instead of compound (1f).

$^1$H-NMR (CDCl$_3$) δ 9.07 (1H, d, J=2.2 Hz), 8.67 (1H, d, J=4.9 Hz), 8.30 (1H, d, J=1.9 Hz), 8.24 (1H, d, J=8.1 Hz), 7.94 (1H, d, J=8.1 Hz), 7.86-7.82 (2H, m), 7.71-7.60 (2H, m), 7.16 (1H, d, J=4.9 Hz), 3.16 (2H, t, J=5.9 Hz), 2.97 (1H, q, J=7.0 Hz), 1.95-1.90 (2H, m), 1.79-1.71 (5H, m), 1.32-1.01 (11H, m); LRMS (ESI) m/z 519 [M+H]$^+$.

Example 31

4-{3-Isopropyl-4-(quinolin-3-yl)-1H-pyrazolo[3,4-b]pyridin-1-yl}-2-(2-morpholinoethylamino)benzamide (31)

According to Example 1(6), 4-{3-isopropyl-4-(quinolin-3-yl)-1H-pyrazolo[3,4-b]pyridin-1-yl}-2-(2-morpholinoethylamino)benzonitrile was prepared using compound (6d) instead of compound (1e) and using 2-morpholinoethylamine instead of trans-aminocyclohexanol and was used in the subsequent reaction without being purified. According to Example 1(7), compound (31) (the second stage yield: 43%) was prepared as a white solid using 4-{3-isopropyl-4-(quinolin-3-yl)-1H-pyrazolo[3,4-b]pyridin-1-yl}-2-(2-morpholinoethylamino)benzonitrile instead of compound (1f).

$^1$H-NMR (CDCl$_3$) δ 9.06 (1H, d, J=1.9 Hz), 8.67 (1H, d, J=4.9 Hz), 8.30 (1H, s), 8.24 (1H, d, J=8.4 Hz), 7.96-7.91 (2H, m), 7.89-7.83 (2H, m), 7.72-7.65 (1H, m), 7.54 (1H, d, J=4.9 Hz), 7.18 (1H, d, J=1.9 Hz), 3.43-3.40 (2H, m), 2.96 (1H, q, J=6.8 Hz), 2.76 (2H, t, J=5.9 Hz), 2.57-2.54 (4H, m), 1.14 (6H, d, J=6.8 Hz); LRMS (ESI) m/z 536 [M+H]$^+$.

Example 32

4-{3-Isopropyl-4-(quinolin-3-yl)-1H-pyrazolo[3,4-b]pyridin-1-yl}-2-(isoxazol-3-ylamino)benzamide (32)

According to Example 1(6), 4-{3-isopropyl-4-(quinolin-3-yl)-1H-pyrazolo[3,4-b]pyridin-1-yl}-2-(isoxazol-3-ylamino)benzonitrile was prepared using compound (6d) instead of compound (1e) and using 3-aminoisoxazole instead of trans-aminocyclohexanol and was used in the subsequent reaction without being purified. According to Example 1(7), compound (32) (the second stage yield: 40%) was prepared as a white solid using 4-{3-isopropyl-4-(quinolin-3-yl)-1H-pyrazolo[3,4-b]pyridin-1-yl}-2-(isoxazol-3-ylamino)benzonitrile instead of compound (1f).

$^1$H-NMR (DMSO-d$_6$) δ 9.14-9.13 (2H, m), 8.77 (1H, d, J=4.9 Hz), 8.73-8.69 (2H, m), 8.14 (2H, t, J=8.6 Hz), 8.02 (2H, s), 7.92-7.85 (1H, m), 7.75-7.70 (1H, m), 7.43 (1H, d, J=4.9 Hz), 6.57 (1H, s), 2.97 (1H, q, J=6.5 Hz), 1.06 (6H, d, J=6.5 Hz); LRMS (ESI) m/z 490 [M+H]$^+$.

Example 33

4-{3-Isopropyl-4-(quinolin-3-yl)-1H-pyrazolo[3,4-b]pyridin-1-yl}-2-(4-morpholinophenylamino)benzamide (33)

According to Example 1(6), 4-{3-isopropyl-4-(quinolin-3-yl)-1H-pyrazolo[3,4-b]pyridin-1-yl}-2-(4-morpholinophenylamino)benzonitrile was prepared using compound (6d) instead of compound (1e) and using 4-morpholinoaniline instead of trans-aminocyclohexanol and was used in the subsequent reaction without being purified. According to Example 1(7), compound (33) (the second stage yield: 11%) was prepared as a white solid using 4-{3-isopropyl-4-(quinolin-3-yl)-1H-pyrazolo[3,4-b]pyridin-1-yl}-2-(4-morpholinophenylamino)benzonitrile instead of compound (1f).

$^1$H-NMR (DMSO-d$_6$) δ 9.10 (1H, s), 8.72 (1H, d, J=4.6 Hz), 8.66 (1H, s), 8.28 (1H, d, J=2.2 Hz), 8.13 (2H, t, J=8.6 Hz), 7.88 (1H, t, J=8.6 Hz), 7.72 (1H, t, J=7.6 Hz), 7.63 (1H, dd, J=2.2, 6.5 Hz), 7.40-7.39 (2H, m), 7.22 (2H, d, J=8.6 Hz), 7.01-6.98 (2H, m), 3.75-3.72 (4H, m), 3.09-3.05 (4H, m), 2.98-2.87 (1H, m), 1.00 (6H, d, J=6.8 Hz); LRMS (ESI) m/z 584 [M+H]$^+$.

Example 34

4-{3-Isopropyl-4-(quinolin-3-yl)-1H-pyrazolo[3,4-b]pyridin-1-yl}-2-{4-(pyrrolidine-1-carbonyl)phenylamino}benzamide (34)

According to Example 1(6), 4-{3-isopropyl-4-(quinolin-3-yl)-1H-pyrazolo[3,4-b]pyridin-1-yl}-2-{4-(pyrrolidine-1-carbonyl)phenylamino}benzonitrile was prepared using compound (6d) instead of compound (1e) and using (4-aminophenyl)(pyrrolidin-1-yl)methanone instead of trans-aminocyclohexanol and was used in the subsequent reaction without being purified. According to Example 1(7), compound (34) (the second stage yield: 59%) was prepared as a white solid using 4-{3-isopropyl-4-(quinolin-3-yl)-1H-pyrazolo[3,4-b]pyridin-1-yl}-2-{4-(pyrrolidine-1-carbonyl)phenylamino}benzonitrile instead of compound (1f).

$^1$H-NMR (DMSO-d$_6$) δ 9.12 (1H, d, J=1.9 Hz), 8.76 (1H, d, J=4.6 Hz), 8.64 (2H, dd, J=1.9, 11.9 Hz), 8.13 (2H, t, J=4.6 Hz), 7.96-7.69 (4H, m), 7.55 (2H, d, J=8.6 Hz), 7.42 (1H, d, J=4.6 Hz), 7.35 (2H, d, J=8.6 Hz), 2.99-2.89 (1H, m), 2.52-2.48 (4H, m), 1.92-1.72 (4H, m), 1.01 (6H, d, J=6.8 Hz); LRMS (ESI) m/z 596 [M+H]$^+$.

Example 35

4-{3-Isopropyl-4-(quinolin-3-yl)-1H-pyrazolo[3,4-b]pyridin-1-yl}-2-{4-(pyrrolidin-1-ylmethyl)phenylamino}benzamide (35)

According to Example 1(6), 4-{3-isopropyl-4-(quinolin-3-yl)-1H-pyrazolo[3,4-b]pyridin-1-yl}-2-{4-(pyrrolidin-1-ylmethyl)phenylamino}benzonitrile was prepared using compound (6d) instead of compound (1e) and using 4-(pyrrolidin-1-ylmethyl)aniline instead of trans-aminocyclohexanol and was used in the subsequent reaction without being purified. According to Example 1(7), compound (35) (the second stage yield: 53%) was prepared as a white solid using 4-{3-isopropyl-4-(quinolin-3-yl)-1H-pyrazolo[3,4-b]pyridin-1-yl}-2-{4-(pyrrolidin-1-ylmethyl)phenylamino}benzonitrile instead of compound (1f).

$^1$H-NMR (DMSO-d$_6$) δ 9.02 (1H, d, J=2.2 Hz), 8.63 (1H, d, J=10.8 Hz), 8.47-8.39 (1H, m), 8.12-8.01 (2H, m), 7.92-7.64 (3H, m), 7.55-7.45 (2H, m), 7.26-7.12 (5H, m), 3.62 (2H, s), 2.78-2.68 (1H, m), 2.40-2.23 (4H, m), 1.72-1.50 (4H, m), 0.92 (6H, d, J=6.5 Hz); LRMS (ESI) m/z 582 [M+H]$^+$.

Example 36

4-{4-(1H-Imidazol-1-yl)-3-isopropyl-1H-pyrazolo[3,4-b]pyridin-1-yl}-2-(trans-4-hydroxycyclohexylamino)benzamide (36)

Example 36(1)

2-Bromo-4-{4-chloro-3-isopropyl-1H-pyrazolo[3,4-b]pyridin-1-yl}benzonitrile (36a)

According to Example 1(5), compound (36a) (93%) was prepared as a white solid using compound (6b) instead of compound (1d).

$^1$H-NMR (DMSO-d$_6$) δ 8.87 (1H, d, J=2.2 Hz), 8.67 (1H, d, J=5.1 Hz), 8.55 (1H, dd, J=8.6, 2.2 Hz), 8.13 (1H, d, J=8.6 Hz), 7.59 (1H, d, J=5.1 Hz), 3.73 (1H, q, J=6.8 Hz), 1.45 (6H, d, J=6.8 Hz); LRMS (ESI) m/z 375 [M+H]$^+$.

Example 36(2)

4-{4-(1H-Imidazol-1-yl)-3-isopropyl-1H-pyrazolo[3,4-b]pyridin-1-yl}-2-bromo-benzonitrile (36b)

A solution of compound (36a) (0.196 g), potassium carbonate (0.145 g), copper(II) oxide (nanopowder) (0.021 g), and imidazole (0.042 g) in DMF (2.0 mL) was stirred at 120° C. for 20 hr. The reaction solution was diluted with chloroform, and insoluble matters were filtered through celite. The solvent was distilled away, and ethyl acetate and ether were added to the residue. The precipitate was collected by filtration to obtain compound (36b) (0.173 g, 81%) as a white solid.

$^1$H-NMR (DMSO-d$_6$) δ 8.93 (1H, d, J=2.0 Hz), 8.87 (1H, d, J=4.9 Hz), 8.60 (1H, dd, J=8.6, 2.0 Hz), 8.22 (1H, s), 8.15 (1H, d, J=8.6 Hz), 7.78 (1H, s), 7.53 (1H, d, J=4.9 Hz), 7.26 (1H, s), 3.12 (1H, q, J=6.8 Hz), 1.11 (6H, d, J=6.8 Hz); LRMS (ESI) m/z 407 [M+H]$^+$.

Example 36(3)

4-{4-(1H-Imidazol-1-yl)-3-isopropyl-1H-pyrazolo[3,4-b]pyridin-1-yl}-2-(trans-4-hydroxycyclohexylamino)benzamide (36)

According to Examples 1(6) and 1(7), compound (36) (the second stage yield: 27%) was prepared as a white solid using (36b) instead of compound (1e).

$^1$H-NMR (DMSO-d$_6$) δ 8.76 (1H, d, J=4.9 Hz), 8.41 (1H, d, J=4.9 Hz), 8.21 (1H, s), 7.85 (1H, brs), 7.75-7.82 (3H, m), 7.39-7.45 (2H, m), 7.25 (1H, s), 7.15 (1H, brs), 4.60 (1H, d, J=4.4 Hz), 3.30-3.60 (2H, m), 3.10 (1H, q, J=6.8 Hz), 1.80-2.20 (4H, m), 1.20-1.45 (4H, m), 1.10 (6H, d, J=6.8 Hz); LRMS (ESI) m/z 460 [M+H]$^+$.

Example 37

2-(Trans-4-hydroxycyclohexylamino)-4-{3-isopropyl-4-(4-phenyl-1H-imidazol-1-yl)-1H-pyrazolo[3,4-b]pyridin-1-yl}benzamide (37)

Example 37(1)

2-Bromo-4-{3-isopropyl-4-(4-phenyl-1H-imidazol-1-yl)-1H-pyrazolo[3,4-b]pyridin-1-yl}benzonitrile (37a)

According to Example 36(2), compound (37a) (72%) was prepared as a white solid using 4-phenyl-1H-imidazole instead of imidazole.

$^1$H-NMR (DMSO-d$_6$) δ 8.96 (1H, d, J=2.2 Hz), 8.91 (1H, d, J=4.9 Hz), 8.63 (1H, dd, J=8.5, 2.2 Hz), 8.31 (1H, s), 8.30 (1H, s), 8.17 (1H, d, J=8.5 Hz), 7.90 (2H, d, J=7.3 Hz), 7.63 (1H, d, J=4.9 Hz), 7.43 (2H, t, J=7.3 Hz), 7.29 (1H, t, J=7.3 Hz), 3.24 (1H, q, J=6.8 Hz), 1.16 (6H, d, J=6.8 Hz); LRMS (ESI) m/z 483 [M+H]$^+$.

Example 37(2)

2-(Trans-4-hydroxycyclohexylamino)-4-{3-isopropyl-4-(4-phenyl-1H-imidazol-1-yl)-1H-pyrazolo[3,4-b]pyridin-1-yl}benzamide (37)

According to Examples 1(6) and 1(7), compound (37) (the second stage yield: 49%) was prepared as a white solid using (37a) instead of compound (1e).

$^1$H-NMR (DMSO-d$_6$) δ 8.80 (1H, d, J=5.1 Hz), 8.43 (1H, d, J=7.3 Hz), 8.29 (2H, s), 7.90 (2H, d, J=7.6 Hz), 7.88 (1H, brs), 7.75-7.83 (2H, m), 7.50 (1H, d, J=5.1 Hz), 7.38-7.47 (3H, m), 7.29 (1H, t, J=7.6 Hz), 7.17 (1H, brs), 4.59 (1H, d, J=4.1 Hz), 3.30-3.60 (2H, m), 3.22 (1H, q, J=6.8 Hz), 1.80-2.20 (4H, m), 1.25-1.85 (4H, m), 1.15 (6H, d, J=6.8 Hz); LRMS (ESI) m/z 536 [M+H]$^+$.

Example 38

3-Chloro-4-{3-isopropyl-4-(quinolin-3-yl)-1H-pyrazolo[3,4-b]pyridin-1-yl}benzamide (38)

Example 38(1)

3-Chloro-4-{3-isopropyl-4-(quinolin-3-yl)-1H-pyrazolo[3,4-b]pyridin-1-yl}benzonitrile (38a)

According to Example 1(5), compound (38a) (79%) was prepared as a white solid using 3-chloro-4-fluorobenzonitrile instead of 2-bromo-4-fluorobenzonitrile.

$^1$H-NMR (DMSO-d$_6$) δ 9.16 (1H, s), 8.73 (1H, s), 8.67 (1H, d, J=4.4 Hz), 8.41 (1H, s), 8.13-8.22 (2H, m), 8.09 (1H, d, J=8.0 Hz), 7.89-8.00 (2H, m), 7.75 (1H, t, J=8.0 Hz), 7.44 (1H, d, J=4.4 Hz), 3.02 (1H, q, J=6.8 Hz), 1.04 (6H, d, J=6.8 Hz); LRMS (ESI) m/z 424 [M+H]$^+$.

Example 38(2)

3-Chloro-4-{3-isopropyl-4-(quinolin-3-yl)-1H-pyrazolo[3,4-b]pyridin-1-yl}benzamide (38)

According to Example 1(7), compound (38) (33%) was prepared as a white solid using compound (38a) instead of compound (1f).

$^1$H-NMR (DMSO-d$_6$) δ 9.17 (1H, d, J=2.4 Hz), 8.73 (1H, s), 8.65 (1H, d, J=4.9 Hz), 8.10-8.30 (4H, m), 8.05 (1H, d, J=8.0 Hz), 7.90 (1H, t, J=8.0 Hz), 7.65-7.80 (3H, m), 7.41 (1H, d, J=4.9 Hz), 3.02 (1H, q, J=6.8 Hz), 1.04 (6H, d, J=6.8 Hz); LRMS (ESI) m/z 442 [M+H]$^+$.

Example 39

6-{3-Isopropyl-4-(quinolin-3-yl)-1H-pyrazolo[3,4-b]pyridin-1-yl}nicotinamide (39)

According to Example 1(5), a crude product of 6-{3-isopropyl-4-(quinolin-3-yl)-1H-pyrazolo[3,4-b]pyridin-1-yl}nicotinonitrile was prepared using 6-chloronicotinonitrile instead of 2-bromo-4-fluorobenzonitrile and was used in the subsequent reaction without being purified. According to Example 1(7), compound (39) (the second stage yield: 51%) was prepared as a white solid using 6-{3-isopropyl-4-(quinolin-3-yl)-1H-pyrazolo[3,4-b]pyridin-1-yl}nicotinonitrile instead of compound (1f).

$^1$H-NMR (DMSO-d$_6$) δ 9.15 (1H, d, J=2.2 Hz), 9.08 (1H, d, J=1.7 Hz), 8.79 (1H, d, J=4.6 Hz), 8.71 (1H, d, J=2.2 Hz), 8.48 (1H, dd, J=8.6, 2.2 Hz), 8.42 (1H, d, J=8.6 Hz), 8.24 (1H, brs), 8.15-8.20 (2H, m), 7.91 (1H, td, J=8.1, 1.7 Hz), 7.75 (1H, t, J=8.1 Hz), 7.66 (1H, brs), 7.48 (1H, d, J=4.6 Hz), 2.98 (1H, q, J=6.8 Hz), 1.07 (6H, d, J=6.8 Hz); LRMS (ESI) m/z 409 [M+H]$^+$.

Example 40

2-(Trans-4-hydroxycyclohexylamino)-4-{3-methyl-4-(quinolin-3-yl)-1H-pyrrolo[2,3-b]pyridin-1-yl}benzamide (40)

Example 40(1)

Tert-butyl 3-ethylpyridin-2-ylcarbamate (40a)

Normal-butyllithium (2.69 M, 157.1 mL) was dropwise added to a solution of tert-butyl 3-methylpyridin-2-ylcarbamate (40.0 g) in THF (550 mL) at an internal temperature of −40 to −20° C., followed by stirring at 0° C. for 1 hr. Subsequently, a solution of methyl iodide (28.6 g) in THF (50 mL) was dropwise added to the reaction solution at an internal temperature of −70 to −60° C., followed by stirring at −78° C. for 30 min. The reaction solution was poured into ice water, followed by extraction with ethyl acetate twice. The organic layers were combined, washed with saturated saline, and dried over anhydrous sodium sulfate. The solvent was distilled away. Hexane (300 mL) was added to the resulting residue, and the precipitate was collected by filtration and dried under reduced pressure to obtain compound (40a) (32.4 g, 76%) as a white solid.

$^1$H-NMR (CDCl$_3$) δ 8.28 (1H, dd, J=4.8 Hz, 1.6 Hz), 7.56-7.54 (1H, m), 7.07 (1H, dd, J=7.7, 4.8 Hz), 6.72 (1H, brs), 2.65 (2H, q, J=7.5 Hz), 1.51 (9H, s), 1.24 (3H, t, J=7.6 Hz); LRMS (ESI) m/z 223 [M+H]$^+$.

Example 40(2)

3-Methyl-1H-pyrrolo[2,3-b]pyridine (40b)

Normal-butyllithium (2.69 M, 118.7 mL) was dropwise added to a solution of compound (40a) (32.4 g) in THF (500 mL) at an internal temperature of −30 to −10° C., followed by stirring at 0° C. for 30 min. Subsequently, a solution of DMF (11.18 g) in THF (50 mL) was added to the reaction solution at an internal temperature of −40° C., followed by increasing the temperature to room temperature. Then, 6 N hydrochloric acid (200 mL) was added to the reaction solution, followed by stirring at 60° C. for 2 hr. After cooling, ethyl acetate (200 mL) and water (100 mL) were added to the reaction solution for distribution. The aqueous layer was added to sodium hydroxide (4 M, 300 mL), and pH was adjusted to 12, followed by stirring for 1 hr. The precipitate was collected by filtration, washed by sprinkling water, and dried under reduced pressure to obtain compound (40b) (16.52 g, 86%) as a white solid.

$^1$H-NMR (CDCl$_3$) δ 9.56 (1H, brs), 8.30 (1H, dd, J=4.6, 1.2 Hz), 7.89 (1H, dd, J=7.8, 1.5 Hz), 7.09-7.06 (2H, m), 2.33 (3H, s); LRMS (ESI) m/z 133 [M+H]$^+$.

Example 40(3)

3-Methyl-1H-pyrrolo[2,3-b]pyridine 7-oxide m-chlorobenzoic acid salt (40c)

According to Example 1(2), compound (40c) (77%) was prepared as a white solid using compound (40b) instead of compound (1a).

$^1$H-NMR (DMSO-d$_6$) δ 12.07 (1H, brs), 8.09 (1H, d, J=6.1 Hz), 7.89-7.87 (2H, m), 7.70-7.67 (1H, m), 7.59 (1H, d, J=7.8 Hz), 7.55-7.51 (1H, m), 7.21 (1H, s), 7.04 (1H, dd, J=7.8, 6.1 Hz), 2.24 (3H, s); LRMS (ESI) m/z 305 [M+H]$^+$.

Example 40(4)

4-Chloro-3-methyl-1H-pyrrolo[2,3-b]pyridine (40d)

According to Example 1(3), compound (40d) (39%) was prepared as a white solid using compound (40c) instead of compound (1b).

$^1$H-NMR (DMSO-d$_6$) δ 11.63 (1H, s), 8.08 (1H, d, J=5.1 Hz), 7.30 (1H, s), 7.07 (1H, d, J=5.1 Hz), 2.42 (3H, s); LRMS (ESI) m/z 167 [M+H]$^+$.

Example 40(5)

3-{3-Methyl-1H-pyrrolo[2,3-b]pyridin-4-yl}quinoline (40e)

According to Example 1(4), compound (40e) (82%) was prepared as a white solid using compound (40d) instead of compound (1c).

$^1$H-NMR (CDCl$_3$) δ 9.53 (1H, brs), 9.08 (1H, d, J=2.2 Hz), 8.38 (1H, d, J=4.6 Hz), 8.27 (1H, d, J=2.0 Hz), 8.21 (1H, d, J=8.5 Hz), 7.92 (1H, d, J=8.3 Hz), 7.82-7.78 (1H, m), 7.66-7.62 (1H, m), 7.17 (1H, s), 7.08 (1H, d, J=4.9 Hz), 1.98 (3H, s); LRMS (ESI) m/z 260 [M+H]$^+$.

Example 40(6)

2-Bromo-4-{3-methyl-4-(quinolin-3-yl)-1H-pyrrolo[2,3-b]pyridin-1-yl}benzonitrile (40f)

According to Example 1(5), compound (40f) (960) was prepared as a white solid using compound (40e) instead of compound (1d).

$^1$H-NMR (DMSO-d$_6$) δ 9.05 (1H, d, J=2.2 Hz), 8.75 (1H, d, J=2.0 Hz), 8.56 (1H, d, J=2.2 Hz), 8.49 (1H, d, J=4.6 Hz), 8.39 (1H, dd, J=8.7, 1.8 Hz), 8.13-8.11 (4H, m), 7.88-7.84 (1H, m), 7.73-7.69 (1H, m), 7.36 (1H, d, J=4.9 Hz), 1.90 (3H, s); LRMS (ESI) m/z 440 [M+H]$^+$.

Example 40(7)

2-(Trans-4-hydroxycyclohexylamino)-4-{3-methyl-4-(quinolin-3-yl)-1H-pyrrolo[2,3-b]pyridin-1-yl}benzonitrile (40h)

According to Example 1(6), compound (40h) (76%) was prepared as a white solid using compound (40f) instead of compound (1e).

$^1$H-NMR (CDCl$_3$) δ 9.06 (1H, d, J=2.2 Hz), 8.44 (1H, d, J=4.9 Hz), 8.27 (1H, d, J=2.0 Hz), 8.22 (1H, d, J=8.3 Hz), 7.93 (1H, d, J=7.8 Hz), 7.84-7.80 (1H, m), 7.68-7.64 (1H, m), 7.51 (1H, d, J=8.5 Hz), 7.47 (1H, d, J=1.7 Hz), 7.37 (1H, s), 7.15 (1H, d, J=4.9 Hz), 7.03 (1H, dd, J=8.5, 1.7 Hz), 4.54 (1H, d, J=7.6 Hz), 3.79-3.72 (1H, m), 3.52-3.43 (1H, m), 2.28-2.25 (2H, m), 2.11-2.07 (2H, m), 1.99 (3H, s), 1.54-1.34 (4H, m); LRMS (ESI) m/z 474 [M+H]$^+$.

Example 40(8)

2-(Trans-4-hydroxycyclohexylamino)-4-{3-methyl-4-(quinolin-3-yl)-1H-pyrrolo[2,3-b]pyridin-1-yl}benzamide (40)

According to Example 1(7), compound (40) (83%) was prepared as a white solid using compound (40h) instead of compound (1f).

$^1$H-NMR (DMSO-d$_6$) δ 9.06 (1H, d, J=2.2 Hz), 8.55 (1H, d, J=2.2 Hz), 8.41-8.39 (2H, m), 8.12 (2H, d, J=8.5 Hz), 7.90 (1H, s), 7.87-7.83 (1H, m), 7.75 (1H, d, J=8.5 Hz), 7.72-7.68 (1H, m), 7.40 (1H, d, J=2.0 Hz), 7.25 (1H, d, J=4.2 Hz), 7.12 (1H, brs), 7.04 (1H, dd, J=8.5, 2.0 Hz), 4.56 (1H, d, J=4.2 Hz), 3.54-3.36 (2H, m), 2.10-2.07 (2H, m), 1.91 (3H, s), 1.87-1.84 (2H, m), 1.39-1.20 (4H, m); LRMS (ESI) m/z 492 [M+H]$^+$.

Example 41

4-{3-Ethyl-4-(quinolin-3-yl)-1H-pyrrolo[2,3-b]pyridin-1-yl}-2-(trans-4-hydroxycyclohexylamino)benzamide (41)

Example 41(1)

Tert-butyl 3-propylpyridin-2-ylcarbamate (41a)

According to Example 40(1), compound (41a) (77%) was prepared as a white solid using ethyl iodide instead of methyl iodide.

$^1$H-NMR (CDCl$_3$) δ 8.29 (1H, dd, J=4.6, 1.7 Hz), 7.52 (1H, dd, J=7.6, 1.7 Hz), 7.05 (1H, dd, J=7.6, 4.6 Hz), 6.73 (1H, brs), 2.59 (2H, t, J=7.6 Hz), 1.60-1.70 (2H, m), 1.52 (9H, s), 0.97 (3H, t, J=7.3 Hz); LRMS (ESI) m/z 237 [M+H]$^+$.

Example 41(2)

3-Ethyl-1H-pyrrolo[2,3-b]pyridine (41b)

According to Example 40(2), compound (41b) (99%) was prepared as a white solid using compound (41a) instead of compound (40a).

$^1$H-NMR (CDCl$_3$) δ 11.05 (1H, brs), 8.31 (1H, d, J=4.9 Hz) 7.92 (1H, dd, J=7.8, 1.0 Hz), 7.13 (1H, s), 7.05 (1H, dd, J=7.8, 4.9 Hz), 2.77 (2H, q, J=7.6 Hz), 1.33 (3H, t, J=7.6); LRMS (ESI) m/z 147 [M+H]$^+$.

Example 41(3)

4-Chloro-3-ethyl-1H-pyrrolo[2,3-b]pyridine (41c)

According to Example 1(2), a crude product of 3-ethyl-1H-pyrrolo[2,3-b]pyridine 7-oxide m-chlorobenzoic acid salt was prepared using compound (41b) instead of compound (1a) and was used in the subsequent reaction without being purified. According to Example 1(3), compound (41c) (the second stage yield: 33%) was prepared as a white solid using 3-ethyl-1H-pyrrolo[2,3-b]pyridine 7-oxide m-chlorobenzoic acid salt instead of compound (1b).

$^1$H-NMR (CDCl$_3$) δ 10.49 (1H, brs), 8.14 (1H, d, J=5.1 Hz) 7.14 (1H, s), 7.05 (1H, d, J=5.1 Hz), 2.99 (2H, q, J=7.6 Hz), 1.33 (3H, t, J=7.6); LRMS (ESI) m/z 181 [M+H]$^+$.

Example 41(4)

4-Chloro-3-ethyl-1-{[2-(trimethylsilyl)ethoxy]methyl}-1H-pyrrolo[2,3-b]pyridine (41d)

Sodium hydride (0.877 g, a 55% dispersion in paraffin liquid) was added to a solution of compound (41c) (3.3 g) in DMF (61 mL) at 0° C., followed by stirring for 10 min. Then, [2-(chloromethoxy)ethyl]trimethylsilane (3.53 mL) was added to the reaction solution, followed by stirring at room temperature for 1 hr. After cooling, ice water was added to the reaction solution, followed by extraction with ethyl acetate. The organic layer was washed with water and saturated saline in this order and was then dried over anhydrous sodium sulfate. After distillation of the solvent, the residue was purified by neutral silica gel column chromatography (n-hexane/ethyl acetate) to obtain compound (41d) (4.30 g, 76%) as a colorless oily substance.

$^1$H-NMR (CDCl$_3$) δ 8.21 (1H, d, J=5.1 Hz), 7.19 (1H, s), 7.10 (1H, d, J=5.1 Hz), 5.68 (2H, s), 3.58 (2H, t, J=8.2 Hz), 3.04 (2H, q, J=7.3 Hz), 1.39 (3H, t, J=7.3 Hz), 0.97 (2H, t, J=8.2 Hz), 0.00 (9H, s); LRMS (ESI) m/z 311 [M+H]$^+$.

Example 41(5)

3-{3-Ethyl-1-[(2-(trimethylsilyl)ethoxy)methyl]-1H-pyrrolo[2,3-b]pyridine}quinoline (41e)

A solution of compound (41d) (4.30 g), quinoline-3-boronic acid (3.59 g), tripotassium phosphate (5.87 g), palladium acetate (0.062 g), and 2-dicyclohexylphosphino-2',6'-dimethoxybiphenyl (Sphos, 0.227 g) in a mixture of n-butanol (69 mL) and water (28 mL) was stirred under a nitrogen atmosphere at 100° C. for 1 hr. The reaction solution was distributed between ethyl acetate and water, and the organic layer was washed with saturated saline. The organic layer after the washing was dried over anhydrous sodium sulfate, and the solvent was distilled away. The residue was purified by neutral silica gel column chromatography (n-hexane/ethyl acetate) to obtain compound (41e) (4.3 g, 77%) as a white solid.

$^1$H-NMR (CDCl$_3$) δ 9.08 (1H, d, J=2.2 Hz), 8.42 (1H, d, J=4.9 Hz), 8.28 (1H, d, J=2.2 Hz), 8.24 (1H, d, J=8.3 Hz), 7.93-7.95 (1H, m), 7.85-7.81 (1H, m), 7.69-7.65 (1H, m), 7.24 (1H, s), 7.08 (1H, d, J=4.9 Hz), 5.75 (2H, s), 3.61-3.66 (2H, m), 2.34-2.39 (2H, m), 0.95-1.01 (5H, m), 0.00 (9H, s); LRMS (ESI) m/z 404 [M+H]$^+$.

Example 41(6)

3-{3-Ethyl-1H-pyrrolo[2,3-b]pyridin-4-yl}quinoline (41f)

Tetrabutylammonium floride (a 1.0 M solution in THF, 32.0 mL) was added to a solution of compound (41e) (4.30 g) in THF (35.5 mL), followed by stirring under reflux for 23 hr. The reaction solution was distributed between ethyl acetate and a saturated aqueous sodium bicarbonate solution, and the organic layer was washed with saturated saline. The organic layer after the washing was dried over anhydrous sodium sulfate, and the solvent was distilled away. The residue was purified by NH silica gel column chromatography (n-hexane/ethyl acetate) to obtain compound (41f) (1.65 g, 57%) as a white solid.

$^1$H-NMR (CDCl$_3$) δ 9.73 (1H, brs), 9.08 (1H, d, J=2.2 Hz), 8.39 (1H, d, J=4.9 Hz), 8.26 (1H, d, J=2.2 Hz), 8.22 (1H, d, J=8.3 Hz), 7.92 (1H, d, J=7.3 Hz), 7.82-7.78 (1H, m), 7.64 (1H, t, J=7.6 Hz), 7.21 (1H, s), 7.06 (1H, dd, J=4.9, 1.0 Hz), 2.36 (2H, q, J=7.6 Hz), 0.94 (3H, dd, J=7.6, 7.1 Hz); LRMS (ESI) m/z 274 [M+H]$^+$.

Example 41(7)

2-Bromo-4-{3-ethyl-4-(quinolin-3-yl)-1H-pyrrolo[2,3-b]pyridin-1-yl}benzonitrile (41h)

According to Example 1(5), compound (41h) (98%) was prepared as a white solid using compound (41f) instead of compound (1d).

$^1$H-NMR (CDCl$_3$) δ 9.04 (1H, d, J=2.0 Hz), 8.46 (1H, d, J=4.6 Hz), 8.41 (1H, d, J=2.2 Hz), 8.25 (1H, d, J=2.2 Hz), 8.22 (1H, d, J=8.5 Hz), 8.10 (1H, dd, J=8.5, 2.2 Hz), 7.93 (1H, d, J=7.8 Hz), 7.78-7.85 (2H, m), 7.67 (1H, t, J=7.6 Hz), 7.39 (1H, s), 7.17 (1H, d, J=4.9 Hz), 2.35 (2H, q, J=7.3 Hz), 0.99 (3H, t, J=7.3 Hz); LRMS (ESI) m/z 454 [M+H]$^+$.

Example 41(8)

4-{3-Ethyl-4-(quinolin-3-yl)-1H-pyrrolo[2,3-b]pyridin-1-yl}-2-(trans-4-hydroxycyclohexylamino)benzamide (41)

According to Example 1(6), 4-{3-ethyl-4-(quinolin-3-yl)-1H-pyrrolo[2,3-b]pyridin-1-yl}-2-(trans-4-hydroxycyclohexylamino)benzonitrile was prepared as a crude product using compound (41h) instead of compound (1e) and was used in the subsequent reaction without being purified. According to Example 1(7), compound (41) (the second stage yield: 51%) was prepared as a white solid using 4-{3-ethyl-4-(quinolin-3-yl)-1H-pyrrolo[2,3-b]pyridin-1-yl}-2-(trans-4-hydroxycyclohexylamino)benzonitrile instead of compound (1f).

$^1$H-NMR (DMSO-d$_6$) δ 9.06 (1H, brs), 8.56 (1H, brs), 8.41-8.44 (2H, m), 8.12-8.16 (2H, m), 7.85-7.87 (3H, m), 7.77 (1H, d, J=8.3 Hz), 7.73-7.70 (1H, m), 7.46 (1H, brs), 7.25 (1H, d, J=4.6 Hz), 7.14 (1H, brs), 7.04 (1H, d, J=8.3 Hz), 4.57 (1H, d, J=3.2 Hz), 3.51 (1H, brs), 3.40 (1H, brs), 2.33 (2H, q, J=7.2 Hz), 2.10-2.13 (2H, m), 1.86-1.88 (2H, m), 1.25-1.40 (4H, m), 0.83 (3H, t, J=7.2 Hz); LRMS (ESI) m/z 506 [M+H]$^+$.

Example 42

Trans-4-{2-carbamoyl-5-{3-ethyl-4-(quinolin-3-yl)-1H-pyrrolo[2,3-b]pyridin-1-yl}phenylamino}cyclohexyl-2-aminoacetate dimethanesulfonate (42)

N-(Tert-butoxycarbonyl)glycine (0.260 g), 1-ethyl-3-(3-dimethylaminopropyl)carbodiimide hydrochloride (0.291 g), and 4-(N,N-dimethylamino)pyridine (0.007 g) were added to a solution of (41) (0.300 g) in DMF (5.93 mL), followed by stirring under argon flow at room temperature for 5 hr. The reaction solution was distributed between ethyl acetate and water, and the organic layer was washed with saturated saline. The organic layer after the washing was dried over anhydrous sodium sulfate, and the solvent was distilled away. The residue was purified by neutral silica gel column chromatography (n-hexane/ethyl acetate) to obtain trans-4-{2-carbamoyl-5-[(3-ethyl-4-(quinolin-3-yl)-1H-pyrrolo[2,3-b]pyridin-1-yl}phenylamino]cyclohexyl-2-(tert-butoxycarbonylamino)acetate (0.360 g, 610) as a colorless oily substance. Subsequently, trifluoroacetic acid (0.87 mL) was added to a solution of the colorless oily substance (0.360 g) in dichloromethane (1.74 mL) at room temperature, followed by stirring for 1 hr. The reaction solvent was distilled away under reduced pressure, and a saturated aqueous sodium bicarbonate solution was added to the residue, followed by extraction with ethyl acetate. The organic layer was washed with saturated saline. The organic layer after the washing was dried over anhydrous sodium sulfate, and then the solvent was distilled away. Dichloromethane (10 mL) and ethanol (3 mL) were added to the residue, and then methanesulfonic acid (0.07 mL) was added thereto, followed by stirring at room temperature for 1 hr. The precipitate was collected by filtration, washed by sprinkling dichloromethane, and dried under reduced pressure to obtain (42) (0.336 g, the third stage yield: 37%) as a yellow solid.

$^1$H-NMR (DMSO-d$_6$) δ 9.29 (1H, d, J=2.2 Hz), 8.90 (1H, s), 8.44 (1H, d, J=4.9 Hz), 8.32-8.21 (3H, m), 8.05-7.99 (1H, m), 7.91-7.79 (2H, m), 7.50 (1H, d, J=1.9 Hz), 7.31 (1H, d, J=4.9 Hz), 7.09 (1H, dd, J=2.2, 6.5 Hz), 4.57-4.45 (2H, brs), 3.86-3.80 (1H, m), 3.58-3.52 (1H, brs), 2.62-2.47 (3H, m), 2.38-2.29 (8H, m), 2.20-2.13 (2H, m), 2.03-1.99 (2H, m), 1.68-1.39 (4H, m), 0.88 (3H, t, J=7.6 Hz); LRMS (ESI) m/z 563 [M+H]$^+$.

Example 43

2-(Trans-4-hydroxycyclohexylamino)-4-{4-(quinolin-3-yl)-3-(trifluoromethyl)-1H-pyrrolo[2,3-b]pyridin-1-yl}benzamide (43)

Example 43(1)

4-Chloro-3-(trifluoromethyl)-1H-pyrrolo[2,3-b]pyridine (43a)

According to Example 40(1), tert-butyl 3-(2,2,2-trifluoroethyl)pyridin-2-ylcarbamate was prepared as a crude product using trifluoromethyl iodide instead of methyl iodide and was used in the subsequent reaction without being purified. According to Example 40(2), a crude product of 3-(trifluoromethyl)-1H-pyrrolo[2,3-b]pyridine was prepared using 3-(2,2,2-trifluoroethyl)pyridin-2-ylcarbamate instead of compound (40a) and was used in the subsequent reaction without being purified. According to Example 1(2), a crude product of 3-(trifluoromethyl)-1H-pyrrolo[2,3-b]pyridine 7-oxide m-chlorobenzoic acid salt was prepared using 3-(trifluoromethyl)-1H-pyrrolo[2,3-b]pyridine instead of compound (1a) and was used in the subsequent reaction without being purified. According to Example 1(3), compound (43a) (the fourth stage yield: 15%) was prepared as a white solid using 3-(trifluoromethyl)-1H-pyrrolo[2,3-b]pyridine 7-oxide m-chlorobenzoic acid salt instead of compound (1b).

$^1$H-NMR (DMSO-d$_6$) δ 8.38 (1H, d, J=5.1 Hz), 8.36 (1H, s), 7.43 (1H, d, J=5.1 Hz); LRMS (ESI) m/z 221 [M+H]$^+$.

Example 43(2)

3-{3-(Trifluoromethyl)-1H-pyrrolo[2,3-b]pyridin-4-yl}quinoline (43b)

According to Example 41(4), 4-chloro-3-(trifluoromethyl)-1-{[2-(trimethylsilyl)ethoxy]methyl}-1H-pyrrolo[2,3-b]pyridine (82%) was prepared as a colorless oily substance using compound (43a) instead of compound (41c); and according to Example 41(5), 3-{3-(trifluoromethyl)-1-[(2-(trimethylsilyl)ethoxy)methyl]-1H-pyrrolo[2,3-b]pyridine}quinoline (82%) was prepared as a colorless oily substance using 4-chloro-3-(trifluoromethyl)-1-{[2-(trimethylsilyl)ethoxy]methyl}-1H-pyrrolo[2,3-b]pyridine instead of compound (41d). According to Example 41(6), compound (43b) (75%) was prepared as a white solid using 3-{3-(trifluoromethyl)-1-[(2-(trimethylsilyl)ethoxy)methyl]-1H-pyrrolo[2,3-b]pyridine}quinoline instead of compound (41e).

$^1$H-NMR (CDCl$_3$) δ 9.12 (1H, d, J=2.2 Hz), 8.29 (1H, d, J=5.1 Hz), 8.26 (1H, d, J=2.2 Hz), 8.20 (1H, d, J=9.0 Hz), 7.96 (1H, J=3.9 Hz), 7.81-7.77 (1H, m), 7.66-7.63 (1H, m), 7.36 (1H, s), 7.15 (1H, d, J=5.1 Hz); LRMS (ESI) m/z 314 [M+H]$^+$.

Example 43(3)

2-Bromo-4-{3-(trifluoromethyl)-4-(quinolin-3-yl)-1H-pyrrolo[2,3-b]pyridin-1-yl}benzonitrile (43c)

According to Example 1(5), compound (43c) (39%) was prepared as a white solid using compound (43b) instead of compound (1d).

$^1$H-NMR (CDCl$_3$) δ 8.97 (1H, d, J=1.7 Hz), 8.58 (1H, d, J=4.6 Hz), 8.33 (1H, d, J=2.2 Hz), 8.25-8.21 (2H, m), 8.02-7.98 (2H, m), 7.91-7.86 (2H, m), 7.84-7.80 (1H, m), 7.67-7.63 (1H, m), 7.31 (1H, d, J=4.9 Hz); LRMS (ESI) m/z 494 [M+H]$^+$.

Example 43(4)

2-(Trans-4-hydroxycyclohexylamino)-4-{4-(quinolin-3-yl)-3-(trifluoromethyl)-1H-pyrrolo[2,3-b]pyridin-1-yl}benzamide (43)

According to Example 1(6), a crude product of 2-(trans-4-hydroxycyclohexylamino)-4-{4-(quinolin-3-yl)-3-(trifluoromethyl)-1H-pyrrolo[2,3-b]pyridin-1-yl}benzonitrile was prepared using (43c) instead of compound (1e) and was used in the subsequent reaction without being purified. According to Example 1(7), compound (43) (the second stage yield: 50%) was prepared as a white solid using 2-(trans-4-hydroxycyclohexylamino)-4-{4-(quinolin-3-yl)-3-(trifluoromethyl)-1H-pyrrolo[2,3-b]pyridin-1-yl}benzonitrile instead of compound (1f).

$^1$H-NMR (DMSO-d$_6$) δ 8.94 (1H, d, J=1.7 Hz), 8.66 (1H, s), 8.56 (1H, d, J=8.5 Hz), 8.46 (1H, s), 8.41 (1H, d, J=7.3 Hz), 8.12 (1H, d, J=8.5 Hz), 8.06 (1H, d, J=8.5 Hz), 7.92 (1H, brs), 7.88-7.84 (1H, m), 7.79 (1H, d, J=7.8 Hz), 7.72-7.68 (1H, m), 7.41 (1H, d, J=4.9 Hz), 7.27 (1H, s), 7.22 (1H, brs), 6.98 (1H, dd, J=8.5, 1.2 Hz), 4.54 (1H, d, J=3.7 Hz), 3.52-3.38 (2H, m), 2.08-2.05 (2H, m), 1.84-1.82 (2H, m), 1.37-1.18 (4H, m); LRMS (ESI) m/z 546 [M+H]$^+$.

Example 44

Trans-4-{2-carbamoyl-5-{4-(quinolin-3-yl)-3-(trifluoromethyl)-1H-pyrrolo[2,3-b]pyridin-1-yl}phenylamino}cyclohexyl-2-aminoacetate dimethanesulfonate (44)

According to Example 42, compound (44) (the third stage yield: 57%) was prepared as a white solid using compound (43) instead of compound (41).

$^1$H-NMR (DMSO-d$_6$) δ 9.00 (1H, s), 8.67 (1H, s), 8.57-8.54 (2H, m), 8.16-8.09 (3H, m), 7.96 (1H, brs), 7.92-7.87 (1H, m), 7.81 (1H, d, J=8.5 Hz), 7.76-7.72 (1H, m), 7.43 (1H, d, J=4.9 Hz), 7.29 (1H, d, J=1.7 Hz), 7.27 (1H, brs), 7.01 (1H, dd, J=8.4, 1.8 Hz), 4.89-4.84 (1H, m), 3.83-3.79 (1H, m), 2.31 (6H, s), 2.14-2.12 (2H, m), 1.98-1.96 (2H, m), 1.63-1.55 (2H, m), 1.46-1.37 (2H, m); LRMS (ESI) m/z 603 [M+H]$^+$.

Example 45

2-(Trans-4-hydroxycyclohexylamino)-4-{3-propyl-4-(quinolin-3-yl)-1H-pyrrolo[2,3-b]pyridin-1-yl}benzamide (45)

Example 45(1)

Tert-butyl 3-butylpyridin-2-ylcarbamate (45a)

According to Example 40(1), compound (45a) (87%) was prepared as a white solid using propyl iodide instead of methyl iodide.

$^1$H-NMR (CDCl$_3$) δ 8.28 (1H, d, J=4.6 Hz), 7.52 (1H, d, J=7.6 Hz), 7.05 (1H, dd, J=7.6, 4.9 Hz), 6.71 (1H, brs), 2.61 (2H, t, J=7.8 Hz), 1.63-1.55 (2H, m), 1.51 (9H, s), 1.42-1.32 (2H, m), 0.94 (3H, t, J=7.3 Hz); LRMS (ESI) m/z 251 [M+H]$^+$.

Example 45(2)

3-Propyl-1H-pyrrolo[2,3-b]pyridine (45b)

According to Example 40(2), compound (45b) (99%) was prepared as a white solid using compound (45a) instead of compound (40a).

$^1$H-NMR (CDCl$_3$) δ 10.45 (1H, brs), 8.30 (1H, dd, J=4.9, 1.5 Hz), 7.93 (1H, dd, J=8.1, 1.5 Hz), 7.13 (1H, s), 7.06 (1H, dd, J=7.8, 4.9 Hz), 2.73 (2H, t, J=7.6 Hz), 1.78-1.69 (2H, m), 0.99 (3H, t, J=7.3 Hz); LRMS (ESI) m/z 161 [M+H]$^+$.

Example 45(3)

4-Chloro-3-propyl-1H-pyrrolo[2,3-b]pyridine (45c)

According to Example 1(2), a crude product of 3-propyl-1H-pyrrolo[2,3-b]pyridine 7-oxide m-chlorobenzoic acid salt was prepared using compound (45b) instead of compound (1a) and was used in the subsequent reaction without being purified. According to Example 1(3), compound (45c) (the second stage yield: 14%) was prepared as a white solid using 3-propyl-1H-pyrrolo[2,3-b]pyridine 7-oxide m-chlorobenzoic acid salt instead of compound (1b).

$^1$H-NMR (CDCl$_3$) δ 9.89 (1H, brs), 8.12 (1H, d, J=5.1 Hz), 7.11 (1H, s), 7.05 (1H, d, J=5.4 Hz), 2.90 (2H, t, J=7.6 Hz), 1.78-1.68 (2H, m), 1.01 (3H, t, J=7.3 Hz); LRMS (ESI) m/z 195 [M+H]$^+$.

Example 45(4)

4-Chloro-3-propyl-1-{[2-(trimethylsilyl)ethoxy]methyl}-1H-pyrrolo[2,3-b]pyridine (45d)

According to Example 41(4), compound (45d) (82%) was prepared as a colorless oily substance using compound (45c) instead of (41c).

$^1$H-NMR (CDCl$_3$) δ 8.14 (1H, d, J=5.1 Hz), 7.12 (1H, s), 7.04 (1H, d, J=5.1 Hz), 5.61 (2H, s), 3.51 (2H, t, J=8.1 Hz), 2.89 (2H, t, J=7.6 Hz), 1.68-1.77 (2H, m), 1.01 (3H, t, J=7.3 Hz), 0.90 (2H, t, J=8.3 Hz), −0.07 (9H, s); LRMS (ESI) m/z 325 [M+H]$^+$.

Example 45(5)

3-{3-Propyl-1-[(2-(trimethylsilyl)ethoxy)methyl]-1H-pyrrolo[2,3-b]pyridine}quinoline (45e)

According to Example 41(5), compound (45e) (75%) was prepared as a colorless oily substance using (45d) instead of compound (41d).

$^1$H-NMR (CDCl$_3$) δ 9.05 (1H, d, J=2.0 Hz), 8.39 (1H, d, J=4.9 Hz), 8.25 (1H, d, J=2.2 Hz), 8.21 (1H, d, J=8.3 Hz), 7.91 (1H, d, J=8.3 Hz), 7.82-7.78 (1H, m), 7.62-7.66 (1H, m), 7.20 (1H, s), 7.05 (1H, d, J=4.9 Hz), 5.72 (2H, s), 3.58-3.62 (2H, m), 2.32 (2H, t, J=7.6 Hz) 1.22-1.17 (2H, m), 0.97-0.93 (2H, m), 0.55 (3H, t, J=7.4 Hz), 0.44 (9H, s); LRMS (ESI) m/z 418 [M+H]$^+$.

Example 45(6)

3-{3-Propyl-1H-pyrrolo[2,3-b]pyridin-4-yl}quinoline (45f)

According to Example 41(6), compound (45f) (71%) was prepared as a white solid using (45e) instead of compound (41e).

$^1$H-NMR (CDCl$_3$) δ 9.07 (1H, d, J=2.2 Hz), 8.38 (1H, d, J=4.9 Hz), 8.26 (1H, d, J=2.2 Hz), 8.21 (1H, d, J=8.1 Hz), 7.92-7.90 (1H, m), 7.82-7.78 (1H, m), 7.66-7.62 (1H, m), 7.18 (1H, s), 7.06 (1H, d, J=4.9 Hz), 2.34 (2H, t, J=7.3 Hz), 1.25-1.15 (2H, m), 0.55 (3H, t, J=7.3 Hz); LRMS (ESI) m/z 288 [M+H]$^+$.

Example 45(7)

2-Bromo-4-{3-propyl-4-(quinolin-3-yl)-1H-pyrrolo[2,3-b]pyridin-1-yl}benzonitrile (45h)

According to Example 1(5), compound (45h) (88%) was prepared as a white solid using compound (45f) instead of compound (1d).

$^1$H-NMR (CDCl$_3$) δ 9.04 (1H, d, J=2.2 Hz), 8.46 (1H, d, J=4.9 Hz), 8.40 (1H, d, J=2.0 Hz), 8.25 (1H, d, J=2.0 Hz), 8.22 (1H, d, J=8.8 Hz), 8.10 (1H, dd, J=8.5, 2.2 Hz), 7.94-7.91 (1H, m), 7.85-7.78 (2H, m), 7.68-7.64 (1H, m), 7.39 (1H, s), 7.17 (1H, d, J=4.9 Hz), 2.35-2.31 (2H, m), 1.29-1.20 (2H, m), 0.57 (3H, t, J=7.3 Hz); LRMS (ESI) m/z 468 [M+H]$^+$.

Example 45(8)

2-(Trans-4-hydroxycyclohexylamino-4-{3-propyl-4-(quinolin-3-yl)-1H-pyrrolo[2,3-b]pyridin-1-yl}benzamide (45)

According to Example 1(6), 2-(trans-4-hydroxycyclohexylamino)-4-{3-propyl-4-(quinolin-3-yl)-1H-pyrrolo[2,3-b]pyridin-1-yl}benzonitrile (36%) was prepared as a white solid using compound (45h) instead of compound (1e). Subsequently, according to Example 1(7), compound (45) (90%) was prepared as a white solid using 2-(trans-4-hydroxycyclohexylamino)-4-{3-propyl-4-(quinolin-3-yl)-1H-pyrrolo[2,3-b]pyridin-1-yl}benzonitrile instead of compound (1f).

$^1$H-NMR (DMSO-d$_6$) δ 9.04 (1H, d, J=2.0 Hz), 8.54 (1H, d, J=1.7 Hz), 8.42-8.39 (2H, m), 8.14-8.10 (2H, m), 7.87-7.83 (3H, m), 7.76-7.69 (2H, m), 7.42 (1H, d, J=1.5 Hz), 7.24 (1H, d, J=4.6 Hz), 7.12 (1H, s), 7.03 (1H, dd, J=8.4, 1.3 Hz), 4.55 (1H, d, J=3.9 Hz), 3.53-3.47 (1H, m), 3.44-3.36 (1H, m), 2.31 (2H, t, J=3.9 Hz), 2.11-2.08 (2H, m), 1.87-1.83 (2H, m), 1.39-1.20 (4H, m), 1.12-1.03 (2H, m), 0.39 (3H, t, J=7.2 Hz); LRMS (ESI) m/z 520 [M+H]$^+$.

Example 46

2-(Trans-4-hydroxycyclohexylamino)-4-{3-vinyl-4-(quinolin-3-yl)-1H-pyrrolo[2,3-b]pyridin-1-yl}benzamide (46)

Example 46(1)

Tert-butyl 3-(3-methoxypropyl)pyridin-2-ylcarbamate (46a)

According to Example 40(1), compound (46a) (96%) was prepared as a white solid using 1-chloro-2-methoxyethane instead of methyl iodide.

$^1$H-NMR (CDCl$_3$) δ 8.35 (1H, dd, J=4.8, 1.8 Hz), 7.81 (1H, brs), 7.46 (1H, dd, J=7.6, 2.0 Hz), 6.98 (1H, dd, J=7.4, 4.8

Hz), 3.39 (3H, s), 3.31 (2H, t, J=5.9 Hz), 2.70 (2H, t, J=7.0 Hz), 1.91-1.85 (2H, m), 1.53 (9H, s); LRMS (ESI) m/z 267 [M+H]$^+$.

Example 46(2)

3-(2-Methoxyethyl)-1H-pyrrolo[2,3-b]pyridine (46b)

According to Example 40(2), compound (46b) (88%) was prepared as a white solid using compound (46a) instead of compound (40a).
$^1$H-NMR (CDCl$_3$) δ 8.29 (1H, d, J=3.9 Hz), 7.95-7.92 (1H, m), 7.16 (1H, s), 7.07 (1H, dd, J=7.8, 4.6 Hz), 3.68 (2H, t, J=6.8 Hz), 3.39 (3H, s), 3.04-3.00 (2H, m); LRMS (ESI) m/z 177 [M+H]$^+$.

Example 46(3)

2-{4-Chloro-1H-pyrrolo[2,3-b]pyridin-3-yl}ethanol (46c)

According to Example 1(2), a crude product of 3-(2-methoxyethyl)-1H-pyrrolo[2,3-b]pyridine 7-oxide m-chlorobenzoic acid salt was prepared using compound (46b) instead of compound (1a) and was used in the subsequent reaction without being purified. According to Example 1(3), compound (46c) (the second stage yield: 10%) was prepared as a white solid using 3-(2-methoxyethyl)-1H-pyrrolo[2,3-b]pyridine 7-oxide m-chlorobenzoic acid salt instead of compound (1b).
$^1$H-NMR (CDCl$_3$) δ 9.76 (1H, brs), 8.18 (1H, d, J=5.1 Hz), 7.28-7.26 (1H, m), 7.09 (1H, d, J=5.1 Hz), 3.82 (2H, t, J=7.1 Hz), 3.40 (2H, t, J=7.1 Hz); LRMS (ESI) m/z 197 [M+H]$^+$.

Example 46(4)

2-Bromo-4-{3-vinyl-4-(quinolin-3-yl)-1H-pyrrolo[2,3-b]pyridin-1-yl}benzonitrile (46d)

According to Example 1(4), a crude product of 3-{3-vinyl-1H-pyrrolo[2,3-b]pyridin-4-yl}quinoline was prepared using compound (46c) instead of compound (1c) and was used in the subsequent reaction without being purified. According to Example 1(5), (46d) (the second stage yield: 8%) was prepared as a white solid using 3-{3-vinyl-1H-pyrrolo[2,3-b]pyridin-4-yl}quinoline instead of compound (1d).
$^1$H-NMR (CDCl$_3$) δ 9.07 (1H, d, J=1.7 Hz), 8.49 (1H, d, J=4.9 Hz), 8.41 (1H, d, J=2.2 Hz), 8.30 (1H, d, J=2.2 Hz), 8.22 (1H, d, J=8.5 Hz), 8.12-8.09 (1H, m), 7.93-7.91 (1H, m), 7.85-7.81 (2H, m), 7.72 (1H, s), 7.66 (1H, dd, J=7.9, 7.2 Hz), 7.25-7.24 (1H, m), 6.25-6.17 (1H, m), 5.48 (1H, d, J=17.3 Hz), 5.01 (1H, d, J=11.2 Hz); LRMS (ESI) m/z 452 [M+H]$^+$.

Example 46(5)

2-(Trans-4-hydroxycyclohexylamino)-4-{3-vinyl-4-(quinolin-3-yl)-1H-pyrrolo[2,3-b]pyridin-1-yl}benzamide (46)

According to Example 1(6), a crude product of 2-(trans-4-hydroxycyclohexylamino)-4-{3-vinyl-4-(quinolin-3-yl)-1H-pyrrolo[2,3-b]pyridin-1-yl}benzonitrile was prepared using (46d) instead of compound (1e) and was used in the subsequent reaction without being purified. According to Example 1(7), compound (46) (the second stage yield: 15%) was prepared as a white solid using 2-(trans-4-hydroxycyclohexylamino)-4-{3-vinyl-4-(quinolin-3-yl)-1H-pyrrolo[2,3-b]pyridin-1-yl}benzonitrile instead of compound (1f).

$^1$H-NMR (DMSO-d$_6$) δ 9.01 (1H, d, J=2.2 Hz), 8.54 (1H, d, J=2.0 Hz), 8.44-8.41 (2H, m), 8.33 (1H, s), 8.15-8.09 (2H, m), 7.88-7.84 (2H, m), 7.71 (1H, d, J=8.5 Hz), 7.73-7.69 (1H, m), 7.42 (1H, d, J=1.7 Hz), 7.31 (1H, d, J=4.9 Hz), 7.16 (1H, brs), 7.05 (1H, dd, J=8.5, 1.5 Hz), 6.14 (1H, dd, J=17.3, 11.0 Hz), 5.53 (1H, d, J=17.3 Hz), 4.90 (1H, d, J=11.0 Hz), 4.55 (1H, d, J=4.4 Hz), 3.53-3.47 (1H, m), 3.44-3.39 (1H, m), 2.11-2.08 (2H, m), 1.86-1.84 (2H, m), 1.38-1.20 (4H, m); LRMS (ESI) m/z 504 [M+H]$^+$.

Example 47

2-(Trans-4-hydroxycyclohexylamino)-4-{4-(quinolin-3-yl)-1H-pyrrolo[2,3-b]pyridin-1-yl}benzamide (47)

Example 47(1)

4-Chloro-1H-pyrrolo[2,3-b]pyridine (47a)

According to Example 1(2), a crude product of 1H-pyrrolo[2,3-b]pyridine 7-oxide m-chlorobenzoic acid salt was prepared using 1H-pyrrolo[2,3-b]pyridine instead of compound (1a) and was used in the subsequent reaction without being purified. According to Example 1(3), compound (47a) (the second stage yield: 65%) was prepared as a white solid using 1H-pyrrolo[2,3-b]pyridine 7-oxide m-chlorobenzoic acid salt instead of the compound.
$^1$H-NMR (CDCl$_3$) δ 11.65 (1H, brs), 8.23 (1H, d, J=5.4 Hz), 7.43 (1H, d, J=3.4 Hz), 7.14 (1H, d, J=5.4 Hz), 6.63 (1H, d, J=3.4 Hz); LRMS (ESI) m/z 153 [M+H]$^+$.

Example 47(2)

3-{1H-Pyrrolo[2,3-b]pyridin-4-yl}quinoline (57b)

According to Example 1(4), compound (47b) (44%) was prepared as a white solid using compound (47a) instead of compound (1c).
$^1$H-NMR (DMSO-d$_6$) δ 11.92 (1H, brs), 9.30 (1H, d, J=2.2 Hz), 8.77 (1H, d, J=2.2 Hz), 8.36 (1H, d, J=4.9 Hz), 8.15 (1H, d, J=8.1 Hz), 8.10 (1H, d, J=8.5 Hz), 7.85-7.81 (1H, m), 7.68 (1H, t, J=7.4 Hz), 7.62 (1H, d, J=3.4 Hz), 7.40 (1H, d, J=4.9 Hz), 6.75 (1H, d, J=3.4 Hz); LRMS (ESI) m/z 246 [M+H]$^+$.

Example 47(3)

2-Bromo-4-{4-(quinolin-3-yl)-1H-pyrrolo[2,3-b]pyridin-1-yl}benzonitrile (47c)

According to Example 1(5), compound (47c) (89%) was prepared as a white solid using compound (47b) instead of compound (1d).
$^1$H-NMR (DMSO-d$_6$) δ 9.30-9.29 (1H, m), 8.82-8.81 (1H, m), 8.78-8.77 (1H, m), 8.57-8.56 (1H, m), 8.44-8.41 (1H, m), 8.36-8.35 (1H, m), 8.19-8.11 (3H, m), 7.89-7.84 (1H, m), 7.74-7.70 (1H, m), 7.67-7.65 (1H, m), 7.14-7.13 (1H, m); LRMS (ESI) m/z 426 [M+H]$^+$.

Example 47(4)

2-(Trans-4-hydroxycyclohexylamino)-4-{4-(quinolin-3-yl)-1H-pyrrolo[2,3-b]pyridin-1-yl}benzonitrile (47d)

According to Example 1(6), compound (47d) (670) was prepared as a white solid using compound (47c) instead of compound (1e).

¹H-NMR (CDCl₃) δ 9.30 (1H, d, J=2.2 Hz), 8.50 (2H, dd, J=9.4, 3.5 Hz), 8.21 (1H, d, J=8.3 Hz), 7.95 (1H, d, J=8.1 Hz), 7.83-7.79 (1H, m), 7.69-7.64 (2H, m), 7.53 (1H, d, J=8.5 Hz), 7.46 (1H, d, J=1.7 Hz), 7.38 (1H, d, J=5.1 Hz), 7.05-7.03 (1H, m), 6.89 (1H, d, J=3.7 Hz), 4.56 (1H, d, J=7.6 Hz), 3.77-3.72 (1H, m), 3.50-3.43 (1H, m), 2.28-2.24 (2H, m), 2.10-2.07 (2H, m), 1.53-1.34 (4H, m); LRMS (ESI) m/z 460 [M+H]⁺.

Example 47 (5)

2-(Trans-4-hydroxycyclohexylamino)-4-{4-(quinolin-3-yl)-1H-pyrrolo[2,3-b]pyridin-1-yl}benzamide (47)

According to Example 1(7), compound (47) (79%) was prepared as a white solid using compound (47d) instead of compound (1f). ¹H-NMR (DMSO-d₆) δ9.31 (1H, d, J=1.7 Hz), 8.80 (1H, s), 8.47 (1H, d, J=4.9 Hz), 8.41 (1H, d, J=7.1 Hz), 8.18-8.11 (3H, m), 7.88-7.84 (2H, m), 7.77 (1H, d, J=8.5 Hz), 7.73-7.69 (1H, m), 7.56 (1H, d, J=4.9 Hz), 7.40 (1H, s), 7.15 (1H, brs), 7.06 (1H, d, J=8.3 Hz), 7.00 (1H, d, J=3.7 Hz), 4.55 (1H, d, J=3.9 Hz), 3.53-3.45 (1H, m), 3.43-3.36 (1H, m), 2.11-2.08 (2H, m), 1.86-1.84 (2H, m), 1.38-1.19 (4H, m); LRMS (ESI) m/z 478 [M+H]⁺.

Example 48

2-(Propylamino)-4-{3-methyl-4-(quinolin-3-yl)-1H-pyrrolo[2,3-b]pyridin-1-yl}benzamide (48)

According to Example 1(6), a crude product of 2-(propylamino)-4-{3-methyl-4-(quinolin-3-yl)-1H-pyrrolo[2,3-b]pyridin-1-yl}benzonitrile was prepared using compound (40f) instead of compound (1e) and using n-propylamine instead of trans-aminocyclohexanol and was used in the subsequent reaction without being purified. According to Example 1(7), compound (48) (the second stage yield: 46%) was prepared as a white solid using 2-(propylamino)-4-{3-methyl-4-(quinolin-3-yl)-1H-pyrrolo[2,3-b]pyridin-1-yl}benzonitrile instead of compound (1f).

¹H-NMR (DMSO-d₆) δ 9.07 (1H, d, J=2.2 Hz), 8.57 (1H, d, J=1.7 Hz), 8.48-8.45 (1H, m), 8.42 (1H, d, J=4.6 Hz), 8.14 (2H, d, J=8.5 Hz), 7.92 (1H, s), 7.88-7.84 (2H, m), 7.78 (1H, d, J=8.8 Hz), 7.73-7.70 (1H, m), 7.29 (1H, d, J=2.0 Hz), 7.26 (1H, d, J=4.9 Hz), 7.15-7.12 (2H, m), 3.20-3.15 (2H, m), 1.93 (3H, s), 1.71-1.62 (2H, m), 1.00 (3H, t, J=7.3 Hz); LRMS (ESI) m/z 436 [M+H]⁺.

Example 49

2-(Pentylamino)-4-{3-methyl-4-(quinolin-3-yl)-1H-pyrrolo[2,3-b]pyridin-1-yl}benzamide (49)

According to Example 1(6), a crude product of 2-(pentylamino)-4-{3-methyl-4-(quinolin-3-yl)-1H-pyrrolo[2,3-b]pyridin-1-yl}benzonitrile was prepared using compound (40f) instead of compound (1e) and using n-pentylamine instead of trans-aminocyclohexanol and was used in the subsequent reaction without being purified. According to Example 1(7), compound (49) (the second stage yield: 55%) was prepared as a white solid using 2-(pentylamino)-4-{3-methyl-4-(quinolin-3-yl)-1H-pyrrolo[2,3-b]pyridin-1-yl}benzonitrile instead of compound (1f).

¹H-NMR (DMSO-d₆) δ 9.07 (1H, d, J=2.2 Hz), 8.56 (1H, d, J=2.0 Hz), 8.47-8.44 (1H, m), 8.42 (1H, d, J=4.9 Hz), 8.14 (2H, d, J=8.8 Hz), 7.92 (1H, s), 7.88-7.84 (2H, m), 7.78 (1H, d, J=8.8 Hz), 7.73-7.70 (1H, m), 7.30 (1H, d, J=2.0 Hz), 7.26 (1H, d, J=4.6 Hz), 7.14-7.11 (2H, m), 3.22-3.18 (2H, m), 1.93 (3H, s), 1.69-1.62 (2H, m), 1.42-1.34 (4H, m), 0.91 (3H, t, J=7.1 Hz); LRMS (ESI) m/z 464 [M+H]⁺.

Example 50

2-(Cyclopropylamino)-4-{3-methyl-4-(quinolin-3-yl)-1H-pyrrolo[2,3-b]pyridin-1-yl}benzamide (50)

According to Example 1(6), a crude product of 2-(cyclopropylamino)-4-{3-methyl-4-(quinolin-3-yl)-1H-pyrrolo[2,3-b]pyridin-1-yl}benzonitrile was prepared using compound (40f) instead of compound (1e) and using cyclopropylamine instead of trans-aminocyclohexanol and was used in the subsequent reaction without being purified. According to Example 1(7), compound (50) (the second stage yield: 15%) was prepared as a white solid using 2-(cyclopropylamino)-4-{3-methyl-4-(quinolin-3-yl)-1H-pyrrolo[2,3-b]pyridin-1-yl}benzonitrile instead of compound (1f).

¹H-NMR (DMSO-d₆) δ 9.08 (1H, d, J=2.4 Hz), 8.57 (1H, d, J=2.2 Hz), 8.53 (1H, s), 8.43 (1H, d, J=4.6 Hz), 8.13 (2H, d, J=8.8 Hz), 7.89-7.84 (3H, m), 7.78 (1H, d, J=8.5 Hz), 7.73-7.69 (2H, m), 7.27 (1H, d, J=4.9 Hz), 7.20-7.17 (2H, m), 1.93 (3H, s), 0.83-0.79 (2H, m), 0.51-0.47 (2H, m); LRMS (ESI) m/z 434 [M+H]⁺.

Example 51

2-(Cyclopentylamino)-4-{3-methyl-4-(quinolin-3-yl)-1H-pyrrolo[2,3-b]pyridin-1-yl}benzamide (51)

According to Example 1(6), a crude product of 2-(cyclopentylamino)-4-{3-methyl-4-(quinolin-3-yl)-1H-pyrrolo[2,3-b]pyridin-1-yl}benzonitrile was prepared using compound (40f) instead of compound (1e) and using cyclopentylamine instead of trans-aminocyclohexanol and was used in the subsequent reaction without being purified. According to Example 1(7), compound (51) (the second stage yield: 36%) was prepared as a white solid using 2-(cyclopentylamino)-4-{3-methyl-4-(quinolin-3-yl)-1H-pyrrolo[2,3-b]pyridin-1-yl}benzonitrile instead of compound (1f).

¹H-NMR (DMSO-d₆) δ 9.07 (1H, d, J=2.2 Hz), 8.57 (1H, d, J=2.0 Hz), 8.51 (1H, d, J=6.3 Hz), 8.43 (1H, d, J=4.6 Hz), 8.14 (2H, d, J=8.8 Hz), 7.90 (1H, s), 7.88-7.84 (2H, m), 7.77 (1H, d, J=8.54 Hz), 7.73-7.70 (1H, m), 7.35 (1H, d, J=2.2 Hz), 7.27 (1H, d, J=4.6 Hz), 7.14 (1H, brs), 7.10 (1H, dd, J=8.5, 2.0 Hz), 3.93-3.86 (1H, m), 2.09-2.04 (2H, m), 1.93 (3H, s), 1.71-1.62 (4H, m), 1.53-1.47 (2H, m); LRMS (ESI) m/z 462 [M+H]⁺.

Example 52

2-(Cyclohexylamino)-4-{3-methyl-4-(quinolin-3-yl)-1H-pyrrolo[2,3-b]pyridin-1-yl}benzamide (52)

According to Example 1(6), a crude product of 2-(cyclohexylamino)-4-{3-methyl-4-(quinolin-3-yl)-1H-pyrrolo[2,3-b]pyridin-1-yl}benzonitrile was prepared using compound (40f) instead of compound (1e) and using cyclohexylamine instead of trans-aminocyclohexanol and was used in the subsequent reaction without being purified. According to Example 1(7), compound (52) (the second stage yield: 25%) was prepared as a white solid using 2-(cyclohexylamino)-4-{3-methyl-4-(quinolin-3-yl)-1H-pyrrolo[2,3-b]pyridin-1-yl}benzonitrile instead of compound (1f).

¹H-NMR (DMSO-d₆) δ 9.07 (1H, d, J=2.2 Hz), 8.57 (1H, d, J=2.2 Hz), 8.52 (1H, d, J=7.6 Hz), 8.41 (1H, d, J=4.9 Hz), 8.14 (2H, d, J=8.3 Hz), 7.90 (1H, s), 7.88-7.84 (2H, m), 7.77 (1H, d, J=8.8 Hz), 7.74-7.70 (1H, m), 7.40 (1H, d, J=2.0 Hz), 7.27 (1H, d, J=4.9 Hz), 7.13 (1H, brs), 7.05 (1H, dd, J=2.0, 8.5 Hz), 3.51-3.43 (1H, m), 2.03-1.99 (2H, m), 1.93 (3H, s), 1.73-1.69 (2H, m), 1.60-1.56 (1H, m), 1.46-1.38 (2H, m), 1.34-1.28 (3H, m); LRMS (ESI) m/z 476 [M+H]$^+$.

Examples 53 and 54

2-(Tetrahydro-2H-pyran-4-ylamino)-4-{3-methyl-4-(quinolin-3-yl)-1H-pyrrolo[2,3-b]pyridin-1-yl}benzamide (53)

4-{3-Methyl-4-(quinolin-3-yl)-1H-pyrrolo[2,3-b]pyridin-1-yl}benzamide (54)

According to Example 1(6), a crude product of 2-(tetrahydro-2H-pyran-4-ylamino)-4-{3-methyl-4-(quinolin-3-yl)-1H-pyrrolo[2,3-b]pyridin-1-yl}benzonitrile was prepared using compound (40f) instead of compound (1e) and using tetrahydro-2H-pyran-4-amine instead of trans-aminocyclohexanol and was used in the subsequent reaction without being purified. According to Example 1(7), (53) (the second stage yield: 4%) was prepared as a white solid using 2-(tetrahydro-2H-pyran-4-ylamino)-4-{3-methyl-4-(quinolin-3-yl)-1H-pyrrolo[2,3-b]pyridin-1-yl}benzonitrile instead of compound (1f). By this reaction, compound (54) (the second stage yield: 21%) was prepared as a white solid.

Compound (53)

$^1$H-NMR (DMSO-d$_6$) δ 9.07 (1H, d, J=2.0 Hz), 8.56-8.53 (2H, m), 8.41 (1H, d, J=4.9 Hz), 8.14 (2H, d, J=8.5 Hz), 7.91-7.84 (3H, m), 7.79 (1H, d, J=8.8 Hz), 7.74-7.70 (1H, m), 7.42 (1H, d, J=1.7 Hz), 7.27-7.26 (1H, m), 7.18 (1H, brs), 7.11 (1H, dd, J=8.5, 1.7 Hz), 3.90-3.86 (2H, m), 3.74-3.65 (1H, m), 3.53-3.48 (2H, m), 2.09-2.04 (2H, m), 1.93 (3H, s), 1.49-1.40 (2H, m); LRMS (ESI) m/z 478 [M+H]$^+$.

Compound (54)

$^1$H-NMR (DMSO-d$_6$) δ 9.06 (1H, s), 8.56 (1H, s), 8.43 (1H, d, J=4.4 Hz), 8.13-8.04 (7H, m), 7.94 (1H, s), 7.87-7.83 (1H, m), 7.72-7.68 (1H, m), 7.40 (1H, brs), 7.28 (1H, d, J=4.6 Hz), 1.92 (3H, s); LRMS (ESI) m/z 379 [M+H]$^+$.

Example 55

2-(4-Hydroxybutylamino)-4-{3-methyl-4-(quinolin-3-yl)-1H-pyrrolo[2,3-b]pyridin-1-yl}benzamide (55)

According to Example 1(6), a crude product of 2-(4-hydroxybutylamino)-4-{3-methyl-4-(quinolin-3-yl)-1H-pyrrolo[2,3-b]pyridin-1-yl}benzonitrile was prepared using compound (40f) instead of compound (1e) and using 4-amino-1-butanol instead of trans-aminocyclohexanol and was used in the subsequent reaction without being purified. According to Example 1(7), compound (55) (the second stage yield: 35%) was prepared as a white solid using 2-(4-hydroxybutylamino)-4-{3-methyl-4-(quinolin-3-yl)-1H-pyrrolo[2,3-b]pyridin-1-yl}benzonitrile instead of compound (1f).

$^1$H-NMR (DMSO-d$_6$) δ 9.06 (1H, d, J=2.2 Hz), 8.55 (1H, d, J=2.2 Hz), 8.44-8.41 (2H, m), 8.12 (2H, d, J=8.8 Hz), 7.90 (1H, s), 7.87-7.83 (2H, m), 7.76 (1H, d, J=8.5 Hz), 7.72-7.68 (1H, m), 7.28-7.24 (2H, m), 7.14-7.11 (2H, m), 4.45 (1H, t, J=5.2 Hz), 3.48-3.43 (2H, m), 3.23-3.18 (2H, m), 1.91 (3H, s), 1.70-1.63 (2H, m), 1.58-1.51 (2H, m); LRMS (ESI) m/z 466 [M+H]$^+$.

Example 56

2-(5-Hydroxypentylamino)-4-{3-methyl-4-(quinolin-3-yl)-1H-pyrrolo[2,3-b]pyridin-1-yl}benzamide (56)

According to Example 1(6), a crude product of 2-(5-hydroxypentylamino)-4-{3-methyl-4-(quinolin-3-yl)-1H-pyrrolo[2,3-b]pyridin-1-yl}benzonitrile was prepared using compound (40f) instead of compound (1e) and using 5-amino-1-pentanol instead of trans-aminocyclohexanol and was used in the subsequent reaction without being purified. According to Example 1(7), compound (56) (the second stage yield: 31%) was prepared as a white solid using 2-(5-hydroxypentylamino)-4-{3-methyl-4-(quinolin-3-yl)-1H-pyrrolo[2,3-b]pyridin-1-yl}benzonitrile instead of compound (1f).

$^1$H-NMR (DMSO-d$_6$) δ 9.05 (1H, d, J=2.2 Hz), 8.55 (1H, d, J=2.2 Hz), 8.45-8.40 (2H, m), 8.12 (2H, d, J=8.5 Hz), 7.90 (1H, s), 7.87-7.83 (2H, m), 7.76 (1H, d, J=8.5 Hz), 7.72-7.68 (1H, m), 7.29 (1H, d, J=2.0 Hz), 7.25 (1H, d, J=4.9 Hz), 7.13-7.10 (2H, m), 4.37 (1H, t, J=5.1 Hz), 3.43-3.39 (2H, m), 3.21-3.16 (2H, m), 1.91 (3H, s), 1.68-1.61 (2H, m), 1.52-1.38 (4H, m); LRMS (ESI) m/z 480 [M+H]$^+$.

Example 57

2-[2-(2-Hydroxyethoxy)ethylamino]-4-{3-methyl-4-(quinolin-3-yl)-1H-pyrrolo[2,3-b]pyridin-1-yl}benzamide (57)

According to Example 1(6), a crude product of 2-[2-(2-hydroxyethoxy)ethylamino]-4-{3-methyl-4-(quinolin-3-yl)-1H-pyrrolo[2,3-b]pyridin-1-yl}benzonitrile was prepared using (40f) instead of compound (1e) and using 2-(2-aminoethoxy)ethanol instead of trans-aminocyclohexanol and was used in the subsequent reaction without being purified. According to Example 1(7), compound (57) (the second stage yield: 18%) was prepared as a white solid using 2-[2-(2-hydroxyethoxy)ethylamino]-4-{3-methyl-4-(quinolin-3-yl)-1H-pyrrolo[2,3-b]pyridin-1-yl}benzonitrile instead of compound (1f).

$^1$H-NMR (DMSO-d$_6$) δ 9.06 (1H, d, J=2.2 Hz), 8.55 (1H, d, J=2.2 Hz), 8.51-8.49 (1H, m), 8.41 (1H, d, J=4.6 Hz), 8.12 (2H, d, J=8.8 Hz), 7.91 (1H, s), 7.87-7.83 (2H, m), 7.76 (1H, d, J=8.5 Hz), 7.72-7.68 (1H, m), 7.28 (1H, d, J=2.0 Hz), 7.25 (1H, d, J=4.6 Hz), 7.18-7.15 (2H, m), 4.58 (1H, dd, J=5.6, 5.1 Hz), 3.68 (2H, t, J=5.5 Hz), 3.55-3.48 (4H, m), 3.39-3.35 (2H, m), 1.91 (3H, s); LRMS (ESI) m/z 482 [M+H]$^+$.

Example 58

2-(2-Hydroxy-2-methylpropylamino)-4-{3-methyl-4-(quinolin-3-yl)-1H-pyrrolo[2,3-b]pyridin-1-yl}benzamide (58)

According to Example 1(6), a crude product of 2-(2-hydroxy-2-methylpropylamino)-4-{3-methyl-4-(quinolin-3-yl)-1H-pyrrolo[2,3-b]pyridin-1-yl}benzonitrile was prepared using compound (40f) instead of compound (1e) and using 1-amino-2-methylpropan-2-ol instead of trans-aminocyclohexanol and was used in the subsequent reaction without being purified. According to Example 1(7), (58) (the second stage yield: 54%) was prepared as a white solid using 2-(2-hydroxy-2-methylpropylamino)-4-{3-methyl-4-(quinolin-3-yl)-1H-pyrrolo[2,3-b]pyridin-1-yl}benzonitrile instead of compound (1f).

¹H-NMR (DMSO-d₆) δ 9.05 (1H, d, J=2.2 Hz), 8.59-8.55 (2H, m), 8.41 (1H, d, J=4.6 Hz), 8.12 (2H, d, J=8.8 Hz), 7.89 (1H, s), 7.87-7.83 (2H, m), 7.75 (1H, d, J=8.5 Hz), 7.72-7.68 (1H, m), 7.25 (1H, d, J=4.8 Hz), 7.20 (1H, d, J=1.7 Hz), 7.15-7.12 (2H, m), 4.57 (1H, s), 3.10 (2H, d, J=4.9 Hz), 1.91 (3H, s), 1.20 (6H, s); LRMS (ESI) m/z 466 [M+H]⁺.

Example 59

2-(3-Isopropoxypropylamino)-4-{3-methyl-4-(quinolin-3-yl)-1H-pyrrolo[2,3-b]pyridin-1-yl}benzamide (59)

According to Example 1(6), a crude product of 2-(3-isopropoxypropylamino)-4-{3-methyl-4-(quinolin-3-yl)-1H-pyrrolo[2,3-b]pyridin-1-yl}benzonitrile was prepared using (40f) instead of compound (1e) and using 3-isopropoxypropylamine instead of trans-aminocyclohexanol and was used in the subsequent reaction without being purified. According to Example 1(7), compound (59) (the second stage yield: 38%) was prepared as a white solid using 2-(3-isopropoxypropylamino)-4-{3-methyl-4-(quinolin-3-yl)-1H-pyrrolo[2,3-b]pyridin-1-yl}benzonitrile instead of compound (1f).

¹H-NMR (DMSO-d₆) δ 9.05 (1H, d, J=2.2 Hz), 8.55 (1H, d, J=2.2 Hz), 8.46-8.43 (1H, m), 8.40 (1H, d, J=4.9 Hz), 8.12 (2H, d, J=8.8 Hz), 7.89 (1H, s), 7.87-7.83 (2H, m), 7.76 (1H, d, J=8.8 Hz), 7.72-7.68 (1H, m), 7.29 (1H, d, J=2.0 Hz), 7.25 (1H, d, J=4.9 Hz), 7.15-7.10 (2H, m), 3.55-3.45 (3H, m), 3.28-3.24 (2H, m), 1.91 (3H, s), 1.85-1.79 (2H, m), 1.07 (3H, s), 1.06 (3H, s); LRMS (ESI) m/z 494 [M+H]⁺.

Example 60

2-[3-(Isopropylamino)propylamino]-4-{3-methyl-4-(quinolin-3-yl)-1H-pyrrolo[2,3-b]pyridin-1-yl}benzamide (60)

According to Example 1(6), a crude product of 2-[3-(isopropylamino)propylamino]-4-{3-methyl-4-(quinolin-3-yl)-1H-pyrrolo[2,3-b]pyridin-1-yl}benzonitrile was prepared using (40f) instead of compound (1e) and using 3-(isopropylamino)propylamine instead of trans-aminocyclohexanol and was used in the subsequent reaction without being purified. According to Example 1(7), compound (60) (the second stage yield: 34%) was prepared as a white solid using 2-[3-(isopropylamino)propylamino]-4-{3-methyl-4-(quinolin-3-yl)-1H-pyrrolo[2,3-b]pyridin-1-yl}benzonitrile instead of compound (1f).

¹H-NMR (CDCl₃) δ 9.07 (1H, d, J=2.2 Hz), 8.44 (1H, d, J=4.9 Hz), 8.27 (1H, d, J=2.2 Hz), 8.21 (1H, d, J=8.5 Hz), 8.10 (1H, s), 7.92 (1H, d, J=7.8 Hz), 7.81 (1H, dt, J=8.5, 3.5 Hz), 7.67-7.63 (1H, m), 7.52 (1H, d, J=8.5 Hz), 7.38 (1H, s), 7.15-7.11 (3H, m), 7.04 (1H, dd, J=8.4, 1.8 Hz), 5.78 (1H, brs), 3.34-3.31 (2H, m), 2.87-2.76 (3H, m), 1.99 (3H, s), 1.95-1.88 (2H, m), 1.08 (3H, s), 1.06 (3H, s); LRMS (ESI) m/z 493 [M+H]⁺.

Example 61

2-(Trans-4-aminocyclohexylamino)-4-{3-methyl-4-(quinolin-3-yl)-1H-pyrrolo[2,3-b]pyridin-1-yl}benzamide (61)

According to Example 1(6), a crude product of 2-(trans-4-aminocyclohexylamino)-4-{3-methyl-4-(quinolin-3-yl)-1H-pyrrolo[2,3-b]pyridin-1-yl}benzonitrile was prepared using (40f) instead of compound (1e) and using trans-1,4-cyclohexanediamine instead of trans-aminocyclohexanol and was used in the subsequent reaction without being purified. According to Example 1(7), compound (61) (the second stage yield: 62%) was prepared as a white solid using 2-(trans-4-aminocyclohexylamino)-4-{3-methyl-4-(quinolin-3-yl)-1H-pyrrolo[2,3-b]pyridin-1-yl}benzonitrile instead of compound (1f).

¹H-NMR (DMSO-d₆) δ 9.06 (1H, brs), 8.55 (1H, brs), 8.40-8.36 (2H, m), 8.13-8.11 (2H, m), 7.90 (1H, s), 7.87-7.83 (2H, m), 7.76-7.69 (2H, m), 7.41 (1H, brs), 7.25 (1H, d, J=4.4 Hz), 7.11 (1H, brs), 7.03 (1H, d, J=7.3 Hz), 3.46-3.40 (1H, m), 2.66-2.55 (1H, m), 2.16-2.04 (2H, m), 1, 92 (3H, s), 1.84-1.75 (2H, m), 1.27-1.13 (4H, m); LRMS (ESI) m/z 491 [M+H]⁺.

Example 62

2-(Trans-4-acetamidocyclohexylamino)-4-{3-methyl-4-(quinolin-3-yl)-1H-pyrrolo[2,3-b]pyridin-1-yl}benzamide (62)

Acetic anhydride (0.012 mL) and triethylamine (0.021 mL) were added to a solution of compound (61) (0.050 g) prepared in Example 61 in dichloromethane (10 mL), followed by stirring at room temperature for 1 hr. The solvent was distilled away under reduced pressure, and water was added to the residue. The precipitate was collected by filtration, washed by sprinkling water and ether, and dried under reduced pressure to obtain (62) (0.043 g, 78%) as a white solid.

¹H-NMR (DMSO-d₆) δ 9.06 (1H, brs), 8.55 (1H, brs), 8.39 (2H, d, J=4.2 Hz), 8.14-8.11 (2H, m), 7.91-7.66 (5H, m), 7.46 (1H, brs), 7.26 (1H, d, J=4.2 Hz), 7.12 (1H, brs), 7.03-7.01 (1H, m), 3.60-3.53 (2H, m), 2.16-2.13 (2H, m), 1.92 (3H, s), 1.87-1.84 (2H, m), 1.78 (3H, s), 1.38-1.21 (4H, m); LRMS (ESI) m/z 533 [M+H]⁺.

Example 63

2-(Trans-4-methylsulfonamidocyclohexylamino)-4-{3-methyl-4-(quinolin-3-yl)-1H-pyrrolo[2,3-b]pyridin-1-yl}benzamide (63)

According to Example 62, compound (63) (17%) was prepared as a white solid using methanesulfonyl chloride instead of acetic anhydride and purifying the residue by NH silica gel column chromatography (chloroform/methanol).

¹H-NMR (DMSO-d₆) δ 9.06 (1H, d, J=1.7 Hz), 8.55 (1H, d, J=2.2 Hz), 8.40-8.38 (2H, m), 8.13 (2H, d, J=8.8 Hz), 7.91 (1H, s), 7.87-7.83 (2H, m), 7.75 (1H, d, J=8.8 Hz), 7.72-7.69 (1H, m), 7.40 (1H, s), 7.12 (1H, brs), 7.06-7.02 (2H, m), 3.40-3.36 (1H, m), 3.22-3.17 (1H, m), 2.92 (3H, s), 2.15-2.12 (2H, m), 1.97-1.94 (2H, m), 1.92 (3H, s), 1.46-1.38 (2H, m), 1.32-1.23 (2H, m); LRMS (ESI) m/z 567 [M+H]⁺.

Example 64

2-(Trans-2-aminocyclohexylamino)-4-{3-methyl-4-(quinolin-3-yl)-1H-pyrrolo[2,3-b]pyridin-1-yl}benzamide (64)

According to Example 1(6), a crude product of 2-(trans-2-aminocyclohexylamino)-4-{3-methyl-4-(quinolin-3-yl)-1H-pyrrolo[2,3-b]pyridin-1-yl}benzonitrile was prepared using (40f) instead of compound (1e) and using trans-1,2-cyclohexanediamine instead of trans-aminocyclohexanol and was used in the subsequent reaction without being purified. According to Example 1(7), compound (64) (the second stage yield: 4%) was prepared as a white solid using 2-(trans-2-aminocyclohexylamino)-4-{3-methyl-4-(quinolin-3-yl)-1H-pyrrolo[2,3-b]pyridin-1-yl}benzonitrile instead of compound (1f).

$^1$H-NMR (DMSO-d$_6$) δ 9.05 (1H, d, J=2.2 Hz), 8.54 (1H, d, J=2.2 Hz), 8.46 (1H, d, J=7.8 Hz), 8.40 (1H, d, J=4.9 Hz), 8.12 (2H, d, J=9.3 Hz), 7.87-7.82 (3H, m), 7.75 (1H, d, J=8.5 Hz), 7.72-7.68 (1H, m), 7.41 (1H, d, J=1.5 Hz), 7.24 (1H, d, J=4.9 Hz), 7.14 (1H, brs), 7.07 (1H, dd, J=8.5, 1.7 Hz), 3.20-3.15 (1H, m), 2.61-2.56 (1H, m), 2.12 (1H, d, J=8.3 Hz), 1.91 (3H, s), 1.86-1.83 (1H, m), 1.66-1.53 (2H, m), 1.36-1.21 (4H, m); LRMS (ESI) m/z 491 [M+H]$^+$.

Example 65

2-(Furan-2-ylmethylamino)-4-{3-methyl-4-(quinolin-3-yl)-1H-pyrrolo[2,3-b]pyridin-1-yl}benzamide (65)

According to Example 1(6), a crude product of 2-(furan-2-ylmethylamino)-4-{3-methyl-4-(quinolin-3-yl)-1H-pyrrolo[2,3-b]pyridin-1-yl}benzonitrile was prepared using compound (40f) instead of compound (1e) and using furfurylamine instead of trans-aminocyclohexanol and was used in the subsequent reaction without being purified. According to Example 1(7), compound (65) (the second stage yield: 32%) was prepared as a white solid using 2-(furan-2-ylmethylamino)-4-{3-methyl-4-(quinolin-3-yl)-1H-pyrrolo[2,3-b]pyridin-1-yl}benzonitrile instead of compound (1f).

$^1$H-NMR (DMSO-d$_6$) δ 9.06 (1H, d, J=2.2 Hz), 8.77-8.74 (1H, m), 8.55 (1H, d, J=2.0 Hz), 8.43 (1H, d, J=4.9 Hz), 8.12 (2H, d, J=8.5 Hz), 7.90-7.83 (3H, m), 7.79 (1H, d, J=8.5 Hz), 7.72-7.68 (1H, m), 7.60 (1H, s), 7.43 (1H, d, J=1.7 Hz), 7.27-7.22 (3H, m), 6.41 (2H, s), 4.48 (2H, d, J=5.6 Hz), 1.91 (3H, s); LRMS (ESI) m/z 474 [M+H]$^+$.

Example 66

2-(3,4-Methylenedioxybenzylamino)-4-{3-methyl-4-(quinolin-3-yl)-1H-pyrrolo[2,3-b]pyridin-1-yl}benzamide (66)

According to Example 1(6), a crude product of 2-(3,4-methylenedioxybenzylamino)-4-{3-methyl-4-(quinolin-3-yl)-1H-pyrrolo[2,3-b]pyridin-1-yl}benzonitrile was prepared using (40f) instead of compound (1e) and using 3,4-methylenedioxybenzylamine instead of trans-aminocyclohexanol and was used in the subsequent reaction without being purified. According to Example 1(7), compound (66) (the second stage yield: 38%) was prepared as a white solid using 2-(3,4-methylenedioxybenzylamino)-4-{3-methyl-4-(quinolin-3-yl)-1H-pyrrolo[2,3-b]pyridin-1-yl}benzonitrile instead of compound (1f).

$^1$H-NMR (DMSO-d$_6$) δ 9.05 (1H, d, J=1.7 Hz), 8.81-8.78 (1H, m), 8.54 (1H, s), 8.39 (1H, d, J=4.6 Hz), 8.12 (2H, d, J=8.1 Hz), 7.90-7.77 (4H, m), 7.72-7.68 (1H, m), 7.35 (1H, s), 7.25-7.13 (3H, m), 6.97 (1H, s), 6.90-6.86 (2H, m), 5.97 (2H, s), 4.38 (2H, d, J=5.4 Hz), 1.89 (3H, s); LRMS (ESI) m/z 528 [M+H]$^+$.

Example 67

2-(Trans-4-hydroxycyclohexylthio)-4-{3-methyl-4-(quinolin-3-yl)-1H-pyrrolo[2,3-b]pyridin-1-yl}benzamide (67)

Trans-4-mercaptocyclohexanol (0.050 g), tris(dibenzylideneacetone)dipalladium(0) (0.008 g), 4,5-bis(diphenylphosphino)-9,9-dimethylxanthene (0.010 g), and N,N-diisopropylethylamine (0.116 mL) were added to a solution of (40f) (0.150 g) prepared in Example 40(6) in 1,4-dioxane (1.71 mL), followed by stirring under nitrogen flow at 120° C. for 6 hr. The reaction solution was distributed between ethyl acetate and water, and the organic layer was washed with saturated saline. The organic layer after the washing was dried over anhydrous sodium sulfate, and the solvent was distilled away. The residue was purified by neutral silica gel column chromatography (n-hexane/ethyl acetate) to obtain a crude product of 2-(trans-4-hydroxycyclohexylthio)-4-{3-methyl-4-(quinolin-3-yl)-1H-pyrrolo[2,3-b]pyridin-1-yl}benzonitrile. Subsequently, an aqueous sodium hydroxide solution (4 M, 0.851 mL) and a 30% hydrogen peroxide solution (0.193 mL) were added to a solution of this 2-(trans-4-hydroxycyclohexylthio)-4-{3-methyl-4-(quinolin-3-yl)-1H-pyrrolo[2,3-b]pyridin-1-yl}benzonitrile in DMSO (0.4 mL) and ethanol (1.6 mL) at room temperature, followed by stirring for 30 min. Water was added to the reaction solution, and the precipitate was collected by filtration, washed by sprinkling water and ether, and then dried under reduced pressure to obtain (67) (0.023 g, the second stage yield: 13%) as a white solid.

$^1$H-NMR (DMSO-d$_6$) δ 9.07 (1H, d, J=2.2 Hz), 8.56 (1H, d, J=2.0 Hz), 8.41 (1H, d, J=2.0 Hz), 8.13 (2H, d, J=8.5 Hz), 7.95 (1H, s), 7.87-7.80 (3H, m), 7.73-7.66 (2H, m), 7.59 (1H, d, J=8.3 Hz), 7.39 (1H, brs), 7.30 (1H, d, J=4.9 Hz), 4.59 (1H, d, J=4.4 Hz), 3.46-3.42 (1H, m), 2.14-2.11 (2H, m), 1.93-1.88 (5H, m), 1.40-1.26 (4H, m); LRMS (ESI) m/z 509 [M+H]$^+$.

Example 68

2-(4-Hydroxyphenylthio)-4-{3-methyl-4-(quinolin-3-yl)-1H-pyrrolo[2,3-b]pyridin-1-yl}benzamide (68)

According to Example 67, compound (68) (the second stage yield: 30%) was prepared as a white solid using 4-mercaptophenol instead of trans-4-mercaptocyclohexanol.

$^1$H-NMR (DMSO-d$_6$) δ 9.00 (1H, d, J=2.2 Hz), 8.50 (1H, d, J=1.7 Hz), 8.22 (1H, d, J=4.9 Hz), 8.11-8.06 (2H, m), 7.93 (1H, brs), 7.85-7.81 (1H, m), 7.70-7.63 (4H, m), 7.51 (1H, dd, J=8.3, 1.7 Hz), 7.45 (1H, brs), 7.35 (2H, d, J=8.3 Hz), 7.19 (1H, d, J=4.6 Hz), 6.84 (2H, d, J=8.3 Hz), 1.83 (3H, s); LRMS (ESI) m/z 503 [M+H]$^+$.

Example 69

2-Bromo-4-{3-methyl-4-(quinolin-3-yl)-1H-pyrrolo[2,3-b]pyridin-1-yl}benzamide (69)

According to Example 1(7), compound (69) (66%) was prepared as a white solid using compound (40f).

$^1$H-NMR (DMSO-d$_6$) δ 9.06 (1H, brs), 8.56 (1H, brs), 8.45 (1H, d, J=4.9 Hz), 8.37 (1H, s), 8.12 (2H, d, J=8.5 Hz), 8.04 (1H, d, J=7.8 Hz), 7.97-7.93 (2H, m), 7.87-7.83 (1H, m), 7.72-7.69 (1H, m), 7.60-7.58 (2H, m), 7.30 (1H, d, J=4.9 Hz), 1.91 (3H, s); LRMS (ESI) m/z 458 [M+H]$^+$.

Example 70

2-(2-Aminocyclohexylamino)-4-{3-ethyl-4-(quinolin-3-yl)-1H-pyrrolo[2,3-b]pyridin-1-yl}benzamide (70)

According to Example 1(6), a crude product of 2-(2-aminocyclohexylamino)-4-{3-ethyl-4-(quinolin-3-yl)-1H-pyrrolo[2,3-b]pyridin-1-yl}benzonitrile was prepared using compound (41h) instead of compound (1e) and using cyclohexane-1,2-diamine instead of trans-aminocyclohexanol and was used in the subsequent reaction without being purified. According to Example 1(7), compound (70) (the second stage yield: 57%) was prepared as a white solid using 2-(2-aminocyclohexylamino)-4-{3-ethyl-4-(quinolin-3-yl)-1H-pyrrolo[2,3-b]pyridin-1-yl}benzonitrile instead of compound (1f).

$^1$H-NMR (DMSO-d$_6$) δ 9.04 (1H, d, J=2.2 Hz), 8.54 (1H, s), 8.47 (1H, d, J=8.1 Hz), 8.39 (1H, d, J=4.6 Hz), 8.14-8.09 (2H, m), 7.87-7.67 (4H, m), 7.45 (1H, s), 7.23 (1H, d, J=4.9 Hz), 7.03 (1H, d, J=8.4 Hz), 2.32 (1H, q, J=7.6 Hz), 2.14-2.10 (1H, m), 1.85-1.82 (1H, m), 1.63-1.56 (4H, m), 1.29-1.09 (4H, m), 0.88 (3H, t, J=7.6 Hz); LRMS (ESI) m/z 505 [M+H]$^+$.

Example 71

4-{3-Ethyl-4-(quinolin-3-yl)-1H-pyrrolo[2,3-b]pyridin-1-yl}-2-(1-methylpiperidin-4-ylamino)benzamide (71)

According to Example 1(6), a crude product of 4-{3-ethyl-4-(quinolin-3-yl)-1H-pyrrolo[2,3-b]pyridin-1-yl}-2-(1-methylpiperidin-4-ylamino)benzonitrile was prepared using compound (41h) instead of compound (1e) and using 4-amino-1-methylpiperidine instead of trans-aminocyclohexanol and was used in the subsequent reaction without being purified. According to Example 1(7), compound (71) (the second stage yield: 62%) was prepared as a white solid using 4-{3-ethyl-4-(quinolin-3-yl)-1H-pyrrolo[2,3-b]pyridin-1-yl}-2-(1-methylpiperidin-4-ylamino)benzonitrile instead of compound (1f).

$^1$H-NMR (DMSO-d$_6$) δ 9.06 (1H, d, J=2.2 Hz), 8.55 (1H, d, J=1.9 Hz), 8.41 (1H, d, J=4.9 Hz), 8.16-8.11 (2H, m), 7.90-7.69 (4H, m), 7.46 (1H, d, J=1.9 Hz), 7.24 (1H, d, J=4.9 Hz), 7.05 (1H, dd, J=1.9, 6.8 Hz), 3.52-3.41 (1H, m), 2.69-2.65 (2H, m), 2.38-2.29 (2H, m), 2.19 (3H, s), 2.15-2.02 (2H, m), 1.53-1.43 (2H, m), 0.83 (3H, t, J=7.6 Hz); LRMS (ESI) m/z 505 [M+H]$^+$.

Example 72

2-(Trans-4-aminocyclohexylamino)-4-{3-ethyl-4-(quinolin-3-yl)-1H-pyrrolo[2,3-b]pyridin-1-yl}benzamide (72)

According to Example 1(6), a crude product of 2-(trans-4-aminocyclohexylamino)-4-{3-ethyl-4-(quinolin-3-yl)-1H-pyrrolo[2,3-b]pyridin-1-yl}benzonitrile was prepared using compound (41h) instead of compound (1e) and using trans-cyclohexane-1,4-diamine instead of trans-aminocyclohexanol and was used in the subsequent reaction without being purified. According to Example 1(7), a (the second stage yield: 57%) was prepared as a white solid using 2-(trans-4-aminocyclohexylamino)-4-{3-ethyl-4-(quinolin-3-yl)-1H-pyrrolo[2,3-b]pyridin-1-yl}benzonitrile instead of compound (1f).

$^1$H-NMR (DMSO-d$_6$) δ 9.06 (1H, d, J=2.2 Hz), 8.56 (1H, d, J=1.6 Hz), 8.42-8.38 (2H, m), 8.16-8.11 (2H, m), 7.89-7.84 (2H, m), 7.78-7.69 (2H, m), 7.59-7.47 (4H, m), 7.25 (1H, d, J=4.9 Hz), 7.02 (1H, d, J=8.4 Hz), 2.34 (1H, q, J=7.3 Hz), 2.15-2.07 (2H, m), 1.87-1.79 (2H, m), 1.26-1.16 (4H, m), 0.83 (3H, t, J=7.3 Hz); LRMS (ESI) m/z 505 [M+H]$^+$.

Example 73

4-{3-Ethyl-4-(quinolin-3-yl)-1H-pyrrolo[2,3-b]pyridin-1-yl}-2-(2-morpholinoethylamino)benzamide (73)

According to Example 1(6), a crude product of 4-{3-ethyl-4-(quinolin-3-yl)-1H-pyrrolo[2,3-b]pyridin-1-yl}-2-(2-morpholinoethylamino)benzonitrile was prepared using compound (41h) instead of compound (1e) and using N-(2-aminoethyl)morpholine instead of trans-aminocyclohexanol and was used in the subsequent reaction without being purified. According to Example 1(7), compound (73) (the second stage yield: 58%) was prepared as a white solid using 4-{3-ethyl-4-(quinolin-3-yl)-1H-pyrrolo[2,3-b]pyridin-1-yl}-2-(2-morpholinoethylamino)benzonitrile instead of compound (1f).

$^1$H-NMR (DMSO-d$_6$) δ 9.06 (1H, d, J=2.2 Hz), 8.56 (1H, d, J=1.9 Hz), 8.52 (1H, t, J=4.9 Hz), 8.42 (1H, d, J=4.9 Hz), 8.16-8.11 (2H, m), 7.89-7.83 (2H, m), 7.78-7.69 (2H, m), 7.32 (1H, d, J=1.9 Hz), 7.25 (1H, d, J=4.9 Hz), 7.15 (1H, dd, J=2.2, 6.5 Hz), 3.62-3.59 (4H, m), 2.64-2.60 (2H, m), 2.33 (2H, q, J=7.3 Hz), 0.84 (3H, t, J=7.3 Hz); LRMS (ESI) m/z 521 [M+H]$^+$.

Example 74

4-{3-Ethyl-4-(quinolin-3-yl)-1H-pyrrolo[2,3-b]pyridin-1-yl}-2-(4-hydroxybutylamino)benzamide (74)

According to Example 1(6), a crude product of 4-{3-ethyl-4-(quinolin-3-yl)-1H-pyrrolo[2,3-b]pyridin-1-yl}-2-(4-hydroxybutylamino)benzonitrile was prepared using compound (41h) instead of compound (1e) and using 4-amino-1-butanol instead of trans-aminocyclohexanol and was used in the subsequent reaction without being purified. According to Example 1(7), compound (74) (the second stage yield: 38%) was prepared as a white solid using 4-{3-ethyl-4-(quinolin-3-yl)-1H-pyrrolo[2,3-b]pyridin-1-yl}-2-(4-hydroxybutylamino)benzonitrile instead of compound (1f).

$^1$H-NMR (DMSO-d$_6$) δ 9.06 (1H, s), 8.56 (1H, s), 8.45-8.42 (2H, m), 8.16-8.13 (2H, m), 7.87-7.69 (2H, m), 7.56-7.52 (2H, m), 7.31 (1H, s), 7.25 (1H, d, J=4.6 Hz), 7.13 (1H, d, J=7.8 Hz), 3.50-3.46 (2H, m), 3.23-3.21 (2H, m), 2.33 (2H, q, J=7.3 Hz), 1.68-1.56 (4H, m), 0.83 (3H, t, J=7.3 Hz); LRMS (ESI) m/z 480 [M+H]$^+$.

Example 75

4-{3-Ethyl-4-(quinolin-3-yl)-1H-pyrrolo[2,3-b]pyridin-1-yl}-2-{2-(ethylamino)ethylamino}benzamide (75)

According to Example 1(6), a crude product of 4-{3-ethyl-4-(quinolin-3-yl)-1H-pyrrolo[2,3-b]pyridin-1-yl}-2-{2-(ethylamino)ethylamino}benzonitrile was prepared using compound (41h) instead of compound (1e) and using N-ethylethylenediamine instead of trans-aminocyclohexanol and was used in the subsequent reaction without being purified. According to Example 1(7), (75) (the second stage yield: 19%) was prepared as a white solid using 4-{3-ethyl-4-(quinolin-3-yl)-1H-pyrrolo[2,3-b]pyridin-1-yl}-2-{2-(ethylamino)ethylamino}benzonitrile instead of compound (1f).

$^1$H-NMR (DMSO-d$_6$) δ 9.04 (1H, d, J=2.2 Hz), 8.53 (1H, d, J=1.9 Hz), 8.46-8.39 (2H, m), 8.14-8.09 (2H, m), 7.87-7.67 (4H, m), 7.30 (1H, d, J=2.2 Hz), 7.22 (1H, d, J=4.9 Hz), 7.11 (1H, dd, J=1.9, 6.8 Hz), 2.79 (2H, t, J=6.1 Hz), 7.59 (2H, q,

J=7.0 Hz), 2.31 (2H, q, J=7.3 Hz), 1.02 (3H, t, J=7.0 Hz), 0.81 (3H, t, J=7.3 Hz); LRMS (ESI) m/z 479 [M+H]$^+$.

Example 76

4-{3-Isopropyl-4-(quinolin-3-yl)-1H-pyrazolo[3,4-b]pyridin-1-yl}-2-(piperidin-4-ylamino)-benzamide (76)

According to Example 1(6), tert-butyl 4-{2-cyano-5-(3-isopropyl-4-(quinolin-3-yl)-1H-pyrazolo[3,4-b]pyridin-1-yl)phenylamino}piperidine-1-carboxylate was prepared using (6d) instead of compound (1e) and using tert-butyl 4-aminopiperidine-carboxylate instead of trans-4-hydroxycyclohexylamine and was used in the subsequent reaction without being purified. According to Example 1(7), tert-butyl 4-[(2-carbamoyl-5-(3-isopropyl-4-(quinolin-3-yl)-1H-pyrazolo[3,4-b]pyridin-1-yl)phenylamino]piperidine-1-carboxylate (the second stage yield: 72%) was prepared using tert-butyl 4-{2-cyano-5-(3-isopropyl-4-(quinolin-3-yl)-1H-pyrazolo[3,4-b]pyridin-1-yl)phenylamino}piperidine-1-carboxylate instead of compound (1f).

Tert-butyl 4-{2-carbamoyl-5-(3-isopropyl-4-(quinolin-3-yl)-1H-pyrazolo[3,4-b]pyridin-1-yl)phenylamino}piperidine-1-carboxylate (0.704 g) was dissolved in trifluoroacetic acid, followed by stirring at room temperature for 1 hr. The reaction solution was distributed between chloroform and saturated sodium bicarbonate water. The organic layer was washed with saturated saline and then dried over anhydrous sodium sulfate. After distillation of the solvent, the residue was purified by neutral silica gel column chromatography (chloroform/methanol) to obtain (76) (0.600 g, 99%) as a white solid.

$^1$H-NMR (DMSO-d$_6$) δ: 9.13 (1H, d, J=1.95 Hz), 8.74 (1H, d, J=4.88 Hz), 8.68 (1H, d, J=1.95 Hz), 8.50 (1H, d, J=7.32 Hz), 8.16 (1H, d, J=8.54 Hz), 8.13 (1H, d, J=8.54 Hz), 7.89 (1H, td, J=7.44, 1.22 Hz), 7.89 (1H, d, J=1.22 Hz), 7.79 (1H, d, J=8.78 Hz), 7.73 (1H, t, J=7.44 Hz), 7.46 (1H, dd, J=8.78, 1.95 Hz), 7.41 (1H, d, J=4.88 Hz), 7.15 (1H, s), 3.49-3.41 (1H, m), 2.99-2.92 (3H, m), 2.61 (2H, t, J=10.37 Hz), 2.01 (2H, d, J=10.37 Hz), 1.32 (2H, q, J=10.37 Hz), 1.04 (6H, d, J=6.83 Hz); LRMS (ESI) m/z 506 [M+H]$^+$.

Example 77

2-(Acetylpiperidin-4-ylamino)-4-{3-isopropyl-4-(quinolin-3-yl)-1H-pyrazolo[3,4-b]pyridin-1-yl}-benzamide (77)

Example 77(1)

4-{3-Isopropyl-4-(quinolin-3-yl)-1H-pyrazolo[3,4-b]pyridin-1-yl}-2-(piperidin-4-ylamino)benzonitrile (77a)

Tert-butyl 4-{2-cyano-5-(3-isopropyl-4-(quinolin-3-yl)-1H-pyrazolo[3,4-b]pyridin-1-yl)phenylamino}piperidine-1-carboxylate obtained in Example 76 was dissolved in trifluoroacetic acid, followed by stirring at room temperature for 1 hr. The reaction solution was distributed between chloroform and saturated sodium bicarbonate water, and the organic layer was washed with saturated saline and then dried over anhydrous sodium sulfate. After distillation of the solvent, the residue was purified by neutral silica gel column chromatography (chloroform/methanol) to obtain (77a) (the second stage yield: 56%) as a white solid.

Example 77(2)

2-(Acetylpiperidin-4-ylamino)-4-{3-isopropyl-4-(quinolin-3-yl)-1H-pyrazolo[3,4-b]pyridin-1-yl}-benzamide (77)

Compound (77a) (0.050 g) and triethylamine (0.017 mL) were dissolved in chloroform (1.0 mL), and acetyl chloride (0.017 mL) was added to the resulting mixture, followed by stirring at room temperature for 15 hr. The reaction solution was distributed between chloroform and water. The organic layer was washed with saturated saline and then dried over anhydrous sodium sulfate. The solvent was distilled away to obtain 2-(acetylpiperidin-4-ylamino)-4-{3-isopropyl-4-(quinolin-3-yl)-1H-pyrazolo[3,4-b]pyridin-1-yl}benzonitrile, which was used in the subsequent reaction without being purified. According to Example 1(7), compound (77) (the second stage yield: 68%) was prepared as a white solid using 2-(acetylpiperidin-4-ylamino)-4-{3-isopropyl-4-(quinolin-3-yl)-1H-pyrazolo[3,4-b]pyridin-1-yl}benzonitrile instead of compound (1f).

$^1$H-NMR (DMSO-d$_6$) δ 9.14 (1H, d, J=1.95 Hz), 8.77 (1H, d, J=4.88 Hz), 8.69 (1H, d, J=1.95 Hz), 8.60 (1H, d, J=7.32 Hz), 8.16 (1H, d, J=8.54 Hz), 8.14 (1H, d, J=8.54 Hz), 7.94 (1H, d, J=1.22 Hz), 7.90 (1H, td, J=7.44, 1.22 Hz), 7.83 (1H, d, J=8.78 Hz), 7.74 (1H, t, J=7.44 Hz), 7.47 (1H, dd, J=8.78, 1.95 Hz), 7.42 (1H, d, J=4.88 Hz), 7.15 (1H, s), 4.14 (1H, d, J=13.66 Hz), 3.79 (1H, d, J=13.66 Hz), 3.65-3.58 (1H, m), 3.02-2.95 (2H, m), 2.20-2.05 (2H, m), 2.03 (3H, s), 1.48 (1H, d, J=10.00 Hz), 1.34 (1H, d, J=10.00 Hz), 1.06 (6H, d, J=6.83 Hz); LRMS (ESI) m/z 548 [M+H]$^+$.

Example 78

2-{1-(2,6-Dihydroxypyrimidine-4-carbonyl)piperidin-4-ylamino}-4-{3-isopropyl-4-(quinolin-3-yl)-1H-pyrazolo[3,4-b]pyridin-1-yl}benzamide (78)

Isoorotic acid (0.021 g), 1-ethyl-3-(3-dimethylaminopropyl)carbodiimide hydrochloride (0.029 g), and 1-hydroxybenzotriazole monohydrate (0.016 g) were added to a solution of compound (77a) (0.050 g) in DMF (1.0 mL), followed by stirring under argon flow at room temperature for 15 hr. The reaction solution was distributed between ethyl acetate and water, and the organic layer was washed with saturated saline. The organic layer after the washing was dried over anhydrous sodium sulfate, and the solvent was distilled away to obtain 2-{1-(2,6-dihydroxypyrimidine-4-carbonyl)piperidin-4-ylamino}-4-{3-isopropyl-4-(quinolin-3-yl)-1H-pyrazolo[3,4-b]pyridin-1-yl}benzonitrile, which was used in the subsequent reaction without being purified. According to Example 1(7), compound (78) (0.026 g, the second stage yield: 39%) was prepared as a white solid using 2-{1-(2,6-dihydroxypyrimidine-4-carbonyl)piperidin-4-ylamino}-4-{3-isopropyl-4-(quinolin-3-yl)-1H-pyrazolo[3,4-b]pyridin-1-yl}benzonitrile instead of compound (1f).

$^1$H-NMR (DMSO-d$_6$) δ: 9.13 (1H, d, J=1.95 Hz), 8.76 (1H, d, J=4.88 Hz), 8.68 (1H, d, J=1.95 Hz), 8.59 (1H, d, J=7.32 Hz), 8.17 (1H, d, J=8.54 Hz), 8.14 (1H, d, J=8.54 Hz), 7.94 (1H, d, J=1.22 Hz), 7.90 (1H, td, J=7.44, 1.22 Hz), 7.83 (1H, d, J=8.78 Hz), 7.74 (1H, t, J=7.44 Hz), 7.63 (2H, s), 7.47 (1H, dd, J=8.78, 1.95 Hz), 7.42 (1H, d, J=4.88 Hz), 7.15 (1H, s), 4.15 (1H, d, J=13.66 Hz), 3.74-3.68 (2H, m), 3.06 (1H, t, J=13.66 Hz), 2.96 (1H, tt, J=6.83, 6.83 Hz), 2.12-2.05 (2H, m), 1.45 (1H, d, J=10.00 Hz), 1.34 (1H, d, J=10.00 Hz), 1.06 (6H, d, J=6.83 Hz); LRMS (ESI) m/z 644 [M+H]$^+$.

Example 79

2-{1-(2-Aminoacetyl)piperidin-4-ylamino}-4-{3-isopropyl-4-(quinolin-3-yl)-1H-pyrazolo[3,4-b]pyridin-1-yl}benzamide (79)

N-(Tert-butoxycarbonyl)glycine (0.021 g), 1-ethyl-3-(3-dimethylaminopropyl)carbodiimide hydrochloride (0.029 g), and 1-hydroxybenzotriazole monohydrate (0.016 g) were added to a solution of compound (77a) (0.050 g) in DMF (1.0 mL), followed by stirring under argon flow at room temperature for 15 hr. The reaction solution was distributed between ethyl acetate and water, and the organic layer was washed with saturated saline. The organic layer after the washing was dried over anhydrous sodium sulfate, and then the solvent was distilled away to obtain tert-butyl 2-{4-(2-cyano-5-(3-isopropyl-4-(quinolin-3-yl)-1H-pyrazolo[3,4-b]pyridin-1-yl)phenylamino)piperidin-1-yl}-2-oxaethylcarbamate, which was used in the subsequent reaction without being purified. According to Example 1(7), tert-butyl 2-{4-(2-carbamoyl-5-(3-isopropyl-4-(quinolin-3-yl)-1H-pyrazolo[3,4-b]pyridin-1-yl)phenylamino)piperidin-1-yl}-2-oxaethylcarbamate was prepared using tert-butyl 2-{4-(2-cyano-5-(3-isopropyl-4-(quinolin-3-yl)-1H-pyrazolo[3,4-b]pyridin-1-yl)phenylamino)piperidin-1-yl}-2-oxaethylcarbamate instead of (1f) and was used in the subsequent reaction without being purified. Tert-butyl 2-{4-(2-carbamoyl-5-(3-isopropyl-4-(quinolin-3-yl)-1H-pyrazolo[3,4-b]pyridin-1-yl)phenylamino)piperidin-1-yl}-2-oxaethylcarbamate was dissolved in trifluoroacetic acid, followed by stirring at room temperature for 1 hr. The reaction solution was distributed between chloroform and saturated sodium bicarbonate water. The organic layer was washed with saturated saline and then dried over anhydrous sodium sulfate. After distillation of the solvent, the residue was purified by neutral silica gel column chromatography (chloroform/methanol) to obtain compound (79) (0.035 g, the third stage yield: 55%) as a white solid.

$^1$H-NMR (DMSO-d$_6$) δ: 9.14 (1H, d, J=1.95 Hz), 8.77 (1H, d, J=4.88 Hz), 8.69 (1H, d, J=1.95 Hz), 8.59 (1H, d, J=7.32 Hz), 8.17 (1H, d, J=8.54 Hz), 8.14 (1H, d, J=8.54 Hz), 7.94 (1H, d, J=1.22 Hz), 7.90 (1H, td, J=7.44, 1.22 Hz), 7.83 (1H, d, J=8.78 Hz), 7.74 (1H, t, J=7.44 Hz), 7.47 (1H, dd, J=8.78, 1.95 Hz), 7.42 (1H, d, J=4.88 Hz), 7.15 (1H, s), 4.15 (1H, d, J=13.66 Hz), 3.74-3.68 (2H, m), 3.31 (2H, s), 3.06 (1H, t, J=13.66 Hz), 2.96 (1H, tt, J=6.83, 6.83 Hz), 2.12-2.05 (2H, m), 1.45 (1H, d, J=10.00 Hz), 1.34 (1H, d, J=10.00 Hz), 1.06 (6H, d, J=6.83 Hz); LRMS (ESI) m/z 563 [M+H]$^+$.

Example 80

4-{3-Isopropyl-4-(quinolin-3-yl)-1H-pyrazolo[3,4-b]pyridin-1-yl}-3-methylbenzamide (80)

4-Fluoro-3-methylbenzonitrile (0.077 g) and cesium carbonate (0.203 g) were added to a solution of compound (6c) (0.150 g) in DMF (1.73 mL), followed by stirring at 80° C. for 18 hr. The reaction solution was distributed between ethyl acetate and water. The organic layer was washed with saturated saline and then dried over anhydrous sodium sulfate. The solvent was distilled away, and the residue was purified by neutral silica gel column chromatography (hexane/ethyl acetate) to obtain 4-{3-isopropyl-4-(quinolin-3-yl)-1H-pyrazolo[3,4-b]pyridin-1-yl}-3-methylbenzonitrile (0.154 g, 73%). This 4-{3-isopropyl-4-(quinolin-3-yl)-1H-pyrazolo[3,4-b]pyridin-1-yl}-3-methylbenzonitrile was dissolved in DMSO (5.0 mL) and ethanol (5.0 mL). A 4 N aqueous sodium hydroxide solution (0.195 mL) and a 30% hydrogen peroxide solution (0.088 mL) were added to the resulting solution, followed by stirring at room temperature for 30 min. Water was added to the reaction solution, and the precipitate was collected by filtration, washed with diethyl ether, and dried under reduced pressure to obtain compound (80) (0.135 g, 83%) as a white solid.

$^1$H-NMR (DMSO-d$_6$) δ: 9.88 (1H, d, J=2.20 Hz), 9.43 (1H, d, J=2.20 Hz), 9.35 (1H, d, J=4.63 Hz), 8.87 (2H, t, J=9.03 Hz), 8.81 (1H, brs), 8.70 (1H, d, J=1.46 Hz), 8.63-8.59 (2H, m), 8.46 (1H, td, J=7.56, 0.73 Hz), 8.30 (1H, d, J=8.05 Hz), 8.20 (1H, brs), 8.09 (1H, d, J=4.63 Hz), 3.72 (1H, tt, J=6.83, 6.83 Hz), 2.94 (3H, s), 1.76 (6H, d, J=6.83 Hz); LRMS (ESI) m/z 422 [M+H]$^+$.

Example 81

4-{3-Isopropyl-4-(quinolin-3-yl)-1H-pyrazolo[3,4-b]pyridin-1-yl}-2-methylbenzamide (81)

According to Example 80, compound (81) (the second stage yield: 59%) was prepared as a white solid using 4-fluoro-2-methylbenzonitrile instead of 4-fluoro-3-methylbenzonitrile.

1H-NMR (DMSO-d$_6$) δ: 9.15 (1H, d, J=2.20 Hz), 8.78 (1H, d, J=4.63 Hz), 8.70 (1H, d, J=2.20 Hz), 8.21 (1H, dd, J=7.56, 1.22 Hz), 8.20 (1H, s), 8.17 (1H, d, J=8.54 Hz), 8.14 (1H, d, J=7.56 Hz), 7.90 (1H, dt, J=1.22, 7.56 Hz), 7.80 (1H, brs), 7.75 (1H, t, J=7.56 Hz), 7.61 (1H, d, J=8.54 Hz), 7.43 (1H, d, J=4.63 Hz), 7.42 (1H, brs), 2.97 (1H, tt, J=6.83, 6.83 Hz), 2.53 (3H, s), 1.07 (6H, d, J=6.83 Hz); LRMS (ESI) m/z 422 [M+H]$^+$.

Example 82

3-Methyl-4-{4-(quinolin-3-yl)-3-(trifluoromethyl)-1H-pyrazolo[3,4-b]pyridin-1-yl}benzamide (82)

4-Fluoro-3-methylbenzonitrile (0.052 g) and cesium carbonate (0.150 g) were added to a solution of compound (1d) (0.092 g) in 1-methyl-2-pyrrolidone (hereinafter referred to as NMP) (1.0 mL), followed by stirring at 120° C. for 60 hr. Water was added to the reaction solution, and the precipitate was collected by filtration and was washed by sprinkling water to obtain 3-methyl-4-{4-(quinolin-3-yl)-3-(trifluoromethyl)-1H-pyrazolo[3,4-b]pyridin-1-yl}benzonitrile (11%). According to Example 1(7), compound (82) (64%) was prepared as a white solid using 3-methyl-4-{4-(quinolin-3-yl)-3-(trifluoromethyl)-1H-pyrazolo[3,4-b]pyridin-1-yl}benzonitrile instead of compound (1f).

$^1$H-NMR (DMSO-d$_6$) δ: 9.06 (1H, d, J=1.95 Hz), 8.84 (1H, d, J=4.63 Hz), 8.62 (1H, d, J=1.95 Hz), 8.16 (1H, d, J=8.54 Hz), 8.14 (1H, brs), 8.10 (1H, d, J=7.56 Hz), 8.03 (1H, d, J=1.46 Hz), 7.94-7.87 (2H, m), 7.73 (1H, t, J=7.56 Hz), 7.66 (1H, d, J=8.29 Hz), 7.64 (1H, d, J=4.63 Hz), 7.55 (1H, brs), 2.17 (3H, s); LRMS (ESI) m/z 448 [M+H]$^+$.

Example 83

2-(Hydroxycyclohexylamino)-4-{3-isopropyl-4-(4-(4-methoxyphenyl)-1H-imidazol-1-yl)-1H-pyrazolo[3,4-b]pyridin-1-yl}benzamide (83)

According to Example 36(2), 2-bromo-4-{3-isopropyl-4-(4-(4-methoxyphenyl)-1H-imidazol-1-yl)-1H-pyrazolo[3,4- b]pyridin-1-yl}benzonitrile was prepared using 4-(4-methoxyphenyl)-1H-imidazole instead of imidazole; and according to Example 36(3), (83) (the third stage yield: 19%) was prepared as a white solid using 2-bromo-4-{3-isopropyl-4-(4-(4-methoxyphenyl)-1H-imidazol-1-yl)-1H-pyrazolo[3,4-b]pyridin-1-yl}benzonitrile instead of compound (36b).

$^1$H-NMR (DMSO-$d_6$) δ: 8.77 (1H, d, J=4.88 Hz), 8.42 (1H, d, J=7.32 Hz), 8.23 (1H, d, J=1.22 Hz), 8.14 (1H, s), 7.82-7.77 (5H, m), 7.47 (1H, d, J=4.88 Hz), 7.43 (1H, dd, J=8.54, 1.95 Hz), 7.17 (1H, brs), 6.99 (2H, d, J=8.54 Hz), 4.59 (1H, d, J=4.15 Hz), 3.78 (3H, s), 3.54-3.47 (1H, m), 3.22 (1H, tt, J=6.59, 6.59 Hz), 2.10 (2H, d, J=11.22 Hz), 1.88 (2H, d, J=11.22 Hz), 1.36-1.23 (5H, m), 1.14 (6H, d, J=6.59 Hz); LRMS (ESI) m/z 566 [M+H]$^+$.

Example 84

2-(Hydroxycyclohexylamino)-4-{3-isopropyl-4-(4-(pyridin-3-yl)-1H-imidazol-1-yl)-1H-pyrazolo[3,4-b]pyridin-1-yl}benzamide (84)

According to Example 83, compound (84) (the third stage yield: 37%) was prepared as a white solid using 4-(pyridin-3-yl)-1H-imidazole dihydrochloride instead of 4-(4-methoxyphenyl)-1H-imidazole.

$^1$H-NMR (DMSO-$d_6$) δ: 9.11 (1H, d, J=1.71 Hz), 8.80 (1H, d, J=4.88 Hz), 8.48 (1H, dd, J=4.76, 1.34 Hz), 8.42 (1H, s), 8.41 (1H, s), 8.36 (1H, s), 8.22 (1H, d, J=7.81 Hz), 7.85 (1H, s), 7.79 (1H, d, J=1.95 Hz), 7.77 (1H, s), 7.51 (1H, d, J=4.88 Hz), 7.45 (1H, dd, J=7.81, 4.88 Hz), 7.44 (1H, dd, J=8.29, 1.71 Hz), 7.16 (1H, brs), 4.58 (1H, d, J=3.90 Hz), 3.55-3.46 (1H, m), 3.19 (1H, tt, J=6.59, 6.59 Hz), 2.10 (2H, d, J=10.25 Hz), 1.88 (2H, d, J=10.25 Hz), 1.38-1.23 (5H, m), 1.14 (6H, d, J=6.59 Hz); LRMS (ESI) m/z 537 [M+H]$^+$.

Example 85

2-(Hydroxycyclohexylamino)-4-{3-isopropyl-4-(4-(pyridin-4-yl)-1H-imidazol-1-yl)-1H-pyrazolo[3,4-b]pyridin-1-yl}benzamide (85)

According to Example 83, compound (85) (the third stage yield: 37%) was prepared as a white solid using 4-(pyridin-4-yl)-1H-imidazole dihydrochloride instead of 4-(4-methoxyphenyl)-1H-imidazole.

$^1$H-NMR (DMSO-$d_6$) δ: 8.82 (1H, d, J=4.88 Hz), 8.61 (2H, d, J=5.12 Hz), 8.57 (1H, s), 8.44 (1H, d, J=7.07 Hz), 8.40 (1H, s), 7.85 (2H, d, J=5.12 Hz), 7.80 (1H, d, J=8.66 Hz), 7.80 (1H, d, J=1.83 Hz), 7.80 (1H, brs), 7.53 (1H, d, J=4.88 Hz), 7.44 (1H, dd, J=8.66, 1.83 Hz), 7.18 (1H, brs), 4.61 (1H, d, J=4.15 Hz), 3.56-3.49 (1H, m), 3.16 (1H, tt, J=6.83, 6.83 Hz), 2.12 (2H, d, J=11.22 Hz), 1.89 (2H, d, J=11.22 Hz), 1.40-1.24 (4H, m), 1.14 (6H, d, J=6.83 Hz); LRMS (ESI) m/z 537 [M+H]$^+$.

Example 86

2-(Hydroxycyclohexylamino)-4-{3-isopropyl-4-(4-(pyrimidin-5-yl)-1H-imidazol-1-yl)-1H-pyrazolo[3,4-b]pyridin-1-yl}benzamide (86)

According to Example 83, compound (86) (the third stage yield: 17%) was prepared as a yellowish-white solid using (pyrimidin-5-yl)-1H-imidazole instead of 4-(4-methoxyphenyl)-1H-imidazole.

$^1$H-NMR (DMSO-$d_6$) δ: 9.27 (2H, s), 9.11 (1H, s), 8.81 (1H, d, J=4.88 Hz), 8.54 (1H, s), 8.43 (1H, d, J=7.07 Hz), 8.41 (1H, s), 7.87 (1H, s), 7.79 (1H, s), 7.52 (1H, d, J=4.88 Hz), 7.52 (1H, brs), 7.43 (1H, d, J=8.05 Hz), 7.17 (1H, s), 4.59 (1H, d, J=4.39 Hz), 3.54-3.46 (1H, m), 3.17 (1H, tt, J=7.07, 7.07 Hz), 2.10 (2H, d, J=9.27 Hz), 1.87 (2H, d, J=9.27 Hz), 1.33-1.25 (5H, m), 1.13 (6H, d, J=7.07 Hz); LRMS (ESI) m/z 538 [M+H]$^+$.

Example 87

2-(Hydroxycyclohexylamino)-4-{3-isopropyl-4-(5-methyl-4-(pyridin-3-yl)-1H-imidazol-1-yl)-1H-pyrazolo[3,4-b]pyridin-1-yl}benzamide (87)

According to Example 83, compound (87) (the third stage yield: 10%) was prepared using 5-methyl-4-(pyridin-3-yl)-1H-imidazole instead of 4-(4-methoxyphenyl)-1H-imidazole.

$^1$H-NMR (DMSO-$d_6$) δ: 8.97 (1H, s), 8.84 (1H, d, J=4.88 Hz), 8.51 (1H, d, J=4.15 Hz), 8.42 (1H, d, J=7.07 Hz), 8.19 (1H, s), 8.12 (1H, d, J=7.81 Hz), 7.86 (1H, brs), 7.80 (1H, s), 7.78 (1H, d, J=7.81 Hz), 7.56-7.41 (3H, m), 7.17 (1H, brs), 4.59 (1H, d, J=4.15 Hz), 3.54-3.47 (1H, m), 2.81 (1H, tt, J=6.59, 6.34 Hz), 2.31 (3H, s), 2.10 (2H, d, J=10.98 Hz), 1.88 (2H, d, J=10.98 Hz), 1.38-1.23 (8H, m), 1.03 (3H, d, J=6.34 Hz); LRMS (ESI) m/z 551 [M+H]$^+$.

Example 88

4-{4-(4-(Furan-2-yl)-1H-imidazol-1-yl)-3-isopropyl-1H-pyrazolo[3,4-b]pyridin-1-yl}-2-(4-hydroxycyclohexylamino)benzamide (88)

According to Example 83, compound (88) (the third stage yield: 3%) was prepared as a white solid using 4-(furan-2-yl)-1H-imidazole instead of 4-(4-methoxyphenyl)-1H-imidazole.

$^1$H-NMR (DMSO-$d_6$) δ: 8.77 (1H, d, J=4.95 Hz), 8.41 (1H, d, J=8.52 Hz), 8.27 (1H, d, J=1.32 Hz), 8.02 (1H, d, J=1.32 Hz), 7.79 (1H, d, J=3.30 Hz), 7.77 (1H, d, J=3.30 Hz), 7.69 (1H, d, J=1.81 Hz), 7.47 (1H, d, J=4.95 Hz), 7.42 (1H, dd, J=8.57, 1.81 Hz), 6.69 (1H, d, J=3.30 Hz), 6.57 (1H, dd, J=3.30, 1.81 Hz), 4.57 (1H, d, J=4.29 Hz), 3.55-3.46 (1H, m), 3.15 (1H, tt, J=6.92, 6.92 Hz), 2.09 (2H, d, J=10.55 Hz), 1.87 (2H, d, J=10.55 Hz), 1.40-1.19 (5H, m), 1.13 (6H, d, J=6.92 Hz); LRMS (ESI) m/z 526 [M+H]$^+$.

Example 89

2-(Hydroxycyclohexylamino)-4-{3-isopropyl-4-(4-(1-methyl-1H-pyrazol-4-yl)-1H-imidazol-1-yl)-1H-pyrazolo[3,4-b]pyridin-1-yl}benzamide (89)

According to Example 83, compound (89) (the third stage yield: 29%) was prepared as a white solid using 4-(1-methyl-1H-pyrazol-4-yl)-1H-imidazole hydrochloride instead of 4-(4-methoxyphenyl)-1H-imidazole.

$^1$H-NMR (DMSO-$d_6$) δ: 8.75 (1H, d, J=4.95 Hz), 8.41 (1H, d, J=7.25 Hz), 8.18 (1H, d, J=1.15 Hz), 7.97 (1H, s), 7.86 (1H, d, J=1.15 Hz), 7.83 (1H, brs), 7.79 (1H, d, J=1.81 Hz), 7.77 (1H, d, J=8.74 Hz), 7.73 (1H, s), 7.44 (1H, d, J=4.95 Hz), 7.42 (1H, dd, J=8.74, 1.81 Hz), 7.15 (1H, brs), 4.57 (1H, d, J=4.45 Hz), 3.87 (3H, s), 3.54-3.47 (1H, m), 3.34-3.30 (1H, m), 3.19 (1H, tt, J=6.76, 6.76 Hz), 2.09 (2H, d, J=10.72 Hz), 1.88 (2H, d, J=10.72 Hz), 1.36-1.23 (4H, m), 1.13 (6H, d, J=6.76 Hz).

Example 90

4-{4-(4-(Furan-3-yl)-1H-imidazol-1-yl)-3-isopropyl-1H-pyrazolo[3,4-b]pyridin-1-yl}-2-(4-hydroxycyclohexylamino)benzamide (90)

According to Example 83, compound (90) (the third stage yield: 23%) was prepared as a white solid using 4-(furan-3-yl)-1H-imidazole instead of 4-(4-methoxyphenyl)-1H-imidazole.

$^1$H-NMR (DMSO-$d_6$) δ: 8.77 (1H, d, J=5.11 Hz), 8.41 (1H, d, J=7.09 Hz), 8.23 (1H, s), 8.01 (1H, s), 7.98 (1H, s), 7.79 (1H, s), 7.77 (1H, d, J=6.76 Hz), 7.71 (1H, s), 7.45 (1H, d, J=5.11 Hz), 7.42 (1H, dd, J=8.41, 1.65 Hz), 6.84 (1H, s), 4.57 (1H, d, J=4.29 Hz), 3.57-3.45 (1H, m), 3.18 (1H, tt, J=6.76, 6.76 Hz), 2.10 (2H, d, J=10.39 Hz), 1.88 (2H, d, J=10.39 Hz), 1.40-1.22 (4H, m), 1.13 (6H, d, J=6.76 Hz); LRMS (ESI) m/z 526 [M+H]$^+$.

Example 91

2-(4-Hydroxycyclohexylamino)-4-{3-isopropyl-(4-(4-(thiophen-3-yl)-1H-imidazol-1-yl)-1H-pyrazolo[3,4-b]pyridin-1-yl}benzamide (91)

According to Example 83, compound (91) (the third stage yield: 17%) was prepared as a white solid using 4-(thiophen-3-yl)-1H-imidazole instead of 4-(4-methoxyphenyl)-1H-imidazole.

$^1$H-NMR (DMSO-$d_6$) δ: 8.77 (1H, d, J=4.78 Hz), 8.42 (1H, d, J=7.25 Hz), 8.24 (1H, s), 8.10 (1H, s), 7.79-7.76 (3H, m), 7.60 (1H, dd, J=4.95, 2.80 Hz), 7.52 (1H, d, J=4.95 Hz), 7.46 (1H, d, J=5.11 Hz), 7.43 (1H, dd, J=8.90, 1.65 Hz), 4.58 (1H, d, J=4.29 Hz), 3.55-3.48 (1H, m), 3.20 (1H, tt, J=6.59, 6.59 Hz), 2.10 (2H, d, J=9.73 Hz), 1.88 (2H, d, J=9.73 Hz), 1.40-1.24 (4H, m), 1.14 (6H, d, J=6.59 Hz); LRMS (ESI) m/z 542 [M+H]$^+$.

Example 92

4-{4-(1'H-1,4'-Biimidazol-1'-yl)-3-isopropyl-1H-pyrazolo[3,4-b]pyridin-1-yl}-2-(4-hydroxycyclohexylamino)benzamide (92)

According to Example 83, compound (92) (the third stage yield: 11%) was prepared as a white solid using 1'H-1,4'-biimidazole instead of 4-(4-methoxyphenyl)-1H-imidazole.

$^1$H-NMR (DMSO-$d_6$) δ: 8.75 (1H, d, J=4.95 Hz), 8.41 (1H, d, J=7.25 Hz), 8.18 (1H, d, J=1.15 Hz), 7.97 (1H, s), 7.86 (1H, d, J=1.15 Hz), 7.80 (1H, s), 7.78 (1H, d, J=7.25 Hz), 7.73 (1H, s), 7.44 (1H, d, J=4.95 Hz), 7.42 (1H, dd, J=8.74, 1.98 Hz), 4.57 (1H, d, J=4.45 Hz), 3.87 (3H, s), 3.57-3.53 (1H, m), 3.35-3.25 (1H, m), 3.19 (1H, tt, J=6.76, 6.76 Hz), 2.09 (2H, d, J=10.72 Hz), 1.88 (2H, d, J=10.72 Hz), 1.36-1.23 (4H, m), 1.13 (6H, d, J=6.76 Hz).

Example 93

2-(Hydroxycyclohexylamino)-4-{3-isopropyl-4-(4-(1-benzyl-1H-pyrazol-4-yl)-1H-imidazol-1-yl)-1H-pyrazolo[3,4-b]pyridin-1-yl}benzamide (93)

According to Example 83, compound (93) (the third stage yield: 49%) was prepared as a white solid using 4-(1-benzyl-1H-pyrazol-4-yl)-1H-imidazole hydrochloride instead of 4-(4-methoxyphenyl)-1H-imidazole.

$^1$H-NMR (DMSO-$d_6$) δ: 8.75 (1H, d, J=4.88 Hz), 8.40 (1H, d, J=7.32 z), 8.19 (1H, s), 8.11 (1H, s), 7.88 (1H, s), 7.79 (2H, d, J=5.61 Hz), 7.78 (1H, d, J=10.98 Hz), 7.42 (1H, d, J=4.88 Hz), 7.41 (1H, dd, J=8.54, 1.95 Hz), 7.38-7.33 (2H, m), 7.32-7.27 (3H, m), 5.36 (2H, s), 4.60 (1H, d, J=4.15 Hz), 3.53-3.48 (1H, m), 3.19 (1H, tt, J=6.83, 6.83 Hz), 2.09 (2H, d, J=11.71 Hz), 1.87 (2H, d, J=11.71 Hz), 1.38-1.22 (4H, m), 1.12 (6H, d, J=6.83 Hz); LRMS (ESI) m/z 616 [M+H]$^+$.

Example 94

4-{4-(4-(1-(Benzyloxyethyl)-1H-pyrazol-4-yl)-1H-imidazol-1-yl)-3-isopropyl-1H-pyrazolo[3,4-b]pyridin-1-yl}-2-(4-hydroxycyclohexylamino)benzamide (94)

According to Example 83, compound (94) (the third stage yield: 53%) was prepared as a white solid using 4-{1-(benzyloxyethyl)-1H-pyrazol-4-yl}-1H-imidazole hydrochloride instead of 4-(4-methoxyphenyl)-1H-imidazole.

$^1$H-NMR (DMSO-$d_6$) δ: 8.76 (1H, d, J=4.88 Hz), 8.40 (1H, d, J=7.07 Hz), 8.19 (1H, d, J=0.98 Hz), 8.03 (1H, s), 7.88 (1H, d, J=0.98 Hz), 7.79 (1H, s), 7.78 (1H, s), 7.78 (1H, d, J=11.22 Hz), 7.56 (1H, s), 7.54 (1H, d, J=10.73 Hz), 7.49 (1H, dd, J=6.83, 3.42 Hz), 7.44-7.41 (2H, m), 7.32-7.24 (2H, m), 4.60 (1H, d, J=4.15 Hz), 4.48 (2H, s), 4.34 (2H, t, J=5.24 Hz), 3.81 (2H, t, J=5.24 Hz), 3.54-3.47 (1H, m), 3.20 (1H, tt, J=6.83, 6.83 Hz), 2.10 (2H, d, J=11.22 Hz), 1.87 (2H, d, J=11.22 Hz), 1.38-1.22 (4H, m), 1.13 (6H, d, J=6.83 Hz); LRMS (ESI) m/z 660 [M+H]$^+$.

Example 95

4-{4-(4-(1H-Pyrazol-4-yl)-1H-imidazol-1-yl)-3-isopropyl-1H-pyrazolo[3,4-b]pyridin-1-yl}-2-(4-hydroxycyclohexylamino)benzamide (95)

Compound (93) (0.010 g) was dissolved in ethanol (1.0 mL). Palladium hydroxide (0.020 g) and cyclohexene (0.5 mL) were added to the resulting solution, followed by stirring under a nitrogen atmosphere at 80° C. for 24 hr. The reaction solution was filtered through celite, and the solvent was distilled away. The residue was purified by neutral silica gel column chromatography (chloroform/methanol) to obtain compound (95) (0.005 g, 56%) as a white solid.

$^1$H-NMR (DMSO-$d_6$) δ: 12.87 (1H, s), 8.76 (1H, d, J=4.88 Hz), 8.40 (1H, d, J=7.07 Hz), 8.19 (1H, d, J=1.22 Hz), 8.02 (1H, s), 7.88 (1H, d, J=1.22 Hz), 7.82 (1H, s), 7.79 (1H, d, J=2.20 Hz), 7.77 (1H, d, J=8.78 Hz), 7.44 (1H, d, J=4.88 Hz), 7.42 (1H, dd, J=8.78, 2.20 Hz), 4.61 (1H, d, J=4.39 Hz), 3.54-3.48 (1H, m), 3.20 (1H, tt, J=6.83, 6.83 Hz), 2.10 (2H, d, J=11.71 Hz), 1.88 (2H, d, J=11.71 Hz), 1.38-1.22 (4H, m), 1.13 (6H, d, J=6.83 Hz); LRMS (ESI) m/z 526 [M+H]$^+$.

Example 96

2-(4-Hydroxycyclohexylamino)-4-{4-(4-(1-hydroxymethyl)-(1H-pyrazol-4-yl)-1H-imidazol-1-yl)-3-isopropyl-1H-pyrazolo[3,4-b]pyridin-1-yl}benzamide (96)

According to Example 95, compound (96) (16%) was prepared as a white solid using compound (94) instead of compound (93).

$^1$H-NMR (DMSO-$d_6$) δ: 8.76 (1H, d, J=4.88 Hz), 8.41 (1H, d, J=7.07 Hz), 8.19 (1H, s), 8.00 (1H, s), 7.88 (1H, s), 7.84 (1H, brs), 7.80 (1H, s), 7.78 (1H, d, J=9.03 Hz), 7.76 (1H, s), 7.43 (1H, d, J=4.88 Hz), 7.42 (1H, dd, J=7.07, 1.71 Hz), 7.15 (1H, brs), 4.93 (1H, t, J=5.45 Hz), 4.59 (1H, d, J=4.39 Hz), 4.17 (2H, t, J=5.45 Hz), 3.76 (2H, q, J=5.45 Hz), 3.54-3.46 (1H, m), 3.20 (1H, tt, J=6.83, 6.83 Hz), 2.10 (2H, d, J=10.98 Hz), 1.88 (2H, d, J=10.98 Hz), 1.38-1.22 (5H, m), 1.13 (6H, d, J=6.83 Hz); LRMS (ESI) m/z 556 [M+H]$^+$.

Example 97

2-(4-Hydroxycyclohexylamino)-4-{3-methyl-4-(4-phenyl-1H-imidazol-1-yl)-1H-pyrrolo[2,3-b]pyridin-1-yl}benzamide (97)

Example 97(1)

4-Chloro-3-methyl-1-{(2-(trimethylsilyl)ethoxy)methyl}-1H-pyrrolo[2,3-b]pyridine (97a)

Compound (40d) (1.0 g) was dissolved in DMF (20 mL), and sodium hydride (0.288 g, a 55% dispersion in paraffin liquid) was added to the resulting solution at 0° C., followed by stirring for 10 min. Then, {2-(chloromethoxy)ethyl}silane (1.16 mL) was added to the reaction solution, followed by stirring at room temperature for 1 hr. Ice water was added to the reaction solution, followed by extraction with ethyl acetate. The organic layer was washed with saturated saline and was then dried over anhydrous sodium sulfate. The solvent was distilled away, and the residue was purified by neutral silica gel column chromatography (hexane/ethyl acetate) to obtain compound (97a) (4.50 g, 84%) as a colorless oily substance.

$^1$H-NMR (CDCl$_3$) δ: 8.21 (1H, d, J=5.12 Hz), 7.19 (1H, s), 7.10 (1H, d, J=5.12 Hz), 5.68 (2H, s), 3.58 (2H, t, J=8.17 Hz), 2.43 (3H, s), 0.97 (2H, t, J=8.17 Hz), 0.00 (9H, s); LRMS (ESI) m/z 297 [M+H]$^+$.

Example 97(2)

3-Methyl-4-(4-phenyl-1H-imidazol-1-yl)-1-{(2-(trimethylsilyl)ethoxy)methyl}-1H-pyrrolo[2,3-b]pyridine (97b)

Compound (97a) (2.00 g), copper(I) oxide (0.048 g), 4,7-dimethoxy-1,10-phenanthroline (0.243 g), cesium carbonate (3.07 g), polyethylene glycol (Mn=3400) (1.35 g), and 4-phenyl-1H-imidazole (1.17 g) were suspended in NMP, followed by stirring at 150° C. for 48 hr. The reaction solution was suspended in ethyl acetate, and insoluble matters were filtered through celite. The filtrate was washed with saturated saline and was then dried over anhydrous sodium sulfate. The solvent was distilled away, and the residue was purified by neutral silica gel column chromatography (hexane/ethyl acetate) to obtain compound (97b) (0.272 g, 10%) as a colorless oily substance.

Example 97(3)

3-Methyl-4-(4-phenyl-1H-imidazol-1-yl)-1H-pyrrolo[2,3-b]pyridine (97c)

Compound (97b) (0.272 g) was dissolved in THF (2.3 mL), and tetrabutylammonium floride (2.0 mL, a 1.0 M solution in THF) was added to the resulting solution, followed by reflux for 24 hr. The reaction solution was concentrated and was then purified by basic silica gel column chromatography (hexane/ethyl acetate) to obtain compound (97c) (0.140 g, 76%) as a white solid.

$^1$H-NMR (DMSO-d$_6$) δ: 11.78 (1H, s), 8.29 (1H, d, J=5.12 Hz), 8.08 (2H, dd, J=8.54, 1.22 Hz), 7.88 (2H, dd, J=8.54, 1.22 Hz), 7.40-7.38 (3H, m), 7.24 (1H, t, J=7.44 Hz), 7.13 (1H, d, J=5.12 Hz), 1.99 (3H, s); LRMS (ESI) m/z 275 [M+H]$^+$.

Example 97(4)

2-Bromo-4-{3-methyl-4-(4-phenyl-1H-imidazol-1-yl)-1H-pyrrolo[2,3-b]pyridin-1-yl}benzonitrile (97d)

Compound (97c) (0.140 g) was dissolved in DMF (1.7 mL), and sodium hydride (0.024 g, a 55% dispersion in paraffin liquid) was added to the resulting solution at 0° C., followed by stirring for 10 min. Then, 2-bromo-4-fluorobenzonitrile (0.112 g) was added to the reaction solution, followed by stirring at 50° C. for 30 min. Ice water was added to the reaction solution, and the precipitate was collected by filtration and was dried under reduced pressure to obtain compound (97d) (0.160 g, 69%) as a white solid.

$^1$H-NMR (DMSO-d$_6$) δ: 8.76 (1H, d, J=2.20 Hz), 8.58 (1H, d, J=5.12 Hz), 8.41 (1H, dd, J=8.66, 2.20 Hz), 8.21-8.19 (4H, m), 7.95 (2H, d, J=8.29 Hz), 7.49 (1H, d, J=5.12 Hz), 7.46 (2H, t, J=7.81 Hz), 7.32 (1H, t, J=7.81 Hz), 2.10 (3H, s); LRMS (ESI) m/z 454 [M+H]$^+$.

Example 97(5)

2-(4-Hydroxycyclohexylamino)-4-{3-methyl-4-(4-phenyl-1H-imidazol-1-yl)-1H-pyrrolo[2,3-b]pyridin-1-yl}benzamide (97)

According to Example 1(6), 2-(4-hydroxycyclohexylamino)-4-{3-methyl-4-(4-phenyl-1H-imidazol-1-yl)-1H-pyrrolo[2,3-b]pyridin-1-yl}benzonitrile (58%) was prepared using compound (97d) instead of (1e); and according to Example 1(7), compound (97) (22%) was prepared as a white solid using 2-(4-hydroxycyclohexylamino)-4-{3-methyl-4-(4-phenyl-1H-imidazol-1-yl)-1H-pyrrolo[2,3-b]pyridin-1-yl}benzonitrile instead of compound (1f).

$^1$H-NMR (DMSO-d$_6$) δ: 8.43-8.39 (2H, m), 8.13 (2H, s), 7.96 (1H, s), 7.89 (2H, d, J=8.90 Hz), 7.87 (1H, brs), 7.75 (1H, d, J=8.54 Hz), 7.40 (2H, t, J=7.32 Hz), 7.32 (2H, s), 7.25 (1H, t, J=7.32 Hz), 7.15 (1H, brs), 7.01 (1H, d, J=8.54 Hz), 4.55 (1H, s), 3.52-3.48 (1H, m), 3.40-3.37 (1H, m), 2.09-2.05 (5H, m), 1.84 (2H, d, J=8.54 Hz), 1.36-1.21 (4H, m); LRMS (ESI) m/z 507 [M+H]$^+$.

Example 98

2-(4-Hydroxycyclohexylamino)-4-{3-methyl-4-(4-(pyridin-3-yl)-1H-imidazol-1-yl)-1H-pyrazolo[2,3-b]pyridin-1-yl}benzamide (98)

Example 98(1)

3-Methyl-4-{4-(pyridin-3-yl)-1H-imidazol-1-yl}-1-{(2-(trimethylsilyl)ethoxy)methyl}-1H-pyrrolo[2,3-b]pyridine (98a)

According to Example 97(2), compound (98a) (11%) was prepared as a colorless oily substance using 4-{pyridin-3-yl}-1H-imidazole hydrochloride instead of 4-phenyl-1H-imidazole.

$^1$H-NMR (CDCl$_3$) δ: 9.10 (1H, d, J=1.71 Hz), 8.57 (1H, dd, J=4.88, 1.71 Hz), 8.43 (1H, d, J=5.12 Hz), 8.23 (1H, dt, J=7.97, 1.71 Hz), 7.88 (1H, d, J=1.22 Hz), 7.64 (1H, d, J=1.22

Hz), 7.40 (1H, dd, J=7.97, 4.88 Hz), 7.26 (1H, d, J=1.22 Hz), 7.10 (1H, d, J=5.12 Hz), 5.72 (2H, s), 3.63-3.59 (2H, m), 2.10 (3H, d, J=1.22 Hz), 1.00-0.96 (2H, m), 0.00 (9H, s); LRMS (ESI) m/z 406 [M+H]$^+$.

Example 98(2)

3-Methyl-4-{4-(pyridin-3-yl)-1H-imidazol-1-yl}-1H-pyrrolo[2,3-b]pyridine (98b)

According to Example 97(3), compound (98b) (62%) was prepared as a white solid using compound (98a) instead of compound (97b).
$^1$H-NMR (DMSO-d$_6$) δ: 11.89 (1H, s), 8.41 (1H, d, J=5.12 Hz), 8.19 (2H, d, J=8.29 Hz), 7.99 (2H, d, J=7.56 Hz), 7.51-7.49 (2H, m), 7.35 (1H, t, J=6.83 Hz), 7.24 (1H, d, J=5.12 Hz), 2.10 (3H, s); LRMS (ESI) m/z 276 [M+H]$^+$.

Example 98(3)

2-Bromo-4-{3-methyl-4-{4-(pyridin-3-yl)-1H-imidazol-1-yl}-1H-pyrrolo[2,3-b]pyridin-1-yl}benzonitrile (98c)

According to Example 97(4), compound (98c) (61%) was prepared as a white solid using compound (98b) instead of compound (97c).
$^1$H-NMR (DMSO-d$_6$) δ: 9.21 (1H, d, J=1.95 Hz), 8.81 (1H, d, J=1.95 Hz), 8.64 (1H, d, J=5.12 Hz), 8.58 (1H, dd, J=4.63, 1.71 Hz), 8.46 (1H, dd, J=8.78, 2.20 Hz), 8.42 (1H, d, J=0.98 Hz), 8.34 (1H, d, J=0.98 Hz), 8.33 (1H, dt, J=8.05, 1.95 Hz), 8.27 (1H, s), 8.24 (1H, d, J=8.78 Hz), 7.55 (1H, d, J=5.12 Hz), 7.54 (1H, dd, J=8.05, 4.63 Hz), 2.15 (3H, s); LRMS (ESI) m/z 455 [M+H]$^+$.

Example 98(4)

2-(4-Hydroxycyclohexylamino)-4-{3-methyl-4-(4-(pyridin-3-yl)-1H-imidazol-1-yl)-1H-pyrazolo[2,3-b]pyridin-1-yl}benzamide (98)

According to Example 1(6), compound (98) (21%) was prepared as a white solid using compound (98c) instead of compound (1e).
$^1$H-NMR (DMSO-d$_6$) δ: 9.11 (1H, s), 8.46-8.42 (3H, m), 8.30 (1H, s), 8.21 (2H, s), 7.97 (1H, s), 7.85 (1H, brs), 7.75 (1H, d, J=7.32 Hz), 7.55 (1H, s), 7.45 (1H, s), 7.32 (2H, s), 7.15 (1H, brs), 7.01 (1H, d, J=7.32 Hz), 4.56 (1H, s), 3.50-3.47 (1H, m), 3.41-3.37 (1H, m), 2.09 (2H, d, J=8.54 Hz), 2.04 (2H, s), 1.83 (2H, d, J=8.54 Hz), 1.35-1.22 (4H, m); LRMS (ESI) m/z 508 [M+H]$^+$.

Example 99

3-Chloro-4-{3-isopropyl-4-(4-(1-methyl-1H-pyrazol-4-yl)-1H-imidazol-1-yl)-1H-pyrazolo[3,4-b]pyridin-1-yl}benzamide (99)

Example 99(1)

3-Chloro-4-{4-chloro-3-isopropyl-1H-pyrazolo[3,4-b]pyridin-1-yl}benzonitrile (99a)

Compound (6b) (0.5 g) was dissolved in DMF (13 mL), and sodium hydride (0.145 g, a 55% dispersion in paraffin liquid) was added to the resulting solution at 0° C., followed by stirring for 30 min. Then, 3-chloro-4-fluorobenzonitrile was added to the reaction solution, followed by stirring at 60° C. for 1 hr. Water was added to the reaction solution. The precipitate was collected by filtration and washed by sprinkling water to obtain compound (99a) (0.72 g, 85%) as a brown solid.
$^1$H-NMR (CDCl$_3$) δ: 8.39 (1H, d, J=4.88 Hz), 7.90 (1H, s), 7.73 (2H, s), 7.21 (1H, d, J=4.88 Hz), 3.80 (1H, tt, J=6.83, 6.83 Hz), 1.49 (6H, d, J=6.83 Hz); LRMS (ESI) m/z 331 [M+H]$^+$.

Example 99(2)

3-Chloro-4-{3-isopropyl-4-(4-(1-methyl-1H-pyrazol-4-yl)-1H-imidazol-1-yl)-1H-pyrazolo[3,4-b]pyridin-1-yl}benzamide (99)

Compound (99a) (0.18 g) was dissolved in DMSO (2.1 mL), and potassium carbonate (0.3 g), copper(II) oxide (nanopowder) (0.086 g), and 4-(1-methyl-1H-pyrazol-4-yl)-1H-imidazole hydrochloride (0.13 g) were added to the resulting solution, followed by stirring at 120° C. for 48 hr. The reaction solution was diluted with chloroform, and insoluble matters were filtered by celite. The solvent was distilled away, and the residue was purified by neutral silica gel column chromatography (chloroform/methanol) to obtain compound (99) (0.045 g, 18%) as a white solid.
$^1$H-NMR (DMSO-d$_6$) δ: 8.65 (1H, dd, J=4.88, 0.98 Hz), 8.25 (1H, brs), 8.22 (1H, s), 8.20 (1H, d, J=0.98 Hz), 8.03 (1H, dd, J=8.29, 0.98 Hz), 7.97 (1H, s), 7.91 (1H, s), 7.75 (1H, d, J=8.29 Hz), 7.74 (1H, s), 7.69 (1H, brs), 7.42 (1H, dd, J=4.88, 0.98 Hz), 3.87 (3H, s), 3.24 (1H, tt, J=6.83, 6.83 Hz), 1.10 (6H, d, J=6.83 Hz); LRMS (ESI) m/z 461 [M+H]$^+$.

Example 100

4-{3-Isopropyl-4-(4-(1-methyl-1H-pyrazol-4-yl)-1H-imidazol-1-yl)-1H-pyrazolo[3,4-b]pyridin-1-yl}-3-methylbenzamide (100)

Example 100(1)

4-Iodo-3-isopropyl-1H-pyrazolo[3,4-b]pyridine (100a)

Normal-butyllithium (a 2.6 M solution in hexane, 41.0 mL) was dropwise added to a solution of N,N-diisopropylamine (16.5 mL) in tetrahydrofuran (hereinafter referred to as THF, 300 mL) under a nitrogen atmosphere at −5 to 0° C., and a solution of 2-fluoro-3-iodo-pyridine (24 g) in THF (200 mL) was dropwise added to the resulting mixture at −78° C., followed by stirring for 15 min. Subsequently, isobutyric anhydride (20.0 mL) was dropwise added to the reaction solution at −78° C., followed by stirring at the same temperature for 1 hr, and then hydrazine monohydrate (10.4 mL) was added to the reaction solution, followed by stirring at 60° C. for 1 hr. The reaction solution was distributed between ethyl acetate and water, and the organic layer was washed with saturated saline. The organic layer after the washing was dried over anhydrous sodium sulfate, and then the solvent was distilled away. The residue was purified by neutral silica gel column chromatography (hexane/ethyl acetate) to obtain compound (100a) (12.9 g, 42%) as a white solid.
$^1$H-NMR (CDCl$_3$) δ: 12.02 (1H, brs), 8.11 (1H, d, J=4.88 Hz), 7.63 (1H, d, J=4.88 Hz), 3.93 (1H, tt, J=6.83, 6.83 Hz), 1.48 (6H, d, J=6.83 Hz); LRMS (ESI) m/z 288 [M+H]$^+$.

Example 100(2)

3-Isopropyl-4-{4-(1-methyl-1H-pyrazol-4-yl)-1H-imidazol-1-yl}-1H-pyrazolo[3,4-b]pyridine (100b)

According to Example 97(1), 4-iodo-3-isopropyl-1-(4-methoxybenzyl)-1H-pyrazolo[3,4-b]pyridine was prepared using (100a) (15.5 g) instead of compound (40d) and using 4-methoxybenzyl chloride instead of {2-(chloromethoxy)ethyl}silane and was used in the subsequent reaction without being purified. According to Example 97(2), 3-isopropyl-1-(4-methoxybenzyl)-4-{4-(1-methyl-1H-pyrazol-4-yl)-1H-imidazol-1-yl}-1H-pyrazolo[3,4-b]pyridine was prepared using 4-iodo-3-isopropyl-1-(4-methoxybenzyl)-1H-pyrazolo[3,4-b]pyridine instead of compound (97a) and using 4-(1-methyl-1H-pyrazol-4-yl)-1H-imidazole hydrochloride instead of 4-phenyl-1H-imidazole and was used in the subsequent reaction without being purified. This 3-isopropyl-1-(4-methoxybenzyl)-4-{4-(1-methyl-1H-pyrazol-4-yl)-1H-imidazol-1-yl}-1H-pyrazolo[3,4-b]pyridine was dissolved in trifluoroacetic acid (60 mL) and anisole (19 mL), followed by reflux for 5 hr. The reaction solution was concentrated and then diluted with acetonitrile, and saturated sodium bicarbonate water was added thereto. The precipitate was collected by filtration and was dried under reduced pressure to obtain compound (100b) (12.3 g, the third stage yield: 63%) as a white solid.

$^1$H-NMR (DMSO-$d_6$) δ: 13.67 (1H, brs), 8.60 (1H, d, J=4.88 Hz), 8.12 (1H, d, J=1.22 Hz), 7.96 (1H, s), 7.81 (1H, d, J=1.22 Hz), 7.73 (1H, s), 7.23 (1H, d, J=4.88 Hz), 3.87 (3H, s), 3.11 (1H, tt, J=6.83, 6.83 Hz), 1.07 (6H, d, J=6.83 Hz); LRMS (ESI) m/z 308 [M+H]$^+$.

Example 100(3)

4-{3-Isopropyl-4-(4-(1-methyl-1H-pyrazol-4-yl)-1H-imidazol-1-yl)-1H-pyrazolo[3,4-b]pyridin-1-yl}-3-methylbenzamide (100)

According to Example 80, compound (100) (the second stage yield: 65%) was prepared as a white solid using compound (100b) instead of compound (6c).

$^1$H-NMR (DMSO-$d_6$) δ: 9.37 (1H, d, J=4.88 Hz), 8.93 (1H, d, J=1.22 Hz), 8.81 (1H, brs), 8.70 (2H, s), 8.62 (1H, d, J=1.22 Hz), 8.60 (1H, dd, J=8.29, 1.71 Hz), 8.46 (1H, s), 8.27 (1H, d, J=8.29 Hz), 8.21 (1H, s), 8.12 (1H, d, J=4.88 Hz), 4.59 (3H, s), 3.94 (1H, tt, J=6.83, 6.83 Hz), 2.90 (3H, s), 1.84 (6H, d, J=6.83 Hz); LRMS (ESI) m/z 441 [M+H]$^+$.

Example 101

4-{3-Isopropyl-4-(4-(1-methyl-1H-pyrazol-4-yl)-1H-imidazol-1-yl)-1H-pyrazolo[3,4-b]pyridin-1-yl}-3-vinylbenzamide (101)

According to Example 80, compound (101) (the second stage yield: 38%) was prepared as a white solid using compound (100b) instead of compound (6c) and using 4-fluoro-3-vinylbenzonitrile instead of 4-fluoro-3-methylbenzonitrile.

$^1$H-NMR (DMSO-$d_6$) δ: 8.62 (1H, d, J=4.88 Hz), 8.36 (1H, d, J=1.95 Hz), 8.22 (1H, brs), 8.20 (1H, d, J=1.22 Hz), 7.98 (1H, s), 7.96 (1H, dd, J=8.29, 1.95 Hz), 7.89 (1H, d, J=1.22 Hz), 7.74 (1H, s), 7.58 (1H, d, J=8.29 Hz), 7.58 (1H, brs), 7.40 (1H, d, J=4.88 Hz), 6.39 (1H, dd, J=17.56, 11.47 Hz), 5.95 (1H, d, J=17.56 Hz), 5.30 (1H, d, J=11.47 Hz), 3.85 (3H, s), 3.23 (1H, tt, J=6.59, 6.59 Hz), 1.11 (6H, d, J=6.59 Hz); LRMS (ESI) m/z 453 [M+H]$^+$.

Example 102

3-Ethyl-4-{3-isopropyl-4-(4-(1-methyl-1H-pyrazol-4-yl)-1H-imidazol-1-yl)-1H-pyrazolo[3,4-b]pyridin-1-yl}benzamide (102)

According to Example 80, compound (102) (the second stage yield: 15%) was prepared as a white solid using compound (100b) instead of compound (6c) and using 3-ethyl-4-fluorobenzonitrile instead of 4-fluoro-3-methylbenzonitrile.

$^1$H-NMR (DMSO-$d_6$) δ: 9.35 (1H, d, J=4.88 Hz), 8.93 (1H, d, J=1.22 Hz), 8.84 (1H, brs), 8.72 (1H, d, J=1.95 Hz), 8.70 (1H, s), 8.63 (1H, d, J=1.22 Hz), 8.60 (1H, dd, J=8.29, 1.95 Hz), 8.46 (1H, s), 8.25 (1H, d, J=8.29 Hz), 8.22 (1H, brs), 8.12 (1H, d, J=4.88 Hz), 4.59 (3H, s), 3.95 (1H, tt, J=6.83, 6.83 Hz), 3.21 (2H, q, J=7.56 Hz), 1.83 (6H, d, J=6.83 Hz), 1.75 (3H, t, J=7.56 Hz); LRMS (ESI) m/z 455 [M+H]$^+$.

Example 103

4-{3-Isopropyl-4-(4-(1-methyl-1H-pyrazol-4-yl)-1H-imidazol-1-yl)-1H-pyrazolo[3,4-b]pyridin-1-yl}-3-propylbenzamide (103)

According to Example 80, compound (103) (the second stage yield: 32%) was prepared as a white solid using compound (100b) instead of compound (6c) and using 4-fluoro-3-propylbenzonitrile instead of 4-fluoro-3-methylbenzonitrile.

$^1$H-NMR (DMSO-$d_6$) δ: 9.35 (1H, d, J=4.88 Hz), 8.93 (1H, d, J=1.22 Hz), 8.83 (2H, brs), 8.70 (2H, s), 8.63 (1H, d, J=1.22 Hz), 8.60 (1H, dd, J=8.05, 1.95 Hz), 8.47 (1H, s), 8.27 (1H, d, J=8.05 Hz), 8.22 (1H, brs), 8.12 (1H, d, J=4.88 Hz), 4.59 (3H, s), 3.95 (1H, tt, J=6.83, 6.83 Hz), 3.21-3.17 (2H, m), 2.15 (2H, ttd, J=7.32, 8.05, 7.32 Hz), 1.84 (6H, d, J=6.83 Hz), 1.45 (3H, t, J=7.32 Hz); LRMS (ESI) m/z 469 [M+H]$^+$.

Example 104

3-Isopropyl-4-{3-isopropyl-4-(4-(1-methyl-1H-pyrazol-4-yl)-1H-imidazol-1-yl)-1H-pyrazolo[3,4-b]pyridin-1-yl}benzamide (104)

According to Example 80, compound (104) (the second stage yield: 25%) was prepared as a white solid using compound (100b) instead of compound (6c) and using 3-isopropyl-4-fluorobenzonitrile instead of 4-fluoro-3-methylbenzonitrile.

$^1$H-NMR (DMSO-$d_6$) δ: 8.63 (1H, d, J=4.88 Hz), 8.22 (1H, s), 8.17 (1H, brs), 8.08 (1H, d, J=1.71 Hz), 7.98 (1H, s), 7.92 (1H, s), 7.88 (1H, dd, J=8.05, 1.71 Hz), 7.75 (1H, s), 7.52 (1H, brs), 7.48 (1H, d, J=8.05 Hz), 7.39 (1H, d, J=4.88 Hz), 3.88 (3H, s), 3.24 (1H, tt, J=6.83, 6.83 Hz), 2.69 (1H, tt, J=6.59, 6.59 Hz), 1.16 (7H, d, J=6.83 Hz), 1.11 (6H, d, J=6.59 Hz); LRMS (ESI) m/z 469 [M+H]$^+$.

Example 105

3-Cyclopropyl-4-{3-isopropyl-4-(4-(1-methyl-1H-pyrazol-4-yl)-1H-imidazol-1-yl)-1H-pyrazolo[3,4-b]pyridin-1-yl}benzamide (105)

According to Example 80, compound (105) (the second stage yield: 2%) was prepared as a white solid using compound (100b) instead of compound (6c) and using 3-cyclopropyl-4-fluorobenzonitrile instead of 4-fluoro-3-methylbenzonitrile.

¹H-NMR (DMSO-d₆) δ: 8.62 (1H, d, J=4.88 Hz), 8.20 (1H, d, J=0.98 Hz), 8.12 (1H, brs), 7.97 (1H, s), 7.89 (1H, d, J=0.98 Hz), 7.83 (1H, dd, J=8.17, 1.83 Hz), 7.74 (1H, s), 7.60 (1H, d, J=1.83 Hz), 7.50 (1H, d, J=8.17 Hz), 7.48 (1H, brs), 7.38 (1H, d, J=4.88 Hz), 3.87 (3H, s), 3.22 (1H, tt, J=6.83, 6.83 Hz), 1.66-1.61 (1H, m), 1.11 (6H, d, J=6.83 Hz), 0.73-0.66 (4H, m); LRMS (ESI) m/z 467 [M+H]⁺.

Example 106

2-Amino-4-{3-isopropyl-4-(4-(1-methyl-1H-pyrazol-4-yl)-1H-imidazol-1-yl)-1H-pyrazolo[3,4-b]pyridin-1-yl}benzamide (106)

Example 106(1)

2-Amino-4-{4-chloro-3-isopropyl-1H-pyrazolo[3,4-b]pyridin-1-yl}benzamide (106a)

Compound (6b) (0.335 g) was dissolved in DMF (8.6 mL), and sodium hydride (0.097 g, a 55% dispersion in paraffin liquid) was added to the resulting solution at 0° C., followed by stirring for 30 min. Then, 4-fluoro-2-nitrobenzonitrile was added to the reaction solution, followed by stirring at 60° C. for 30 min. Water was added to the reaction solution, and the precipitate was collected by filtration and washed by sprinkling water to obtain 4-{4-chloro-3-isopropyl-1H-pyrazolo[3,4-b]pyridin-1-yl}-2-nitrobenzonitrile (0.5 g, 85%). 4-{4-Chloro-3-isopropyl-1H-pyrazolo[3,4-b]pyridin-1-yl}-2-nitrobenzonitrile (0.35 g) and ammonium chloride (0.35 g) were dissolved in a solvent mixture of THF (3 mL), methanol (3 mL), and water (3 mL). Iron (0.57 g) was added to the resulting solution, followed by stirring at 70° C. for 1 hr. Insoluble matters were filtered by celite, and the solvent was distilled away. The precipitate was washed with water and was collected by filtration to obtain compound (106a) (0.32 g, 95%) as a white solid.

¹H-NMR (DMSO-d₆) δ: 8.57 (1H, d, J=4.88 Hz), 7.70 (1H, d, J=9.27 Hz), 7.60 (1H, d, J=1.95 Hz), 7.47 (1H, d, J=4.88 Hz), 7.45 (1H, dd, J=9.27, 1.95 Hz), 6.92 (2H, brs), 3.73 (1H, tt, J=6.83, 6.83 Hz), 1.43 (6H, d, J=6.83 Hz); LRMS (ESI) m/z 330 [M+H]⁺.

Example 106(2)

2-Amino-4-{3-isopropyl-4-(4-(1-methyl-1H-pyrazol-4-yl)-1H-imidazol-1-yl)-1H-pyrazolo[3,4-b]pyridin-1-yl}benzamide (106)

According to Example 99(2), compound (106) (12%) was prepared as a yellow solid using compound (106a) instead of compound (99a).

¹H-NMR (DMSO-d₆) δ: 8.76 (1H, d, J=4.88 Hz), 8.18 (1H, s), 7.97 (1H, s), 7.86 (1H, s), 7.78 (1H, brs), 7.73 (1H, s), 7.72 (1H, d, J=8.66 Hz), 7.65 (1H, d, J=1.95 Hz), 7.50 (1H, dd, J=8.66, 1.95 Hz), 7.44 (1H, d, J=4.88 Hz), 7.11 (1H, brs), 6.94 (2H, s), 3.86 (3H, s), 3.16 (1H, tt, J=6.83, 6.83 Hz), 1.13 (6H, d, J=6.83 Hz); LRMS (ESI) m/z 442 [M+H]⁺.

Example 107

3-Amino-4-{3-isopropyl-4-(4-(1-methyl-1H-pyrazol-4-yl)-1H-imidazol-1-yl)-1H-pyrazolo[3,4-b]pyridin-1-yl}benzamide (107)

Example 107(1)

3-Amino-4-{4-chloro-3-isopropyl-1H-pyrazolo[3,4-b]pyridin-1-yl}benzonitrile (107a)

According to Example 106(1), compound (107a) (50%) was prepared as a dark brown solid using 4-chloro-3-nitrobenzonitrile instead of 4-fluoro-2-nitrobenzonitrile.

¹H-NMR (DMSO-d₆) δ: 8.47 (1H, d, J=4.88 Hz), 7.50 (1H, d, J=8.05 Hz), 7.44 (1H, d, J=4.88 Hz), 7.26 (1H, s), 7.08 (1H, d, J=8.05 Hz), 5.71 (2H, s), 3.71 (1H, tt, J=6.83, 6.83 Hz), 1.41 (6H, d, J=6.83 Hz); LRMS (ESI) m/z 311 [M+H]⁺.

Example 107(2)

3-Amino-4-{3-isopropyl-4-(4-(1-methyl-1H-pyrazol-4-yl)-1H-imidazol-1-yl)-1H-pyrazolo[3,4-b]pyridin-1-yl}benzamide (107)

According to Example 99(2), 3-amino-4-{3-isopropyl-4-(4-(1-methyl-1H-pyrazol-4-yl)-1H-imidazol-1-yl)-1H-pyrazolo[3,4-b]pyridin-1-yl}benzonitrile was prepared using compound (107a) instead of compound (99a) and was used in the subsequent reaction without being purified. This 3-amino-4-{3-isopropyl-4-(4-(1-methyl-1H-pyrazol-4-yl)-1H-imidazol-1-yl)-1H-pyrazolo[3,4-b]pyridin-1-yl}benzonitrile was dissolved in DMSO, and a 30% hydrogen peroxide solution and a 4 M aqueous sodium hydroxide solution were added to the resulting solution, followed by stirring at room temperature for 30 min. The reaction solution was distributed between ethyl acetate and waster, and the organic layer was washed with saturated saline. The organic layer after the washing was dried over anhydrous sodium sulfate, and then the solvent was distilled away. The residue was purified by neutral silica gel column chromatography (chloroform/methanol) to obtain (107) (the second stage yield: 18%) as a white solid.

¹H-NMR (DMSO-d) δ: 8.65 (1H, d, J=4.88 Hz), 8.19 (1H, s), 7.98 (1H, s), 7.91 (1H, brs), 7.86 (1H, s), 7.74 (1H, s), 7.43 (1H, d, J=1.46 Hz), 7.40 (1H, d, J=3.90 Hz), 7.39 (1H, d, J=4.88 Hz), 7.31 (1H, brs), 7.19 (1H, dd, J=8.05, 1.46 Hz), 3.87 (3H, s), 3.18 (1H, tt, J=6.83, 6.83 Hz), 1.11 (6H, d, J=6.83 Hz); LRMS (ESI) m/z 442 [M+H]⁺.

Example 108

3-(Dimethylamino)-4-{3-isopropyl-4-(4-(1-methyl-1H-pyrazol-4-yl)-1H-imidazol-1-yl)-1H-pyrazolo[3,4-b]pyridin-1-yl}benzamide (108)

Compound (107a) (0.08 g) and iodomethane (0.16 mL) were dissolved in DMF, and sodium hydride (0.028 g, a 55% dispersion in paraffin liquid) was added to the resulting solution at 0° C., followed by stirring at room temperature for 1 hr. The reaction solution was distributed between ethyl acetate and water, and the organic layer was washed with saturated saline. The organic layer after the washing was dried over anhydrous sodium sulfate, and then the solvent was distilled away to obtain 3-(dimethylamino)-4-(4-chloro-3-isopropyl-1H-pyrazolo[3,4-b]pyridin-1-yl)benzonitrile, which was used in the subsequent reaction without being purified. According to Example 107(2), compound (108) (0.014 g, the third stage yield: 12%) was prepared using 3-(dimethylamino)-4-(4-chloro-3-isopropyl-1H-pyrazolo[3,4-b]pyridin-1-yl)benzonitrile instead of compound (107a).

$^1$H-NMR (DMSO-d$_6$) δ: 8.60 (1H, d, J=4.88 Hz), 8.19 (1H, d, J=1.22 Hz), 8.09 (1H, brs), 7.97 (1H, s), 7.89 (1H, d, J=1.22 Hz), 7.74 (1H, s), 7.59 (1H, d, J=1.71 Hz), 7.46 (1H, dd, J=8.05, 1.71 Hz), 7.45 (1H, d, J=1.71 Hz), 7.35 (1H, d, J=4.88 Hz), 7.31 (1H, d, J=8.05 Hz), 3.87 (3H, s), 3.21 (1H, tt, J=6.83, 6.83 Hz), 2.41 (6H, s), 1.10 (6H, d, J=6.83 Hz); LRMS (ESI) m/z 470 [M+H]$^+$.

Example 109

2-(Ethylamino)-4-{3-isopropyl-4-(4-(1-methyl-1H-pyrazol-4-yl)-1H-imidazol-1-yl)-1H-pyrazolo[3,4-b]pyridin-1-yl}benzamide (109)

Compound (100b) (1.00 g), copper iodide (0.248 g), cesium carbonate (2.12 g), and 4-bromo-2-(ethylamino)benzonitrile (0.932 g) were suspended in 1,4-dioxane (10 mL), and N,N'-dimethylethylenediamine (0.560 mL) was added to the suspension, followed by stirring at 150° C. for 20 hr. The reaction solution was distributed between chloroform and water. The organic layer was washed with a 2 N aqueous sodium hydroxide solution and dried over magnesium sulfate, and then the solvent was distilled away. The residue was purified by neutral silica gel column chromatography (chloroform/methanol) to obtain 2-(ethylamino)-4-{3-isopropyl-4-(4-(1-methyl-1H-pyrazol-4-yl)-1H-imidazol-1-yl)-1H-pyrazolo[3,4-b]pyridin-1-yl}benzamide (1.13 g, 77%) as a white solid. 2-(Ethylamino)-4-{3-isopropyl-4-(4-(1-methyl-1H-pyrazol-4-yl)-1H-imidazol-1-yl)-1H-pyrazolo[3,4-b]pyridin-1-yl}benzamide (0.700 g) was dissolved in DMSO (10 mL), and a 30% hydrogen peroxide solution (0.310 mL) and a 4 N aqueous sodium hydroxide solution (1.16 mL) were added to the resulting solution, followed by stirring at room temperature for 10 min. Water was added to the reaction solution, and the precipitate was collected by filtration and was dried under reduced pressure to obtain compound (109) (0.655 g, 90%) as a white solid.

$^1$H-NMR (DMSO-d$_6$) δ: 8.78 (1H, d, J=4.88 Hz), 8.35 (1H, t, J=5.24 Hz), 8.19 (1H, d, J=1.46 Hz), 7.98 (1H, s), 7.87 (1H, d, J=1.46 Hz), 7.80 (1H, d, J=8.78 Hz), 7.74 (1H, s), 7.70 (1H, d, J=1.95 Hz), 7.48 (1H, dd, J=8.78, 1.95 Hz), 7.45 (1H, d, J=4.88 Hz), 7.19 (1H, brs), 3.88 (3H, s), 3.26-3.18 (3H, m), 1.28 (3H, t, J=7.07 Hz), 1.14 (6H, d, J=6.83 Hz); LRMS (ESI) m/z 470 [M+H]$^+$.

Example 110

4-{3-Isopropyl-4-(4-(1-methyl-1H-pyrazol-4-yl)-1H-imidazol-1-yl)-1H-pyrazolo[3,4-b]pyridin-1-yl}-2-(methylamino)benzamide (110)

According to Example 109, compound (110) (the second stage yield: 30%) was prepared as a white solid using 4-bromo-2-(methylamino)benzonitrile instead of 4-bromo-2-(ethylamino)benzonitrile.

$^1$H-NMR (DMSO-d$_6$) δ: 8.77 (1H, d, J=4.88 Hz), 8.30 (1H, q, J=4.88 Hz), 8.18 (1H, s), 7.97 (1H, s), 7.86 (1H, s), 7.79 (1H, d, J=8.54 Hz), 7.73 (1H, s), 7.64 (1H, d, J=1.71 Hz), 7.49 (1H, dd, J=8.54, 1.71 Hz), 7.43 (1H, d, J=4.88 Hz), 3.86 (3H, s), 3.17 (1H, tt, J=6.83, 6.83 Hz), 2.87 (3H, d, J=4.88 Hz), 1.13 (6H, d, J=6.83 Hz); LRMS (ESI) m/z 456 [M+H]$^+$.

Example 111

4-{3-Isopropyl-4-(4-(1-methyl-1H-pyrazol-4-yl)-1H-imidazol-1-yl)-1H-pyrazolo[3,4-b]pyridin-1-yl}-2-(isopropylamino)benzamide (111)

According to Example 109, compound (111) (the second stage yield: 36%) was prepared as a white solid using 4-bromo-2-(isopropylamino)benzonitrile instead of 4-bromo-2-(ethylamino)benzonitrile.

$^1$H-NMR (DMSO-d$_6$) δ: 8.78 (1H, d, J=4.88 Hz), 8.39 (1H, d, J=7.07 Hz), 8.19 (1H, d, J=1.22 Hz), 7.98 (1H, s), 7.87 (1H, d, J=1.22 Hz), 7.79 (1H, d, J=8.54 Hz), 7.75 (1H, d, J=1.95 Hz), 7.74 (1H, s), 7.44 (1H, d, J=4.88 Hz), 7.42 (1H, dd, J=8.54, 1.95 Hz), 3.88 (3H, s), 3.69 (1H, dtt, J=7.07, 6.34, 6.34 Hz), 3.19 (1H, tt, J=6.83, 6.83 Hz), 1.26 (6H, d, J=6.34 Hz), 1.14 (6H, d, J=6.83 Hz); LRMS (ESI) m/z 484 [M+H]$^+$.

Example 112

2-(Tert-butylamino)-4-{3-isopropyl-4-(4-(1-methyl-1H-pyrazol-4-yl)-1H-imidazol-1-yl)-1H-pyrazolo[3,4-b]pyridin-1-yl}benzamide (112)

According to Example 109, compound (112) (the second stage yield: 62%) was prepared using 4-bromo-2-(tert-butylamino)benzonitrile instead of 4-bromo-2-(ethylamino)benzonitrile.

$^1$H-NMR (DMSO-d$_6$) δ: 8.77 (1H, d, J=4.88 Hz), 8.64 (1H, s), 8.19 (1H, s), 8.11 (1H, d, J=1.71 Hz), 7.98 (1H, s), 7.88 (1H, s), 7.77 (1H, d, J=8.54 Hz), 7.74 (1H, s), 7.44 (1H, d, J=4.88 Hz), 7.43 (1H, dd, J=8.54, 1.71 Hz), 3.88 (3H, s), 3.20 (1H, tt, J=6.83, 6.83 Hz), 1.45 (9H, s), 1.14 (6H, d, J=6.83 Hz); LRMS (ESI) m/z 498 [M+H]$^+$.

Example 113

2-(2,2-Difluoroethylamino)-4-{3-isopropyl-4-(4-(1-methyl-1H-pyrazol-4-yl)-1H-imidazol-1-yl)-1H-pyrazolo[3,4-b]pyridin-1-yl}benzamide (113)

According to Example 109, compound (113) (the second stage yield: 27%) was prepared as a white solid using 4-bromo-2-(2,2-difluoroethylamino)benzonitrile instead of 4-bromo-2-(ethylamino)benzonitrile.

$^1$H-NMR (DMSO-d$_6$) δ: 8.78 (1H, d, J=5.12 Hz), 8.18 (1H, d, J=1.22 Hz), 7.97 (1H, s), 7.96 (1H, d, J=1.71 Hz), 7.86 (1H, d, J=1.22 Hz), 7.77 (1H, dd, J=8.54, 1.71 Hz), 7.73 (1H, d, J=0.73 Hz), 7.71 (1H, d, J=8.54 Hz), 7.47 (1H, d, J=5.12 Hz), 6.64 (1H, t, J=6.22 Hz), 6.22 (1H, tt, J=55.62, 3.74 Hz), 3.86 (3H, s), 3.78-3.68 (2H, m), 3.19 (1H, tt, J=6.83, 6.83 Hz), 1.12 (6H, d, J=6.83 Hz); LRMS (ESI) m/z 506 [M+H]$^+$.

Example 114

4-{3-Isopropyl-4-(4-(1-methyl-1H-pyrazol-4-yl)-1H-imidazol-1-yl)-1H-pyrazolo[3,4-b]pyridin-1-yl}-2-(2,2,2-trifluoroethylamino)benzamide (114)

According to Example 109, compound (114) (the second stage yield: 1%) was prepared using 4-bromo-2-(2,2,2-trifluoroethyl)benzonitrile instead of 4-bromo-2-(ethylamino)benzonitrile.

$^1$H-NMR (DMSO-d$_6$) δ: 8.90 (1H, t, J=6.59 Hz), 8.78 (1H, d, J=4.88 Hz), 8.19 (1H, s), 7.99 (1H, s), 7.88 (2H, s), 7.87 (1H, d, J=9.27 Hz), 7.74 (1H, s), 7.66 (1H, dd, J=9.27, 1.95

Hz), 7.46 (1H, d, J=4.88 Hz), 4.21-4.14 (2H, m), 3.88 (3H, s), 3.21 (1H, tt, J=7.07, 7.07 Hz), 1.14 (6H, d, J=7.07 Hz); LRMS (ESI) m/z 524 [M+H]$^+$.

Example 115

4-{3-Isopropyl-4-(4-(1-methyl-1H-pyrazol-4-yl)-1H-imidazol-1-yl)-1H-pyrazolo[3,4-b]pyridin-1-yl}-2-{2-(pyrrolidin-1-yl)ethylamino}benzamide (115)

According to Example 109, compound (115) (the second stage yield: 5%) was prepared using 5-bromo-2-{2-(pyrrolidin-1-yl)ethylamino}benzonitrile instead of 4-bromo-2-(ethylamino)benzonitrile.

$^1$H-NMR (DMSO-d$_6$) δ: 8.77 (1H, d, J=4.88 Hz), 8.50 (1H, t, J=4.88 Hz), 8.19 (1H, s), 7.98 (1H, s), 7.87 (1H, s), 7.78 (1H, d, J=8.54 Hz), 7.74 (1H, s), 7.72 (1H, d, J=1.71 Hz), 7.50 (1H, dd, J=8.54, 1.71 Hz), 7.45 (1H, d, J=4.88 Hz), 3.88 (3H, s), 3.30 (2H, dt, J=4.88, 6.34 Hz), 3.19 (1H, tt, J=6.83, 6.83 Hz), 2.72 (2H, t, J=6.34 Hz), 2.56-2.53 (4H, m), 1.72-1.70 (4H, m), 1.14 (6H, d, J=6.83 Hz); LRMS (ESI) m/z 539 [M+H]$^+$.

Example 116

5-{3-Isopropyl-4-(4-(1-methyl-1H-pyrazol-4-yl)-1H-imidazol-1-yl)-1H-pyrazolo[3,4-b]pyridin-1-yl}picolinamide (116)

According to Example 109, compound (116) (the second stage yield: 7%) was prepared as a white solid using 5-bromopicolinenitrile instead of 4-bromo-2-(ethylamino)benzonitrile.

$^1$H-NMR (DMSO-d$_6$) δ: 9.60 (1H, d, J=2.44 Hz), 8.84 (1H, dd, J=8.78, 2.44 Hz), 8.83 (1H, d, J=4.88 Hz), 8.26 (1H, d, J=8.78 Hz), 8.20 (1H, d, J=1.22 Hz), 8.13 (1H, brs), 7.98 (1H, s), 7.88 (1H, d, J=1.22 Hz), 7.74 (1H, s), 7.69 (1H, brs), 7.52 (1H, d, J=4.88 Hz), 3.87 (3H, s), 3.23 (1H, tt, J=6.83, 6.83 Hz), 1.15 (6H, d, J=6.83 Hz); LRMS (ESI) m/z 428 [M+H]$^+$.

Example 117

5-{3-Isopropyl-4-(4-(1-methyl-1H-pyrazol-4-yl)-1H-imidazol-1-yl)-1H-pyrazolo[3,4-b]pyridin-1-yl}-6-methylpicolinamide (117)

According to Example 109, compound (117) (the second stage yield: 5%) was prepared as a yellow solid using 5-bromo-6-methylpicolinenitrile instead of 4-bromo-2-(ethylamino)benzonitrile.

$^1$H-NMR (DMSO-d$_6$) δ: 8.68 (1H, d, J=4.88 Hz), 8.21 (1H, d, J=1.22 Hz), 8.14 (1H, brs), 8.13 (1H, d, J=8.05 Hz), 8.07 (1H, d, J=8.05 Hz), 7.98 (1H, s), 7.90 (1H, d, J=1.22 Hz), 7.76 (1H, brs), 7.74 (1H, s), 7.44 (1H, d, J=4.88 Hz), 3.87 (3H, s), 3.24 (1H, tt, J=6.83, 6.83 Hz), 2.46 (3H, s), 1.12 (6H, d, J=6.83 Hz); LRMS (ESI) m/z 442 [M+H]$^+$.

Example 118

5-{3-Isopropyl-4-(4-(1-methyl-1H-pyrazol-4-yl)-1H-imidazol-1-yl)-1H-pyrazolo[3,4-b]pyridin-1-yl}-4-methylpicolinamide (118)

According to Example 109, compound (118) (the second stage yield: 2%) was prepared using 5-bromo-4-methylpicolinenitrile instead of 4-bromo-2-(ethylamino)benzonitrile.

$^1$H-NMR (DMSO-d$_6$) δ: 8.75 (1H, s), 8.69 (1H, d, J=4.88 Hz), 8.22 (1H, d, J=1.22 Hz), 8.20 (1H, brs), 8.19 (1H, s), 7.99 (1H, s), 7.90 (1H, d, J=1.22 Hz), 7.76 (1H, brs), 7.75 (1H, s), 7.46 (1H, d, J=4.88 Hz), 3.88 (3H, s), 3.26 (1H, tt, J=6.83, 6.83 Hz), 2.33 (3H, s), 1.13 (6H, d, J=6.83 Hz); LRMS (ESI) m/z 442 [M+H]$^+$.

Example 119

5-{3-Isopropyl-4-(4-(1-methyl-1H-pyrazol-4-yl)-1H-imidazol-1-yl)-1H-pyrazolo[3,4-b]pyridin-1-yl}-3-methylpicolinamide (119)

According to Example 109, compound (119) (the second stage yield: 4%) was prepared using 5-bromo-3-methylpicolinenitrile instead of 4-bromo-2-(ethylamino)benzonitrile.

$^1$H-NMR (DMSO-d$_6$) δ: 9.40 (1H, d, J=2.20 Hz), 8.84 (1H, d, J=4.88 Hz), 8.57 (1H, d, J=2.20 Hz), 8.21 (1H, d, J=0.73 Hz), 8.03 (1H, brs), 7.99 (1H, s), 7.89 (1H, d, J=0.73 Hz), 7.75 (1H, s), 7.53 (1H, brs), 7.52 (1H, d, J=4.88 Hz), 3.88 (3H, s), 3.23 (1H, tt, J=6.83, 6.83 Hz), 2.69 (3H, s), 1.16 (6H, d, J=6.83 Hz); LRMS (ESI) m/z 442 [M+H]$^+$.

Example 120

4-{3-Isopropyl-4-(4-(1-methyl-1H-pyrazol-4-yl)-1H-imidazol-1-yl)-1H-pyrazolo[3,4-b]pyridin-1-yl}-3-(isopropylamino)benzamide (120)

Example 120(1)

4-{4-Chloro-3-isopropyl-1H-pyrazolo[3,4-b]pyridin-1-yl}-3-(isopropylamino)benzonitrile (120a)

Compound (107a) (0.100 g) and sodium triacetoxyborohydride (0.130 g) were suspended in dichloromethane (1.6 mL), and trifluoroacetic acid (0.3 mL) and acetone (0.050 mL) were added to the resulting suspension at 0° C., followed by stirring at 0° C. for 20 min. Saturated sodium bicarbonate water was added to the reaction solution, and the organic layer was washed with saturated saline. The organic layer after the washing was dried over anhydrous sodium sulfate, and the solvent was distilled away. Methanol and water were added to the residue, and the precipitate was collected by filtration and dried under reduced pressure to obtain compound (120a) (0.100 g, 93%) as a brown solid.

$^1$H-NMR (DMSO-d$_6$) δ: 8.51 (1H, d, J=5.12 Hz), 7.64 (1H, d, J=8.05 Hz), 7.48 (1H, d, J=5.12 Hz), 7.27 (1H, s), 7.13 (1H, d, J=8.05 Hz), 5.75 (1H, d, J=7.56 Hz), 3.80-3.72 (2H, m), 1.42 (6H, d, J=6.83 Hz), 1.13 (6H, d, J=6.34 Hz); LRMS (ESI) m/z 354 [M+H]$^+$.

Example 120(2)

4-{3-Isopropyl-4-(4-(1-methyl-1H-pyrazol-4-yl)-1H-imidazol-1-yl)-1H-pyrazolo[3,4-b]pyridin-1-yl}-3-(isopropylamino)benzamide (120)

According to Example 107(2), compound (120) (the second stage yield: 47%) was prepared as a white solid using compound (120a) instead of compound (107a).

$^1$H-NMR (DMSO-d$_6$) δ: 8.68 (1H, d, J=4.88 Hz), 8.19 (1H, s), 8.01 (1H, s), 7.98 (1H, s), 7.88 (1H, s), 7.74 (1H, s), 7.53 (1H, d, J=8.29 Hz), 7.42 (1H, d, J=4.88 Hz), 7.38 (1H, s), 7.37 (1H, d, J=1.22 Hz), 7.26 (1H, dd, J=8.29, 1.22 Hz), 5.37 (1H, d, J=7.07 Hz), 3.87 (3H, s), 3.76 (1H, ttd, J=6.59, 6.59, 7.07

Hz), 3.21 (1H, tt, J=6.83, 6.83 Hz), 1.14 (6H, d, J=6.83 Hz), 1.12 (6H, d, J=6.59 Hz); LRMS (ESI) m/z 484 [M+H]⁺.

Example 121

3-(Ethylamino)-4-{3-isopropyl-4-(4-(1-methyl-1H-pyrazol-4-yl)-1H-imidazol-1-yl)-1H-pyrazolo[3,4-b]pyridin-1-yl}benzamide (121)

Example 121(1)

4-{4-Chloro-3-isopropyl-1H-pyrazolo[3,4-b]pyridin-1-yl}-3-(ethylamino)benzamide (121a)

According to Example 120(1), compound (121a) (92%) was prepared as a brown solid using acetaldehyde instead of acetone.
¹H-NMR (DMSO-d₆) δ: 8.49 (1H, d, J=5.12 Hz), 7.56 (1H, d, J=7.81 Hz), 7.46 (1H, d, J=5.12 Hz), 7.22 (1H, s), 7.13 (1H, d, J=7.81 Hz), 5.80 (1H, t, J=4.88 Hz), 3.74 (1H, tt, J=7.07, 7.07 Hz), 2.75 (2H, q, J=6.83 Hz), 1.43 (6H, d, J=7.07 Hz), 0.71 (3H, t, J=6.83 Hz); LRMS (ESI) m/z 340 [M+H]⁺.

Example 121(2)

3-(Ethylamino)-4-{3-isopropyl-4-(4-(1-methyl-1H-pyrazol-4-yl)-1H-imidazol-1-yl)-1H-pyrazolo[3,4-b]pyridin-1-yl}benzamide (121)

According to Example 107(2), compound (121) (45%) was prepared using compound (121a) instead of compound (107a).
¹H-NMR (DMSO-d₆) δ: 9.39 (1H, d, J=4.88 Hz), 8.90 (1H, d, J=1.22 Hz), 8.73 (1H, brs), 8.71 (1H, s), 8.59 (1H, d, J=1.22 Hz), 8.47 (1H, s), 8.20 (1H, d, J=8.05 Hz), 8.13 (1H, d, J=4.88 Hz), 8.10 (1H, brs), 8.06 (1H, d, J=1.71 Hz), 7.98 (1H, dd, J=8.05, 1.71 Hz), 6.13 (1H, t, J=5.24 Hz), 4.59 (3H, s), 3.95-3.86 (3H, m), 1.87 (3H, t, J=7.07 Hz), 1.85 (6H, d, J=6.83 Hz); LRMS (ESI) m/z 470 [M+H]⁺.

Example 122

4-{3-Isopropyl-4-(4-(1-methyl-1H-pyrazol-4-yl)-1H-imidazol-1-yl)-1H-pyrazolo[3,4-b]pyridin-1-yl}-3-(propylamino)benzamide (122)

Example 122(1)

4-{4-Chloro-3-isopropyl-1H-pyrazolo[3,4-b]pyridin-1-yl}-3-(propylamino)benzamide (122a)

According to Example 120(1), compound (122a) (97%) was prepared as a brownish-yellow solid using propionaldehyde dimethylacetal instead of acetone.
¹H-NMR (DMSO-d₆) δ: 8.48 (1H, d, J=5.12 Hz), 7.55 (1H, d, J=8.05 Hz), 7.46 (1H, d, J=5.12 Hz), 7.22 (1H, d, J=1.34 Hz), 7.11 (1H, dd, J=8.05, 1.34 Hz), 5.83 (1H, t, J=5.37 Hz), 3.74 (1H, tt, J=6.83, 6.83 Hz), 3.08 (2H, q, J=6.34 Hz), 1.54-1.51 (2H, m), 1.42 (6H, d, J=6.83 Hz), 0.90 (3H, t, J=7.44 Hz); LRMS (ESI) m/z 354 [M+H]⁺.

Example 122(2)

4-{3-Isopropyl-4-(4-(1-methyl-1H-pyrazol-4-yl)-1H-imidazol-1-yl)-1H-pyrazolo[3,4-b]pyridin-1-yl}-3-(propylamino)benzamide (122)

According to Example 107(2), compound (122) (the second stage yield: 54%) was prepared using compound (122a) instead of compound (107a).
¹H-NMR (DMSO-d₆) δ: 9.39 (1H, d, J=4.88 Hz), 8.90 (1H, s), 8.74 (1H, brs), 8.71 (1H, s), 8.59 (1H, s), 8.47 (1H, s), 8.20 (1H, d, J=8.29 Hz), 8.13 (1H, d, J=4.88 Hz), 8.10 (1H, brs), 8.06 (1H, s), 7.97 (1H, d, J=8.29 Hz), 6.18 (1H, t, J=5.12 Hz), 4.59 (3H, s), 3.93 (1H, tt, J=6.83, 6.83 Hz), 3.84 (2H, q, J=6.18 Hz), 2.27 (2H, tdt, J=7.07, 5.12, 7.02 Hz), 1.84 (6H, d, J=6.83 Hz), 1.65 (3H, t, J=7.07 Hz); LRMS (ESI) m/z 484 [M+H]⁺.

Example 123

3-(2,2-Difluoroethylamino)4-{3-isopropyl-4-(4-(1-methyl-1H-pyrazol-4-yl)-1H-imidazol-1-yl)-1H-pyrazolo[3,4-b]pyridin-1-yl}benzamide (123)

Example 123(1)

4-{4-Chloro-3-isopropyl-1H-pyrazolo[3,4-b]pyridin-1-yl}-3-(2,2-difluoroethylamino)benzonitrile (123a)

According to Example 120(1), compound (123a) (93%) was prepared as a yellow solid using difluoroacetaldehyde ethyl hemiacetal instead of acetone.
¹H-NMR (DMSO-d₆) δ: 8.49 (1H, d, J=5.12 Hz), 7.58 (1H, d, J=8.05 Hz), 7.48 (1H, s), 7.47 (1H, d, J=5.12 Hz), 7.22 (1H, dd, J=8.05, 1.46 Hz), 6.14 (1H, tt, J=55.86, 3.90 Hz), 6.10 (1H, t, J=6.10 Hz), 3.73 (1H, tt, J=6.83, 6.83 Hz), 3.70-3.61 (2H, m), 1.43 (6H, d, J=6.83 Hz); LRMS (ESI) m/z 376 [M+H]⁺.

Example 123(2)

4-{3-Isopropyl-4-(4-(1-methyl-1H-pyrazol-4-yl)-1H-imidazol-1-yl)-1H-pyrazolo[3,4-b]pyridin-1-yl}-3-(2,2-difluoroethylamino)benzamide (123)

According to Example 107(2), compound (123) (220) was prepared as a yellow solid using compound (123a) instead of (107a).
¹H-NMR (DMSO-d₆) δ: 8.68 (1H, d, J=4.88 Hz), 8.31 (1H, s), 8.18 (1H, d, J=1.22 Hz), 8.05 (1H, brs), 7.99 (1H, s), 7.87 (1H, d, J=1.22 Hz), 7.75 (1H, s), 7.51 (1H, d, J=8.05 Hz), 7.48 (1H, d, J=1.71 Hz), 7.43 (1H, brs), 7.42 (1H, d, J=4.88 Hz), 7.34 (1H, dd, J=8.05, 1.71 Hz), 6.18 (1H, tt, J=55.74, 3.82 Hz), 5.80 (1H, t, J=6.22 Hz), 3.88 (3H, s), 3.71-3.61 (2H, m), 3.22 (1H, tt, J=6.83, 6.83 Hz), 1.12 (6H, d, J=6.83 Hz); LRMS (ESI) m/z 506 [M+H]⁺.

Example 124

3-Cyano-4-{3-isopropyl-4-(4-(1-methyl-1H-pyrazol-4-yl)-1H-imidazol-1-yl)-1H-pyrazolo[3,4-b]pyridin-1-yl}benzamide (124)

Example 124(1)

3-Cyano-4-(4-iodo-3-isopropyl-1H-pyrazolo[3,4-b]pyridin-1-yl)benzamide (124a)

According to Example 97(4), 5-form-2-(4-iodo-3-isopropyl-1H-pyrazolo[3,4-b]pyridin-1-yl)benzonitrile (32%) was prepared using (100a) instead of compound (97c) and using 2-fluoro-5-formbenzonitrile instead of 2-bromo-4-fluorobenzonitrile. 5-Form-2-(4-iodo-3-isopropyl-1H-pyrazolo[3,4-b]pyridin-1-yl)benzonitrile (0.470 g), sodium chlorite (0.377 g), sodium dihydrogenphosphate (0.134 g), and 2-methyl-2-butene (0.540 mL) were dissolved in tert-butanol (7.5 mL) and water (2.2 mL), followed by stirring at room temperature for 1 hr. The reaction solution was distributed between chloroform and water. The organic layer was dried over anhydrous sodium sulfate to obtain 3-cyano-4-(4-iodo-3-isopropyl-1H-pyrazolo[3,4-b]pyridin-1-yl)benzoic acid, which was used in the subsequent reaction without being purified. This 3-cyano-4-(4-iodo-3-isopropyl-1H-pyrazolo[3,4-b]pyridin-1-yl)benzoic acid, HATU (0.373 g), and diisopropylethylamine (0.758 mL) were dissolved in DMF (3.0 mL), and ammonia water (0.660 mL, 23% in water) was added to the resulting solution, followed by stirring at 50° C. for 20 hr. Water was added to the reaction solution, and the precipitate was collected by filtration and dried under reduced pressure to obtain compound (124a) (0.325 g, the second stage yield: 67%) as a white solid.

$^1$H-NMR (DMSO-$d_6$) δ: 8.49 (1H, d, J=2.20 Hz), 8.34 (1H, dd, J=8.66, 2.20 Hz), 8.27 (1H, d, J=8.66 Hz), 8.26 (1H, brs), 8.22 (1H, d, J=4.88 Hz), 7.95 (1H, d, J=4.88 Hz), 7.72 (1H, brs), 3.96 (1H, tt, J=6.59, 6.59 Hz), 1.47 (6H, d, J=6.59 Hz); LRMS (ESI) m/z 432 [M+H]$^+$.

Example 124(2)

3-Cyano-4-{3-isopropyl-4-(4-(1-methyl-1H-pyrazol-4-yl)-1H-imidazol-1-yl)-1H-pyrazolo[3,4-b]pyridin-1-yl}benzamide (124)

According to Example 97(2), compound (124) (13%) was prepared as a white solid using compound (124a) instead of compound (97a) and using 4-(1-methyl-1H-pyrazol-4-yl)-1H-imidazole hydrochloride instead of 4-phenyl-1H-imidazole.

$^1$H-NMR (DMSO-$d_6$) δ: 8.77 (1H, dd, J=4.88, 0.98 Hz), 8.52 (1H, s), 8.36 (1H, t, J=8.78 Hz), 8.32 (1H, s), 8.30 (1H, d, J=0.49 Hz), 8.27 (1H, brs), 8.23 (1H, s), 7.98 (1H, s), 7.91 (1H, s), 7.74 (2H, s), 7.53 (1H, dd, J=4.88, 0.98 Hz), 3.87 (3H, s), 3.25 (1H, tt, J=6.59, 6.59 Hz), 1.14 (6H, d, J=6.59 Hz); LRMS (ESI) m/z 452 [M+H]$^+$.

Example 125

3-Formyl-4-{3-isopropyl-4-(4-(1-methyl-1H-pyrazol-4-yl)-1H-imidazol-1-yl)-1H-pyrazclo[3,4-b]pyridin-1-yl}benzamide (125)

Example 125(1)

3-Formyl-4-{4-iodo-3-isopropyl-1H-pyrazolo[3,4-b]pyridin-1-yl}benzonitrile (125a)

Compound (100a) (2.0 g), cesium carbonate (3.41 g), and 4-fluoro-3-formylbenzonitrile (1.25 g) were suspended in acetonitrile (23 mL), followed by reflux for 3 hr. The reaction solution was distributed between chloroform and water, and the organic layer was washed with saturated saline. The organic layer after the washing was dried over anhydrous sodium sulfate, and then the solvent was distilled away. The residue was purified by neutral silica gel column chromatography (hexane/ethyl acetate) to obtain compound (125a) (2.00 g, 67%) as a white solid.

$^1$H-NMR (DMSO-$d_6$) δ: 9.93 (1H, s), 8.30-8.24 (3H, m), 8.20 (1H, d, J=4.88 Hz), 7.96 (1H, d, J=4.88 Hz), 3.95 (1H, tt, J=6.83, 6.83 Hz), 1.44 (6H, d, J=6.83 Hz); LRMS (ESI) m/z 417 [M+H]$^+$.

Example 125(2)

3-Formyl-4-{3-isopropyl-4-(4-(1-methyl-1H-pyrazol-4-yl)-1H-imidazol-1-yl)-1H-pyrazolo[3,4-b]pyridin-1-yl}benzamide (125)

According to Example 97(2), 3-formyl-4-{3-isopropyl-4-(4-(1-methyl-1H-pyrazol-4-yl)-1H-imidazol-1-yl)-1H-pyrazolo[3,4-b]pyridin-1-yl}benzonitrile was prepared using compound (125a) instead of compound (97a) and using 4-(1-methyl-1H-pyrazol-4-yl)-1H-imidazole hydrochloride instead of 4-phenyl-1H-imidazole and was used in the subsequent reaction without being purified. According to Example 1(7), compound (125) (the second stage yield: 17%) was prepared as a white solid using 3-formyl-4-{3-isopropyl-4-(4-(1-methyl-1H-pyrazol-4-yl)-1H-imidazol-1-yl)-1H-pyrazolo[3,4-b]pyridin-1-yl}benzonitrile instead of compound (1f).

$^1$H-NMR (DMSO-$d_6$) δ: 9.89 (1H, d, J=0.98 Hz), 8.69 (1H, d, J=4.88 Hz), 8.43 (1H, s), 8.29 (1H, dd, J=8.29, 2.20 Hz), 8.26 (1H, brs), 8.16 (1H, s), 8.01 (1H, d, J=8.29 Hz), 7.95 (1H, s), 7.85 (1H, s), 7.70 (1H, s), 7.58 (1H, brs), 7.46 (2H, d, J=4.88 Hz), 3.83 (3H, s), 3.20 (1H, tt, J=6.83, 6.83 Hz), 1.09 (6H, d, J=6.83 Hz); LRMS (ESI) m/z 455 [M+H]$^+$.

Example 126

3-{(Dimethylamino)methyl}-4-{3-isopropyl-4-(4-(1-methyl-1H-pyrazol-4-yl)-1H-imidazol-1-yl)-1H-pyrazolo[3,4-b]pyridin-1-yl}benzamide (126)

Compound (125a) (0.500 g), 2-picoline-borane complex (0.166 g), and dimethylamine (0.216 mL) were dissolved in acetic acid (1.0 mL) and methanol (10 mL), followed by stirring at room temperature for 12 hr. The reaction solution was concentrated, and the residue was purified by basic silica gel column chromatography (hexane/ethyl acetate) to obtain 3-{(dimethylamino)methyl}-4-{4-iodo-3-isopropyl-1H-pyrazolo[3,4-b]pyridin-1-yl}benzonitrile (0.213 g, 40%). This 3-{(dimethylamino)methyl}-4-{4-iodo-3-isopropyl-1H-pyrazolo[3,4-b]pyridin-1-yl}benzonitrile was dissolved in DMSO (1.6 mL), and a hydrogen peroxide solution (30 wt %) (0.060 mL) and a 4 mol % aqueous sodium hydroxide solution (0.132 mL) were added to the resulting solution, followed by stirring at room temperature for 20 min. Water was added to the reaction solution, and the precipitate was collected by filtration and was dried under reduced pressure to obtain 3-{(dimethylamino)methyl}-4-{4-iodo-3-isopropyl-1H-pyrazolo[3,4-b]pyridin-1-yl}benzamide (0.144 g, 65%). According to Example 97(2), compound (126) (64%) was prepared as a white solid using 3-{(dimethylamino)methyl}-4-{4-iodo-3-isopropyl-1H-pyrazolo[3,4-b]pyridin-1-yl}benzamide instead of compound (97a) and using 4-(1-methyl-1H-pyrazol-4-yl)-1H-imidazole hydrochloride instead of 4-phenyl-1H-imidazole.

$^1$H-NMR (DMSO-$d_6$) δ: 8.58 (1H, d, J=4.88 Hz), 8.16 (1H, d, J=1.22 Hz), 8.12 (1H, d, J=1.95 Hz), 8.08 (1H, brs), 7.94 (1H, s), 7.90 (1H, dd, J=8.05, 1.95 Hz), 7.86 (1H, d, J=1.22 Hz), 7.70 (1H, s), 7.54 (1H, d, J=8.05 Hz), 7.44 (1H, brs), 7.34 (1H, d, J=4.88 Hz), 3.83 (3H, s), 3.33 (2H, s), 3.19 (1H, tt, J=6.38, 6.38 Hz), 1.90 (6H, s), 1.08 (6H, d, J=6.83 Hz); LRMS (ESI) m/z 484 [M+H]$^+$.

Example 127

4-{3-Isopropyl-4-(4-(1-methyl-1H-pyrazol-4-yl)-1H-imidazol-1-yl)-1H-pyrazolo[3,4-b]pyridin-1-yl}-3-(morpholinomethyl)benzamide (127)

According to Example 126, compound (127) (the third stage yield: 28%) was prepared using morpholine instead of dimethylamine.
$^1$H-NMR (DMSO-d$_6$) δ: 8.57 (1H, d, J=4.88 Hz), 8.14 (1H, d, J=1.22 Hz), 8.08 (1H, brs), 8.03 (1H, d, J=2.20 Hz), 7.95 (1H, s), 7.93 (1H, dd, J=8.05, 2.20 Hz), 7.83 (1H, d, J=1.22 Hz), 7.72 (1H, s), 7.57 (1H, d, J=8.05 Hz), 7.47 (1H, brs), 7.34 (1H, d, J=4.88 Hz), 3.83 (3H, s), 3.43 (2H, s), 3.20 (2H, tt, J=6.59, 6.59 Hz), 3.08-3.06 (4H, m), 1.96-1.94 (4H, m), 1.07 (6H, d, J=6.59 Hz); LRMS (ESI) m/z 526 [M+H]$^+$.

Example 128

4-{3-Isopropyl-4-(4-(1-methyl-1H-pyrazol-4-yl)-1H-imidazol-1-yl)-1H-pyrazolo[3,4-b]pyridin-1-yl}-3-methoxybenzamide (128)

According to Example 80, compound (128) (the second stage yield: 17%) was prepared as a white solid using compound (100b) instead of compound (6c) and using 4-fluoro-3-methoxybenzonitrile instead of 4-fluoro-3-methylbenzonitrile.
$^1$H-NMR (DMSO-d$_6$) δ: 8.60 (1H, d, J=4.88 Hz), 8.21 (1H, s), 8.17 (1H, brs), 7.98 (1H, s), 7.89 (1H, s), 7.74 (2H, s), 7.65 (1H, d, J=8.05 Hz), 7.56 (1H, brs), 7.51 (1H, d, J=8.05 Hz), 7.35 (1H, d, J=4.88 Hz), 3.88 (3H, s), 3.80 (3H, s), 3.21 (1H, tt, J=6.83, 6.83 Hz), 1.10 (6H, d, J=6.83 Hz); LRMS (ESI) m/z 456 [M+H]$^+$.

Example 129

4-{3-Isopropyl-4-(4-(1-methyl-1H-pyrazol-4-yl)-1H-imidazol-1-yl)-1H-pyrazolo[3,4-b]pyridin-1-yl}-2,3-dimethylbenzamide (129)

According to Example 80, compound (129) (the second stage yield: 20%) was prepared as a white solid using compound (100b) instead of compound (6c) and using 4-fluoro-2,3-dimethylbenzonitrile instead of 4-fluoro-3-methylbenzonitrile.
$^1$H-NMR (DMSO-d$_6$) δ: 8.61 (1H, d, J=4.88 Hz), 8.21 (1H, d, J=1.22 Hz), 7.98 (1H, s), 7.90 (1H, d, J=1.22 Hz), 7.85 (1H, brs), 7.75 (1H, s), 7.53 (1H, brs), 7.38 (1H, d, J=4.88 Hz), 7.33 (1H, d, J=8.05 Hz), 7.28 (1H, d, J=8.05 Hz), 3.88 (3H, s), 3.23 (1H, tt, J=6.83, 6.83 Hz), 2.37 (3H, s), 1.93 (3H, s), 1.11 (6H, d, J=6.83 Hz); LRMS (ESI) m/z 455 [M+H]$^+$.

Example 130

2-Fluoro-4-{3-isopropyl-4-(4-(1-methyl-1H-pyrazol-4-yl)-1H-imidazol-1-yl)-1H-pyrazolo[3,4-b]pyridin-1-yl}-3-methylbenzamide (130)

According to Example 109, compound (130) (the second stage yield: 29%) was prepared as a white solid using 4-bromo-2-fluoro-3-methylbenzonitrile instead of 4-bromo-2-(ethylamino)benzonitrile.
$^1$H-NMR (DMSO-d$_6$) δ: 8.67 (1H, d, J=4.88 Hz), 8.21 (1H, d, J=1.22 Hz), 7.99 (1H, s), 7.90 (1H, d, J=1.22 Hz), 7.87 (1H, brs), 7.76 (1H, brs), 7.75 (1H, s), 7.65 (1H, t, J=7.93 Hz), 7.43 (1H, d, J=4.88 Hz), 7.42 (1H, d, J=7.93 Hz), 3.88 (3H, s), 3.24 (1H, tt, J=6.83, 6.83 Hz), 2.08 (3H, d, J=2.20 Hz), 1.12 (6H, d, J=6.83 Hz); LRMS (ESI) m/z 459 [M+H]$^+$.

Example 131

3-Ethyl-2-fluoro-4-{3-isopropyl-4-(4-(1-methyl-1H-pyrazol-4-yl)-1H-imidazol-1-yl)-1H-pyrazolo[3,4-b]pyridin-1-yl}benzamide (131)

According to Example 109, compound (131) (the second stage yield: 22%) was prepared as a white solid using 4-bromo-3-ethyl-2-fluorobenzonitrile instead of 4-bromo-2-(ethylamino)benzonitrile.
$^1$H-NMR (DMSO-d$_6$) δ: 8.66 (1H, d, J=5.12 Hz), 8.22 (1H, d, J=1.22 Hz), 7.99 (1H, s), 7.91 (1H, d, J=1.22 Hz), 7.89 (1H, brs), 7.76 (1H, brs), 7.75 (1H, s), 7.65 (1H, t, J=7.93 Hz), 7.43 (1H, d, J=7.93 Hz), 7.43 (1H, d, J=5.12 Hz), 3.88 (3H, s), 3.24 (1H, tt, J=6.83, 6.83 Hz), 2.46 (2H, q, J=7.44 Hz), 1.12 (6H, d, J=6.83 Hz), 1.08 (3H, t, J=7.44 Hz); LRMS (ESI) m/z 473 [M+H]$^+$.

Example 132

2-(Ethylamino)-4-{3-isopropyl-4-(4-(1-methyl-1H-pyrazol-4-yl)-1H-imidazol-1-yl)-1H-pyrazolo[3,4-b]pyridin-1-yl}-3-methylbenzamide (132)

According to Example 109, compound (132) (the second stage yield: 45%) was obtained as a white solid using 4-bromo-2-(ethylamino)-3-methylbenzonitrile instead of 4-bromo-2-(ethylamino)benzonitrile.
$^1$H-NMR (DMSO-d$_6$) δ: 8.64 (1H, d, J=4.88 Hz), 8.21 (1H, d, J=1.22 Hz), 8.08 (1H, brs), 7.98 (1H, s), 7.90 (1H, d, J=1.22 Hz), 7.75 (1H, s), 7.56 (1H, d, J=8.54 Hz), 7.50 (1H, brs), 7.38 (1H, d, J=4.88 Hz), 6.99 (1H, d, J=8.29 Hz), 6.54 (1H, t, J=6.59 Hz), 3.88 (3H, s), 3.22 (1H, tt, J=6.83, 6.83 Hz), 3.08 (2H, dq, J=6.59, 6.83 Hz), 1.92 (3H, s), 1.13 (3H, t, J=6.83 Hz), 1.12 (6H, d, J=6.83 Hz); LRMS (ESI) m/z 484 [M+H]$^+$.

Examples 133 and 134

3-Ethyl-2-(ethylamino)-4-{3-isopropyl-4-(4-(1-methyl-1H-pyrazol-4-yl)-1H-imidazol-1-yl)-1H-pyrazolo[3,4-b]pyridin-1-yl}benzamide (133)

2-Amino-3-ethyl-4-{3-isopropyl-4-(4-(1-methyl-1H-pyrazol-4-yl)-1H-imidazol-1-yl)-1H-pyrazolo[3,4-b]pyridin-1-yl}benzamide (134)

According to Example 109, compound (133) (the second stage yield: 6%) was prepared as a white solid using 4-bromo-3-ethyl-2-(ethylamino)benzonitrile instead of 4-bromo-2-(ethylamino)benzonitrile. Compound (134) (the second stage yield: 2%) was prepared as a white solid by this reaction.

Compound (133)
$^1$H-NMR (DMSO-d$_6$) δ: 8.61 (1H, d, J=4.88 Hz), 8.21 (1H, d, J=1.22 Hz), 8.03 (1H, brs), 7.98 (1H, s), 7.91 (1H, d, J=1.22 Hz), 7.75 (1H, s), 7.50 (1H, brs), 7.46 (1H, d, J=8.05 Hz), 7.37 (1H, d, J=4.88 Hz), 6.90 (1H, d, J=8.05 Hz), 5.76 (1H, t, J=6.59 Hz), 3.88 (3H, s), 3.22 (1H, tt, J=6.83, 6.83 Hz), 3.09 (2H, dq, J=6.59, 7.07 Hz), 2.44 (2H, q, J=7.32 Hz), 1.14 (3H, t, J=7.07 Hz), 1.11 (6H, d, J=6.83 Hz), 0.82 (3H, t, J=7.32 Hz); LRMS (ESI) m/z 498 [M+H]$^+$.

Compound (134)
$^1$H-NMR (DMSO-d$_6$) δ: 8.78 (1H, d, J=4.88 Hz), 8.35 (1H, t, J=4.88 Hz), 8.19 (1H, d, J=0.98 Hz), 7.99 (1H, s), 7.88 (1H, d, J=0.98 Hz), 7.88 (1H, brs), 7.80 (1H, d, J=8.54 Hz), 7.74

(1H, s), 7.70 (1H, d, J=1.95 Hz), 7.48 (1H, dd, J=8.54, 1.95 Hz), 7.45 (1H, d, J=4.88 Hz), 7.20 (1H, s), 3.88 (3H, s), 3.27-3.17 (3H, m), 1.28 (3H, t, J=7.20 Hz), 1.14 (6H, d, J=6.59 Hz); LRMS (ESI) m/z 470 [M+H]$^+$.

Example 135

4-{3-Isopropyl-4-(4-(pyridin-3-yl)-1H-imidazol-1-yl)-1H-pyrazolo[3,4-b]pyridin-1-yl}-3-methylbenzamide (135)

Example 135(1)

3-Isopropyl-4-{4-(pyridin-3-yl)-1H-imidazol-1-yl}-1H-pyrazolo[3,4-b]pyridine (135a)

According to Example 100(2), compound (135a) (the third stage yield: 31%) was prepared as a white solid using 4-(pyridin-3-yl)-1H-imidazole hydrochloride instead of 4-(1-methyl-1H-pyrazol-4-yl)-1H-imidazole hydrochloride.

$^1$H-NMR (DMSO-d$_6$) δ: 13.73 (1H, s), 9.11 (1H, d, J=1.71 Hz), 8.64 (1H, d, J=4.88 Hz), 8.48 (1H, dd, J=4.76, 1.71 Hz), 8.38 (1H, d, J=1.46 Hz), 8.30 (1H, d, J=1.46 Hz), 8.22 (1H, dt, J=8.05, 1.71 Hz), 7.45 (1H, dd, J=8.05, 4.76 Hz), 7.31 (1H, d, J=4.88 Hz), 3.11 (1H, tt, J=6.83, 6.83 Hz), 1.08 (6H, d, J=6.83 Hz); LRMS (ESI) m/z 305 [M+H]$^+$.

Example 135(2)

4-{3-Isopropyl-4-(4-(pyridin-3-yl)-1H-imidazol-1-yl)-1H-pyrazolo[3,4-b]pyridin-1-yl}-3-methylbenzamide (135)

According to Example 80, compound (135) (the second stage yield: 65%) was prepared as a white solid using compound (135a) instead of compound (6c).

$^1$H-NMR (DMSO-d$_6$) δ: 9.11 (1H, d, J=1.71 Hz), 8.69 (1H, d, J=4.88 Hz), 8.48 (1H, dd, J=4.76, 1.71 Hz), 8.46 (1H, d, J=1.22 Hz), 8.38 (1H, d, J=1.22 Hz), 8.23 (1H, dt, J=7.89, 1.95 Hz), 8.09 (1H, brs), 7.98 (1H, d, J=1.83 Hz), 7.88 (1H, dd, J=8.29, 1.83 Hz), 7.55 (1H, d, J=8.29 Hz), 7.49 (1H, brs), 7.47 (1H, d, J=4.88 Hz), 7.46 (1H, dd, J=4.63, 7.89 Hz), 3.25-3.18 (1H, m), 2.19 (3H, s), 1.12 (6H, d, J=6.59 Hz); LRMS (ESI) m/z 438 [M+H]$^+$.

Example 136

3-Ethyl-4-{3-isopropyl-4-(4-(pyridin-3-yl)-1H-imidazol-1-yl)-1H-pyrazolo[3,4-b]pyridin-1-yl}benzamide (136)

According to Example 80, compound (136) (the second stage yield: 12%) was prepared as a white solid using compound (135a) instead of compound (6c) and using 4-fluoro-3-ethylbenzonitrile instead of 4-fluoro-3-methylbenzonitrile.

$^1$H-NMR (DMSO-d$_6$) δ: 9.13 (1H, d, J=1.46 Hz), 8.68 (1H, d, J=4.88 Hz), 8.50 (1H, dd, J=4.63, 1.46 Hz), 8.48 (1H, d, J=1.22 Hz), 8.40 (1H, d, J=1.22 Hz), 8.24 (1H, dt, J=7.89, 1.95 Hz), 8.13 (1H, brs), 8.01 (1H, d, J=1.95 Hz), 7.90 (1H, dd, J=8.05, 1.95 Hz), 7.54 (1H, d, J=8.05 Hz), 7.52 (1H, brs), 7.48 (1H, d, J=4.88 Hz), 7.47 (1H, dd, J=4.63, 7.89 Hz), 3.23 (1H, tt, J=6.59, 6.59 Hz), 2.50 (2H, q, J=7.56 Hz), 1.13 (6H, d, J=6.59 Hz), 1.04 (3H, t, J=7.56 Hz); LRMS (ESI) m/z 452 [M+H]$^+$.

Example 137

3-Isopropyl-4-{3-isopropyl-4-(4-(pyridin-3-yl)-1H-imidazol-1-yl)-1H-pyrazolo[3,4-b]pyridin-1-yl}benzamide (137)

According to Example 80, compound (137) (the second stage yield: 22%) was prepared as a white solid using compound (135a) instead of compound (6c) and using 3-isopropyl-4-fluorobenzonitrile instead of 4-fluoro-3-methylbenzonitrile.

$^1$H-NMR (DMSO-d$_6$) δ: 9.12 (1H, d, J=1.71 Hz), 8.68 (1H, d, J=4.88 Hz), 8.50 (1H, dd, J=4.76, 1.71 Hz), 8.48 (1H, d, J=1.22 Hz), 8.40 (1H, d, J=1.22 Hz), 8.24 (1H, dt, J=8.17, 1.95 Hz), 8.17 (1H, brs), 8.09 (1H, d, J=1.95 Hz), 7.89 (1H, dd, J=8.17, 1.95 Hz), 7.52 (1H, brs), 7.50-7.45 (3H, m), 3.23 (1H, tt, J=6.83, 6.83 Hz), 2.70 (1H, tt, J=7.07, 7.07 Hz), 1.17 (6H, d, J=7.07 Hz), 1.12 (6H, d, J=6.83 Hz); LRMS (ESI) m/z 466 [M+H]$^+$.

Example 138

3-Cyclopropyl-4-{3-isopropyl-4-(4-(pyridin-3-yl)-1H-imidazol-1-yl)-1H-pyrazolo[3,4-b]pyridin-1-yl}benzamide (138)

According to Example 80, compound (138) (the second stage yield: 2%) was prepared as a white solid using compound (135a) instead of compound (6c) and using 3-cyclopropyl-4-fluorobenzonitrile instead of 4-fluoro-3-methylbenzonitrile.

$^1$H-NMR (DMSO-d$_6$) δ: 9.11 (1H, d, J=1.71 Hz), 8.67 (1H, d, J=4.88 Hz), 8.49 (1H, dd, J=4.76, 1.71 Hz), 8.46 (1H, d, J=1.22 Hz), 8.38 (1H, d, J=1.22 Hz), 8.24 (1H, dt, J=7.97, 1.95 Hz), 8.13 (1H, brs), 7.84 (1H, dd, J=8.17, 1.95 Hz), 7.61 (1H, d, J=1.95 Hz), 7.51 (1H, d, J=8.17 Hz), 7.49 (1H, brs), 7.47 (1H, d, J=4.78 Hz), 7.45 (1H, d, J=4.88 Hz), 3.21 (1H, tt, J=6.83, 6.83 Hz), 1.67-1.61 (1H, m), 1.12 (6H, d, J=6.83 Hz), 0.74-0.67 (4H, m); LRMS (ESI) m/z 464 [M+H]$^+$.

Example 139

2-(Ethylamino)-4-{3-isopropyl-4-(4-(pyridin-3-yl)-1H-imidazol-1-yl)-1H-pyrazolo[3,4-b]pyridin-1-yl}benzamide (139)

According to Example 109, compound (139) (the second stage yield: 52%) was prepared as a white solid using compound (135a) instead of compound (100b).

$^1$H-NMR (DMSO-d$_6$) δ: 9.10 (1H, d, J=1.65 Hz), 8.81 (1H, d, J=4.95 Hz), 8.48 (1H, dd, J=4.70, 1.57 Hz), 8.42 (1H, d, J=0.99 Hz), 8.35 (2H, d, J=0.99 Hz), 8.22 (1H, dt, J=7.97, 2.02 Hz), 7.80 (1H, d, J=8.74 Hz), 7.69 (1H, d, J=2.02 Hz), 7.51 (1H, d, J=4.95 Hz), 7.49-7.43 (2H, m), 3.27-3.12 (3H, m), 1.27 (3H, t, J=7.09 Hz), 1.14 (6H, d, J=6.92 Hz); LRMS (ESI) m/z 467 [M+H]$^+$.

Example 140

4-{3-Isopropyl-4-(4-(pyridin-3-yl)-1H-imidazol-1-yl)-1H-pyrazolo[3,4-b]pyridin-1-yl}-2-(isopropylamino)benzamide (140)

According to Example 109, compound (140) (the second stage yield: 19%) was prepared as a white solid using compound (135a) and 4-bromo-2-(isopropylamino)benzonitrile instead of compound (100b) and 4-bromo-2-(ethylamino) benzonitrile, respectively.

$^1$H-NMR (DMSO-d$_6$) δ: 9.10 (1H, d, J=1.65 Hz), 8.81 (1H, d, J=4.95 Hz), 8.48 (1H, dd, J=4.78, 1.65 Hz), 8.42 (1H, d, J=0.99 Hz), 8.38 (1H, d, J=7.09 Hz), 8.35 (1H, d, J=0.99 Hz), 8.22 (1H, dt, J=7.91, 1.98 Hz), 7.79 (1H, d, J=8.74 Hz), 7.74 (1H, d, J=1.98 Hz), 7.50 (1H, d, J=4.95 Hz), 7.46 (1H, dd, J=7.91, 4.78 Hz), 7.42 (1H, dd, J=8.74, 1.98 Hz), 3.69 (1H, td, J=6.26, 6.26, 7.09 Hz), 3.18 (1H, tt, J=6.76, 6.76 Hz), 1.25 (6H, d, J=6.26 Hz), 1.14 (6H, d, J=6.76 Hz); LRMS (ESI) m/z 481 [M+H]$^+$.

Example 141

2-(Tert-butylamino)-4-{3-isopropyl-4-(4-(pyridin-3-yl)-1H-imidazol-1-yl)-1H-pyrazolo[3,4-b]pyridin-1-yl}benzamide (141)

According to Example 109, compound (141) (the second stage yield: 58%) was prepared as a white solid using compound (135a) and 4-bromo-2-(tert-butylamino)benzonitrile instead of compound (100b) and 4-bromo-2-(ethylamino) benzonitrile, respectively.

$^1$H-NMR (DMSO-d$_6$) δ: 9.10 (1H, d, J=1.98 Hz), 8.80 (1H, d, J=4.95 Hz), 8.63 (1H, s), 8.48 (1H, d, J=4.78 Hz), 8.42 (1H, s), 8.36 (1H, s), 8.22 (1H, d, J=7.91 Hz), 8.10 (1H, d, J=1.98 Hz), 7.77 (1H, d, J=8.74 Hz), 7.50 (1H, d, J=4.95 Hz), 7.48-7.41 (2H, m), 3.19 (1H, tt, J=6.76, 6.76 Hz), 1.45 (9H, s), 1.13 (6H, d, J=6.76 Hz); LRMS (ESI) m/z 495 [M+H]$^+$.

Example 142

4-{3-Isopropyl-4-(4-(pyridin-3-yl)-1H-imidazol-1-yl)-1H-pyrazolo[3,4-b]pyridin-1-yl}-3-methoxybenzamide (142)

According to Example 80, compound (142) (the second stage yield: 33%) was prepared as a white solid using compound (135a) and 4-fluoro-3-methoxybenzonitrile instead of compound (6c) and 4-fluoro-3-methylbenzonitrile, respectively.

$^1$H-NMR (DMSO-d$_6$) δ: 9.12 (1H, s), 8.65 (1H, d, J=4.88 Hz), 8.49 (1H, d, J=4.63 Hz), 8.46 (1H, d, J=1.22 Hz), 8.39 (1H, d, J=1.22 Hz), 8.24 (1H, dt, J=8.05, 1.95 Hz), 8.18 (1H, brs), 7.76 (1H, d, J=1.71 Hz), 7.65 (1H, dd, J=8.05, 1.71 Hz), 7.57 (1H, brs), 7.52 (1H, d, J=8.05 Hz), 7.47 (1H, dd, J=4.63, 8.55 Hz), 7.43 (1H, d, J=4.88 Hz), 3.80 (3H, s), 3.21 (1H, tt, J=6.83, 6.83 Hz), 1.11 (6H, d, J=6.83 Hz); LRMS (ESI) m/z 454 [M+H]$^+$.

Example 143

4-{4-(4-(1H-Pyrazol-4-yl)-1H-imidazol-1-yl)-3-isopropyl-1H-pyrazolo[3,4-b]pyridin-1-yl}-2-(isopropylamino)benzamide (143)

Example 143(1)

4-{4-(4-(1-(Benzyloxymethyl)-1H-pyrazol-4-yl)-1H-imidazol-1-yl)-3-isopropyl-1H-pyrazolo[3,4-b]pyridin-1-yl}-2-bromo-benzonitrile (143a)

According to Example 99(2), compound (143a) (71%) was prepared as a gray solid using compound (36a) instead of compound (99a) and using 4-(1-(benzyloxymethyl)-1H-pyrazol-4-yl)-1H-imidazole instead of 4-(1-methyl-1H-pyrazol-4-yl)-1H-imidazole hydrochloride.

$^1$H-NMR (DMSO-d$_6$) δ: 8.96 (1H, d, J=1.95 Hz), 8.88 (1H, d, J=5.12 Hz), 8.62 (1H, dd, J=8.66, 1.95 Hz), 8.25 (2H, s), 8.17 (1H, d, J=8.66 Hz), 7.98 (1H, d, J=1.22 Hz), 7.92 (1H, s), 7.58 (1H, d, J=5.12 Hz) 7.38-7.28 (5H, m), 5.57 (2H, s), 4.58 (2H, s), 3.24 (1H, tt, J=6.83, 6.83 Hz), 1.16 (6H, d, J=6.83 Hz); LRMS (ESI) m/z 593 [M+H]$^+$.

Example 143(2)

4-{4-(4-(1H-Pyrazol-4-yl)-1H-imidazol-1-yl)-3-isopropyl-1H-pyrazolo[3,4-b]pyridin-1-yl}-2-(isopropylamino)benzamide (143)

According to Example 1(6), 4-{4-(4-(1-(benzyloxymethyl)-1H-pyrazol-4-yl)-1H-imidazol-1-yl)-3-isopropyl-1H-pyrazolo[3,4-b]pyridin-1-yl}-2-(isopropylamino)benzonitrile (65%) was prepared using compound (143a) and isopropylamine instead of compound (1e) and trans-4-hydroxycyclohexylamine, respectively, and this 4-{4-(4-(1-(benzyloxymethyl)-1H-pyrazol-4-yl)-1H-imidazol-1-yl)-3-isopropyl-1H-pyrazolo[3,4-b]pyridin-1-yl}-2-(isopropylamino)benzonitrile was dissolved in anisole and trifluoroacetic acid, followed by stirring at 70° C. for 3 hr. The reaction solution was distributed between chloroform and a 2 M aqueous sodium hydroxide solution. The organic layer was dried over anhydrous sodium sulfate, and the solvent was distilled away to obtain 4-{4-(4-(1H-pyrazol-4-yl)-1H-imidazol-1-yl)-3-isopropyl-1H-pyrazolo[3,4-b]pyridin-1-yl}-2-(isopropylamino)benzonitrile, which was used in the subsequent reaction without being purified. Lastly, according to Example 1(7), compound (143) (the second stage yield: 43%) was prepared as a white solid using 4-{4-(4-(1H-pyrazol-4-yl)-1H-imidazol-1-yl)-3-isopropyl-1H-pyrazolo[3,4-b]pyridin-1-yl}-2-(isopropylamino)benzonitrile instead of compound (1f).

$^1$H-NMR (DMSO-d$_6$) δ: 12.87 (1H, s), 8.78 (1H, d, J=4.88 Hz), 8.35 (1H, t, J=5.00 Hz), 8.20 (1H, d, J=1.22 Hz), 8.02 (1H, s), 7.89 (1H, d, J=1.22 Hz), 7.82 (1H, s), 7.80 (1H, d, J=8.78 Hz), 7.71 (1H, d, J=2.20 Hz), 7.48 (1H, dd, J=8.78, 2.20 Hz), 7.44 (1H, d, J=4.88 Hz), 3.26-3.16 (3H, m), 1.28 (3H, t, J=7.07 Hz), 1.15 (6H, d, J=6.83 Hz); LRMS (ESI) m/z 470 [M+H]$^+$.

Example 144

4-{4-(4-(1H-Pyrazol-4-yl)-1H-imidazol-1-yl)-3-isopropyl-1H-pyrazolo[3,4-b]pyridin-1-yl}-2-(ethylamino)benzamide (144)

According to Example 143(2), compound (144) (the third stage yield: 27%) was prepared as a white solid using ethylamine (2.0 M in THF) instead of isopropylamine.

$^1$H-NMR (DMSO-d$_6$) δ: 12.88 (1H, s), 8.78 (1H, d, J=4.88 Hz), 8.39 (1H, d, J=7.07 Hz), 8.20 (1H, d, J=1.22 Hz), 8.02 (1H, s), 7.89 (1H, s), 7.82 (1H, s), 7.80 (1H, d, J=8.78 Hz), 7.75 (1H, d, J=1.95 Hz), 7.44 (1H, d, J=4.88 Hz), 7.43 (1H, dd, J=8.75, 1.95 Hz), 3.69 (1H, dtt, J=7.07, 6.34, 6.34 Hz), 3.21 (1H, tt, J=6.83, 6.83 Hz), 1.26 (6H, d, J=6.34 Hz), 1.15 (6H, d, J=6.83 Hz); LRMS (ESI) m/z 456 [M+H]$^+$.

Example 145

3-Chloro-4-{4-(4-(1-ethyl-1H-pyrazol-4-yl)-1H-imidazol-1-yl)-3-isopropyl-1H-pyrazolo[3,4-b]pyridin-1-yl}benzamide (145)

According to Example 99(2), compound (145) (42%) was prepared as a white solid using 4-(1-ethyl-1H-pyrazol-4-yl)-

1H-imidazole hydrochloride instead of 4-(1-methyl-1H-pyrazol-4-yl)-1H-imidazole hydrochloride.

$^1$H-NMR (DMSO-$d_6$) δ: 8.65 (1H, d, J=4.95 Hz), 8.25 (1H, brs), 8.22 (1H, d, J=1.32 Hz), 8.20 (1H, d, J=1.81 Hz), 8.03 (1H, dd, J=8.24, 1.81 Hz), 8.02 (1H, s), 7.90 (1H, d, J=1.32 Hz), 7.76 (1H, d, J=8.24 Hz), 7.75 (1H, s), 7.69 (1H, brs), 7.41 (1H, d, J=4.95 Hz), 4.16 (2H, q, J=7.25 Hz), 3.23 (1H, tt, J=6.76, 6.76 Hz), 1.40 (3H, t, J=7.25 Hz), 1.11 (6H, d, J=6.76 Hz); LRMS (ESI) m/z 475 [M+H]$^+$.

Example 146

4-{4-(4-(1-Ethyl-1H-pyrazol-4-yl)-1H-imidazol-1-yl)-3-isopropyl-1H-pyrazolo[3,4-b]pyridin-1-yl}-2-(ethylamino)benzamide (146)

According to Example 83, compound (146) (the third stage yield: 36%) was prepared as a white solid using 4-(1-ethyl-1H-pyrazol-4-yl)-1H-imidazole hydrochloride instead of 4-(4-methoxyphenyl)-1H-imidazole and using ethylamine (2.0 M in THF) instead of 4-hydroxycyclohexylamine.

$^1$H-NMR (DMSO-$d_6$) δ: 8.77 (1H, d, J=4.95 Hz) 8.34 (1H, t, J=5.11 Hz), 8.18 (1H, d, J=1.15 Hz), 8.02 (1H, s), 7.86 (1H, d, J=1.15 Hz), 7.79 (1H, d, J=8.74 Hz), 7.74 (1H, s), 7.69 (1H, d, J=2.14 Hz), 7.46 (1H, dd, J=8.74, 2.14 Hz), 7.43 (1H, d, J=4.95 Hz), 4.16 (2H, q, J=7.25 Hz), 3.27-3.16 (3H, m), 1.40 (3H, t, J=7.25 Hz), 1.27 (3H, t, J=7.09 Hz), 1.13 (6H, d, J=6.76 Hz); LRMS (ESI) m/z 484 [M+H]$^+$.

Example 147

4-{4-(4-(1-(Difluoromethyl)-1H-pyrazol-4-yl)-1H-imidazol-1-yl)-3-isopropyl-1H-pyrazolo[3,4-b]pyridin-1-yl}-2-(ethylamino)benzamide (147)

According to Example 83, compound (147) (the third stage yield: 22%) was prepared as a white solid using 4-(1-difluoromethyl-1H-pyrazol-4-yl)-1H-imidazole hydrochloride instead of 4-(4-methoxyphenyl)-1H-imidazole and using ethylamine (2.0 M in THF) instead of 4-hydroxycyclohexylamine.

$^1$H-NMR (DMSO-$d_6$) δ: 8.79 (1H, d, J=4.88 Hz), 8.50 (1H, s), 8.33 (1H, t, J=5.00 Hz), 8.27 (1H, d, J=1.22 Hz), 8.14 (1H, s), 8.06 (1H, d, J=1.22 Hz), 7.84 (1H, t, J=59.28 Hz), 7.79 (1H, d, J=8.78 Hz), 7.69 (1H, d, J=1.95 Hz), 7.46 (1H, d, J=4.88 Hz), 7.46 (1H, dd, J=8.78, 1.95 Hz), 3.25-3.13 (3H, m), 1.27 (3H, t, J=7.07 Hz), 1.13 (6H, d, J=6.59 Hz); LRMS (ESI) m/z 506 [M+H]$^+$.

Example 148

4-{4-(4-(1-(Hydroxyethyl)-1H-pyrazol-4-yl)-1H-imidazol-1-yl)-3-isopropyl-1H-pyrazolo[3,4-b]pyridin-1-yl}-2-(isopropyl)benzamide (148)

Example 148(1)

4-{4-(4-(1-(Benzyloxyethyl)-1H-pyrazol-4-yl)-1H-imidazol-1-yl)-3-isopropyl-1H-pyrazolo[3,4-b]pyridin-1-yl}-2-(isopropyl)benzamide (148a)

According to Example 83, compound (148a) (the third stage yield: 38%) was prepared as a white solid using 4-(1-benzyloxyethyl-1H-pyrazol-4-yl)-1H-imidazole hydrochloride instead of 4-(4-methoxyphenyl)-1H-imidazole and using isopropylamine instead of 4-hydroxycyclohexylamine.

Example 148(2)

4-{4-(4-(1-(Hydroxyethyl)-1H-pyrazol-4-yl)-1H-imidazol-1-yl)-3-isopropyl-1H-pyrazolo[3,4-b]pyridin-1-yl}-2-(isopropyl)benzamide (148)

According to Example 95, compound (148) (60%) was prepared as a white solid using compound (148a) instead of compound (93).

$^1$H-NMR (DMSO-$d_6$) δ: 8.77 (1H, d, J=4.88 Hz), 8.38 (1H, d, J=6.83 Hz), 8.19 (1H, d, J=1.10 Hz), 7.99 (1H, s), 7.88 (1H, d, J=1.10 Hz), 7.85 (1H, brs), 7.78 (1H, d, J=8.78 Hz), 7.76 (1H, s), 7.74 (1H, d, J=1.95 Hz), 7.43 (1H, d, J=4.88 Hz), 7.42 (1H, dd, J=8.78, 1.95 Hz), 7.16 (1H, brs), 4.93 (1H, t, J=5.45 Hz), 4.17 (2H, t, J=5.45 Hz), 3.76 (2H, q, J=5.45 Hz), 3.68 (1H, dtt, J=6.34, 6.34, 6.84 Hz), 3.19 (1H, tt, J=6.59, 6.59 Hz), 1.25 (6H, d, J=6.34 Hz), 1.13 (6H, d, J=6.59 Hz); LRMS (ESI) m/z 514 [M+H]$^+$.

Example 149

4-{3-Isopropyl-4-(4-(pyridin-4-yl)-1H-imidazol-1-yl)-1H-pyrazolo[3,4-b]pyridin-1-yl}-3-methylbenzamide (149)

According to Example 99(1), 4-(4-chloro-3-isopropyl-1H-pyrazolo[3,4-b]pyridin-1-yl)-3-methylbenzonitrile was prepared using 4-fluoro-3-methylbenzonitrile instead of 4-fluoro-3-chlorobenzonitrile; and according to Example 107 (2), compound (149) (the third stage yield: 2%) was prepared using 4-(4-chloro-3-isopropyl-1H-pyrazolo[3,4-b]pyridin-1-yl)-3-methylbenzonitrile instead of compound (107a) and using 4-(pyridin-4-yl)-1H-imidazole instead of 4-(1-methyl-1H-pyrazol-1-yl)-1H-imidazole hydrochloride.

$^1$H-NMR (DMSO-$d_6$) δ: 9.11 (1H, d, J=1.46 Hz), 8.69 (1H, d, J=4.88 Hz), 8.48 (1H, dd, J=4.76, 1.46 Hz), 8.46 (1H, d, J=1.22 Hz), 8.38 (1H, d, J=1.22 Hz), 8.23 (1H, dt, J=7.97, 1.95 Hz), 8.09 (1H, brs), 7.98 (1H, d, J=1.71 Hz), 7.88 (1H, dd, J=8.29, 1.71 Hz), 7.55 (1H, d, J=8.29 Hz), 7.49 (1H, brs), 7.47 (1H, d, J=4.88 Hz), 7.46 (1H, dd, J=7.97, 4.76 Hz), 3.21 (1H, tt, J=6.59, 6.59 Hz), 2.19 (3H, s), 1.12 (7H, d, J=6.59 Hz); LRMS (ESI) m/z 438 [M+H]$^+$.

Example 150

4-{1-(1-(4-Carbamoyl-2-chlorophenyl)-3-isopropyl-1H-pyrazolo[3,4-b]pyridin-4-yl)-1H-imidazol-4-yl}-N-isopropylbenzamide (150)

Example 150(1)

4-{1-(1-(Carbamoyl-2-chlorophenyl)-3-isopropyl-1H-pyrazolo[3,4-b]pyridin-4-yl)-1H-imidazol-4-yl}benzoic acid (150a)

According to Example 107(2), compound (150a) (the second stage yield: 21%) was prepared as a white solid using compound (99a) and ethyl-4-(1H-imidazol-4-yl)benzoate instead of compound (107a) and 4-(1-methyl-1H-pyrazol-1-yl)-1H-imidazole hydrochloride, respectively.

Example 150(2)

4-{1-(1-(4-Carbamoyl-2-chlorophenyl)-3-isopropyl-1H-pyrazolo[3,4-b]pyridin-4-yl)-1H-imidazol-4-yl}-N-isopropylbenzamide (150)

Compound (150a) (0.07 g), 1-ethyl-3-(3-dimethylamino-propyl)-carbodiimide hydrochloride (0.035 g), hydroxybenzotriazole monohydrate (0.025 g), and isopropylamine (0.085 mL) were dissolved in DMF (0.6 mL), followed by stirring at room temperature for 3 hr. The reaction solution was distributed between chloroform and water, and the organic layer was washed with saturated saline and was dried over anhydrous sodium sulfate. The solvent was distilled away, and the residue was purified by neutral silica gel column chromatography (chloroform/methanol) to obtain compound (150) (36%) as a white solid.

$^1$H-NMR (DMSO-$d_6$) δ: 8.69 (1H, d, J=4.95 Hz), 8.44 (1H, d, J=1.15 Hz), 8.36 (1H, d, J=1.32 Hz), 8.25 (1H, brs), 8.20 (1H, d, J=1.98 Hz), 8.18 (1H, d, J=6.92 Hz), 8.04 (1H, dd, J=8.24, 1.98 Hz), 7.96-7.90 (4H, m), 7.76 (1H, d, J=8.24 Hz), 7.69 (1H, brs), 7.49 (1H, d, J=4.95 Hz), 4.11 (1H, dtt, J=6.76, 6.76, 4.95 Hz), 3.23 (1H, tt, J=6.59, 6.59 Hz), 1.18 (6H, d, J=6.59 Hz), 1.12 (6H, d, J=6.76 Hz); LRMS (ESI) m/z 542 [M+H]$^+$.

Example 151

4-{1-(1-(4-Carbamoyl-2-chlorophenyl)-3-isopropyl-1H-pyrazolo[3,4-b]pyridin-4-yl)-1H-imidazol-4-yl}-N,N-dimethylbenzamide (151)

According to Example 150(2), compound (151) (16%) was prepared as a white solid using N,N-dimethylamine instead of isopropylamine.

$^1$H-NMR (DMSO-$d_6$) δ: 8.69 (1H, d, J=4.95 Hz), 8.41 (1H, d, J=1.15 Hz), 8.35 (1H, d, J=0.99 Hz), 8.25 (1H, brs), 8.20 (1H, d, J=1.98 Hz), 8.04 (1H, dd, J=8.24, 1.98 Hz), 7.94 (2H, d, J=8.08 Hz), 7.76 (1H, d, J=8.24 Hz), 7.69 (1H, brs), 7.48 (1H, d, J=4.95 Hz), 7.46 (2H, d, J=8.08 Hz), 3.25 (1H, tt, J=6.76, 6.76 Hz), 2.98 (6H, s), 1.12 (6H, d, J=6.76 Hz); LRMS (ESI) m/z 528 [M+H]$^+$.

Example 152

4-{4-(4-(4-Carbamoylphenyl)-1H-imidazol-1-yl)-3-isopropyl-1H-pyrazolo[3,4-b]pyridin-1-yl}-3-chlorobenzamide (152)

According to Example 150(2), compound (152) (32%) was prepared as a white solid using ammonia water (23% in water) instead of isopropylamine.

$^1$H-NMR (DMSO-$d_6$) δ: 8.69 (1H, d, J=4.95 Hz), 8.44 (1H, d, J=1.32 Hz), 8.36 (1H, d, J=1.32 Hz), 8.26 (1H, brs), 8.20 (1H, d, J=1.81 Hz), 8.04 (1H, dd, J=8.24, 1.81 Hz), 7.97-7.92 (5H, m), 7.76 (1H, d, J=8.24 Hz), 7.69 (1H, brs), 7.49 (1H, d, J=4.95 Hz), 7.33 (1H, brs), 3.23 (1H, tt, J=6.76, 6.76 Hz), 1.13 (6H, d, J=6.76 Hz); LRMS (ESI) m/z 500 [M+H]$^+$.

Example 153

3-Chloro-4-{4-(4-(1-methyl-1H-pyrazol-4-yl)-1H-imidazol-1-yl)-3-(trifluoromethyl)-1H-pyrazolo[3,4-b]pyridin-1-yl}benzamide (153)

Example 153(1)

4-Iodo-3-(trifluoromethyl)-1H-pyrazolo[3,4-b]pyridine (153a)

Normal-butyllithium (a 2.76 M solution in hexane, 37.0 mL) was dropwise added to a solution of N,N-diisopropylamine (15.0 mL) in tetrahydrofuran (hereinafter referred to as THF, 200 mL) under a nitrogen atmosphere at −5 to 0° C., and a solution of 2-fluoro-3-iodo-pyridine (21.8 g) in THF (250 mL) was dropwise added to the resulting solution at −78° C., followed by stirring for 15 min. Subsequently, ethyl 2,2,2-trifluoroacetate (14.0 mL) was dropwise added to the reaction solution at −78° C., followed by stirring at the same temperature for 1 hr, and then hydrazine monohydrate (9.5 mL) was added to the reaction solution, followed by stirring at 60° C. for 1 hr. The reaction solution was distributed between ethyl acetate and water, and the organic layer was washed with saturated saline. The organic layer after the washing was dried over anhydrous sodium sulfate, and then the solvent was distilled away. The residue was purified by neutral silica gel column chromatography (hexane/ethyl acetate) to obtain compound (153a) (21.0 g, 69%) as a white solid.

$^1$H-NMR (DMSO-$d_6$) δ: 8.10 (1H, dd, J=4.63, 2.20 Hz), 7.73 (1H, dd, J=4.63, 2.20 Hz); LRMS (ESI) m/z 314 [M+H]$^+$.

Example 153(2)

3-Chloro-4-{4-iodo-3-(trifluoromethyl)-1H-pyrazolo[3,4-b]pyridin-1-yl}benzamide (153b)

Compound (153a) (5.0 g), cesium carbonate (7.82 g), and 3-chloro-4-fluorobenzonitrile (3.0 g) were suspended in acetonitrile (50 mL), followed by stirring at 70° C. for 24 hr. The reaction solution was distributed between ethyl acetate and an aqueous ammonium chloride solution, and the organic layer was washed with saturated saline. The organic layer after the washing was dried over anhydrous sodium sulfate, and then the solvent was distilled away. Ethanol was added to the residue, and the precipitate was collected by filtration to obtain 3-chloro-4-{4-iodo-3-(trifluoromethyl)-1H-pyrazolo[3,4-b]pyridin-1-yl}benzamide (4.77 g, 66%). 3-Chloro-4-{4-iodo-3-(trifluoromethyl)-1H-pyrazolo[3,4-b]pyridin-1-yl}benzamide (2.53 g) was dissolved in DMSO (28 mL). A hydrogen peroxide solution (30 wt %) (0.700 mL) and a 4 mol % aqueous sodium hydroxide solution (1.41 mL) were added to the resulting solution, followed by stirring at room temperature for 20 min. Water was added to the reaction solution, and the precipitate was collected by filtration and was dried under reduced pressure to obtain compound (153b) (2.26 g, 86%).

$^1$H-NMR (DMSO-$d_6$) δ: 8.32 (1H, d, J=4.88 Hz), 8.28 (1H, br s), 8.22 (1H, d, J=1.71 Hz), 8.14 (1H, d, J=4.88 Hz), 8.06 (1H, dd, J=8.05, 1.71 Hz), 7.91 (1H, d, J=8.05 Hz), 7.74 (1H, brs); LRMS (ESI) m/z 466 [M+H]$^+$.

Example 153(3)

3-Chloro-4-{4-(4-(1-methyl-1H-pyrazol-4-yl)-1H-imidazol-1-yl)-3-(trifluoromethyl)-1H-pyrazolo[3,4-b]pyridin-1-yl}benzamide (153)

According to Example 99(2), compound (153) (71%) was prepared using compound (153b) instead of compound (99a).

$^1$H-NMR (DMSO-$d_6$) δ: 8.86 (1H, d, J=4.88 Hz), 8.30 (1H, brs), 8.25 (1H, d, J=1.95 Hz), 8.10 (1H, s), 8.08 (1H, dd, J=8.29, 1.95 Hz), 7.96 (1H, s), 7.92 (1H, d, J=8.29 Hz), 7.79 (1H, s), 7.76 (1H, brs), 7.71 (1H, s), 7.69 (1H, d, J=4.88 Hz), 3.87 (3H, s); LRMS (ESI) m/z 487 [M+H]$^+$.

Example 154

3-Methyl-4-{4-(4-(1-methyl-1H-pyrazol-4-yl)-1H-imidazol-1-yl)-3-(trifluoromethyl)-1H-pyrazolo[3,4-b]pyridin-1-yl}benzamide (154)

Example 154(1)

4-Hydrazinyl-3-methylbenzonitrile (154a)

Hydrazine monohydrate (180 mL) was added to 4-fluoro-3-methylbenzonitrile (5.0 g), followed by stirring at 100° C. for 4 hr. Water was added to the reaction solution, and the precipitate was collected by filtration and was dried under reduced pressure to obtain compound (154a) (4.33 g, 79%).

$^1$H-NMR (DMSO-$d_6$) δ: 7.41 (1H, dd, J=8.66, 1.59 Hz), 7.26 (1H, d, J=1.59 Hz), 7.14 (1H, brs), 7.07 (1H, d, J=8.66 Hz), 2.02 (3H, s); LRMS (ESI) m/z 148 [M+H]$^+$.

Example 154(2)

4-{5-Amino-3-(trifluoromethyl)-1H-pyrazolo-1-yl}-3-methylbenzonitrile (154b)

Compound (154a) (0.300 g) and 4,4,4-trifluoro-3-oxobutanenitrile (0.419 g) were dissolved in ethanol (6.8 mL) and methanesulfonic acid (0.68 mL), followed by reflux for 12 hr. The reaction solution was distributed between ethyl acetate and water, and the organic layer was washed with saturated saline. The organic layer after the washing was dried over anhydrous sodium sulfate, and the solvent was distilled away. The residue was purified by neutral silica gel column chromatography (hexane/ethyl acetate) to obtain compound (154b) (0.255 g, 47%).

$^1$H-NMR (DMSO-$d_6$) δ: 7.95 (1H, s), 7.82 (1H, d, J=8.05 Hz), 7.53 (1H, d, J=8.05 Hz), 5.74 (1H, s), 5.69 (2H, s), 2.10 (3H, s); LRMS (ESI) m/z 267 [M+H]$^+$.

Example 154(3)

4-{5-((2,2-Dimethyl-4,6-dioxo-1,3-dioxan-5-ylidene)methylamino)-3-(trifluoromethyl)-1H-pyrazolo-1-yl}-3-methylbenzonitrile (154c)

Compound (154b) (0.153 g) and 5-methoxymethylene Meldrum's acid (0.129 g) were dissolved in 2-propanol (2.00 mL), followed by stirring at 100° C. for 1 hr. The reaction solution was cooled to room temperature, and the precipitate was collected by filtration, washed with diethyl ether, and dried under reduced pressure to obtain compound (154c) (0.159 mg, 66%).

$^1$H-NMR (DMSO-$d_6$) δ: 11.07 (1H, d, J=7.56 Hz), 8.46 (1H, d, J=7.56 Hz), 8.04 (1H, d, J=1.71 Hz), 7.91 (1H, dd, J=8.05, 1.71 Hz), 7.76 (1H, d, J=8.05 Hz), 7.39 (1H, s), 2.17 (3H, s), 1.62 (6H, s); LRMS (ESI) m/z 420 [M+H]$^+$.

Example 154(4)

3-Methyl-4-{4-oxo-3-(trifluoromethyl)-4,7-dihydro-1H-pyrazolo[3,4-b]pyridin-1-yl}benzonitrile (154d)

Compound (154c) (2.9 g) was added to Dothem (21.0 mL), followed by stirring at 200° C. for 1 hr. The reaction solution was cooled to room temperature, and the precipitate was collected by filtration, washed with hexane, and dried under reduced pressure to obtain compound (154d) (2.20 g, 97%).

$^1$H-NMR (DMSO-$d_6$) δ: 8.32 (1H, brs), 8.02 (1H, d, J=1.46 Hz), 7.89 (1H, dd, J=8.29, 1.46 Hz), 7.74 (1H, d, J=8.29 Hz), 6.78 (1H, brs), 2.15 (3H, s); LRMS (ESI) m/z 319 [M+H]$^+$.

Example 154(5)

4-{4-Chloro-3-(trifluoromethyl)-1H-pyrazolo[3,4-b]pyridin-1-yl}-3-methylbenzonitrile (154e)

Compound (154d) (2.20 g) was dissolved in chloroform (14 mL), and thionyl chloride (1.00 mL) and DMF (0.148 mL) were added to the resulting solution, followed by reflux for 3 hr. Water was added to the reaction solution for distribution. The organic layer was washed with saturated sodium bicarbonate water. The organic layer after the washing was dried over anhydrous sodium sulfate, and the solvent was distilled away. 2-Propanol was added to the residue, and the precipitate was collected by filtration and then dried under reduced pressure to obtain compound (154e) (1.60 g, 71%).

$^1$H-NMR (DMSO-$d_6$) δ: 8.69 (1H, d, J=5.12 Hz), 8.07 (1H, d, J=1.34 Hz), 7.95 (1H, dd, J=8.05, 1.34 Hz), 7.81 (1H, d, J=8.05 Hz), 7.77 (1H, d, J=4.88 Hz), 2.18 (3H, s); LRMS (ESI) m/z 337 [M+H]$^+$.

Example 154(6)

3-Methyl-4-{4-(4-(1-methyl-1H-pyrazol-4-yl)-1H-imidazol-1-yl)-3-(trifluoromethyl)-1H-pyrazolo[3,4-b]pyridin-1-yl}benzamide (154)

Compound (154e) (1.66 g), copper(I) oxide (0.070 g), 4,7-dimethoxy-1,10-phenanthroline (0.214 g), cesium carbonate (5.46 g), polyethylene glycol (Mn=3400) (0.250 g), and 4-(1-methyl-1H-pyrazol-4-yl)-1H-imidazole hydrochloride (1.20 g) were suspended in DMSO (15 mL), followed by stirring at 120° C. for 2 hr. The reaction solution was diluted with ethyl acetate, and insoluble matters were filtered by celite. The filtrate was distributed between ethyl acetate and water, and the organic layer was washed with saturated saline. The organic layer after the washing was dried over anhydrous sodium sulfate, and the solvent was distilled away to obtain 3-methyl-4-{4-(4-(1-methyl-1H-pyrazol-4-yl)-1H-imidazol-1-yl)-3-(trifluoromethyl)-1H-pyrazolo[3,4-b]pyridin-1-yl}benzonitrile, which was used in the subsequent reaction without being purified. TFA (5.0 mL) and sulfuric acid (0.5 mL) were added to this 3-methyl-4-{4-(4-(1-methyl-1H-pyrazol-4-yl)-1H-imidazol-1-yl)-3-(trifluoromethyl)-1H-pyrazolo[3,4-b]pyridin-1-yl}benzonitrile, followed by stirring at room temperature for 2 days. The reaction solution was cooled in an ice bath and was neutralized with sodium hydroxide. The reaction solution was distributed between ethyl acetate and water, and the organic layer was washed with saturated saline. The organic layer after the washing was dried over anhydrous sodium sulfate, and the solvent was distilled away. Ethanol was added to the residue, and the precipitate was collected by filtration and dried under reduced pressure to obtain compound (154) (0.881 g, the second stage yield: 38%).

$^1$H-NMR (DMSO-$d_6$) δ: 9.57 (1H, d, J=4.88 Hz), 8.87 (1H, brs), 8.81 (1H, s), 8.75 (1H, d, J=1.46 Hz), 8.69 (1H, s), 8.64 (1H, dd, J=8.17, 1.46 Hz), 8.50 (1H, s), 8.44 (1H, s), 8.39 (1H, d, J=4.88 Hz), 8.36 (1H, d, J=8.17 Hz), 8.28 (1H, brs), 4.59 (3H, s), 2.88 (3H, s); LRMS (ESI) m/z 466 [M+H]$^+$.

Example 155

3-Ethyl-4-{4-(4-(1-methyl-1H-pyrazol-4-yl)-1H-imidazol-1-yl)-3-(trifluoromethyl)-1H-pyrazolo[3,4-b]pyridin-1-yl}benzamide (155)

Example 155(1)

3-Ethyl-4-hydrazinylbenzonitrile (155a)

According to Example 154(1), compound (155a) (0.370 g, 28%) was prepared using 3-ethyl-4-fluorobenzonitrile (1.22 g) instead of 4-fluoro-3-methylbenzonitrile.

Example 155(2)

4-{5-Amino-3-(trifluoromethyl)-1H-pyrazolo-1-yl}-3-ethylbenzonitrile (155b)

According to Example 154(2), compound (155b) (0.220 g, 33%) was prepared using compound (155a) (0.370 g) instead of compound (154a).
$^1$H-NMR (CDCl$_3$) δ: 7.72 (1H, d, J=1.95 Hz), 7.64 (1H, dd, J=8.05, 1.95 Hz), 7.46 (1H, d, J=8.05 Hz), 5.88 (1H, s), 3.72 (2H, s), 2.56 (2H, q, J=7.56 Hz), 1.15 (3H, t, J=7.56 Hz); LRMS (ESI) m/z 281 [M+H]$^+$.

Example 155(3)

4-{5-((2,2-Dimethyl-4,6-dioxo-1,3-dioxan-5-ylidene)methylamino)-3-(trifluoromethyl)-1H-pyrazolo-1-yl}-3-ethylbenzonitrile (155c)

According to Example 154(3), compound (155c) (0.286 g, 84%) was prepared using compound (155b) (0.220 g) instead of compound (154b).

Example 155(4)

3-Ethyl-4-{4-oxo-3-(trifluoromethyl)-4,7-dihydro-1H-pyrazolo[3,4-b]pyridin-1-yl}benzonitrile (155d)

According to Example 154(4), compound (155d) (0.148 g, 68%) was prepared using compound (155c) (0.286 g) instead of compound (154c).
$^1$H-NMR (CDCl$_3$) δ: 8.36 (1H, brs), 7.74 (1H, d, J=1.71 Hz), 7.65 (1H, dd, J=8.05, 1.71 Hz), 7.59 (2H, d, J=8.05 Hz), 6.71 (1H, brs), 2.57 (2H, q, J=7.56 Hz), 1.12 (3H, t, J=7.56 Hz); LRMS (ESI) m/z 333 [M+H]$^+$.

Example 155(5)

4-{4-Chloro-3-(trifluoromethyl)-1H-pyrazolo[3,4-b]pyridin-1-yl}-3-methylbenzonitrile (155e)

According to Example 154(5), compound (155e) (0.064 g, 41%) was prepared using compound (155d) (0.148 g) instead of compound (154d).
$^1$H-NMR (CDCl$_3$) δ: 8.52 (1H, d, J=4.88 Hz), 7.78 (1H, d, J=1.95 Hz), 7.70 (1H, dd, J=8.05, 1.95 Hz), 7.57 (1H, d, J=8.05 Hz), 7.43 (1H, d, J=4.88 Hz), 2.56 (2H, q, J=7.56 Hz), 1.12 (3H, t, J=7.56 Hz); LRMS (ESI) m/z 351 [M+H]$^+$.

Example 155(6)

3-Methyl-4-{4-(4-(1-methyl-1H-pyrazol-4-yl)-1H-imidazol-1-yl)-3-(trifluoromethyl)-1H-pyrazolo[3,4-b]pyridin-1-yl}benzamide (155)

According to Example 154(6), compound (155) (0.008 g, 9%) was prepared using compound (155e) (0.064 g) instead of compound (154e).
$^1$H-NMR (DMSO-d$_6$) δ: 9.56 (1H, d, J=4.88 Hz), 8.90 (1H, brs), 8.81 (1H, s), 8.77 (1H, d, J=1.95 Hz), 8.69 (1H, s), 8.65 (1H, dd, J=8.05, 1.95 Hz), 8.51 (1H, s), 8.44 (1H, s), 8.39 (1H, d, J=4.88 Hz), 8.34 (1H, d, J=8.05 Hz), 8.30 (1H, brs), 4.59 (3H, s), 3.15 (2H, q, J=7.44 Hz), 1.76 (3H, t, J=7.44 Hz); LRMS (ESI) m/z 481 [M+H]$^+$.

Example 156

4-{4-(4-(1-Methyl-1H-pyrazol-4-yl)-1H-imidazol-1-yl)-3-(trifluoromethyl)-1H-pyrazolo[3,4-b]pyridin-1-yl}-3-propylbenzamide (156)

Example 156(1)

4-{5-Amino-3-(trifluoromethyl)-1H-pyrazolo-1-yl}-3-ethylbenzonitrile (156a)

According to Example 154(1), 4-hydrazinyl-3-propylbenzonitrile was prepared using 4-fluoro-3-propylbenzonitrile (1.00 g) instead of 4-fluoro-3-methylbenzonitrile; and according to Example 154(2), compound (156a) (0.340 g, the second stage yield: 19%) was prepared using 4-hydrazinyl-3-propylbenzonitrile instead of compound (154a).
$^1$H-NMR (CDCl$_3$) δ: 7.70 (1H, d, J=1.95 Hz), 7.64 (1H, dd, J=8.05, 1.95 Hz), 7.46 (1H, d, J=8.05 Hz), 5.88 (1H, s), 3.71 (2H, s), 2.51 (2H, t, J=7.81 Hz), 1.53 (2H, dtt, J=7.32, 7.32, 7.81 Hz), 0.87 (3H, t, J=7.32 Hz); LRMS (ESI) m/z 295 [M+H]$^+$.

Example 156(2)

4-{5-((2,2-Dimethyl-4,6-dioxo-1,3-dioxan-5-ylidene)methylamino)-3-(trifluoromethyl)-1H-pyrazolo-1-yl}-3-propylbenzonitrile (156b)

According to Example 154(3), compound (156b) (0.482 g, 93%) was prepared using compound (156a) (0.340 g) instead of compound (154b).
$^1$H-NMR (CDCl$_3$) δ: 11.20 (1H, d, J=13.17 Hz), 8.38 (1H, d, J=13.17 Hz), 7.78 (1H, d, J=1.71 Hz), 7.73 (1H, dd, J=8.05, 1.71 Hz), 7.45 (1H, d, J=8.05 Hz), 6.63 (1H, s), 2.43 (2H, t, J=7.68 Hz), 1.53 (2H, dtt, J=7.32, 7.32, 7.68 Hz), 0.85 (3H, t, J=7.32 Hz); LRMS (ESI) m/z 449 [M+H]$^+$.

Example 156(3)

4-{4-Oxo-3-(trifluoromethyl)-4,7-dihydro-1H-pyrazolo[3,4-b]pyridin-1-yl}-3-propylbenzonitrile (156c)

According to Example 154(4), compound (156c) (0.300 g, 81%) was prepared using compound (156b) (0.482 g) instead of compound (154c).
$^1$H-NMR (CDCl$_3$) δ: 8.40 (1H, brs), 7.73 (1H, d, J=1.71 Hz), 7.67 (1H, dd, J=8.05, 1.71 Hz), 7.60 (1H, d, J=8.05 Hz), 6.75 (1H, brs), 2.52 (2H, t, J=7.81 Hz), 1.49 (2H, dtt, J=7.32, 7.32, 7.81 Hz), 0.81 (3H, t, J=7.32 Hz); LRMS (ESI) m/z 347 [M+H]$^+$.

Example 156(4)

4-{4-Chloro-3-(trifluoromethyl)-1H-pyrazolo[3,4-b]pyridin-1-yl}-3-propylbenzonitrile (156d)

According to Example 154(5), compound (156d) (0.250 g, 79%) was prepared using compound (156c) (0.300 g) instead of compound (154d).

$^1$H-NMR (CDCl$_3$) δ: 8.52 (1H, d, J=4.88 Hz), 7.76 (1H, d, J=1.83 Hz), 7.69 (1H, dd, J=8.05, 1.83 Hz), 7.57 (1H, d, J=8.05 Hz), 7.43 (1H, d, J=4.88 Hz), 2.50 (2H, t, J=7.68 Hz), 1.50 (2H, dtt, J=7.32, 7.32, 7.68 Hz), 0.80 (3H, t, J=7.32 Hz); LRMS (ESI) m/z 365 [M+H]$^+$.

Example 156(5)

3-Methyl-4-{4-(4-(1-methyl-1H-pyrazol-4-yl)-1H-imidazol-1-yl)-3-(trifluoromethyl)-1H-pyrazolo[3,4-b]pyridin-1-yl}benzamide (156)

According to Example 154(6), compound (156) (0.0.97 g, 34%) was prepared using compound (156d) (0.250 g) instead of compound (154e).

$^1$H-NMR (DMSO-d$_6$) δ: 8.84 (1H, d, J=4.88 Hz), 8.16 (1H, s), 8.09 (1H, brs), 8.03 (1H, d, J=1.95 Hz), 7.97 (1H, s), 7.92 (1H, dd, J=8.05, 1.95 Hz), 7.78 (1H, s), 7.71 (1H, s), 7.66 (1H, d, J=4.88 Hz), 7.62 (1H, d, J=8.05 Hz), 7.56 (1H, brs), 3.87 (3H, s), 2.41 (2H, t, J=7.68 Hz), 1.44 (2H, ttd, J=7.68, 7.32, 7.32 Hz), 0.71 (3H, t, J=7.32 Hz); LRMS (ESI) m/z 495 [M+H]$^+$.

Example 157

2-Amino-4-{4-(4-(1-methyl-1H-pyrazol-4-yl)-1H-imidazol-1-yl)-3-(trifluoromethyl)-1H-pyrazolo[3,4-b]pyridin-1-yl}benzamide (157)

Example 157(1)

2-Amino-4-{4-iodo-3-(trifluoromethyl)-1H-pyrazolo[3,4-b]pyridin-1-yl}benzamide (157a)

According to Example 106(1), compound (157a) (2.47 g, the second stage yield: 58%) was prepared using compound (153a) (3.00 g) instead of compound (6b).

$^1$H-NMR (DMSO-d$_6$) δ: 8.40 (1H, d, J=4.88 Hz), 8.14 (1H, d, J=4.88 Hz), 7.86 (1H, brs), 7.76 (1H, d, J=8.78 Hz), 7.50 (1H, d, J=2.20 Hz), 7.32 (1H, dd, J=8.78, 2.20 Hz), 7.20 (1H, brs), 6.98 (2H, s); LRMS (ESI) m/z 448 [M+H]$^+$.

Example 157(2)

2-Amino-4-{4-(4-(1-methyl-1H-pyrazol-4-yl)-1H-imidazol-1-yl)-3-(trifluoromethyl)-1H-pyrazolo[3,4-b]pyridin-1-yl}benzamide (157)

According to Example 99(2), compound (157) (46%) was prepared using compound (157a) instead of compound (99a).

$^1$H-NMR (DMSO-d$_6$) δ: 8.96 (1H, d, J=4.88 Hz), 8.22 (1H, s), 7.99 (1H, s), 7.88 (1H, brs), 7.81 (1H, s), 7.78 (1H, d, J=8.78 Hz), 7.73 (1H, s), 7.71 (1H, d, J=4.88 Hz), 7.55 (1H, d, J=1.95 Hz), 7.38 (1H, dd, J=8.78, 1.95 Hz), 7.23 (1H, brs), 3.87 (3H, s); LRMS (ESI) m/z 468 [M+H]$^+$.

Example 158

3-Amino-4-{4-(4-(1-methyl-1H-pyrazol-4-yl)-1H-imidazol-1-yl)-3-(trifluoromethyl)-1H-pyrazolo[3,4-b]pyridin-1-yl}benzamide (158)

Example 158(1)

3-Amino-4-{4-iodo-3-(trifluoromethyl)-1H-pyrazolo[3,4-b]pyridin-1-yl}benzonitrile (158a)

Compound (153a) (5.00 g), cesium carbonate (6.72 g), and 4-chloro-3-nitrobenzonitrile (3.21 g) were suspended in acetonitrile (50 mL), followed by stirring at 70° C. for 4 hr. A saturated aqueous ammonium chloride solution was added to the reaction solution, and the precipitate was collected by filtration and dried under reduced pressure to obtain 4-{4-iodo-3-(trifluoromethyl)-1H-pyrazolo[3,4-b]pyridin-1-yl}-3-nitrobenzonitrile (7.19 g, 98%). The obtained 4-{4-iodo-3-(trifluoromethyl)-1H-pyrazolo[3,4-b]pyridin-1-yl}-3-nitrobenzonitrile (7.19 g) was suspended in THF (50 mL), MeOH (50 mL), and water (50 mL), and ammonium chloride (7.20 g) and iron powder (8.76 g) were added to the resulting suspension, followed by stirring at 80° C. for 2 hr. The reaction solution was diluted with ethyl acetate, and insoluble matters were filtered by celite. The solvent of the filtrate was distilled away, and water was added to the residue. Insoluble matters were collected by filtration and dried under reduced pressure to obtain compound (158a) (6.44 g, 96%).

$^1$H-NMR (DMSO-d$_6$) δ: 8.26 (1H, d, J=4.63 Hz), 8.08 (1H, d, J=4.63 Hz), 7.42 (1H, d, J=8.05 Hz), 7.23 (1H, s), 7.04 (1H, d, J=8.05 Hz), 5.80 (2H, s); LRMS (ESI) m/z 430 [M+H]$^+$.

Example 158(2)

3-Amino-4-{4-iodo-3-(trifluoromethyl)-1H-pyrazolo[3,4-b]pyridin-1-yl}benzamide (158b)

Compound (158a) (0.100 g) was dissolved in DMSO (1.2 mL). A hydrogen peroxide solution (30 wt %) (0.053 mL) and a 4 mol % aqueous sodium hydroxide solution (0.233 mL) were added to the resulting solution, followed by stirring at room temperature for 20 min. Water was added to the reaction solution, and the precipitate was collected by filtration and was dried under reduced pressure to obtain compound (158b) (0.090 g).

$^1$H-NMR (DMSO-d$_6$) δ: 8.25 (1H, d, J=4.63 Hz), 8.06 (1H, d, J=4.63 Hz), 7.94 (1H, brs), 7.38 (1H, s), 7.36 (1H, brs), 7.24 (1H, d, J=8.05 Hz), 7.11 (1H, d, J=8.05 Hz), 5.40 (2H, s); LRMS (ESI) m/z 448 [M+H]$^+$.

Example 158(3)

3-Amino-4-{4-(4-(1-methyl-1H-pyrazol-4-yl)-1H-imidazol-1-yl)-3-(trifluoromethyl)-1H-pyrazolo[3,4-b]pyridin-1-yl}benzamide (158)

According to Example 99(2), compound (155) (0.040 g, 36%) was prepared using compound (158b) (0.090 g) instead of compound (99a).

$^1$H-NMR (DMSO-d$_6$) δ: 9.52 (1H, d, J=4.88 Hz), 8.73 (1H, s), 8.70 (1H, s), 8.67 (1H, brs), 8.45 (2H, s), 8.33 (1H, d, J=4.88 Hz), 8.12 (1H, d, J=1.71 Hz), 8.09 (1H, brs), 8.02 (1H, d, J=8.05 Hz), 7.86 (1H, dd, J=8.05, 1.71 Hz), 6.13 (2H, s), 4.59 (3H, s); LRMS (ESI) m/z 468 [M+H]⁺.

Example 159

3-(Dimethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (159)

Compound (158a) (0.100 g) and iodomethane (0.18 mL) were dissolved in DMF (6.0 mL), and sodium hydride (0.038 g, a 55% dispersion in paraffin liquid) was added to the resulting solution under ice cooling, followed by stirring for 1 hr. The reaction solution was distributed between ethyl acetate and water, and the organic layer was washed with saturated saline. The organic layer after the washing was dried over anhydrous sodium sulfate, and then the solvent was distilled away to obtain 3-(dimethylamino)-4-{4-iodo-3-(trifluoromethyl)-1H-pyrazolo[3,4-b]pyridin-1-yl}benzonitrile, which was used in the subsequent reaction without being purified. This 3-(dimethylamino)-4-{4-iodo-3-(trifluoromethyl)-1H-pyrazolo[3,4-b]pyridin-1-yl}benzonitrile was dissolved in DMSO (3.0 mL), and a hydrogen peroxide solution (30 wt %) (0.060 mL) and a 4 mol % aqueous sodium hydroxide solution (0.15 mL) were added to the resulting solution, followed by stirring at room temperature for 20 min. Water was added to the reaction solution, and the precipitate was collected by filtration and dried under reduced pressure to obtain 3-(dimethylamino)-4-{4-iodo-3-(trifluoromethyl)-1H-pyrazolo[3,4-b]pyridin-1-yl}benzamide. Lastly, according to Example 99(2), compound (159) (0.025 g, the third stage yield: 17%) was prepared using 3-(dimethylamino)-4-{4-iodo-3-(trifluoromethyl)-1H-pyrazolo[3,4-b]pyridin-1-yl}benzamide instead of compound (99a).

¹H-NMR (DMSO-d₆) δ: 8.83 (1H, d, J=4.88 Hz), 8.14 (1H, brs), 8.08 (1H, s), 7.96 (1H, s), 7.77 (1H, s), 7.71 (1H, s), 7.66 (1H, d, J=1.71 Hz), 7.63 (1H, d, J=4.88 Hz), 7.52 (1H, dd, J=8.05, 1.71 Hz), 7.52 (1H, brs), 7.45 (1H, d, J=8.05 Hz), 3.87 (3H, s), 2.43 (6H, s); LRMS (ESI) m/z 496 [M+H]⁺.

Example 160

2-(Isopropylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (160)

Compound (157a) (0.200 g), sodium triacetoxyborohydride (0.189 g), and isopropenyl methyl ether (0.102 mL) were dissolved in dichloroethane (2.0 mL) and acetic acid (0.50 mL), followed by stirring at 0° C. for 1 hr. The reaction solution was distributed between ethyl acetate and saturated sodium bicarbonate water, and the organic layer was washed with saturated saline and was dried over anhydrous sodium sulfate. The solvent was distilled away to obtain 4-{4-iodo-3-(trifluoromethyl)-1H-pyrazolo[3,4-b]pyridin-1-yl}-2-(isopropyl)benzamide, which was used in the subsequent reaction without being purified. According to Example 99(2), compound (160) (the second stage yield: 30%) was prepared as a white solid using 4-{4-iodo-3-(trifluoromethyl)-1H-pyrazolo[3,4-b]pyridin-1-yl}-2-(isopropyl)benzamide instead of compound (99a).

¹H-NMR (DMSO-d₆) δ: 8.94 (1H, d, J=4.88 Hz), 8.38 (1H, d, J=7.07 Hz), 8.04 (1H, s), 7.96 (1H, s), 7.84 (1H, d, J=8.78 Hz), 7.74 (1H, s), 7.71 (1H, s), 7.67 (1H, d, J=4.88 Hz), 7.54 (1H, d, J=1.95 Hz), 7.26 (1H, dd, J=8.78, 1.95 Hz), 3.86 (3H, s), 3.68 (1H, dtt, J=7.07, 6.34, 6.34 Hz), 1.24 (6H, d, J=6.34 Hz); LRMS (ESI) m/z 510 [M+H]⁺.

Example 161

2-(Ethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (161)

According to Example 160, compound (161) (the second stage yield: 27%) was prepared as a white solid using acetaldehyde dimethyl acetal instead of isopropenyl methyl ether.

¹H-NMR (DMSO-d₆) δ: 8.94 (1H, d, J=4.88 Hz), 8.33 (1H, t, J=5.00 Hz), 8.04 (1H, s), 7.96 (1H, s), 7.85 (1H, d, J=8.54 Hz), 7.74 (1H, s), 7.71 (1H, s), 7.67 (1H, d, J=4.88 Hz), 7.49 (1H, d, J=1.95 Hz), 7.32 (1H, dd, J=8.54, 1.95 Hz), 3.86 (3H, s), 3.21 (2H, dq, J=5.00, 7.20 Hz), 1.25 (3H, t, J=7.20 Hz); LRMS (ESI) m/z 496 [M+H]⁺.

Example 162

3-(Ethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (162)

Example 162(1)

3-(Ethylamino)-4-{4-iodo-3-(trifluoromethyl)-1H-pyrazolo[3,4-b]pyridin-1-yl}benzamide (162a)

Compound (158a) (1.50 g) and iodoethane (2.8 mL) were dissolved in DMF (35 mL), and sodium hydride (0.335 g, a 55% dispersion in paraffin liquid) was added to the resulting solution under ice cooling, followed by stirring for 20 min. Water was added to the reaction solution, and the precipitate was collected by filtration and dried under reduced pressure to obtain 3-(ethylamino)-4-{4-iodo-3-(trifluoromethyl)-1H-pyrazolo[3,4-b]pyridin-1-yl}benzonitrile, which was used in the subsequent reaction without being purified. This 3-(ethylamino)-4-{4-iodo-3-(trifluoromethyl)-1H-pyrazolo[3,4-b]pyridin-1-yl}benzonitrile was dissolved in DMSO (15 mL), and a hydrogen peroxide solution (30 wt %) (0.563 mL) and a 4 mol % aqueous sodium hydroxide solution (2.48 mL) were added to the resulting solution, followed by stirring at room temperature for 20 min. Water was added to the reaction solution, and the precipitate was collected by filtration and was dried under reduced pressure to obtain compound (162a) (1.29 g, the second stage yield: 78%) as a white solid.

¹H-NMR (DMSO-d₆) δ: 8.24 (1H, d, J=4.88 Hz), 8.06 (1H, d, J=4.88 Hz), 8.03 (1H, brs), 7.41 (1H, brs), 7.28 (1H, d, J=1.71 Hz), 7.23 (1H, d, J=8.05 Hz), 7.14 (1H, dd, J=8.05, 1.71 Hz), 5.41 (1H, t, J=5.61 Hz), 3.12 (2H, dq, J=5.61, 7.07 Hz), 1.05 (3H, t, J=7.07 Hz); LRMS (ESI) m/z 476 [M+H]⁺.

Example 162(2)

3-(Ethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (162)

According to Example 99(2), compound (162) (0.435 g, 32%) was prepared using (162a) (1.29 g) instead of compound (99a).

¹H-NMR (DMSO-d₆) δ: 9.52 (1H, d, J=4.88 Hz), 8.77 (1H, brs), 8.75 (1H, s), 8.70 (1H, s), 8.45 (2H, s), 8.34 (1H, d, J=4.88 Hz), 8.15 (1H, brs), 8.04 (1H, d, J=1.46 Hz), 8.01 (1H, d, J=8.05 Hz), 7.90 (1H, dd, J=8.05, 1.46 Hz), 6.09 (1H, t, J=5.61 Hz), 4.60 (3H, s), 3.87 (2H, dq, J=5.61, 7.07 Hz), 1.79 (3H, t, J=7.07 Hz); LRMS (ESI) m/z 496 [M+H]⁺.

Example 163

4-{4-(4-(1-Methyl-1H-pyrazol-4-yl)-1H-imidazol-1-yl)-3-(trifluoromethyl)-1H-pyrazolo[3,4-b]pyridin-1-yl}-3-(propylamino)benzamide (163)

Example 163(1)

4-{4-Iodo-3-(trifluoromethyl)-1H-pyrazolo[3,4-b]pyridin-1-yl}-3-(propylamino)-benzamide (163a)

According to Example 120(1), compound (163a) (the second stage yield: 66%) was prepared as a yellow solid using compound (158b) instead of compound (107a) and using propionaldehyde instead of acetone.
¹H-NMR (DMSO-d₆) δ: 8.24 (1H, d, J=4.63 Hz), 8.05 (1H, d, J=4.63 Hz), 8.03 (1H, brs), 7.41 (1H, brs), 7.28 (1H, s), 7.24 (1H, d, J=8.05 Hz), 7.13 (1H, d, J=8.05 Hz), 5.44 (1H, t, J=5.37 Hz), 3.04 (2H, td, J=7.32, 5.37 Hz), 1.47 (2H, ttd, J=7.32, 7.32, 7.32 Hz), 0.83 (3H, t, J=7.32 Hz); LRMS (ESI) m/z 490 [M+H]⁺.

Example 163(2)

4-{4-(4-(1-Methyl-1H-pyrazol-4-yl)-1H-imidazol-1-yl)-3-(trifluoromethyl)-1H-pyrazolo[3,4-b]pyridin-1-yl}-3-(propylamino)benzamide (163)

According to Example 99(2), compound (163) (40%) was prepared using (163a) instead of compound (99a).
¹H-NMR (DMSO-d₆) δ: 9.23 (1H, d, J=1.46 Hz), 9.10 (2H, d, J=9.03 Hz), 8.83 (1H, d, J=1.22 Hz), 8.76 (1H, d, J=7.56 Hz), 8.70 (1H, d, J=9.03 Hz), 8.67 (1H, s), 8.44 (1H, s), 4.58 (5H, s), 3.83-3.74 (2H, m), 2.26-2.20 (2H, m), 1.58 (3H, q, J=6.67 Hz); LRMS (ESI) m/z 510 [M+H]⁺.

Example 164

3-(Isopropylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (164)

Example 164(1)

4-{4-Iodo-3-(trifluoromethyl)-1H-pyrazolo[3,4-b]pyridin-1-yl}-3-(isopropylamino)benzamide (164a)

According to Example 120(1), compound (164a) (1.04 g, the second stage yield: 97%) was prepared using compound (158b) (1.00 g) instead of compound (107a).
¹H-NMR (DMSO-d₆) δ: 8.23 (1H, d, J=4.88 Hz), 8.04 (1H, d, J=4.88 Hz), 8.01 (1H, brs), 7.39 (1H, brs), 7.32 (1H, s), 7.20 (1H, d, J=8.05 Hz), 7.12 (1H, d, J=8.05 Hz), 5.07 (1H, d, J=8.05 Hz), 3.73 (1H, ttd, J=6.10, 6.10, 8.05 Hz), 1.05 (6H, d, J=6.10 Hz); LRMS (ESI) m/z 490 [M+H]⁺.

Example 164(2)

3-(Isopropylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (164)

According to Example 99(2), compound (164) (0.760 g, 71%) was prepared using (164a) (1.04 g) instead of compound (99a).
¹H-NMR (DMSO-d₆) δ: 8.80 (1H, d, J=4.88 Hz), 8.05 (1H, brs), 8.03 (1H, s), 7.97 (1H, s), 7.73 (1H, s), 7.72 (1H, s), 7.62 (1H, d, J=4.88 Hz), 7.43 (1H, brs), 7.37 (1H, d, J=1.71 Hz), 7.28 (1H, d, J=8.05 Hz), 7.18 (1H, dd, J=8.05, 1.71 Hz), 5.03 (1H, d, J=8.05 Hz), 3.87 (3H, s), 3.08 (1H, ttd, J=6.34, 6.34, 8.05 Hz), 1.09 (6H, d, J=6.34 Hz); LRMS (ESI) m/z 510 [M+H]⁺.

Example 165

3-(Cyclobutylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (165)

Example 165(1)

3-(Cyclobutylamino)-4-{4-iodo-3-(trifluoromethyl)-1H-pyrazolo[3,4-b]pyridin-1-yl}benzamide (165a)

According to Example 120(1), compound (165a) (1.02 g, the second stage yield: 71%) was prepared using compound (158b) (1.20 g) instead of compound (107a) and using cyclobutanone (0.430 mL) instead of acetone.
¹H-NMR (DMSO-d₆) δ: 8.24 (1H, d, J=4.88 Hz), 8.06 (1H, d, J=4.88 Hz), 8.01 (1H, brs), 7.41 (1H, brs), 7.22 (1H, d, J=1.71 Hz), 7.21 (1H, d, J=8.05 Hz), 7.15 (1H, dd, J=8.05, 1.71 Hz), 5.63 (1H, d, J=6.83 Hz), 3.98 (1H, dtt, J=6.83, 6.38, 6.38 Hz), 2.31-2.24 (2H, m), 1.84-1.74 (2H, m), 1.68-1.61 (2H, m); LRMS (ESI) m/z 502 [M+H]⁺.

Example 165(2)

3-(Cyclobutylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (165)

According to Example 99(2), compound (165) (0.350 g, 39%) was prepared using (165a) (0.870 g) instead of compound (99a).
¹H-NMR (DMSO-d₆) δ: 8.80 (1H, d, J=4.88 Hz), 8.03 (2H, s), 7.98 (1H, s), 7.73 (2H, s), 7.62 (1H, d, J=4.88 Hz), 7.42 (1H, brs), 7.27 (1H, d, J=8.05 Hz), 7.25 (1H, d, J=1.83 Hz), 7.20 (1H, dd, J=8.05, 1.83 Hz), 5.57 (1H, d, J=6.83 Hz), 4.00 (1H, ttd, J=7.07, 7.07, 6.83 Hz), 2.33-2.27 (2H, m), 1.82-1.76 (2H, m), 1.68-1.65 (2H, m); LRMS (ESI) m/z 522 [M+H]⁺.

Example 166

3-(Cyclopentylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (166)

Example 166(1)

3-(Cyclopentylamino)-4-{4-iodo-3-(trifluoromethyl)-1H-pyrazolo[3,4-b]pyridin-1-yl}benzamide (166a)

According to Example 120(1), compound (166a) (1.15 g, the second stage yield: 78%) was prepared using compound (158b) (1.20 g) instead of compound (107a) and using cyclopentanone (0.506 mL) instead of acetone.
¹H-NMR (DMSO-d₆) δ: 8.25 (1H, d, J=4.63 Hz), 8.06 (1H, d, J=4.63 Hz), 8.02 (1H, brs), 7.42 (1H, brs), 7.35 (1H, d, J=1.59 Hz), 7.23 (1H, d, J=8.05 Hz), 7.15 (1H, dd, J=8.05, 1.59 Hz), 5.22 (1H, d, J=7.07 Hz), 3.89 (1H, dtt, J=7.07, 6.22, 6.22 Hz), 1.94-1.86 (2H, m), 1.60-1.47 (4H, m), 1.41-1.35 (2H, m); LRMS (ESI) m/z 516 [M+H]$^+$.

Example 166(2)

3-(Cyclopentylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (166)

According to Example 99(2), compound (166) (0.630 g, 65%) was prepared using (166a) (0.900 g) instead of compound (99a).

$^1$H-NMR (DMSO-d$_6$) δ: 8.80 (1H, d, J=4.63 Hz), 8.04 (1H, brs), 8.03 (1H, s), 7.97 (1H, s), 7.73 (1H, s), 7.72 (1H, s), 7.62 (1H, d, J=4.88 Hz), 7.43 (1H, brs), 7.38 (1H, d, J=1.46 Hz), 7.31 (1H, d, J=8.05 Hz), 7.20 (1H, dd, J=8.05, 1.46 Hz), 5.18 (1H, d, J=6.83 Hz), 3.87 (3H, s), 3.10-3.05 (1H, m), 1.95-1.88 (2H, m), 1.60-1.49 (4H, m), 1.42-1.35 (2H, m); LRMS (ESI) m/z 536 [M+H]$^+$.

Example 167

3-(2,2-Difluoroethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (167)

According to Example 120(1), 3-(2,2-difluoroethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzonitrile (the second stage yield: 95%) was prepared using compound (158a) instead of compound (107a) and using 2,2-difluoroacetaldehyde ethyl hemiacetal instead of acetone; and according to Example 99(2), compound (167) (8%) was prepared as a yellow solid using 3-(2,2-difluoroethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzonitrile instead of compound (99a).

$^1$H-NMR (DMSO-d$_6$) δ: 8.79 (1H, d, J=4.88 Hz), 8.08 (1H, brs), 8.02 (1H, s), 7.98 (1H, s), 7.72 (2H, s), 7.62 (1H, d, J=4.88 Hz), 7.48 (1Hbrs), 7.46 (1H, d, J=1.71 Hz), 7.33 (1H, d, J=8.29 Hz), 7.26 (1H, dd, J=8.29, 1.71 Hz), 5.70 (1H, t, J=6.34 Hz), 3.57 (1H, ddt, J=5.12, 4.63, 11.71 Hz), 3.08 (2H, dt, J=11.71, 6.24 Hz); LRMS (ESI) m/z 532 [M+H]$^+$.

Example 168

3-(2-Methoxyethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (168)

According to Example 120(1), 3-(2-methoxyethylamino)-4-{4-iodo-3-(trifluoromethyl)-1H-pyrazolo[3,4-b]pyridin-1-yl}benzamide was prepared using compound (158b) (0.20 g) instead of compound (107a) and using 1,1,2-triethoxyethane (0.1170 mL) instead of acetone; and according to Example 99(2), compound (168) (0.030 g, the third stage yield: 12%) was prepared using 3-(2-methoxyethylamino)-4-{4-iodo-3-(trifluoromethyl)-1H-pyrazolo[3,4-b]pyridin-1-yl}benzamide (0.125 g) instead of compound (99a).

$^1$H-NMR (DMSO-d$_6$) δ: 8.81 (1H, dd, J=4.88, 0.73 Hz), 8.06 (1H, brs), 8.03 (1H, s), 7.97 (1H, s), 7.73 (1H, s), 7.72 (1H, s), 7.63 (1H, dd, J=4.88, 0.73 Hz), 7.44 (1H, brs), 7.37 (1H, d, J=1.22 Hz), 7.36 (1H, d, J=8.05 Hz), 7.22 (1H, dd, J=8.05, 1.22 Hz), 5.45 (1H, t, J=5.37 Hz), 3.87 (3H, s), 3.42 (3H, t, J=5.73 Hz), 3.22 (3H, s); LRMS (ESI) m/z 526 [M+H]$^+$.

Example 169

3-Cyano-4-{4-(4-(1-methyl-1H-pyrazol-4-yl)-1H-imidazol-1-yl)-3-(trifluoromethyl)-1H-pyrazolo[3,4-b]pyridin-1-yl}benzamide (169)

According to Example 124(1), 3-cyano-{4-iodo-3-(trifluoromethyl)-1H-pyrazolo[3,4-b]pyridine}benzamide (the third stage yield: 6%) was prepared as a white solid using compound (153a) instead of compound (100a). According to Example 99, compound (169) (the second stage yield: 16%) was prepared using 3-cyano-{4-iodo-3-(trifluoromethyl)-1H-pyrazolo[3,4-b]pyridine}benzamide instead of compound (99a).

$^1$H-NMR (DMSO-d$_6$) δ: 8.96 (1H, d, J=4.88 Hz), 8.62 (1H, d, J=1.95 Hz), 8.45 (1H, dd, J=8.54, 1.95 Hz), 8.36 (1H, brs), 8.22 (1H, d, J=8.54 Hz), 8.13 (1H, s), 7.99 (1H, s), 7.85 (1H, brs), 7.82 (1H, s), 7.77 (1H, d, J=4.88 Hz), 7.73 (1H, s), 3.89 (3H, s); LRMS (ESI) m/z 478 [M+H]$^+$.

Example 170

3-Bromo-4-{4-(4-(1-methyl-1H-pyrazol-4-yl)-1H-imidazol-1-yl)-3-(trifluoromethyl)-1H-pyrazolo[3,4-b]pyridin-1-yl}benzamide (170)

Example 170(1)

3-Bromo-4-{4-iodo-3-(trifluoromethyl)-1H-pyrazolo[3,4-b]pyridin-1-yl}benzamide (170a)

According to Example 153(2), compound (170a) (1.53 g, the second stage yield: 55%) was prepared using 3-bromo-4-fluorobenzonitrile instead of 3-chloro-4-fluorobenzonitrile.

$^1$H-NMR (DMSO-d$_6$) δ: 8.32 (1H, d, J=4.88 Hz), 8.28 (1H, br s), 8.22 (1H, d, J=1.71 Hz), 8.14 (1H, d, J=4.88 Hz), 8.06 (1H, dd, J=8.05, 1.71 Hz), 7.91 (1H, d, J=8.05 Hz), 7.74 (1H, brs); LRMS (ESI) m/z 511 [M+H]$^+$.

Example 170(2)

3-Bromo-4-{4-(4-(1-methyl-1H-pyrazol-4-yl)-1H-imidazol-1-yl)-3-(trifluoromethyl)-1H-pyrazolo[3,4-b]pyridin-1-yl}benzamide (170)

According to Example 99(2), compound (170) (0.860 g, 54%) was prepared using compound (170a) (1.53 g) instead of compound (99a).

$^1$H-NMR (DMSO-d$_6$) δ: 8.86 (1H, d, J=4.88 Hz), 8.39 (1H, d, J=1.71 Hz), 8.30 (1H, brs), 8.12 (1H, dd, J=8.29, 1.95 Hz), 8.11 (1H, s), 7.97 (1H, s), 7.89 (1H, d, J=8.29 Hz), 7.79 (1H, s), 7.75 (1H, brs), 7.72 (1H, s), 7.69 (1H, d, J=4.88 Hz), 3.87 (3H, s); LRMS (ESI) m/z 531 [M+H]$^+$.

Example 171

3-Fluoro-4-{4-(4-(1-methyl-1H-pyrazol-4-yl)-1H-imidazol-1-yl)-3-(trifluoromethyl)-1H-pyrazolo[3,4-b]pyridin-1-yl}benzamide (171)

Example 171(1)

3-Fluoro-4-{4-iodo-3-(trifluoromethyl)-1H-pyrazolo[3,4-b]pyridin-1-yl}benzamide (171a)

According to Example 153(2), compound (171a) (0.747 g, the second stage yield: 55%) was prepared using 3,4-difluorobenzonitrile instead of 3-chloro-4-fluorobenzonitrile.

¹H-NMR (DMSO-d₆) δ: 8.35 (1H, d, J=4.88 Hz), 8.25 (1H, brs), 8.16 (1H, d, J=4.88 Hz), 8.01 (1H, dd, J=10.86, 1.46 Hz), 7.95 (1H, td, J=8.29, 1.46 Hz), 7.93 (1H, td, J=8.29, 6.83 Hz), 7.73 (1H, s); LRMS (ESI) m/z 451 [M+H]⁺.

Example 171(2)

3-Fluoro-4-{4-(4-(1-methyl-1H-pyrazol-4-yl)-1H-imidazol-1-yl)-3-(trifluoromethyl)-1H-pyrazolo[3,4-b]pyridin-1-yl}benzamide (171)

According to Example 99(2), compound (171) (0.430 g, 73%) was prepared using compound (171a) (0.650 g) instead of compound (99a).

¹H-NMR (DMSO-d₆) δ: 9.62 (1H, d, J=4.88 Hz), 8.98 (1H, brs), 8.82 (1H, s), 8.76 (1H, dd, J=10.98, 1.46 Hz), 8.72-8.66 (3H, m), 8.51 (1H, d, J=0.73 Hz), 8.47 (1H, brs), 8.44 (1H, s), 8.43 (1H, d, J=4.88 Hz), 4.59 (3H, s); LRMS (ESI) m/z 471 [M+H]⁺.

Example 172

6-{4-(4-(1-Methyl-1H-pyrazol-4-yl)-1H-imidazol-1-yl)-3-(trifluoromethyl)-1H-pyrazolo[3,4-b]pyridin-1-yl}biphenyl-3-carboxamide (172)

Compound (153) (0.030 g), phenylboronic acid (0.014 g), palladium acetate (0.001 g), tricyclohexylphosphine (0.004 g), and potassium phosphate (0.050 g) were dissolved in toluene (0.5 mL) and water (0.025 mL), followed by stirring using microwaves at 130° C. for 10 min. The reaction solution was distributed between chloroform and water, and the organic layer was washed with saturated saline and then dried over anhydrous sodium sulfate. The solvent was distilled away, and the residue was purified by neutral silica gel column chromatography (chloroform/methanol) to obtain compound (172) (0.002 g, 6%) as a white solid.

¹H-NMR (DMSO-d₆) δ: 8.70 (1H, dd, J=4.88, 0.98 Hz), 8.28 (1H, brs), 8.16 (1H, s), 8.12 (1H, dd, J=8.05, 1.46 Hz), 8.00 (1H, s), 7.96 (1H, s), 7.85 (1H, d, J=8.05 Hz), 7.71 (2H, s), 7.64 (1H, brs), 7.56 (1H, dd, J=4.88, 0.98 Hz), 7.22-7.19 (3H, m), 7.04-7.01 (2H, m), 3.86 (3H, s); LRMS (ESI) m/z 529 [M+H]⁺.

Example 173

3-(Cyclopropyl)-4-{4-(4-(1-methyl-1H-pyrazol-4-yl)-1H-imidazol-1-yl)-3-(trifluoromethyl)-1H-pyrazolo[3,4-b]pyridin-1-yl}benzamide (173)

According to Example 172, compound (173) (7%) was prepared as a white solid using cyclohexylboronic acid instead of phenylboronic acid.

¹H-NMR (DMSO-d₆) δ: 8.83 (1H, d, J=4.88 Hz), 8.17 (1H, brs), 8.08 (1H, s), 7.96 (1H, s), 7.87 (1H, dd, J=8.29, 1.95 Hz), 7.77 (1H, s), 7.71 (1H, s), 7.65 (1H, d, J=4.88 Hz), 7.64 (1H, d, J=1.95 Hz), 7.61 (1H, d, J=8.29 Hz), 7.54 (1H, brs), 3.87 (3H, s), 1.52-1.48 (1H, m), 0.75-0.71 (4H, m); LRMS (ESI) m/z 493 [M+H]⁺.

Example 174

4-{4-(4-(1-Methyl-1H-pyrazol-4-yl)-1H-imidazol-1-yl)-3-(trifluoromethyl)-1H-pyrazolo[3,4-b]pyridin-1-yl}-3-(prop-1-en-2-yl)benzamide (174)

According to Example 172, compound (174) (7%) was prepared as a white solid using propenylboronic acid and X-phos instead of phenylboronic acid and tricyclohexylphosphine, respectively.

¹H-NMR (DMSO-d₆) δ: 8.83 (1H, d, J=4.88 Hz), 8.22 (1H, s), 8.07 (1H, s), 8.04 (1H, s), 8.02 (1H, dd, J=8.29, 1.95 Hz), 7.96 (1H, s), 7.77 (1H, s), 7.72 (1H, d, J=8.29 Hz), 7.71 (1H, s), 7.63 (1H, d, J=4.88 Hz), 7.60 (1H, brs), 4.87 (1H, s), 4.55 (1H, s), 3.86 (3H, s), 1.80 (3H, s); LRMS (ESI) m/z 493 [M+H]⁺.

Example 175

3-Methyl-4-{4-(4-(pyridin-3-yl)-1H-imidazol-1-yl)-3-(trifluoromethyl)-1H-pyrazolo[3,4-b]pyridin-1-yl}benzamide (175)

According to Example 154(6), compound (175) (the second stage yield: 5%) was prepared as a white solid using 4-(pyridin-3-yl)-1H-imidazole dihydrochloride instead of 4-(1-methyl-1H-pyrazol-4-yl)-1H-imidazole hydrochloride.

¹H-NMR (DMSO-d₆) δ: 9.10 (1H, s), 8.91 (1H, d, J=4.88 Hz), 8.50 (1H, d, J=4.88 Hz), 8.35 (1H, s), 8.27 (1H, s), 8.22 (1H, dt, J=8.05, 1.89 Hz), 8.16 (1H, brs), 8.04 (1H, s), 7.94 (1H, dd, J=8.29, 1.89 Hz), 7.76 (1H, d, J=4.88 Hz), 7.67 (1H, d, J=8.29 Hz), 7.57 (1H, brs), 7.48 (1H, dd, J=8.05, 4.88 Hz), 2.18 (3H, s); LRMS (ESI) m/z 464 [M+H]⁺.

Example 176

2-Amino-4-{4-(4-(pyridin-3-yl)-1H-imidazol-1-yl)-3-(trifluoromethyl)-1H-pyrazolo[3,4-b]pyridin-1-yl}benzamide (176)

Compound (157a) (0.080 g) was dissolved in DMSO (1.2 mL), and potassium carbonate (0.160 g), copper(II) oxide (nanopowder) (0.009 g), and 4-(pyridin-3-yl)-1H-imidazole hydrochloride (0.053 g) were added to the resulting solution, followed by stirring at 120° C. for 4 hr. The reaction solution was diluted with ethyl acetate, and insoluble matters were filtered by celite. The solvent was distilled away, and the residue was purified by neutral silica gel column chromatography (chloroform/methanol) to obtain compound (176) (0.031 g, 30%).

¹H-NMR (DMSO-d₆) δ: 9.07 (1H, dd, J=1.95, 0.98 Hz), 8.99 (1H, dd, J=4.88, 0.98 Hz), 8.48 (1H, d, J=4.88 Hz), 8.30 (1H, s), 8.22 (1H, s), 8.19 (1H, d, J=8.05 Hz), 7.88 (1H, brs), 7.79 (1H, d, J=8.78 Hz), 7.75 (1H, dd, J=4.88, 0.98 Hz), 7.55 (1H, d, J=2.20 Hz), 7.45 (1H, dd, J=8.05, 4.88 Hz), 7.38 (1H, dd, J=8.78, 2.20 Hz), 7.22 (1H, brs), 7.00 (2H, s); LRMS (ESI) m/z 465 [M+H]⁺.

Example 177

3-Amino-4-{4-(4-(pyridin-3-yl)-1H-imidazol-1-yl)-3-(trifluoromethyl)-1H-pyrazolo[3,4-b]pyridin-1-yl}benzamide (177)

According to Example 176, compound (177) (45%) was prepared using compound (158b) instead of compound (157a).

¹H-NMR (DMSO-d₆) δ: 9.09 (1H, s), 8.85 (1H, dd, J=4.88, 0.98 Hz), 8.49 (1H, d, J=4.39 Hz), 8.26 (1H, s), 8.21 (1H, d, J=7.81 Hz), 8.17 (1H, s), 7.95 (1H, brs), 7.69 (1H, dd, J=4.88, 0.98 Hz), 7.46 (1H, dd, J=7.81, 4.88 Hz), 7.40 (1H, d, J=1.22 Hz), 7.37 (1H, brs), 7.30 (1H, d, J=8.05 Hz), 7.14 (1H, dd, J=8.05, 1.22 Hz), 5.42 (2H, s); LRMS (ESI) m/z 465 [M+H]⁺.

Example 178

2-(Ethylamino)-4-{4-(4-(pyridin-3-yl)-1H-imidazol-1-yl)-3-(trifluoromethyl)-1H-pyrazolo[3,4-b]pyridin-1-yl}benzamide (178)

According to Example 161, compound (178) (the second stage yield: 30%) was prepared as a white solid using 4-(4-(pyridin-3-yl)-1H-imidazole hydrochloride instead of 4-(1-methyl-1H-pyrazol-4-yl)-1H-imidazole hydrochloride.

$^1$H-NMR (DMSO-d$_6$) δ: 9.07 (1H, d, J=1.95 Hz), 9.01 (1H, d, J=4.88 Hz), 8.48 (1H, dd, J=4.88, 1.95 Hz), 8.35 (1H, t, J=4.88 Hz), 8.31 (1H, s), 8.23 (1H, s), 8.21 (1H, d, J=7.56 Hz), 8.20 (1H, dt, J=8.05, 1.95 Hz), 7.87 (1H, d, J=8.29 Hz), 7.77 (1H, d, J=4.88 Hz), 7.51 (1H, d, J=2.20 Hz), 7.45 (1H, dd, J=8.05, 4.88 Hz), 7.34 (1H, dd, J=8.29, 2.07 Hz), 3.23 (2H, dq, J=4.88, 7.07 Hz), 1.27 (3H, t, J=7.07 Hz); LRMS (ESI) m/z 493 [M+H]$^+$.

Example 179

2-(Isopropylamino)-4-{4-(4-(pyridin-3-yl)-1H-imidazol-1-yl)-3-(trifluoromethyl)-1H-pyrazolo[3,4-b]pyridin-1-yl}benzamide (179)

According to Example 160, compound (179) (the second stage yield: 14%) was prepared as a white solid using 4-(4-(pyridin-3-yl)-1H-imidazole hydrochloride instead of 4-(1-methyl-1H-pyrazol-4-yl)-1H-imidazole hydrochloride.

$^1$H-NMR (DMSO-d$_6$) δ: 9.07 (1H, d, J=1.95 Hz), 8.99 (1H, d, J=4.88 Hz), 8.48 (1H, dd, J=4.88, 1.95 Hz), 8.38 (1H, d, J=7.32 Hz), 8.30 (1H, s), 8.22 (1H, s), 8.20 (1H, dt, J=8.05, 1.95 Hz), 7.85 (1H, d, J=8.54 Hz), 7.75 (1H, d, J=4.88 Hz), 7.54 (1H, d, J=2.20 Hz), 7.45 (1H, dd, J=8.05, 4.88 Hz), 7.26 (1H, dd, J=8.54, 2.20 Hz), 3.69 (1H, dtt, J=7.32, 6.34, 6.34 Hz), 1.24 (6H, d, J=6.34 Hz); LRMS (ESI) m/z 507 [M+H]$^+$.

Example 180

3-(Ethylamino)-4-{4-(4-(pyridin-3-yl)-1H-imidazol-1-yl)-3-(trifluoromethyl)-1H-pyrazolo[3,4-b]pyridin-1-yl}benzamide (180)

According to Example 176, compound (180) (36%) was prepared using compound (162a) instead of compound (157a).

$^1$H-NMR (DMSO-d$_6$) δ: 9.10 (1H, d, J=1.46 Hz), 8.84 (1H, d, J=4.88 Hz), 8.49 (1H, dd, J=4.88, 1.46 Hz), 8.27 (1H, s), 8.22 (1H, dt, J=8.05, 1.95 Hz), 8.19 (1H, s), 8.05 (1H, brs), 7.69 (1H, d, J=4.88 Hz), 7.46 (1H, dd, J=8.05, 4.88 Hz), 7.44 (1H, brs), 7.32 (1H, d, J=1.71 Hz), 7.29 (1H, d, J=8.05 Hz), 7.19 (1H, dd, J=8.05, 1.71 Hz), 5.38 (1H, t, J=5.49 Hz), 3.15 (2H, dq, J=5.49, 7.07 Hz), 1.07 (3H, t, J=7.07 Hz); LRMS (ESI) m/z 493 [M+H]$^+$.

Example 181

3-(Isopropylamino)-4-{4-(4-(pyridin-3-yl)-1H-imidazol-1-yl)-3-(trifluoromethyl)-1H-pyrazolo[3,4-b]pyridin-1-yl}benzamide (181)

According to Example 176, compound (181) (28%) was prepared using compound (164a) instead of compound (157a).

$^1$H-NMR (DMSO-d$_6$) δ: 9.09 (1H, d, J=1.46 Hz), 8.85 (1H, d, J=4.88 Hz), 8.49 (1H, dd, J=4.88, 1.46 Hz), 8.28 (1H, s), 8.21 (1H, dt, J=7.81, 1.46 Hz), 8.20 (1H, s), 8.05 (1H, brs), 7.70 (1H, d, J=4.88 Hz), 7.46 (1H, dd, J=7.81,4.88 Hz), 7.43 (1H, brs), 7.38 (1H, d, J=1.71 Hz) 7.29 (1H, d, J=8.05 Hz), 7.19 (1H, dd, J=8.05, 1.71 Hz), 5.04 (1H, d, J=8.05 Hz), 3.78 (1H, ttd, J=6.34, 6.34, 8.05 Hz), 1.09 (7H, d, J=6.34 Hz); LRMS (ESI) m/z 507 [M+H]$^+$.

Example 182

3-(Cyclobutylamino)-4-{4-(4-(pyridin-3-yl)-1H-imidazol-1-yl)-3-(trifluoromethyl)-1H-pyrazolo[3,4-b]pyridin-1-yl}benzamide (182)

According to Example 176, compound (182) (49%) was prepared using compound (165a) instead of compound (157a).

$^1$H-NMR (DMSO-d$_6$) δ: 9.10 (1H, s), 8.85 (1H, d, J=4.88 Hz), 8.49 (1H, d, J=4.88 Hz), 8.27 (1H, s), 8.22 (1H, dt, J=7.81, 1.71 Hz), 8.19 (1H, s), 8.03 (1H, brs), 7.70 (1H, d, J=4.88 Hz), 7.46 (1H, dd, J=7.81, 4.88 Hz), 7.43 (1H, brs), 7.28 (1H, d, J=8.05 Hz), 7.26 (1H, d, J=1.46 Hz), 7.20 (1H, dd, J=8.05, 1.46 Hz), 5.59 (1H, d, J=6.59 Hz), 4.01 (1H, ttd, J=7.32, 7.32, 6.59 Hz), 2.33-2.27 (2H, m), 1.85-1.76 (2H, m), 1.70-1.64 (2H, m); LRMS (ESI) m/z 519 [M+H]$^+$.

Example 183

3-(Cyclopentylamino)-4-{4-(4-(pyridin-3-yl)-1H-imidazol-1-yl)-3-(trifluoromethyl)-1H-pyrazolo[3,4-b]pyridin-1-yl}benzamide (183)

According to Example 176, compound (183) (50%) was prepared using compound (168a) instead of compound (157a).

$^1$H-NMR (DMSO-d$_6$) δ: 9.09 (1H, d, J=1.71 Hz), 8.85 (1H, d, J=4.88 Hz), 8.49 (1H, dd, J=4.63, 1.71 Hz), 8.27 (1H, s), 8.22 (1H, dt, J=7.81, 1.95 Hz), 8.20 (1H, s), 8.05 (1H, brs), 7.70 (1H, d, J=4.88 Hz), 7.46 (1H, dd, J=7.81, 4.63 Hz), 7.43 (1H, brs), 7.39 (1H, d, J=1.71 Hz), 7.32 (1H, d, J=8.05 Hz), 7.20 (1H, dd, J=8.05, 1.71 Hz), 5.19 (1H, d, J=6.83 Hz), 3.92 (1H, ttd, J=6.34, 6.34, 6.83 Hz), 1.95-1.89 (2H, m), 1.60-1.50 (4H, m), 1.43-1.35 (2H, m); LRMS (ESI) m/z 533 [M+H]$^+$.

Example 184

3-Amino-4-{4-(4-(1-ethyl-1H-pyrazol-4-yl)-1H-imidazol-1-yl)-3-(trifluoromethyl)-1H-pyrazolo[3,4-b]pyridin-1-yl}benzamide (184)

According to Example 176, compound (184) (36%) was prepared using compound (158b) instead of compound (157a) and using 4-(1-ethyl-1H-pyrazol-4-yl)-1H-imidazole hydrochloride instead of 4-(pyridin-3-yl)-1H-imidazole hydrochloride.

$^1$H-NMR (DMSO-d$_6$) δ: 8.80 (1H, dd, J=4.76, 0.73 Hz), 8.02 (1H, s), 8.01 (1H, s), 7.94 (1H, brs), 7.73 (1H, s), 7.72 (1H, s), 7.60 (1H, dd, J=4.76, 0.73 Hz), 7.39 (1H, d, J=1.22 Hz), 7.36 (1H, brs), 7.29 (1H, d, J=8.05 Hz), 7.14 (1H, dd, J=8.05, 1.22 Hz), 5.40 (2H, s), 4.16 (2H, q, J=7.16 Hz), 1.40 (3H, t, J=7.16 Hz); LRMS (ESI) m/z 482 [M+H]$^+$.

Example 185

4-{4-(4-(1-Ethyl-1H-pyrazol-4-yl)-1H-imidazol-1-yl)-3-(trifluoromethyl)-1H-pyrazolo[3,4-b]pyridin-1-yl}-3-(ethylamino)benzamide (185)

According to Example 176, compound (185) (35%) was prepared using compound (162a) instead of compound (157a) and using 4-(1-ethyl-1H-pyrazol-4-yl)-1H-imidazole hydrochloride instead of 4-(pyridin-3-yl)-1H-imidazole hydrochloride.

$^1$H-NMR (DMSO-d$_6$) δ: 8.79 (1H, d, J=4.88 Hz), 8.05 (1H, brs), 8.02 (2H, s), 7.74 (1H, s), 7.72 (1H, s), 7.61 (1H, d, J=4.88 Hz), 7.42 (1H, brs), 7.32 (1H, d, J=1.71 Hz), 7.28 (1H, d, J=8.05 Hz), 7.18 (1H, dd, J=8.05, 1.71 Hz), 5.36 (1H, t, J=5.85 Hz), 4.16 (2H, q, J=7.24 Hz), 3.15 (2H, dq, J=7.07, 5.85 Hz), 1.40 (3H, t, J=7.24 Hz), 1.07 (3H, t, J=7.07 Hz); LRMS (ESI) m/z 510 [M+H]$^+$.

Example 186

3-Amino-4-{4-(4-(1-isopropyl-1H-pyrazol-4-yl)-1H-imidazol-1-yl)-3-(trifluoromethyl)-1H-pyrazolo[3,4-b]pyridin-1-yl}benzamide (186)

According to Example 176, compound (186) (35%) was prepared using compound (158b) instead of compound (157a) and using 4-(1-isopropyl-1H-pyrazol-4-yl)-1H-imidazole hydrochloride instead of 4-(pyridin-3-yl)-1H-imidazole hydrochloride.

$^1$H-NMR (DMSO-d$_6$) δ: 8.80 (1H, dd, J=4.88, 0.98 Hz), 8.04 (1H, s), 8.00 (1H, s), 7.94 (1H, brs), 7.73 (1H, s), 7.72 (1H, s), 7.60 (1H, dd, J=4.88, 0.98 Hz), 7.39 (1H, s), 7.36 (1H, brs), 7.29 (1H, d, J=8.05 Hz), 7.13 (1H, d, J=8.05 Hz), 5.40 (2H, s), 4.53 (1H, tt, J=6.59, 6.59 Hz), 1.45 (3H, d, J=6.59 Hz), 1.44 (3H, d, J=6.59 Hz); LRMS (ESI) m/z 496 [M+H]$^+$.

Example 187

3-(Ethylamino)-4-{4-(4-(1-isopropyl-1H-pyrazol-4-yl)-1H-imidazol-1-yl)-3-(trifluoromethyl)-1H-pyrazolo[3,4-b]pyridin-1-yl}benzamide (187)

According to Example 176, compound (187) (40%) was prepared using compound (162a) instead of compound (157a) and using 4-(1-isopropyl-1H-pyrazol-4-yl)-1H-imidazole hydrochloride instead of 4-(pyridin-3-yl)-1H-imidazole hydrochloride.

$^1$H-NMR (DMSO-d$_6$) δ: 8.79 (1H, d, J=4.88 Hz), 8.05 (1H, brs), 8.04 (1H, s), 8.02 (1H, s), 7.74 (1H, s), 7.73 (1H, s), 7.60 (1H, d, J=4.88 Hz), 7.42 (1H, brs), 7.32 (1H, d, J=1.71 Hz), 7.29 (1H, d, J=8.05 Hz), 7.18 (1H, dd, J=8.05, 1.71 Hz), 5.36 (1H, t, J=5.61 Hz), 4.53 (1H, tt, J=6.59, 6.59 Hz), 3.07 (2H, dq, J=5.61, 7.31 Hz), 1.45 (6H, d, J=6.59 Hz), 1.17 (3H, t, J=7.32 Hz); LRMS (ESI) m/z 524 [M+H]$^+$.

Example 188

3-Chloro-4-{4-(4-(1-(hydroxymethyl)-1H-pyrazol-4-yl)-1H-imidazol-1-yl)-3-(trifluoromethyl)-1H-pyrazolo[3,4-b]pyridin-1-yl}benzamide (188)

Compound (153a) (0.200 g), cesium carbonate (0.880 g), and 3-chloro-4-fluorobenzonitrile (0.154 g) were suspended in DMSO (50 mL), followed by stirring at 60° C. for 24 hr. The reaction solution was distributed between ethyl acetate and water, and the organic layer was washed with saturated saline. The organic layer after the washing was dried over anhydrous sodium sulfate, and then the solvent was distilled away to obtain 3-chloro-4-{4-iodo-3-(trifluoromethyl)-1H-pyrazolo[3,4-b]pyridin-1-yl}benzonitrile, which was used in the subsequent reaction without being purified. This 3-chloro-4-{4-chloro-3-(trifluoromethyl)-1H-pyrazolo[3,4-b]pyridin-1-yl}benzonitrile, 4-(1-(hydroxymethyl)-1H-pyrazol-4-yl)-1H-imidazole hydrochloride (0.129 g), potassium carbonate (0.263 g), and copper(II) oxide (nanopowder) (0.020 g) were suspended in DMF (2.5 mL), followed by stirring at 120° C. for 24 hr. The reaction solution was diluted with ethyl acetate, and insoluble matters were filtered by celite. The solvent of the filtrate was distilled away, and the residue was purified by neutral silica gel column chromatography (chloroform/methanol) to obtain compound (188) (0.012 g, 3%).

$^1$H-NMR (DMSO-d$_6$) δ: 8.86 (1H, d, J=4.88 Hz), 8.30 (1H, brs), 8.25 (1H, d, J=1.71 Hz), 8.10 (1H, s), 8.08 (1H, dd, J=8.29, 1.71 Hz), 7.98 (1H, s), 7.92 (1H, d, J=8.29 Hz), 7.80 (1H, s), 7.76 (1H, brs), 7.74 (1H, s), 7.69 (1H, d, J=4.88 Hz), 4.93 (1H, t, J=5.37 Hz), 4.17 (2H, t, J=5.49 Hz), 3.75 (2H, q, J=5.53 Hz); LRMS (ESI) m/z 503 [M+H]$^+$.

Example 189

4-{4-(4-(1-Benzyl-1H-pyrazol-4-yl)-1H-imidazol-1-yl)-3-isopropyl-1H-pyrazolo[3,4-b]pyridin-1-yl}-3-chlorobenzamide (189)

According to Example 107(2), compound (189) (the second stage yield: 15%) was prepared as a white solid using compound (99a) and 4-(1-benzyl-1H-pyrazol-4-yl)-1H-imidazole hydrochloride instead of compound (107a) and 4-(1-methyl-1H-pyrazol-4-yl)-1H-imidazole hydrochloride, respectively.

$^1$H-NMR (DMSO-d$_6$) δ: 8.66 (1H, d, J=4.95 Hz), 8.26 (1H, brs), 8.23 (1H, d, J=1.15 Hz), 8.21 (1H, d, J=1.81 Hz), 8.12 (1H, s), 8.04 (1H, dd, J=8.24, 1.81 Hz), 7.93 (1H, d, J=1.15 Hz), 7.81 (1H, s), 7.76 (1H, d, J=8.24 Hz), 7.70 (1H, brs), 7.42 (1H, d, J=4.78 Hz), 7.38-7.29 (5H, m), 5.37 (2H, s), 3.24 (1H, tt, J=6.76, 6.76 Hz), 1.12 (6H, d, J=6.76 Hz).

Test Example 1

Measurement of HSP90-Binding Activity

First, a solution of purified HSP90 was prepared as follows. A plasmid, pET-HSP90N, expressing an HSP90 N-terminal protein having a His tag at the N-terminal was constructed by inserting a human HSP90 alpha gene (NCBI Reference Sequences Register No. NM_005348) region, which encodes amino acids corresponding to from the 2nd amino acid to the 236th amino acid of human HSP90 alpha protein (NCBI Reference Sequences Register No. NP_005339, full length: 732 amino acids), into pET-19b (Novagen Inc.). The pET-HSP90N was introduced into *Escherichia coli* cells (BL21 (DE3), Stratagene Inc.), and then the *Escherichia coli* cells were cultured in the presence of 0.5 mM isopropyl-beta-D-thiogalactopyranoside (Sigma-Aldrich Corp.) at 37° C. for 4 hr. The *Escherichia coli* cells were collected, suspended in a lysis buffer (50 mM Tris-HCl (pH 7.5), 200 mM NaCl), and sonicated. The sonicated cell solution was centrifuged (40000×g, 20 min) to obtain supernatant as a crude extract. The extract was fractionated by Ni Sepharose High Performance (GE Healthcare Japan Corporation) chromatography and HiLoad 26/60 Superdex 75 pg (GE Healthcare Japan Corporation), and the fraction in which HSP90 protein was concentrated was adjusted to a 50 mM Tris-HCl (pH 7.5)/ 20% glycerol solution as a purified HSP90 solution. The purified HSP90 solution was divided and stored at −80° C. until use.

The HSP90-binding activity was measured by an AlphaScreen competitive assay system. The purified HSP90 solution was diluted with a binding buffer (50 mM Tris-HCl (pH 7.5), 150 mM NaCl, 0.1% Triton-X100, 1 mM DTT, 0.1% BSA)

and added to a 384-well plate (No. 3673, Corning Incorporated) containing test substances. After reaction at room temperature for 2 hr, biotin-labeled geldanamycin was added to each reaction solution in an amount of 40 nM, followed by reaction for further 1 hr. Detection mix (20 mM HEPES-KOH (pH 7.5), 0.5% BSA, 0.04 mg/mL Nickel Chelate Acceptor beads, 0.04 mg/mL Streptavidin-coated Donor beads) (No. 6760619C, Perkin Elmer, Inc.) was added to each well in the same amount as that of the reaction solution. After reaction in a dark place at room temperature for 1 hr, the fluorescence intensity in each well was measured with a multilabel plate reader, EnVision (Perkin Elmer, Inc.). The inhibition rate (%) of biotin-labeled geldanamycin binding by a compound of the present invention was determined by the following equation using the fluorescence signal of a test substance-free group (control) as a control. Each compound was added thereto, and the concentration ($IC_{50}$ (μM)) of a compound to inhibit the binding of biotin-labeled geldanamycin to 50% of that of the control was determined as a relative index of HSP90 binding.

Inhibition rate (%)=$(C-T)/C \times 100$

T: signal in a well to which a test substance was added
C: signal in a well to which no test substance was added The results were that compounds of the present invention showed highly satisfactory HSP90-binding activities whereas none of comparative compounds showed HSP90-binding activity (Table 1).

Test Example 2

Measurement of Cell Growth Inhibition

Cell growth was measured by a crystal violet staining method. SK-BR-3 cells (HTB-30) purchased from American Type Culture Collection were seeded in a 96-well plate (No. 353075, BD Biosciences) at a concentration of 5000 cells/well. The cells were cultured in a 5% $CO_2$ incubator at 37° C. for 24 hr, and then test substances were added to the plate, followed by culturing for further 72 hr. A 25% glutaraldehyde solution (No. 17025-25, Nacalai Tesque Inc.) was added to each well in an amount of 20 μL for 200 μL of the culture medium, and the plate was left to stand at room temperature for 20 min for fixing the cells. The plate was washed with water and dried, and then 100 μL of a solution of 0.05% crystal violet (No. 038-17792, Wako Pure Chemical Industries, Ltd.) in 20% methanol was added to each well. The plate was left to stand at room temperature for 20 min for staining the cells. The plate was washed with water and dried, and 100 μL of a solution mixture of 0.05 M $NaH_2PO_4$ and ethanol (mixture in equal amounts) was added to each well. Absorbance at 540 nm was measured with a microplate reader (MTP-450, Corona Electric Co., Ltd.) as an index of the number of cells in each well. The inhibition rate (%) of cell growth by a compound of the present invention was determined by the following equation using the absorbance of a test substance-free group (control) as a control. Each compound was added thereto, and the concentration ($IC_{50}$ (μM)) of a compound to inhibit the number of cells to 50% of that of the control was determined.

Inhibition rate (%)=$(C-T)/C \times 100$

T: absorbance in a well to which a test substance was added
C: absorbance in a well to which no test substance was added The results were that compounds of the present invention inhibited the growth of breast cancer SK-BR-3 cells whereas none of comparative compounds inhibited the growth of SK-BR-3 cells (Table 1 and 2).

TABLE 1

| Example | HSP-binding activity $IC_{50}$ (μM) | Cell growth inhibition $IC_{50}$ (μM) |
|---|---|---|
| 1 | 0.12 | 0.02 |
| 2 | 0.13 | 0.03 |
| 3 | 0.17 | 0.02 |
| 4 | 1.60 | 0.82 |
| 5 | 0.16 | 0.11 |
| 6 | 0.15 | 0.03 |
| 7 | 0.34 | 0.23 |
| 11 | 0.55 | 0.16 |
| 13 | 0.43 | 0.15 |
| 14 | 0.69 | 0.18 |
| 18 | 3.01 | 0.59 |
| 19 | 1.19 | 0.47 |
| 20 | 3.05 | 0.67 |
| 22 | 0.18 | 0.16 |
| 23 | 0.49 | 0.19 |
| 24 | 0.23 | 0.03 |
| 25 | 1.27 | 0.07 |
| 27 | 0.24 | 0.13 |
| 28 | 0.40 | 0.28 |
| 29 | 0.32 | 0.24 |
| 31 | 0.33 | 0.10 |
| 33 | 1.14 | 0.07 |
| 34 | 0.57 | 0.05 |
| 35 | 1.50 | 0.28 |
| 36 | 1.88 | 3.21 |
| 37 | 0.25 | 0.10 |
| 38 | 0.51 | 0.67 |
| 40 | 0.27 | 0.09 |
| 41 | 0.12 | 0.03 |
| 42 | 0.19 | 0.03 |
| 43 | 0.10 | 0.01 |
| 44 | 0.13 | 0.01 |
| 45 | 0.09 | 0.01 |
| 46 | 0.15 | 0.02 |
| 53 | 0.35 | 0.20 |
| 55 | 2.81 | 0.92 |
| 58 | 0.46 | 0.21 |
| 60 | 1.37 | 1.53 |
| 61 | 0.60 | 0.36 |
| 62 | 0.61 | 0.21 |
| 63 | 0.47 | 0.17 |
| 64 | 0.42 | 0.59 |
| 67 | 0.36 | 0.51 |
| 70 | 0.23 | 0.08 |
| 71 | 0.25 | 0.10 |
| 72 | 0.26 | 0.11 |
| 73 | 0.59 | 0.36 |
| 74 | 0.34 | 0.27 |
| 75 | 0.31 | 0.24 |
| 76 | 0.19 | 0.04 |
| 77 | 0.18 | 0.01 |
| 78 | 0.36 | 0.65 |
| 79 | 0.25 | 0.02 |
| 80 | 0.47 | 0.29 |
| 81 | 1.03 | 0.63 |
| 82 | 0.83 | 0.23 |
| 83 | 0.40 | 0.11 |
| 84 | 0.10 | 0.02 |
| 85 | 0.10 | 0.03 |
| 86 | 0.24 | 0.27 |
| 87 | 0.14 | 0.03 |
| 88 | 0.68 | 0.23 |
| 89 | 0.07 | 0.01 |
| 90 | 0.23 | 0.04 |
| 91 | 0.43 | 0.07 |
| 92 | 0.13 | 0.07 |
| 93 | 0.32 | 0.07 |
| 94 | 0.47 | 0.20 |
| 95 | 0.06 | 0.02 |
| 96 | 0.06 | 0.06 |
| 97 | 0.24 | 0.07 |
| 98 | 0.07 | 0.01 |
| 99 | 0.52 | 0.69 |
| 100 | 0.15 | 0.30 |
| 101 | 0.22 | 0.29 |
| 102 | 0.21 | 0.17 |

TABLE 1-continued

| Example | HSP-binding activity IC$_{50}$ (μM) | Cell growth inhibition IC$_{50}$ (μM) |
| --- | --- | --- |
| 103 | 0.12 | 0.17 |
| 104 | 0.12 | 0.20 |

TABLE 2

| Example | HSP-binding activity IC$_{50}$ (μM) | Cell growth inhibition IC$_{50}$ (μM) |
| --- | --- | --- |
| 105 | 0.14 | 0.25 |
| 106 | 0.34 | 0.65 |
| 107 | 0.20 | 0.90 |
| 109 | 0.18 | 0.08 |
| 110 | 0.31 | 0.49 |
| 111 | 0.19 | 0.08 |
| 112 | 0.25 | 0.04 |
| 113 | 0.26 | 0.07 |
| 114 | 0.49 | 0.18 |
| 115 | 0.16 | 0.24 |
| 118 | 0.21 | 0.55 |
| 120 | 0.20 | 0.14 |
| 121 | 0.18 | 0.16 |
| 122 | 0.18 | 0.13 |
| 123 | 0.19 | 0.12 |
| 124 | 0.35 | 0.59 |
| 126 | 0.23 | 1.13 |
| 127 | 0.23 | 1.56 |
| 128 | 0.09 | 0.15 |
| 129 | 0.29 | 1.13 |
| 130 | 0.69 | 1.89 |
| 131 | 0.70 | 0.92 |
| 132 | 0.12 | 0.10 |
| 133 | 0.16 | 0.15 |
| 134 | 0.20 | 0.11 |
| 135 | 0.40 | 0.69 |
| 136 | 0.13 | 0.27 |
| 137 | 0.28 | 0.43 |
| 138 | 0.19 | 0.53 |
| 139 | 0.57 | 0.28 |
| 140 | 0.76 | 0.19 |
| 141 | 0.41 | 0.14 |
| 142 | 0.12 | 0.22 |
| 143 | 0.17 | 0.03 |
| 144 | 0.42 | 0.11 |
| 145 | 0.63 | 1.50 |
| 146 | 0.77 | 0.21 |
| 147 | 0.81 | 0.36 |
| 148 | 0.40 | 0.24 |
| 149 | 0.39 | 0.69 |
| 150 | 0.93 | 1.33 |
| 151 | 0.66 | 1.54 |
| 152 | 1.01 | 1.28 |
| 153 | 0.13 | 0.24 |
| 154 | 0.14 | 0.12 |
| 155 | 0.11 | 0.04 |
| 156 | 0.07 | 0.04 |
| 157 | 0.13 | 0.19 |
| 158 | 0.10 | 0.20 |
| 159 | 0.21 | 0.29 |
| 160 | 0.16 | 0.02 |
| 161 | 0.17 | 0.06 |
| 162 | 0.11 | 0.09 |
| 163 | 0.10 | 0.06 |
| 164 | 0.11 | 0.07 |
| 165 | 0.12 | 0.07 |
| 166 | 0.14 | 0.11 |
| 167 | 0.10 | 0.08 |
| 168 | 0.07 | 0.06 |
| 169 | 0.23 | 0.27 |
| 170 | 0.21 | 0.37 |
| 171 | 0.10 | 0.13 |
| 172 | 1.07 | 0.87 |
| 173 | 0.12 | 0.08 |
| 174 | 0.32 | 0.38 |
| 175 | 0.37 | 0.29 |
| 176 | 0.42 | 0.41 |
| 177 | 0.27 | 0.39 |
| 178 | 0.53 | 0.08 |
| 179 | 0.38 | 0.07 |
| 180 | 0.19 | 0.14 |
| 181 | 0.14 | 0.12 |
| 182 | 0.20 | 0.13 |
| 183 | 0.33 | 0.15 |
| 184 | 0.23 | 0.41 |
| 185 | 0.19 | 0.21 |
| 186 | 0.80 | 1.93 |
| 187 | 0.62 | 0.71 |
| Comparative Example 1 | >100 | >10 |
| Comparative Example 2 | >100 | >10 |
| Comparative Example 3 | >10 | >10 |
| Comparative Example 4 | >10 | >10 |
| Comparative Example 5 | >100 | >10 |
| Comparative Example 6 | >100 | >10 |

Comparative tests of the compounds of the present invention were performed by testing the binding of the compounds to HSP90 of the compound of the present invention and testing the effect for inhibition of growth of SKBR cancer cell line by the compounds, using the compounds described in Examples of Patent Document 2 as comparative compounds. The comparative compounds hardly exhibited inhibition activities in both tests even at high concentrations. Note that the comparative compounds were synthesized in accordance with the methods described in Patent Document 2 (Table 3).

TABLE 3

| Compound | Structure |
| --- | --- |
| Comparative Example 1 | (structure image) |

TABLE 3-continued

| Compound | Structure |
|---|---|
| Comparative Example 2 | 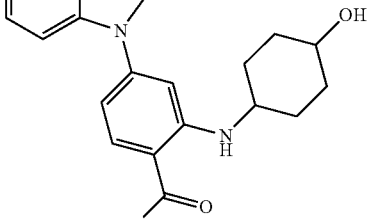 |
| Comparative Example 3 | 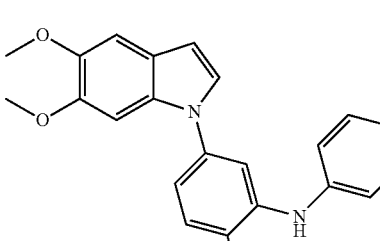 |
| Comparative Example 4 | 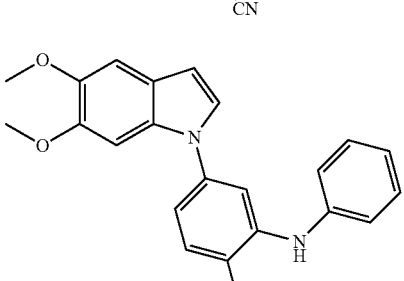 |
| Comparative Example 5 | 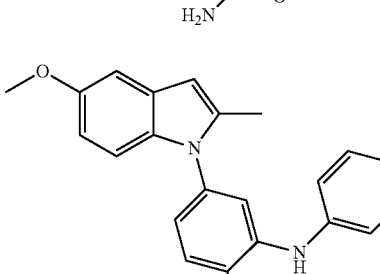 |
| Comparative Example 6 | 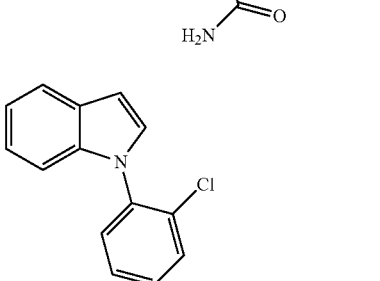 |

The invention claimed is:

1. A compound of formula (I)

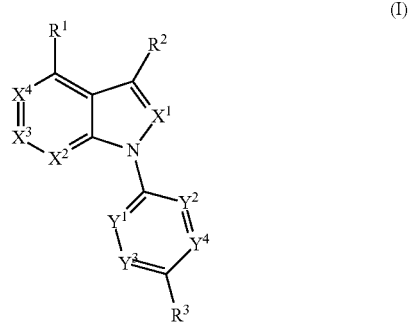

or a salt thereof,
wherein:
$X^1$ is CH or N;
any one of $X^2$, $X^3$, and $X^4$ is N, and the others are CH;
any one or two of $Y^1$, $Y^2$, $Y^3$, and $Y^4$ is C—$R^4$, and the others are each independently CH or N;
$R^1$ is an optionally substituted monocyclic or bicyclic unsaturated heterocyclic group comprising 1 to 4 heteroatoms selected from the group consisting of N, S, and O;
$R^2$ is a hydrogen atom, an optionally substituted alkyl group comprising 1 to 6 carbon atoms, or an optionally substituted alkenyl group comprising 2 to 6 carbon atoms;
$R^3$ is a cyano group or —CO—$R^5$;
each $R^4$ is independently a hydrogen atom, a halogen atom, a cyano group, an optionally substituted alkyl group comprising 1 to 6 carbon atoms, an alkenyl group comprising 2 to 6 carbon atoms, an alkoxy group comprising 1 to 6 carbon atoms, an aromatic hydrocarbon group, —N($R^6$)($R^7$), —S—$R^8$, or —CO—$R^9$;
$R^5$ is an amino group optionally comprising a hydroxyl group, or an optionally substituted mono- or di-alkylamino group;
$R^6$ and $R^7$ are each independently a hydrogen atom, an optionally substituted alkyl group comprising 1 to 6 carbon atoms, a halogenoalkyl group comprising 1 to 6 carbon atoms, an optionally substituted cycloalkyl group comprising 3 to 7 carbon atoms, an optionally substituted aralkyl group, an optionally substituted aromatic hydrocarbon group, an optionally substituted saturated heterocyclic group, or an optionally substituted unsaturated heterocyclic group,
or
$R^6$ and $R^7$ form a saturated heterocyclic group, together with the nitrogen atom to which they are bonded;
$R^8$ is an optionally substituted cycloalkyl group comprising 3 to 7 carbon atoms or an optionally substituted aromatic hydrocarbon group; and
$R^9$ is a hydrogen atom, a hydroxyl group, an amino group optionally comprising a hydroxyl group, or an optionally substituted mono- or di-alkylamino group,
wherein the optional substituents are selected from the group consisting of a halogen atom, a hydroxyl group, a cyano group, a nitro group, an alkyl group, a halogenoalkyl group, a cycloalkyl group, a cycloalkyl-alkyl group, an aralkyl group, a hydroxyalkyl group, an alkenyl group, an alkenyl group, an alkoxy group, a halogenoalkoxy group, an alkoxy-alkyl group, a cycloalkoxy group, a cycloalkyl-alkoxy group, an aralkyloxy group, an aralkyloxy-alkyl group, an alkylthio group, a cycloalkyl-alkylthio group, an amino group, a monoalkylamino, dialkylamino group, a cycloalkyl-alkylamino group, an acyl group, an acyloxy group, an oxo group, a carboxyl group, an alkoxycarbonyl group, an aralkyloxycarbonyl group, a carbamoyl group, a saturated heterocyclic group, an unsaturated heterocyclic group, an aromatic hydrocarbon group and a saturated heterocyclic oxy group;

with the proviso that if $R^1$ is substituted with the saturated or unsaturated heterocyclic group or the aromatic hydrocarbon group, the saturated or unsaturated heterocyclic group and the aromatic hydrocarbon group is optionally substituted with a substituent selected from the group consisting of a halogen atom, a hydroxyl group, a cyano group, a nitro group, an alkyl group, a halogenoalkyl group, a cycloalkyl group, a cycloalkylalkyl group, an aralkyl group, a hydroxyalkyl group, an alkenyl group, an alkynyl group, an alkoxy group, a halogenoalkoxy group, an alkoxy-alkyl group, a cycloalkoxy group, a cycloalkyl-alkoxy group, an aralkyloxy group, an aralkyloxy-alkyl group, an alkylthio group, a cycloalkyl-alkylthio group, an amino group, a monoalkylamino, dialkylamino group, a cycloalkyl-alkylamino group, an acyl group, an acyloxy group, an oxo group, a carboxyl group, an alkoxycarbonyl group, an aralkyloxycarbonyl group, a carbamoyl group, a saturated heterocyclic group, an unsaturated heterocyclic group, an aromatic hydrocarbon group and a saturated heterocyclic oxy group.

2. The compound or salt of claim 1, wherein $R^1$ is an optionally substituted monocyclic 5- to 6-membered unsaturated heterocyclic group comprising 1 to 3 heteroatoms selected from the group consisting of N, S, and O, or an optionally substituted bicyclic 9- to 10-membered unsaturated heterocyclic group comprising 1 to 3 heteroatoms selected from the group consisting of N, S, and O.

3. The compound or salt of claim 1, wherein $R^2$ is an alkyl group comprising 1 to 6 carbon atoms optionally comprising a halogen atom, or an alkenyl group comprising 2 to 6 carbon atoms.

4. The compound or salt of claim 1, wherein $R^3$ is —CO—$R^5$, and $R^5$ is an amino group or a mono- or di-(C1-C6 alkyl)amino group.

5. The compound or salt of claim 1, wherein $X^2$ is N, and $X^3$ and $X^4$ are CH.

6. The compound or salt of claim 1, wherein $R^1$ is selected from the group consisting of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group, and an optionally substituted 5,6,7,8-tetrahydroquinolin-3-yl group.

7. The compound or salt of claim 1 wherein:
$Y^1$ and $Y^3$ are CH, any one or two of $Y^2$ and $Y^4$ are C-$R^4$, and the other is CH; and
$R^4$ is a halogen atom, an alkyl group comprising 1 to 6 carbon atoms optionally comprising a mono- or di-(C1-C6 alkyl)amino group or a monocyclic 5- to 7-membered saturated heterocyclic group comprising one or two heteroatoms selected from the group consisting of N, S, and O, an alkoxy group comprising 1 to 6 carbon atoms, —N($R^6$)($R^7$), —S$R^8$, or —CO—$R^9$.

8. The compound or salt of claim 1, wherein:
$R^6$ is a hydrogen atom or an optionally substituted alkyl group comprising 1 to 6 carbon atoms, and $R^7$ is a hydrogen atom, an optionally substituted alkyl group comprising 1 to 6 carbon atoms, an optionally substituted cycloalkyl group comprising 3 to 7 carbon atoms, an optionally substituted aralkyl group comprising 7 to 12 carbon atoms, an optionally substituted aromatic hydrocarbon group comprising 6 to 14 carbon atoms, a monocyclic or bicyclic optionally substituted saturated heterocyclic group comprising 1 to 4 heteroatoms selected from the group consisting of N, S, and O, or a monocyclic or bicyclic optionally substituted unsaturated heterocyclic group comprising 1 to 4 heteroatoms selected from the group consisting of N, S, and O,
or
$R^6$ and $R^7$ form a 5- to 7-membered saturated heterocyclic group, together with the nitrogen atom to which they are bonded;
$R^8$ is an optionally substituted cycloalkyl group comprising 3 to 7 carbon atoms, or an optionally substituted aromatic hydrocarbon group comprising 6 to 14 carbon atoms; and
$R^9$ is a hydrogen atom, a hydroxyl group, an amino group or a mono- or di-(C1-C6 alkyl)amino group.

9. A pharmaceutical product comprising a compound or salt of claim 1.

10. A pharmaceutical composition comprising a compound or salt of claim 1, and a pharmaceutically acceptable carrier.

11. The compound or salt of claim 1, which is selected from the group consisting of
(2-(hydroxycyclohexylamino)-4-{3-isopropyl-4-(4-(4-methoxyphenyl)-1H-imidazol-1-yl)-1H-pyrazolo[3,4-b]pyridin-1-yl}benzamide);
2-(4-Hydroxycyclohexylamino)-4-{3-methyl-4-(4-(pyridin-3-yl)-1H-imidazol-1-yl)-1H-pyrazolo[2,3-b]pyridin-1-yl}benzamide;
4-{3-Isopropyl-4-(4-(1-methyl-1H-pyrazol-4-yl)-1H-imidazol-1-yl)-1H-pyrazolo[3,4-b]pyridin-1-yl }-3-methylbenzamide;
3-Ethyl-4-{3-isopropyl-4-(4-(1-methyl-1H-pyrazol-4-yl)-1H-imidazol-1-yl)-1H-pyrazolo[3,4-b]pyridin-1-yl}benzamide;
3-(Ethylamino)-4-{4-(4-(4-(1-methyl -1H-pyrazol-4-yl)-1H-imidazol-1-yl)-3-(trifluoromethyl)-1H-pyrazolo[3,4-b]pyridin-1-yl}benzamide;
2-(Ethylamino)-4-{4-(4-(pyridin-3-yl)-1H-imidazol-1-yl)-3-(trifluoromethyl)-1H-pyrazolo[3,4-b]pyridin-1-yl}benzamide;
3-(Isopropylamino)-4-{4-(4-(pyridin-3-yl)-1H-imidazol-1-yl)-3-(trifluoromethyl)-1H-pyrazolo[3,4-b]pyridin-1-yl}benzamide; and
a salt thereof.

12. A pharmaceutical composition comprising the compound or salt of claim 11, and a pharmaceutically acceptable carrier.

* * * * *

UNITED STATES PATENT AND TRADEMARK OFFICE
CERTIFICATE OF CORRECTION

PATENT NO. : 8,779,142 B2
APPLICATION NO. : 13/378527
DATED : July 15, 2014
INVENTOR(S) : Makoto Kitade et al.

Page 1 of 1

It is certified that error appears in the above-identified patent and that said Letters Patent is hereby corrected as shown below:

Column 78, line 62, "2-(Hydroxycyclohexylamino)-4-{3-isopropyol-4-(4" should read
--2-(4-Hydroxycyclohexylamino)-4-{3-isopropyol-4-(4- --.

Column 79, line 18, "2-(Hydroxycyclohexylamino)-4-{3-isopropyol-4-(4" should read
--2-(4-Hydroxycyclohexylamino)-4-{3-isopropyol-4-(4- --;

line 38, "2-(Hydroxycyclohexylamino)-4-{3-isopropyol-4-(4" should read
--2-(4-Hydroxycyclohexylamino)-4-{3-isopropyol-4-(4- --;

line 57, "2-(Hydroxycyclohexylamino)-4-{3-isopropyol-4-(4-" should read
--2-(4-Hydroxycyclohexylamino)-4-{3-isopropyol-4-(4- --.

Column 80, line 9, "2-(Hydroxycyclohexylamino)-4-{3-isopropyol-4-(5-" should read
--2-(4-Hydroxycyclohexylamino)-4-{3-isopropyol-4-(5- --;

line 51, "2-(Hydroxycyclohexylamino)-4-{3-isopropyol-4-(4-" should read
--2-(4-Hydroxycyclohexylamino)-4-{3-isopropyol-4-(4- --.

Column 84, line 52, "(pyridin-3-yl)-1H-imidazol-1-yl)-1H-pyrazolo[2,3-b]" should read
--(pyridin-3-yl)-1H-imidazol-1-yl)-1H-pyrrolo[2,3-b]--.

Column 85, line 39, "(pyridin-3-yl)-1H-imidazol-1-yl)-1H-pyrazolo[2,3-b]" should read
--(pyridin-3-yl)-1H-imidazol-1-yl)-1H-pyrrolo[2,3-b]--.

Signed and Sealed this
Sixteenth Day of December, 2014

Michelle K. Lee
*Deputy Director of the United States Patent and Trademark Office*